US009914924B2

(12) United States Patent
Aronin et al.

(10) Patent No.: US 9,914,924 B2
(45) Date of Patent: Mar. 13, 2018

(54) METHODS AND COMPOSITIONS FOR TREATING NEUROLOGICAL DISEASE

(71) Applicant: University of Massachusetts, Boston, MA (US)

(72) Inventors: Neil Aronin, Newtonville, MA (US); Phillip Zamore, Northboro, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 14/589,807

(22) Filed: Jan. 5, 2015

(65) Prior Publication Data

US 2015/0232840 A1 Aug. 20, 2015

Related U.S. Application Data

(63) Continuation of application No. 13/238,991, filed on Sep. 21, 2011, now abandoned, which is a continuation of application No. 12/823,917, filed on Jun. 25, 2010, now abandoned, which is a continuation of application No. 11/506,448, filed on Aug. 18, 2006, now abandoned.

(60) Provisional application No. 60/709,985, filed on Aug. 18, 2005, provisional application No. 60/833,234, filed on Jul. 25, 2006.

(51) Int. Cl.
C12N 15/11 (2006.01)
C12N 15/113 (2010.01)
A61K 31/7088 (2006.01)
C12Q 1/68 (2018.01)
A61K 47/48 (2006.01)

(52) U.S. Cl.
CPC ........ *C12N 15/113* (2013.01); *A61K 31/7088* (2013.01); *C12Q 1/6883* (2013.01); *A61K 47/48123* (2013.01); *C12N 2310/14* (2013.01); *C12N 2310/315* (2013.01); *C12N 2310/321* (2013.01); *C12N 2310/3515* (2013.01); *C12N 2320/32* (2013.01); *C12Q 2600/136* (2013.01); *C12Q 2600/158* (2013.01); *C12Q 2600/178* (2013.01)

(58) Field of Classification Search
CPC .......... C12N 2310/14; C12N 2310/315; C12N 2310/321
See application file for complete search history.

(56) References Cited

U.S. PATENT DOCUMENTS

| 4,842,996 A | 6/1989 | Huynh-Dinh et al. |
| 5,328,470 A | 7/1994 | Nebel et al. |
| 5,686,288 A * | 11/1997 | MacDonald ........... C07K 14/47 435/320.1 |
| 5,814,014 A | 9/1998 | Elsberry et al. |
| 5,965,722 A | 10/1999 | Ecker et al. |
| 6,093,180 A | 8/2000 | Elsberry |
| 6,107,094 A | 8/2000 | Crooke |
| 6,245,427 B1 | 6/2001 | Duzgunes et al. |
| 6,358,932 B1 | 3/2002 | Monia |
| 6,361,940 B1 | 3/2002 | Van Ness et al. |
| 6,476,205 B1 | 11/2002 | Buhr et al. |
| 6,506,559 B1 | 1/2003 | Fire et al. |
| 7,241,618 B2 | 7/2007 | Agami et al. |
| 7,320,965 B2 | 1/2008 | Sah et al. |
| 7,459,547 B2 | 12/2008 | Zamore et al. |
| 7,892,793 B2 | 2/2011 | Xu |
| 7,947,658 B2 | 5/2011 | Aronin et al. |
| 8,680,063 B2 | 3/2014 | Aronin et al. |
| 2002/0012968 A1 | 1/2002 | Carroll et al. |
| 2002/0086356 A1 | 7/2002 | Tuschl et al. |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0069195 A1 | 4/2003 | Farrar et al. |
| 2003/0108923 A1 | 6/2003 | Tuschl et al. |
| 2003/0144232 A1 | 7/2003 | Agami et al. |
| 2003/0144239 A1 | 7/2003 | Agami et al. |
| 2003/0162734 A1 | 8/2003 | Miller et al. |
| 2003/0180756 A1 | 9/2003 | Shi et al. |
| 2003/0190635 A1 | 10/2003 | McSwiggen |
| 2004/0023390 A1 | 2/2004 | Davidson et al. |
| 2004/0096843 A1 | 5/2004 | Rossi et al. |
| 2004/0162255 A1 | 8/2004 | Kaemmerer |
| 2004/0171030 A1 | 9/2004 | Baker et al. |
| 2004/0175703 A1 | 9/2004 | Kreutzer et al. |
| 2004/0180351 A1 | 9/2004 | Giese et al. |
| 2004/0192629 A1 | 9/2004 | Xu et al. |
| 2004/0203145 A1 | 10/2004 | Zamore et al. |
| 2004/0214198 A1 | 10/2004 | Rana |
| 2004/0219671 A1 | 11/2004 | McSwiggen et al. |
| 2004/0220132 A1 | 11/2004 | Kaemmerer |
| 2004/0229266 A1 | 11/2004 | Tuschl et al. |
| 2004/0241854 A1 | 12/2004 | Davidson et al. |
| 2004/0248299 A1 | 12/2004 | Jayasena et al. |
| 2004/0259247 A1 | 12/2004 | Tuschl et al. |
| 2004/0259248 A1 | 12/2004 | Tuschl et al. |
| 2005/0020521 A1 | 1/2005 | Rana |

(Continued)

FOREIGN PATENT DOCUMENTS

| CA | 2432341 A1 | 7/2002 |
| CA | 2432350 A1 | 7/2002 |
| DE | 10160151 A1 | 6/2003 |
| DE | 10302421 A1 | 7/2004 |
| EP | 1389637 A1 | 2/2004 |
| EP | 1527176 B1 | 1/2007 |
| EP | 1857547 A2 | 11/2007 |
| WO | 1994/019493 A1 | 9/1994 |

(Continued)

OTHER PUBLICATIONS

US 5,814,014, 09/1998, Elsberry et al. (withdrawn)

(Continued)

*Primary Examiner* — Brian A Whiteman
(74) *Attorney, Agent, or Firm* — Lathrop Gage LLP; James H. Velema, Esq.

(57) ABSTRACT

This invention relates to methods and compositions for treating neurological disease, and more particularly to methods of delivering iRNA agents to neural cells for the treatment of neurological diseases.

20 Claims, 5 Drawing Sheets

(56) References Cited

U.S. PATENT DOCUMENTS

| | | |
|---|---|---|
| 2005/0026278 A1 | 2/2005 | Tuschl et al. |
| 2005/0037988 A1 | 2/2005 | Zamore et al. |
| 2005/0042646 A1 | 2/2005 | Davidson et al. |
| 2005/0059005 A1 | 3/2005 | Tuschl et al. |
| 2005/0074757 A1 | 4/2005 | Kreutzer et al. |
| 2005/0096284 A1 | 5/2005 | McSwiggen |
| 2005/0106731 A1 | 5/2005 | Davidson et al. |
| 2005/0107325 A1* | 5/2005 | Manoharan ...... A61K 47/48123 514/44 A |
| 2005/0130184 A1 | 6/2005 | Xu et al. |
| 2005/0130919 A1 | 6/2005 | Xu et al. |
| 2005/0137155 A1 | 6/2005 | McSwiggen et al. |
| 2005/0176045 A1 | 8/2005 | Fedorov et al. |
| 2005/0181382 A1 | 8/2005 | Zamore et al. |
| 2005/0182005 A1 | 8/2005 | Tuschl et al. |
| 2005/0186586 A1 | 8/2005 | Zamore et al. |
| 2005/0186591 A1 | 8/2005 | Bumcrot et al. |
| 2005/0191638 A1 | 9/2005 | McSwiggen |
| 2005/0227256 A1 | 10/2005 | Hutvagner et al. |
| 2005/0227940 A1 | 10/2005 | Rossi et al. |
| 2005/0233342 A1* | 10/2005 | Manoharan ........... C12N 15/111 435/6.13 |
| 2005/0234006 A1 | 10/2005 | Tuschl et al. |
| 2005/0234007 A1 | 10/2005 | Tuschl et al. |
| 2005/0244858 A1 | 11/2005 | Rossi et al. |
| 2005/0246794 A1 | 11/2005 | Khvorova et al. |
| 2005/0255086 A1 | 11/2005 | Davidson et al. |
| 2005/0255487 A1* | 11/2005 | Khvorova ............ A61K 31/713 435/6.11 |
| 2005/0256072 A1 | 11/2005 | Aronin et al. |
| 2005/0273868 A1 | 12/2005 | Rana |
| 2005/0277133 A1 | 12/2005 | McSwiggen |
| 2005/0277610 A1 | 12/2005 | Rossi et al. |
| 2006/0009402 A1 | 1/2006 | Zamore et al. |
| 2006/0009408 A1 | 1/2006 | Davidson et al. |
| 2006/0069050 A1 | 3/2006 | Rana |
| 2006/0128650 A1 | 6/2006 | Xu |
| 2006/0134787 A1 | 6/2006 | Zamore et al. |
| 2006/0166910 A1 | 7/2006 | Tuschl et al. |
| 2006/0178328 A1 | 8/2006 | Kaemmerer |
| 2006/0178334 A1 | 8/2006 | Rossi et al. |
| 2006/0212950 A1 | 9/2006 | Tuschl et al. |
| 2006/0257912 A1 | 11/2006 | Kaemmerer et al. |
| 2006/0270623 A1* | 11/2006 | McSwiggen ............ A61K 48/00 514/44 A |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0031844 A1 | 2/2007 | Khvorova et al. |
| 2007/0039072 A1 | 2/2007 | Khvorova et al. |
| 2007/0093445 A1 | 4/2007 | Tuschl et al. |
| 2007/0104688 A1 | 5/2007 | Rossi et al. |
| 2007/0105803 A1 | 5/2007 | Manoharan et al. |
| 2007/0111228 A1 | 5/2007 | Jayasena et al. |
| 2007/0161590 A1 | 7/2007 | Van Bilsen et al. |
| 2007/0161591 A1 | 7/2007 | Aronin et al. |
| 2007/0161595 A1 | 7/2007 | Bumcrot et al. |
| 2007/0207974 A1 | 9/2007 | Khvorova et al. |
| 2007/0259827 A1 | 11/2007 | Aronin et al. |
| 2007/0261126 A1 | 11/2007 | Kaemmerer et al. |
| 2007/0265220 A1 | 11/2007 | Rossi et al. |
| 2008/0039415 A1 | 2/2008 | Stewart et al. |
| 2008/0274989 A1* | 11/2008 | Davidson ............. C12N 15/113 514/44 A |
| 2009/0186410 A1 | 1/2009 | Aronin et al. |
| 2009/0118206 A1 | 5/2009 | Aronin et al. |
| 2010/0267810 A1 | 10/2010 | Aronin et al. |
| 2011/0027882 A1 | 2/2011 | Manoharan et al. |
| 2011/0160286 A1 | 6/2011 | Xu |
| 2011/0251257 A1 | 10/2011 | Manoharan et al. |
| 2012/0214861 A1 | 8/2012 | Aronin et al. |
| 2013/0261166 A1 | 10/2013 | Manoharan et al. |
| 2014/0370597 A1 | 12/2014 | Aronin et al. |

FOREIGN PATENT DOCUMENTS

| | | |
|---|---|---|
| WO | 1998/048009 A2 | 10/1998 |
| WO | 2001/075164 A2 | 10/2001 |
| WO | 2002/044321 A2 | 6/2002 |
| WO | 2002/055692 A3 | 6/2002 |
| WO | 2002/055693 A2 | 7/2002 |
| WO | 2003/001335 A2 | 1/2003 |
| WO | 2003/006477 A1 | 1/2003 |
| WO | 2003/013437 A2 | 2/2003 |
| WO | 2003/020931 A2 | 3/2003 |
| WO | 2003/035869 A1 | 5/2003 |
| WO | 2003/050306 A1 | 6/2003 |
| WO | 2003/056012 A1 | 7/2003 |
| WO | 2003/068797 A1 | 8/2003 |
| WO | 2003/070895 A2 | 8/2003 |
| WO | 2003/080807 A2 | 10/2003 |
| WO | 2004/013280 A2 | 2/2004 |
| WO | 2004/013310 A2 | 2/2004 |
| WO | 2004/013355 A1 | 2/2004 |
| WO | 2004/014933 A1 | 2/2004 |
| WO | 2004/015107 A2 | 2/2004 |
| WO | 2004/029212 A2 | 4/2004 |
| WO | 2004/042027 A2 | 5/2004 |
| WO | 2004/045543 A2 | 6/2004 |
| WO | 2004/046324 A2 | 6/2004 |
| WO | 2004/047872 A2 | 6/2004 |
| WO | 2004/058940 A2 | 7/2004 |
| WO | 2004/065601 A2 | 8/2004 |
| WO | 2004/080406 A2 | 9/2004 |
| WO | 2004/111072 A2 | 12/2004 |
| WO | 2004/111191 A2 | 12/2004 |
| WO | 2005/001043 A2 | 1/2005 |
| WO | 2005/003350 A2 | 1/2005 |
| WO | 2005/007875 A2 | 1/2005 |
| WO | 2005/007877 A2 | 1/2005 |
| WO | 2005/019453 A2 | 3/2005 |
| WO | 2005/023991 A2 | 3/2005 |
| WO | 2005/027980 A1 | 3/2005 |
| WO | 2005/045034 A2 | 5/2005 |
| WO | 2005/062937 A2 | 7/2005 |
| WO | 2005/069987 A2 | 8/2005 |
| WO | 2005/078096 A2 | 8/2005 |
| WO | 2005/079532 A2 | 9/2005 |
| WO | 2005/079533 A2 | 9/2005 |
| WO | 2005/089287 A2 | 9/2005 |
| WO | 2005/116212 A2 | 12/2005 |
| WO | 2006/015389 A2 | 2/2006 |
| WO | 2006/121960 A2 | 11/2006 |
| WO | 2007/002904 A2 | 1/2007 |
| WO | 2007/022470 A2 | 2/2007 |
| WO | 2007/047692 A2 | 4/2007 |
| WO | 2007/087451 A2 | 8/2007 |
| WO | 2008/005562 A2 | 1/2008 |
| WO | 2008/021136 A2 | 2/2008 |
| WO | 2008/021157 A1 | 2/2008 |
| WO | 2008/143774 A2 | 11/2008 |
| WO | 2008/147887 A1 | 12/2008 |

OTHER PUBLICATIONS

Abdelgany, Amr et al., "Allele-specific silencing of a pathogenic mutant acetylcholine receptor subunit by RNA interference," Human Molecular Genetics, vol. 12(20):2637-2644 (2003).

Akhtar, Saghir et al., "Nonviral delivery of synthetic siRNAs in vivo," The Journal of Clinical Investigation, vol. 117 (2007) (12):3623-3632.

Amarzguioui, Mohammed et al., "Rational design and in vitro and in vivo delivery of Dicer substrate si RNA," Nature Protocols, vol. 1(2):508-517 (2006)

Amarzguioui, Mohammed et al., "Tolerance for mutations and chemical modifications in a siRNA," Nucleic Acids Research, vol. 31(2):589-595 (2003).

Ambros, Victor et al., "MicroRNAs and Other Tiny Endogenous RNAs in C. elegans," Current Biology, vol. 13:807-818 (2003).

Aoki, Yuji et al., "Potential tumor-targeting peptide vector of histidylated oligolysine conjugated to a tumor-homing RGD motif," Cancer Gene Therapy, vol. 8:783-787 (2001).

(56) References Cited

OTHER PUBLICATIONS

Aravin, Alexei A. et al., "The Small RNA Profile during *Drosophila melanogaster* Development," Developmental Cell, vol. 5:337-350 (2003).
Aronin, Neil et al., "Are there multiple pathways in the pathogenesis of Huntington's disease?" Phil. Trans. R. Soc. Lond. B, vol. 354:995-1003 (1999).
Aronin, Neil et al., "CAG Expansion Affects the Expression of Mutant Huntingtin in the Huntington's Disease Brain," Neuron, vol. 15:1193-1201 (1995).
Bagella, Luigi et al., "Cloning of Murine CDK9/PITALRE and Its Tissue-Specific Expression in Development," Journal of Cellular Physiology, vol. 177:206-213 (1998).
Bailly, Christian et al., "The use of diaminopurine to investigate structural properties of nucleic acids and molecular recognition between ligands and DNA," Nucleic Acids Research, vol. 26(19):4309-4314 (1998).
Bartel, D.P., "MicroRNAs: Genomics, Biogenesis, Mechanism, and Function," Cell, vol. 116(2):281-297 (2004).
Bass, Brenda L., "The short answer," Nature, vol. 411:428-429 (2001).
Behding, Anders et al., "In vitro photochemical cataract in mice lacking copper-zinc superoxide dismutase," Free Radical Biology & Medicine, vol. 31(6):738-744 (2001).
Bernstein, Emily et al., "Role for a bidentate ribonuclease in the initiation step of RNA interference," Nature, vol. 409:363-366 (2001).
Bijsterbosch, Martin K. et al., "Modulation of plasma protein binding and in vivo liver cell uptake of phosphorothioate oligodeoxynucleotides by cholesterol conjugation," Nucleic Acids Research, vol. 28(14):2717-2725 (2000).
Boden, Daniel et al., "Efficient Gene Transfer of HIV-1-Specific Short Hairpin RNA into Human Lymphocytic Cells Using Recombinant Adeno-associated Virus Vectors," Molecular Therapy, vol. 9(3):396-402 (2004).
Boden, Daniel et al., "Enhanced gene silencing of HIV-1 specific siRNA using microRNA designed hairpins," Nucleic Acids Research, vol. 32(3):1154-1158 (2004).
Bohnsack, Markus T. et al., "Exportin 5 is a RanGTP-dependent dsRNA-binding protein that mediates nuclear export of pre-miRNAs," RNA, vol. 10:185-191 (2004).
Bonnet, Eric et al., "Evidence that microRNA precursors, unlike other non-coding RNAs, have lower folding free energies than random sequences," Bioinformatics, vol. 20(17):2911-2917 (2004).
Boudreau, Ryan L. et al., "Nonallele-specific Silencing of Mutant and Wild-type Huntingtin Demonstrates Therapeutic Efficacy in Huntington's Disease Mice," Molecular Therapy, doi:10.1038/mt. 2009.17 (2009).
Boutla, Alexandra et al, "Developmental defects by antisense-mediated inactivation of micro-RNAs 2 and 13 in *Drosophila* and the identification of putative target genes," Nucleic Acids Research, vol. 31(17):4973-4980 (2003).
Boutla, Alexandra et al., "Short 5'-phosphorylated double-stranded RNAs induce RNA interference in *Drosophila*," Current Biology, vol. 11:1776-1780 (2001).
Brecht, John et al:, "Trans-splicing and polyadenylation of let-7 microRNA primary transcripts," RNA, vol. 10:1586-1594 (2004).
Brennecke, Julius et al., "bantam Encodes a Developmentally Regulated microRNA that Controls Cell Proliferation and Regulates the Proapoptotic Gene hid in *Drosophila*," Cell, vol. 113:25-36 (2003).
Brennecke, Julius et al., "Principles of MicroRNA-Target Recognition," PLoS Biology, vol. 3(3):404-418 (2005).
Brennecke, Julius et al., "Towards a complete description of the microRNA complement of animal genomes," Genome Biology, vol. 4:228.1-228.3 (2003).
Brown, Kirk M. et al., "Target accessibility dictates the potency of human RISC," Nature Structural & Molecular Biology, vol. 12(5):469-470 (2005).
Brummelkamp, Thijn R. et al., "Stable suppression of tumorigenicity by virus-mediated RNA interference," Cell, vol. 2:243-247 (2002).

Brummelkamp, Thijn, R. et al., "A System for Stable Expression of Short Interfering RNAs in Mammalian Cells," Science, vol. 296(5567):550-553 (2002).
Bumcrot, David et al., "RNAi therapeutics: a potential new class of pharmaceutical drugs," Nature Chemical Biology, vol. 2(12):711-719 (2006).
Burgess, Kevin et al., "Photolytic Mass Laddering for Fast Characterization of Oligomers on Single Resin Beads," J. Org. Chem., vol. 62:5662-5663 (1997).
Caccone, Adalgisa et al., "Calibration of the Change in Thermal Stability of DNA Duplexes and Degree of Base Pair Mismatch," J. Mol. Evol., vol. 27:212-216 (1988).
Cai, Xuezhong et al., "Human microRNA are processed from capped, polyadenylated transcripts that can also function as mRNAs," RNA, vol. 10:1957-1966 (2004).
Calegari, Federico et al., "Tissue-specific RNA interference in postimplantation mouse embryos with endoribonuclease-prepared short interfering RNA," Proc. Natl. Acad. Sci. USA, vol. 99(22):14236•14240 (2002).
Caplen, Natasha J. et al., "dsRNA-mediated gene silencing in cultured *Drosophila* cells: a tissue culture model for the analysis of RNA interference," Gene, vol. 252:95-105 (2000).
Caplen, Natasha J. et al., "Rescue of polyglutamine-mediated cytotoxicity by double-stranded RNA-mediated RNA interference," Human Molecular Genetics, vol. 11(2):175-184 (2002).
Caplen, Natasha J. et al., "Specific inhibition of gene expression by small double-stranded RNAs in invertebrate and vertebrate systems," Proc. Natl. Acad. Sci. USA, vol. 98(17):9742-9747 (2001).
Caplen, Natasha J., "RNAi as a gene therapy approach," Expert Opin. Biol. Tiler., vol. 3(4):575-586 (2003).
Carthew, Richard W., "Gene silencing by double-stranded RNA," Current Opinion in Cell Biology, vol. 13:244-248 (2001).
Catalanotto, Caterina et al., "Gene silencing in worms and fungi," Nature, vol. 404:245 (2000).
Catalanotto, Caterina et al., "Involvement of small RNAs and role of the qde genes in the gene silencing pathway in Neurospora," Genes & Development, vol. 16:790-795 (2002).
Caudy, Amy A. et al., "Fragile X-related protein and VIG associate with the RNA interference machinery," Genes & Development, vol. 16:2491-2496 (2002).
Chalk, A.M. et al., "siRNAdb: a database of siRNA sequences," Nucleic Acids Research, vol. 33:D131-D134 (2005).
Chaloin, L. et al., "Design of Carrier Peptide-Oligonucleotide Conjugates with Rapid Membrane Translocation and Nuclear Localization Properties," Biochemical and Biophysical Research Communications, vol. 243:601-608 (1998).
Check, Erika, "RNA to the rescue?" Nature, vol. 425:10-12 (2003).
Chen, Shu-Hsia et al., "Gene therapy for brain tumors: Regression of experimental gliomas by adenovirus-mediated gene transfer in vivo," Proc. Natl. Acad. Sci. USA, vol. 91:3054-3057 (1994).
Chen, Zongyu J. et al., "Sleeping Beauty-mediated down-regulation of huntingtin expression by RNA interference," Biochemical and Biophysical Research Communication, vol. 329:646•652 (2005).
Chi, Jen-Tsan et al., "Genomewide view of gene silencing by small interfering RNAs," Proc. Natl. Acad. Sci. USA, vol. 100(11):6343-6346 (2003).
Chiu, Ya-Lin et al., "RNAi in Human Cells: Basic Structural and Functional Features of Small Interfering RNA," Molecular Cell, vol. 10:549-561 (2002).
Chiu, Ya-Lin et al., "siRNA function in RNAi: A chemical modification analysis," RNA, vol. 9:1034-1048 (2003).
Cleveland, Don W. et al., "From Cheroot to Lou Gehrig: Deciphering Selective Motor Neuron Death in ALS," Nature, vol. 2:806-819 (2001)
Cogoni, Carlo et al., "Gene silencing in Neurospora crassa requires a protein homologous to RNA-dependent RNA polymerase," Nature, vol. 399:166-168 (1999).
Cogoni, Carlo et al., "Isolation of quelling-defective (qde) mutants impaired in posttranscriptional transgene-induced gene silencing in Neurospora crassa," Proc. Natl. Acad. Sci. USA, vol. 94:10233-10238 (1997).
Cogoni, Carlo et al., "Posttranscriptional Gene Silencing in Neurospora by a Real DNA Helicase," Science, vol. 286:2342-2344 (1999)
Conte, Darryl Jr. et al., "RNA Interference in Caenorhabditis Elegans," Current Protocols in Molecular Biology, F.M. Asubel et al., eds., John Wiley & Sons, pp. 26.3.1-26.3.20 (2003)

(56) References Cited

OTHER PUBLICATIONS

Corey, David R., "Chemical modification: the key to clinical application of RNA interference?" The Journal of Clinical Investigation, vol. 117(12):3615-3622 (2007).
Cullen, Bryan R., "Enhancing and confirming the specificity of RNAi experiments," Nature Methods, vol. 3(9):677-681 (2006).
Czauderna, Frank et al., "Structural variations and stabilising modifications of synthetic siRNAs in mammalian cells," Nucleic Acids Research, vol. 31(11):2705-2716 (2003).
Dalmay, Tamas et al., "An RNA-Dependent RNA Polymerase Gene in *Arabidopsis* Is Required for Posttranscriptional Gene Silencing Mediated by a Transgene but Not by a Virus," Cell, vol. 101:543-553 (2000).
Dalmay, Tamas et al., "SDE3 encodes an RNA helicase required for posttranscriptional gene silencing in *Arabidopsis*," The EMBO Journal, vol. 20(8):2069-2077 (2001).
Davidson, Beverly L. et al., "Molecular medicine for the brain: silencing of disease genes with RNA interference," Lancet Neural., vol. 3:145-149 (2004).
Denli, Ahmet M. et al., "Processing of primary microRNAs by the Microprocessor complex," Nature, vol. 432:231-235 (2004).
Derossi, Daniele et al., "The Third Helix of the Antennapedia Homeodomain Translocates through Biological Membranes," The Journal of Biological Chemistry, vol. 269(14):10444•10450 (1994).
Devroe, Eric et al., "Retrovirus-delivered siRNA," BMC Biotechnology, vol. 2:15-19 (2002).
DiFiglia, M. et al., "Therapeutic silencing of mutant huntingtin with siRNA attenuates striate' and cortical neuropathology and behavioral deficits," Proc. Natl. Acad. Sci. USA, vol. 104(43):17204-17209 (2007).
DiFiglia, Marian et al., "Aggregation of Huntingtin in Neuronal Intranuclear Inclusions and Dystrophic Neurites in Brain," Science, vol. 277:1990-1993 (1997).
DiFiglia, Marian et al., "Huntingtin Is a Cytoplasmic Protein Associated with Vesicles in Human and Rat Brain Neurons," Neuron, vol. 14:1075-1081 (1995).
Ding, Hongliu et al., "Selective silencing by RNAi of a dominant allele that causes amyotrophic lateral sclerosis," Aging Cell, vol. 2:209-217 (2003).
Doench, John G. et al., "siRNAs can function as miRNAs," Genes & Development, vol. 17:438-442 (2003).
Doench, John G. et al., "Specificity of microRNA target selection in translational repression," Genes & Development, vol. 18:504-511 (2004).
Dostie, Josee et al, "Numerous microRNPs in neuronal cells containing novel microRNAs," RNA, vol. 9:180-186 (2003).
Du, Quan et al., "A systematic analysis of the silencing effects of an active siRNA at all single-nucleotide mismatched target sites," Nucleic Acids Research, vol. 33(5):1671-1677 (2005).
Duprez, Laurence, et al., "Pathology of the TSH Receptor," Journal of Pediatric Endocrinology & Metabolism, vol. 12:295-302 (1999).
Dykxhoorn, Derek M. et al., "Determinants of specific RNA interference-mediated silencing of human 13-globin alleles differing by a single nucleotide polymorphism," Proc. Natl. Acad. Sci. USA, vol. 103(15):5953-5958 (2006).
Elbashir, S.M., et al., "Duplexes of 21-nucleotide RNAs mediate RNA interferences in cultured mammalian cells," Nature, vol. 411:494-498 (2001).
Elbashir, Sayda M. et al., "Functional anatomy of siRNAs for the mediating efficient RNAi in *Drosophila melanogaster* embryo lysate," The EMBO Journal, vol. 20(23):6877-6888 (2001).
Elbashir, Sayda M. et al., "RNA interference is mediated by 21- and 22-nucleotide RNAs," Genes & Development, vol. 15:188-200 (2001).
Elmquist, Anna et al., "VE-Cadherin-Derived Cell-Penetrating Peptide, pVEC, with Carrier Functions," Experimental Cell Research, vol. 269:237-244 (2001).
Enright, Anton J. et al, "MicroRNA targets in *Drosophila*," Genome Biology, vol. 5:R1.1-R1.14 (2003).

Epa, W. Ruwan et al., "Enhanced Downregulation of the p75 Nerve Growth Factor Receptor by Cholesteryl and Bis-Cholesteryl Antisense Oligonucleotides," Antisense & Nucleic Acid Drug Development, vol. 8:489-498 (1998).
Fagard, Mathilde et al., "AG01, QDE-2, and RDE-1 are related proteins required for post-transcriptional gene silencing in plants, quelling in fungi, and RNA interference in animals," Proc. Natl. Acad. Sci. USA, vol. 97(21):11650-11654 (2000).
Fire, Andrew et al., "Potent and specific genetic interference by double-stranded RNA in Caenorhabditis elegans," Nature, vol. 391:806-811 (1998).
Flood, Dorothy G. et al., "Hindlimb Motor Neurons Require Cu/Zn Superoxide Dismutase for Maintenance of Neuromuscular Junctions," American Journal of Pathology, vol. 155(2):663•672 (1999).
Fluiter, K. et al., "Killing cancer by targeting genes that cancer cells have lost: Allele-specific inhibition, a novel approach to the treatment of genetic disorders," CMLS, Cell. WI. Life Sci., vol. 60:834-843 (2003).
Fluiter, Kees et al., "Tumor Genotype-specific Growth Inhibition in Vivo by Antisense Oligonucleotides against a Polymorphic Site of the Large Subunit of Human RNA Polymerase II," Cancer Research, vol. 62:2024-2028 (2002).
Förstermann, K. et al, "Normal microRNA maturation and germline stem cell maintenance requires loquacious, a double-stranded RNA-binding domain protein," PLOS Biology, vol. 3(7):1-15 (2005).
Francis, Ross et al., "aph-1 and pen-2 Are Required for Notch Pathway Signaling, γ-Secretase Cleavage of pAPP, and Presenilin Protein Accumulation," Development Cell, vol. 3:85-97 (2002).
Fressinaud, Edith et al., "Molecular Genetics of Type 2 von Willebrand Disease," International Journal of Hematology, vol. 75:9-18 (2002).
Gante, Joachim, "Azapeptides," Synthesis, 1989(6): 405-413 (1989).
Gaudette, Mara et al., "Current status of SOD1 mutations in familial amyotrophic lateral sclerosis," Amyotrophic Lateral Sclerosis, vol. 1(2):83-89 (2000).
Gewirtz, Alan M., "On future's doorstep: RNA interference and the pharmacopeia of tomorrow," The Journal of Clinical Investigation, vol. 117(12):3612-3614 (2007).
Ghildiyal, M. et al., "Small silencing RNAs: an expanding universe," Nat. Rev. Genet., vol. 10(2):94-108 (2009).
Goto, J. et al., "Suppression of Huntingtin Gene Expression by siRNA: A Possible Therapeutic Tool for Huntington's Disease," Neurology, vol. 60(5 Suppl. 1):A286 (2003).
Griffiths-Jones, Sam, "The microRNA Registry," Nucleic Acids Research, vol. 32:D109-D111 (2004).
Grimm, Dirk et al., "Therapeutic application of RNAi: is mRNA targeting finally ready for prime time?" The Journal of Clinical Investigation, vol. 117(12):3633-3641 (2007).
Grishok, A. et al.,"Genes and Mechanisms related to RNA interference regulate expression of the small temporal RNAs that control C. elegans development timing," Cell, vol. 106:23-34 (2001).
Grishok, Alla et al., "Genetic Requirements for Inheritance of RNAi in C. elegans," Science, vol. 287:2494-2497 (2000).
Grishok, Alla 'et al., "RNAi (Nematodes Caenorhabditis elegans)," Advances in Genetics, vol. 46:339-360 (2002).
Grzelinski, Marius et al, "RNA Interference-Mediated Gene Silencing of Pleiotrophin Through Polyethylenimine-Complexed Small Interfering RNAs In Vivo Exerts Antitumoral Effects in Glioblastoma Xenografts," Human Gene Therapy, 17:751-766 (2006).
McManus, Michael T. et al., "Gene Silencing in Mammals by Small Interfering RNAs," Nature Reviews Genetics, vol. (2002) 3:737-747.
McManus, Michael T. et al., "Gene silencing using micro-RNA designed hairpins," RNA, vol. 8:842-850 (2002).
Meister, Gunter et al., "Sequence-specific inhibition of microRNA- and siRNA-induced RNA silencing," RNA, vol. 10:544-550 (2004).
Merriam-Webster online, "engineer," retrieved online at http://www.merriam-webster.com/dictonary (2008).
Merriam-Webster online, "pharmaceutical," retrieved online at http://www.merriam-webster.com/dictonary (2009).

(56) References Cited

OTHER PUBLICATIONS

Mi, Zhibao et al., "Characterization of a Class of Cationic Peptides Able to Facilitate Efficient Protein Transduction in Vitro and in Vivo," Molecular Therapy, vol. 2(4):339-347 (2000)
Miller et al. "Allele-specific silencing of dominant disease genes," Proc. Natl. Acad. Sci. USA, 100(12): 7195-7200 (2003).
Miller, Victor M. et al., "Targeting Alzheimer's disease genes with RNA interference: an efficient strategy for silencing mutant alleles," Nucleic Acids Research, vol. 32(2):661-668 (2004).
Mitchell, D.J. et al., "Polyarginine enters cells more efficiently than other polycationic homopolymers," J. Peptide Res., vol. 56:318-325 (2000).
Miyagishi, Makoto et al., "U6 promoter-driven, siRNAs with four uridine 3' overhangs efficiently suppress targeted gene expression in mammalian cells," Nature Biotechnology, vol. 19:497-500 (2002).
Molecular Biology of the Cell, Fourth Edition, "DNA Replication Mechanisms," retrieved online at http://www.ncbi.nlm.nih.gov/books/bv.fcgi?highlight=DNA&rid=mboc4.section.754 (2008).
Molecular Biology of the Cell, Fourth Edition, "Figure 4-4," retrieved online at http://www.ncbi.nlm.nih.gov/books/bv.fcgi?rid=mboc4.figgrp (2008).
Molecular Biology of the Cell, Fourth Edition, "The Chemical Composition of a Cell," retrieved online at http://www.ncbi.nlm.nih.gov/books/bv.fcgi?highlight=hydrogen,dna,bond&rid=mboc4.section16 5 (2008).
Molecular Biology of the Cell, Fourth Edition, Wobble base-pairing between codons and anticodons, retrieved online at http://www.ncbi.nlm.nih.gov/books/bv.fcgi?highlight=inosine&rid=mboc4.figgrp.1058 (2008).
Moss, Eric G. et al., "The Cold Shock Domain Protein LIN-28 Controls Developmental Timing in C. elegans and Is Regulated by the lin-4 RNA," Cell, vol. 88:637-646 (1997).
Moss, Eric G., "Silencing unhealthy alleles naturally," Trends in Biotechnology, vol. 21(5):185-187 (2003).
Mourelatos, Zissimos et al., "miRNPs: a novel class of ribonucleoproteins containing numerous microRNAs," Genes & Development, vol. 16:720-728 (2002).
Mourrain, Philippe et al., "*Arabidopsis* SGS2 and SGS3 Genes Are Required for Posttranscriptional Gene Silencing and Natural Virus Resistance," Cell, vol. 101:533-542 (2000).
Müller, Jørn et al., "Severe testotoxicosis phentype associated with Asp578-->Tyr mutation of the lutrophin/choriogonadotrophin receptor gene," J. Med. Genet., vol. 35:340-341 (1998).
Murchison, Elizabeth P. et al., "miRNAs on the move: miRNA biogenesis and the RNAi machinery," Current Opinion in Cell Biology, vol. 16:223-229 (2004).
Nellemann, Christine et al., "Inhibition of Huntingtin Synthesis by Antisense Oligodeoxynucleotides," Molecular and Cellular Neuroscience, vol. 16:313-323 (2000).
Holen, Torgeir et al., "Similar behaviour of single-strand and double-strand siRNAs suggests they act through a common RNAi pathway," Nucleic Acids Research, vol. 31(9):2401-2407 (2003).
Nykänen, Antti et al., "ATP Requirements and Small Interfering RNA Structure in the RNA Interference Pathway," Cell, vol. 107:309-321 (2001).
Ohnishi, Yusuke et al., "Enhancement of Allele Discrimination by Introduction of Nucleotide Mismatches into siRNA in Allele-Specific Gene Silencing by RNAi," PLoS One, vol. 3(5):e2248 (2008).
Oldridge, Michael et al., "Dominant mutations in ROR2, encoding an orphan receptor tyrosine kinase, cause brachydactyly type B," Nature Genetics, vol. 24:275-278 (2000).
Olsen, Philip H. et al., "The lin-4 Regulatory RNA Controls Developmental Timing in Caenorhabditis elegans by Blocking LIN-14 Protein Synthesis after the Initiation of Translation," Developmental Biology, vol. 216:671-680 (1999).
Opalinska, Joanna B. et al., "Nucleic Acid Therapeutic for Hematologic Malignancies—Theoretical Considerations," Ann. N.Y. Acad. Sci., vol. 1082:124-136 (2006).

Opalinska, Joanna B. et al., "Nucleic-Acid Therapeutics: Basic Principles and Recent Applications," Nature Reviews, Drug Discovery, vol. 1:503-514 (2002).
Orrell, Richard W. et al., "Clinical implications of the genetics of ALS and other motor neuron diseases," Neurology, vol. 57:9-17 (2001).
Paddison, Patrick J. et al., "Short hairpin RNAs (shRNAs) induce sequence-specific silencing in mammalian cells," Genes & Development, vol. 16:948-958 (2002).
Parrish, Susan et al., "Functional Anatomy of a dsRNA Trigger: Differential Requirement for the Two Trigger Strands in RNA Interference," Molecular Cell, vol. 6:1077-1087 (2000).
Paul, Cynthia P. et al., "Effective expression of small interfering RNA in human cells," Nature Biotechnology, vol. 29:505-508 (2002).
Persengiev, Stephan P. et al., "Nonspecific, concentration-dependent stimulation and repression of mammalian gene expression by small interfering RNAs (siRNAs)," RNA, vol. 10:12-18 (2004).
Pfister, Edith L. et al., "Five siRNAs Targeting Three SNPs May Provide Therapy for Three-Quarters of Huntington's Disease Patients," Current Biology, vol. 19:774-778 (2009).
Pooga, Margus et al., "Cell penetration by transportan," FASEB J., vol. 12:67-77 (1998).
Poy, Matthew N. et al., "A pancreatic islet-specific microRNA regulates insulin secretion," Nature, vol. 432:226-230 (2004).
Pusch, Oliver et al., "Nucleotide sequence homology requirements of HIV-1-specific short hairpin RNA," Nucleic Acids Research, vol. 31(22):6444-6449 (2003).
Puttaparthi, Krishna et al., "Disease Progression in a Transgenic Model of Familial Amyotrophic Lateral Sclerosis Is Dependent on Both Neuronal and Non-Neuronal Zinc Binding Proteins," The Journal of Neuroscience, vol. 22 (20):8790-8796 (2002).
Qin, Zheng-Hong et al., "Autophagy regulates the processing of amino terminal huntingtin fragments," Human Molecular Genetics, vol. 12(24):3231-3244 (2003).
Radunović, Aleksandar et al., "ALSODatabase: Database of SOD1 (and other) gene mutations in ALS on the internet," Amyot. Lat. Scler. Other Motor Neuron Disord., vol. 1:45-49 (1999).
Ralph, G. Scott et al., "Silencing mutant SOD1 using RNAi protects against neurodegeneration and extends survival in an ALS model," Nature Medicine, vol. 11(4):429-433 (2005).
Raoul, Cédric et al., "Lentiviral-mediated silencing of SOD1 through RNA interference retards disease onset and progression in a mouse model of ALS," Nature Medicine, vol. 11(4):423-428 (2005).
Reich, Samuel J. et al., "Small interfering RNA (siRNA) targeting VEGF effectively inhibits ocular neovascularization in a mouse model," Molecular Vision, vol. 9:910-916 (2003).
Reinhart, Brenda J. et al., "MicroRNAs in plants," Genes & Development, vol. 16:1616-1626 (2002).
Reinhart, Brenda J. et al., "The 21-nucleotide let-7 RNA regulates developmental timing in Caenorhabditis elegans," Nature, vol. 403:901-906 (2000).
Reynolds, Angela et al., "Rational siRNA design for RNA interference," Nature Biotechnology, vol. 22(3):326-330 (2004).
Rival, Thomas et al., "Decreasing Glutamate Buffering Capacity Triggers Oxidative Stress and Neuropil Degeneration in the *Drosophila* Brain," Current Biology, vol. 14:599-605 (2004).
Rose, Scott D. et al., "Functional polarity is introduced by Dicer processing of short substrate RNAs," Nucleic Acids Research, vol. 33(13):4140-4156 (2005).
Saenger, Wolfram, Principles of Nucleic Acid Structure, Springer-Verlag, New York, Charles R. Cantor (ed.) (1984).
Sahin-Tóth, Miklos et al., "Gain-of-Function Mutations Associated with Hereditary Pancreatitis Enhance Autoactivation of Human Cationic Trypsinogen," Biochemical and Biophysical Research Communications, vol. 278:286-289 (2000).
Kremer, Berry et al., "A Worldwide Study of the Huntington's Disease Mutation: The Sensitivity and Specificity of Measuring CAG Repeats," New England Journal of Medicine, vol. 330(20):1401-1406 (1994).
Krol, Jacek et al., "Structural Features of MicroRNA (miRNA) Precursors and Their Relevance to miRNA Biogenesis and Small

(56) References Cited

OTHER PUBLICATIONS

Interfering RNA/Short Hairpin RNA Design," The Journal of Biological Chemistry, vol. 279(40):42230-42239 (2004).
Kunst, Catherine B. et al., "Mutations in SOD1 associated with amyotrophic lateral sclerosis cause novel protein interactions," Nature Genetics, vol. 15:91-94 (1997).
Kwong, J.Q. et al., "RNAi-mediated inhibition of mutated htt in Huntington's disease models," Society for Neuroscience, Abstract, Presentation No. 208.18 (2003).
Laforet, Genevieve A. et al., "Changes in Cortical and Striatal Neurons Predict Behavioral and Electrophysiological Abnormalities in a Transgenic Murine Model of Huntington's Disease," The Journal of Neuroscience, vol. 21 (23):9112-9123 (2001).
Lagos-Quintana, M. et al., "Identification of novel genes coding for small expressed RNAs," Science, vol. 294 (2001) (5543):853-858.
Lagos-Quintana, Mariana et al., "Identification of Tissue-Specific MicroRNAs from Mouse," Current Biology, vol. 12:735-739 (2002).
Lagos-Quintana, Mariana et al., "New MicroRNAs from mouse and human," RNA, vol. 9:175-179 (2003).
Lai, Eric C., "Micro RNAs are complementary to 3' UTR sequence motifs that mediate negative post-transcriptional regulation," Nature Genetics, vol. 30:363-364 (2002).
Lam, Kit S. et al., "A new type of synthetic peptide library for identifying ligand-binding activity," Nature, vol. 354:82-84 (1991).
Lania, Andrea, et al., "G protein mutations in endocrine diseases," European Journal of Endocrinology, vol. 145:543-559 (2001).
Lau, Nelson C. et al., "An Abundant Class of Tiny RNAs with Probable Regulatory Roles in Caenorhabditis elegans," Science, vol. 294:858-862 (2001).
Lee, Nan Sook et al., "Expression of small interfering RNAs targeted against HIV-1 rev transcripts in human cells," Nature Biotechnology, vol. 19:500-505 (2002).
Lee, Rosalind C. et al., "An Extensive Class of Small RNAs in Caenorhabditis elegans," Science, vol. 294:862-864 (2001).
Lee, Rosalind C. et al., "The C. elegans Heterochronic Gene lin-4 Encodes Small RNAs with Antisense Complementarity to lin-14," Cell, vol. 75:843-854 (1993).
Lee, Sang-Kyung et al., "Lentiviral delivery of short hairpin RNAs protects CD4 T cells from multiple clades and primary isolates of HIV," Blood, vol. 106(3):818-826 (2005).
Lee, Yoontae et al., "MicroRNA genes are transcribed by RNA polymerase II," The EMBO Journal, vol. 23:4051-4060 (2004).
Lee, Yoontae et al., "MicroRNA maturation: stepwise processing and subcellular localization," The EMBO Journal, vol. 21(17):4663-4670 (2002).
Lee, Yoontae et al., "The nuclear RNase III Drosha initiates microRNA processing," Nature, vol. 425:415-419 (2003).
Lewis, Benjamin P. et al., "Conserved Seed Pairings, Often Flanked by Adenosines, Indicates that Thousands of Human Genes are MicroRNA Targets," Cell, vol. 120:15-20 (2005).
Lewis, Benjamin P. et al., "Prediction of Mammalian MicroRNA Targets," Cell, vol. 115:787-798 (2003).
Lewis, David L. et al., "Efficient delivery of siRNA for inhibition of gene expression in postnatal mice," Nature Genetics, vol. 32:107-108 (2002).
Li, Bao-jian et al., "Using siRNA in prophylactic and therapeutic regimens against SARS coronavirus in Rhesus macaque," Nature Medicine, vol. 11(9):944-951 (2005).
Li, Zhaoyang et al., "Specific inhibition of HIV-1 replication by short hairpin RNAs targeting human cyclin T1 without inducing apoptosis," FEES Letters, vol. 579:3100-3106 (2005).
Liang, Xue-hai et al., "Small nucleolar RNA interference induced by antisense or double-stranded RNA in trypanosomatids," Proc. Natl. Acad. Sci. USA, vol. 100(13):7521-7526 (2003).
Lieberman, Judy et al., "Interfering with disease: opportunities and roadblocks to harnessing RNA interference," Trends in Molecular Medicine, vol. 9(9):397-403 (2003).
Lim, Lee P. et al., "Microarray analysis shows that some microRNAs downregulate large numbers of target mRNAs," Nature, vol. 433:769-773 (2005).
Lim, Lee P. et al., "The microRNAs of Caenorhabditis elegans," Genes & Development, vol. 17:991-1008 (2003).
Lim, Lee P. et al., "Vertebrate MicroRNA Genes," Science, vol. 299:1540 (2003).
Limbach, Patrick A. et al., "Summary: the modified nucleosides of RNA," Nucleic Acids Research, vol. 22(12): 2183-2196 (1994).
Lipardi, Concetta et al., "RNAi as Random Degradative PCR: siRNA Primers Convert mRNA into dsRNAs that Are Degraded to Generate New siRNAs," Cell, vol. 107:297-307 (2001).
Liu, Qinghua et al., "R2D2, a Bridge Between the Initiation and Effector Steps of the *Drosophila* RNAi Pathway," Science, vol. 301:1921-1925 (2003).
Liu, Wanzhao et al., "Linking SNPs to CAG repeat length in Huntington's disease patients," Nature Methods, vol. 5 (11):951-953 (2008).
Lombardi, Maria Stella et al., "A majority of Huntington's disease patients may be treatable by individualized allele-specific RNA interference," Experimental Neurology, vol. 312-319 (2009).
Lorenz, Christina et al., "Steroid and lipid conjugates of siRNAs to enhance cellular uptake and gene silencing in liver cells," Bioorganic & Medicinal Chemistry Letters, vol. 14:4975-4977 (2004).
Lund, Elsebet et al., "Nuclear Export of MicroRNA Precursors," Science, vol. 303:95-98 (2004).
Luyten, Ingrid et al., "Hybridization properties of base-modified oligonucleotides within the double and triple helix motif," Eur. J. Med. Chem., vol. 33:515-576 (1998).
MacDonald, Marcy E. et al., "A Novel Gene Containing a Trinucleotide Repeat That Is Expanded and Unstable on Huntington's Disease Chromosomes," Cell, vol. 72:971-983 (1993).
Mahato, Ram I. et al., "Modulation of gene expression by antisense and antigene oligodeoxynucleotides and small interfering RNA," Expert Opinion on Drug Delivery, vol. 2(1):3-28 (2005).
Mallory, Allison C. et al., "MicroRNA control of PHABULOSA in leaf development: importance of pairing to the microRNA 5' region," The EMBO Journal, vol. 23:3356-3364 (2004).
Manoharan, Muthiah et al., "Oligonucleotide Conjugates: Alteration of the Pharmacokinetic Properties of Antisense Agents," Nucleoside & Nucleotides, vol. 14(3-5):969-973 (1995).
Manoharan, Muthiah, "Oligonucleotide Conjugates as Potential Antisense Drugs with Improved Uptake, Biodistribution, Targeted Delivery, and Mechanism of Action," Antisense & Nucleic Acid Drug Development, vol. 12:103-128 (2002).
Martinez, Javier et al., "Single-Stranded Antisense siRNAs Guide Target RNA Cleavage in RNAi," Cell, vol. 110:563-574 (2002).
Martinez, Luis Alfonso et al., "Synthetic small inhibiting RNAs: Efficient tools to inactivate oncogenic mutations and restore p53 pathways," Proc. Natl. Acad. Sci. USA, vol. 99(23):14849-14854 (2002).
Matz, Paul G. et al., "Cell Death After Exposure to Subarachnoid Hemolysate Correlates Inversely With Expression of CuZn-Superoxide Dismutase," Stroke, vol. 31:2450-2458 (2000).
Matzuk, Martin M. et al., "Ovarian Function in Superoxide Dismutase 1 and 2 Knockout Mice," Endocrinology, vol. 139 (9):4008-4011 (1998).
Maxwell, Michele M. et al., "RNA interference-mediated silencing of mutant superoxide dismutase rescues cyclosporin A-induced death in cultured neuroblastoma cells," Proc. Natl. Acad. Sci. USA, vol. 101(9):3178-3183 (2004).
McCaffrey, Anton P. et al., "A story of mice and men," Gene Therapy, vol. 9:1563 (2002).
McCaffrey, Anton P. et al., "RNA interference in adult mice," Nature, vol. 418:38-39 (2002}.
McFadden, Sandra L. et al., "Anatomical, Metabolic and Genetic Aspects of Age-related Hearing Loss in Mice," Audiology, vol. 40:313-321 (2001).
Gualberto, Antonio, et al., "An oncogenic form of p53 confers a dominant, gain-of-function phenotype that disrupts spindle checkpoint control," Proc. Natl. Acad. Sci. USA, vol. 95:5166-5171 (1998).

(56) References Cited

OTHER PUBLICATIONS

Ha, Ilho et al., "A bulged lin-4/lin-14 RNA duplex is sufficient for Caenorhabditis elegans lin-14 temporal gradient formation," Genes & Development, vol. 10:3041-3050 (1996).
Haley, Benjamin et al., "In vitro analysis of RNA interference in *Drosophila melanogaster*," Methods, vol. 30:330-336 (2003).
Haley, Benjamin et al., "Kinetic analysis of the RNAi enzyme complex," Nature Structural & Molecular Biology, vol. 11 (7):599-606 (2004).
Halldórsson, Bjarni V. et al., "Optimal Selection of SNP Markers for Disease Association Studies," Hum. Hered., vol. 58:190-202 (2004).
Hamada, Makiko et al., "Effects on RNA Interference in Gene Expression (RNAi) in Cultured Mammalian Cells of Mismatches and the Introduction of Chemical Modifications at the 3'-Ends of siRNAs," Antisense and Nucleic Acid Drug Development, vol. 12:301-309 (2002).
Hamilton, Andrew J. et al., "A Species of Small Antisense RNA in Posttranscriptional Gene Silencing in Plants," Science, vol. 286:950-952 (1999).
Hammond, Scott M. et al., "An RNA-directed nuclease mediates post-transcriptional gene silencing in *Drosophila* cells," Nature, vol. 404:293-296 (2000).
Hammond, Scott M. et al., "Argonaute2, a Link Between Genetic and Biochemical Analyses of RNAi," Science, vol. 293:1146-1150 (2001).
Hammond, Scott M. et al., "Post-Transcriptional Gene Silencing by Double-Stranded RNA," Nature, vol. 2:110-119 (2001).
Hannon, Gregory J. et al., "Unlocking the potential of the human genome with RNA interference," Nature, vol. 431:371-378 (2004).
Harborth, Jens et al., "Identification of essential genes in cultured mammalian cells using small interfering RNAs," Journal of Cell Science, vol. 114:4557-4565 (2001).
Harper, Scott Q. et at., "RNA interference improves motor and neuropathological abnormalities in a Huntington's disease mouse model," Proc. Natl. Acad. Sci. USA, vol. 102(16):5820-5825 (2005).
Haubner, Roland et al., "Glycosylated RGD-Containing Peptides: Tracer for Tumor Targeting and Angiogenesis Imaging with Improved Biokinetics," The Journal of Nuclear Medicine, vol. 42(2):326-336 (2001).
Heale, Bret S.E. et al., "siRNA target site secondary structure predictions using local stable substructures," Nucleic Acids Research, vol. 33(3):1-10 (2005).
Hirota, Seiichi et al., "Gain-of-function mutation at the extracellular domain of KIT in gastrointestinal stromal tumours," Journal of Pathology, vol. 193:505-510 (2001).
Hirota, Seiichi, et al., "Gain-of-Function Mutations of c-kit in Human Gastrointestinal Stromal Tumors," Science, vol. 279:577-580 (1998).
Hixon, M.L. et al., "Gain of function properties of mutant p53 proteins at the mitotic spindle cell cycle checkpoint," Histology and Histopathology, vol. 15:551-556 (2000).
Ho, L.W., et al., "The molecular biology of Huntington's disease," Psychological Medicine, vol. 31:3-14 (2001).
Hoehn, Margaret M. et al., "Parkinsonism: onset, progression, and mortality," Neurology, vol. 17(5):427-442 (1967).
Hohjoh, Hirohiko, "Enhancement of RNAi activity by improved siRNA duplexes," FEBS Letters, vol. 557:193-198 (2004).
Hojo, S. et al., "Heterogeneous point mutations of the p53 gene in pulmonary fibrosis," Eur. Respir. J., vol. 12:1404-1408 (1998).
Holen, Torgeir et al., "Positional effects of short interfering RNAs targeting the human coagulation trigger Tissue Factor," Nucleic Acids Research, vol. 30(8):1757-1766 (2002).
Holmes, Christopher P., et al., "Strategies for Combinatorial Organic Synthesis: Solution and Polymer-Supported Synthesis of 4-Thiazolidinones and 4-Metathiazanones Derived from Amino Acids," J. Org. Chem., vol. 60:7328-7333 (1995).
Hsieh, Andrew C. et al., "A library of siRNA duplexes targeting the phosphoinositide 3-kinase pathway: determinants of gene silencing for use in cell-based screens," Nucleic Acids Research, vol. 32(3):893-901 (2004).
Hu-Lieskovan, Siwen et al., "Sequence-Specific Knockdown of EWS-FLI1 by Targeted, Nonviral Delivery of Small Interfering Inhibits Tumor Growth in a Murine Model of Metastatic Ewing's Sarcoma," Cancer Res., vol. 65 (19):8984-8992 (2005).
Hutvágner, György et al.,"A cellular function for the RNA-interference enzyme dicer in the maturation of the let-7 small temporal RNA," Science, vol. 293:834-838 (2001).
Hutvágner, György et al., "A microRNA in a Multiple-Turnover RNAi Enzyme Complex," Science, vol. 297:2056-2060 (2002).
Hutvágner, György et al., "RNAi: nature abhors a double-strand," Curr. Opin. Genet. Dev., vol. 12:225-232 (2002).
Jackson, Aimee L. et al., "Expression profiling reveals off-target gene regulation by RNAi," Nature Biotechnology, vol. 21(6):635-637 (2003).
Jackson, Aimee L. et al., "Position-specific chemical modification of siRNAs reduces 'off-target' transcript silencing," RNA, vol. 12:1197-1205 (2006).
Jackson, Aimee L. et al., "Widespread siRNA 'off-target' transcript silencing mediated by seed region sequence complementarity," RNA, vol. 12:1179-1187 (2006).
Jacque, Jean-Marc et al., "Modulation of HIV-1 replication by RNA interference," Nature, vol. 418:435-438 (2002).
Kato, Shinsuke et al., "New consensus research on neuropathological aspects of familial amyotrophic lateral sclerosis with superoxide dismutase 1 (SOD1) gene mutations: Inclusions containing SOD1 in neurons and astrocytes," ALS, vol. 1:163-184 (2000).
Kawase, Makoto et al., "Exacerbation of Delayed Cell Injury After Transient Global Ischemia in Mutant Mice With CuZn Superoxide Dismutase Deficiency," Stroke, vol. 30:1962-1968 (1999).
Ketting, René et al., "Dicer functions in RNA interference and in synthesis of small RNA involved in developmental timing in C. elegans," Genes & Development, vol. 15:2654-2659 (2001).
Ketting, René F. et a., "mut-7 of C. elegans, Required for Transposon Silencing and RNA Interference, Is a Homolog of Werner Syndrome Helicase and RNaseD," Cell, vol. 99:133-141 (1999).
Ketting, René F. et al., "A genetic link between co-suppression and RNA interference in C. elegans," Nature, vol. 404:296-298 (2000).
Khan, Alim et al., "Sustained Polymeric Delivery of Gene Silencing Antisense ODNs, siRNA, DNAzymes and Ribozymes: In Vitro and In Vivo Studies," Journal of Drug Targeting, vol. 12:393-404 (2004).
Khvorova, A. et al.,"Functional siRNAs and miRNAs exhibit strand bias," Cell, vol. 115:209-216 (2003).
Kierzek, Ryszard et al., "Thermodynamics of single Mismatches in RNA Duplexes," Biochemistry, vol. 38:14214-14223 (1999).
Kim, Daniel H. et al., "Strategies for silencing human disease using RNA interference," Nature Reviews Genetics, vol. 8:173-184 (2007).
Kim, Dong-Ho et al., "Synthetic dsRNA Dicer substrates enhances RNAi potency and efficacy," Nature Biotechnology, vol. 23(2):222-226 (2005).
Kim, V.N. et al.,"MicroRNA Biogenesis: Coordinated cropping and dicing," Nature Reviews, vol. 6:376-385 (2005).
Kiriakidou, Marianthi et al., "A combined computational-experimental approach predicts human microRNA targets," Genes & Development, vol. 18:1165-1178 (2004).
Klug, N. et al., "A selective antisense oligonucleotide against the G93A mutant of the Cu/Zn-SOD1 mRNA, applied to the mouse brain," European Journal of Physiology, vol. 441(Suppl. 6):R205, No. P20-7 (2001).
Knight, Scott W: et al., "A Role for the RNase III Enzyme DCR-1 in RNA Interference and Germ Line Development in Caenorhabditis elegans," Science, vol. 293:2269-2271 (2001).
Kondo, Takeo et al., "Reduction of CuZn-Superoxide Dismutase Activity Exacerbates Neuronal Cell Injury and Edema Formation after Transient Focal Cerebral Ischemia," The Journal of Neuroscience, vol. 17(11):4180-4189 (1997).

(56) References Cited

OTHER PUBLICATIONS

Kopp, P., "Human Genome and Diseases: Review, The TSH receptor and its role in thyroid disease," Cell. Mol. Life Sci., vol. 58:1301-1322 (2001).
Kosaki, Kenjiro et al., "PTPN11 (Protein-Tyrosine Phosphatase, Nonreceptor-Type II) Mutations in Seven Japanese Patients with Noonan Syndrome," The Journal of Clinical Endocrinology & Metabolism, vol. 87(8):3529-3533 (2002).
Final Office Action issued for U.S. Appl. No. 11/506,448. dated Jun. 26, 2009, 16 pages.
Final Office Action issued for U.S. Appl. No. 13/238,991. dated Dec. 4, 2013, 11 pages.
GenBank Accession No. NM_002111, "*Homo sapiens* huntingtin (HTT), mRNA," [Online from http://www.ncbi.nlm.nih.gov/nuccore/NM_002111], deposited 1992, 13 pages.
Non-final Office Action issued for U.S. Appl. No. 11/506,448. dated Sep. 12, 2008, 27 pages.
Non-final Office Action issued for U.S. Appl. No. 12/823,917. dated Mar. 21, 2011, 13 pages.
Pending Claims for UMY-041 filed with U.S. Appl. No. 10/715,229, dated Nov. 17, 2003.
Rangone, H. et al., "Phosphorylation of Arfaptin 2 at Ser260 by Akt Inhibits PolyQ-huntingtin-induced toxicity by rescuing proteasome impairment," J. Biol. Chem., vol. 280(23):22021-22028 (2005).
Savitt, Joseph M. et al., "Diagnosis and treatment of Parkinson disease: molecules to medicine," J. Clin. Invest., vol. 116:1744-1754 (2006).
Saxena, Sandeep et al., "Small RNAs with Imperfect Match to Endogenous mRNA Repress Translation: Implications for Off-Target Activity of Small Inhibitory RNA in Mammalian Cells," The Journal of Biological Chemistry, vol. 278 (45):44312-44319 (2003).
Scadden, A.D.J. et al., "Editing of RNA reduces the production of siRNAs," EMBO Reports, vol. 21(12):1109-1111 (2001).
Scherer, Lisa et al."Therapeutic Applications of RNA Interference: Recent Advances in siRNA," Advances in Genetics, vol. 52:1-21 (2004).
Scherer, Lisa J. et al., "Approaches for the sequence-specific knockdown of mRNA," Nature Biotechnology, vol. 21 (12):1457-1465 (2003).
Scherer, Lisa J. et al., "Rapid Assessment of Anti-HIV siRNA Efficacy Using PCR-Derived Pol III shRNA Cassettes," Molecular Therapy, vol. 10(3):597-603 (2004).
Scherer, Lisa J. et al., "Recent Applications of RNAi in Mammalian Systems," Current Pharmaceutical Biotechnology, vol. 5:355-360 (2004).
Schmidt, Charlie, "Negotiating the RNAi patent thicket," Nature Biotechnology, vol. 25(3):273-275 (2007).
Schwarz, Dianne S. et al., "Asymmetry in the Assembly of the RNAi Enzyme Complex," Cell, vol. 115:199-208 (2003).
Schwarz, Dianne S. et al., "Designing siRNA That Distinguish between Genes That Differ by a Single Nucleotide," PloS Genetics, vol. 2(9):1307-1318 (2006) .
Schwarz, Dianne S. et al., "Evidence that siRNAs Function as Guides, Not Primers, in the *Drosophila* and Human RNAi Pathways," Molecular Cell, vol. 10:537-548 (2002).
Schwarz, Dianne S. et al., "The RNA-Induced Silencing Complex Is a Mg2+-Dependent Endonuclease," Current Biology, vol. 14:787-791 (2004).
Schwarz, Dianne S. et al., "Why do miRNAs live in the miRNP?," Genes & Development, vol. 16:1025-1031 (2002).
Seggerson, Kathy et al., "Two Genetic Circuits Repress the Caenorhabditis elegans Heterochronic Gene lin-28 after Translation Initiation," Developmental Biology, vol. 243:215-225 (2002).
Semizarov, Dimitri et al, "Specificity of short interfering RNA determined through gene expression signatures," Natl. Proc. Acad. Sci. USA, 100(11):6347-52 (2003).
Shackel, Nick A. et al., "Intrahepatic Gene Silencing by RNA Interference," Gastroenterology, vol. 126(1):356-358 (2004).
Sharp, Phillip A. et al., "RNA Interference," Science, vol. 287:2431-2432 (2000).
Sharp, Phillip A., "RNA Interference—2001," Genes & Development, vol. 15:485-490 (2001).
Shefner, J.M. et al., "Mice lacking cytosolic copper/zinc superoxide dismutase display a distinctive motor axonopathy," Neurology, vol. 53:1239-1246 (1999).
Shi, Yang, "Mammalian RNAi for the masses," Trends in Genetics, vol. 19(1):9-12 (2003).
Siddique, Teepu et al., ."Molecular genetic basis of familial ALS," Neurology, vol. 47(Suppl. 2):S27-S35 (1996).
Sijen, Titia et al., "One the Role of RNA Amplification in dsRNA-Triggered Gene Silencing," Cell, vol. 107:465-476 (2001).
Simeoni, Federica et al., "Insight into the mechanism of the peptide-based gene delivery system MPG: implications for delivery of siRNA into mammalian cells," Nucleic Acids Research, vol. 31(11):2717-2724 (2003).
Simon, E.S. et al., "Creutzfeldt-Jakob Disease Profile in Patients Homozygous for the PRNP E200K Mutation," Annals of Neurology, vol. 47(2):257-260 (2000).
Slack, Frank J. et al., "The lin-41 RBCC Gene Acts in the C. elegans Heterochronic Pathway between the let-7 Regulatory RNA and the LIN-29 Transcription Factor," Molecular Cell, vol. 5:659-669 (2000).
Sledz, Carol A. et al., "Activation of the interferon system by short-interfering RNAs," Nature Cell Biology, vol. 5 (9):834-838 (2003).
Snøve, Ola Jr., et al., "Chemical Modifications Rescue Off-Target Effects of RNAi," ACS Chemical Biology, vol. 1 (5):274-276 (2006).
Song, Erwei et al., "RNA interference targeting Fas protects mice from fulminant hepatitis," Nature Medicine, vol. 9 (3):347-351 (2003).
Soutschek, Jurgen et al., "Therapeutic silencing of an endogenous gene by systemic administration of modified siRNAs," Nature, vol. 432:173-178 (2004).
Stark, Alexander et al., "Identification of *Drosophila* MicroRNA Targets," PLoS Biology, vol. 1(3):397-409 (2003).
Sui, Guangchao et al., "A DNA vector-based RNAi technology to suppress gene expression in mammalian cells," Proc. Natl. Acad. Sci. USA, vol. 99(8):5515-5520 (2002).
Sundaralingam Muttaiya et al., "Hydrogen and hydration of DNA and RNA oligonucleotides," Biophysical Chemistry, vol. 95:273-282 (2002).
Tabara, Hiroaki et al., "The dsRNA Binding Protein RDE-4 Interacts with RDE-1, DCR-1, and a DExH-Box Helicase to Direct RNAi in C. elegans," Cell, vol. 109:861-871 (2002).
Tabara, Hiroaki et al., "The rcle-1 Gene, RNA Interference and Transposon Silencing in C. elegans," Cell, vol. 99:123-132 (1999).
Tan, P-H et al., "Gene knockdown with intrathecal siRNA of NMDA receptor NR2B subunit reduces formalin-induced nociception in the rat," Gene Therapy, vol. 12:59-66 (2005).
Tang, Guiliang et al., "A biochemical framework for RNA silencing in plants," Genes & Development, vol. 17:49-63 (2003).
Tang, Guiliang et al., "Biochemical Dissection of RNA Silencing in Plants," Methods in Molecular Biology, vol. 257:223-243 (2004).
Taylor, J. Paul et al., "Toxic Proteins in Neurodegenerative Disease," Science, vol. 296:1991-1995 (2002).
Ten Asbroek, Anneloor L.M.A. et al., "Polymorphisms,in the large subunit of human RNA polymerase II as target for allele-specific inhibition," Nucleic Acids Research, vol. 28(5):1133-1138 (2000).
Thakker, Deepak R. et al., "Neurochemical and behavioral consequences of widespread gene knockdown in the adult mouse brain by using nonviral RNA interference," Proc. Natl. Acad. Sci. USA, vol. 101(49):17270-17275 (2004).
Tijsterman, Marcel et al., "PPW-1, a PAZ/PIWI Protein Required for Efficient Germline RNAi, Is Defective in a Natural Isolate of C. elegans," Current Biology, vol. 12:1535-1540 (2002).
Tijsterman, Marcel et al., "RNA Helicase MUT-14-Dependent Gene Silencing Triggered in C. elegans by Short Antisense RNAs," Science, vol. 295:694-697 (2002).
Tomari, Yukihide et al., "A Protein Sensor for siRNA Asymmetry," Science, vol. 306:1377-1380 (2004).
Tomari, Yukihide et al., "Perspective: machines for RNAi," Genes & Development, vol. 19:517-529 (2005).

(56) References Cited

OTHER PUBLICATIONS

Tomari, Yukihide et al., "RISC Assembly Defects in the *Drosophila* RNAi Mutant armitage," Cell, vol. 116:831-841 (2004).
Tuschl, Thomas et al., "siRNAs and miRNAs," Keystone Symposia, Abstract Book (2004).
Tuschl, Thomas et al., "Small Interfering RNAs: A Revolutionary Tool for the Analysis of Gene Function and Gene Therapy," Molecular Interventions, vol. 2(3)1 68-167 (2002).
Tuschl, Thomas et al., "Targeted mRNA degradation by double-stranded RNA in vitro," Genes & Development, vol. 13:3191-3197 (1999).
Tuschl, Thomas, "Expanding small RNA interference," Nature Biotechnology, vol. 20:446-448, (2002).
Van Bilsen, P.H.J. et al., "Identification and Allele-Specific Silencing of the Mutant Huntingtin Allele in Huntington's Disease Patient-Derived Fibroblasts," Human Gene Therapy, vol. 19:710-718 (2008).
Vargason, Jeffrey M. et al., "Size selective recognition of siRNA by an RNA silencing suppressor," Cell, vol. 115:799-811 (2003).
Veldink, Jan H. et al., "The future of motor neuron disease: The Challenge Is in the Genes," J. Neurol., vol. 241:491-500 (2004).
Vella, Monica C. et al., "The C. elegans microRNA let-7 binds to imperfect let-7 complementary sites from the lin-41 3'UTR,"Genes & Development, vol. 18:132-137 (2004).
Victor, Martin et al "HAT activity is essential for CBP-1-dependent transcription and differentiation in Caenorhabditis elegans," EMBO Reports, vol. 31(1):50-55 (2002).
Vivès, Eric et al., "A Truncated HIV-1 Tat Protein Basic Domain Rapidly Translocates through the Plasma Membrane and Accumulates in the Cell Nucleus," The Journal of Biological Chemistry, vol. 272(25):16010-16017 (1997).
Wang, J. et al., "Fas siRNA Reduces Apoptotic Cell Death of Allogeneic-Transplanted Hepatocytes in Mouse Spleen," Transplantation Proceedings, vol. 35(4):1594-1595 (2003).
Warby, Simon C. et al., "CAG Expansion in the Huntington Disease Gene Is Associated with a Specific and Targetable Predisposing Haplogroup," The American Journal of Human Genetics, vol. 84:351-366 (2009).
Wianny, Florence et al., "Specific interference with gene function by double-stranded RNA in early mouse development," Nature Cell Biology, vol. 2(2):70-75 (2000).
Wightman, Bruce et al., "Posttranscriptional Regulation of the Heterochronic Gene lin-14 by lin-4 Mediates Temporal Pattern Formation in C. elegans," Cell, vol. 75:855-862 (1993).
Wikipedia, "Human genetic variation," retrieved online at: <http://en.wikipedia.org/wiki/Human_genetic_variation> (2008).
Wu-Sharf, Dancia et al., "Transgene and Transposon Silencing in Chlamydomonas reinhardtii by a DEAH-Box RNA Helicase," Science, vol. 290:1159-1162 (2000).
Xia, Haibin et al., "siRNA-mediated gene silencing in vitro and in vivo," Nature Biotechnology, vol. 20:1006-1010 (2002).
Xia, Xu Gang et al., "An enhanced U6 promoter for synthesis of short hairpin RNA," Nucleic Acids Research, vol. 31 (17):e100 (2003).
Xia, Xu Gang et al., "An RNAi strategy for treatment of amyotrophic lateral sclerosis caused by mutant Cu,Zn superoxide dismutase," Journal of Neurochemistry, vol. 92(2):362-367 (2005).
Xie, Jun et al., "RNAi knockdown of Par-4 inhibits neurosynaptic degeneration in ALS-linked mice," Journal of Neurochemistry, vol. 92:59-71 (2005).
Xie, Zhongcong et al., "Effects of RNA Interference-mediated Silencing of gamma-Secretase Complex Components on Cell Sensitivity to Caspase-3 Activation," The Journal of Biological Chemistry, vol. 279(33):34130-34137 (2004).
Xu, Peizhang et al., "The *Drosophila* MicroRNA Mir-14 Suppresses Cell Death and Is Required for Normal Fat Metabolism," Current Biology, vol. 13:790-795 (2003).
Yi, Rui et al., "Exportin-5 mediates the nuclear export of pre-microRNAs and short hairpin RNAs," Genes & Development, vol. 17:3011-3016 (2003).
Yohrling, George J. et al., "Mutant huntingtin increases nuclear corepressor function and enhances ligand-dependent nuclear hormone receptor activation," Molecular and Cellular Neuroscience, vol. 23:28-38 (2003).
Yu, Jenn-Yah et al., "RNA interference by expression of short-interfering RNAs and hairpin RNAs in mammalian cells," Proc. Natl. Acad. Sci. USA, vol. 99(9):6047-6052 (2002).
Zamore, Phillip D. et al., "RNAi: Double-Stranded RNA Directs the ATP-Dependent Cleavage of mRNA at 21 to 23 Nucleotide Intervals," Cell, vol. 101:25-33 (2000).
Zamore, Phillip D. et al., "siRNAs knock down hepatitis," Nature Medicine, vol. 9(3):266-267 (2003).
Zeng, Yan et al, "Sequence requirements for micro RNA processing and function in human cells," RNA, vol. 9:112-123 (2003).
Zeng, Yan et al., "Both Natural and Designed Micro RNAs Can Inhibit the Expression in Cognate mRNAs When Expressed in Human Cells," Molecular Cell, vol. 9:1327-1333 (2002).
Zeng, Yan et al., "MicroRNAs and small interfering RNAs can inhibit mRNA expression by similar mechanisms," Proc. Natl. Acad. Sci. USA, vol. 100(17):9779-9784 (2003).
Zeng, Yan et al., "Structural requirements for pre-microRNA binding and nuclear export by Exportin 5," Nucleic Acids Research, vol. 32(16):4776-4785 (2004).
Zhang, J. et al., "Targeted Gene Silencing by Small Interfering RNA-Based Knock-Down Technology," Current Pharmaceutical Biotechnology, vol. 5(1):1-7 (2004).
Zhang, Heidi et al., "Human Dicer preferentially cleaves dsRNAs at their termini without a requirement for ATP," The EMBO Journal, vol. 21(21):5875-5885 (2002).
Zhang, Yingjie et al., "Engineering Mucosal RNA Interference in Vivo," Molecular Therapy, vol. 14(3):336-342 (2006).
Zhou, Hongxia et al., "An RNA polymerase II construct synthesizes short-hairpin RNA with a quantitative indicator and mediates highly efficient RNAi," Nucleic Acids Research, vol. 33 6 :e62 (2005).
Zimmermann, Tracy S. et al, "RNAi-mediated Gene Silencing in Non-human Primates," Nature, vol. 441, 111-114 (2006).
Zitzmann, Sabine et al., "Arginine-Glycine-Aspartic Acid (RGD)-Peptide Binds to Both Tumor and Tumor-Endothelial Cells in Vivo," Cancer Research, vol. 62:5139-5143 (2002).
Zuccato, Chiara et al., "Loss of Huntingtin-Mediated BDNF Gene Transcription in Huntington's Disease," Science, vol. 293:493-498 (2001)
European Office Action for Application No. 047783980, dated Sep. 29, 2009.
European Office Action for Application No. 06836174.0, dated Dec. 10, 2008.
German Application, File No. 101 55 280.7, dated Oct. 26, 2001.
German Application, File No. 101 58 411.3, dated Nov. 29, 2001.
German Application, File No. 101 60 151.4, dated Dec. 7, 2001.
German Application, File No. 102 35 620.3, dated Aug. 2, 2002.
International Preliminary Report on Patentability for Application No. PCT/US2006/03474, dated Apr. 2, 2008.
International Preliminary Report on Patentability for Application No. PCT/US2006/038704, dated Dec. 11, 2007.
International Search Report for Application No. PCT/US2005/029011, dated Apr. 13, 2006.
Invitation to Pay Additional Fees for Application No. PCT/US2005/029011, dated Feb. 20, 2006.
Supplementary European Search Report for Application No. 06836174, dated Dec. 10, 2008.
Supplementary Partial European Search Report for Application No. 04753972, dated Oct. 31, 2006.
Dharmacon RNA Technologies. On-Target siRNA. Company Brochure (2003).
Dharmacon RNA Technologies. Products for RNA Interference. Company brochure (2003).

* cited by examiner

Striatum

Striatum near globus pallidus

Striatum near globus pallidus

Striatum near globus pallidus

A

B

METHODS AND COMPOSITIONS FOR TREATING NEUROLOGICAL DISEASE

RELATED APPLICATIONS

This application is a continuation of co-pending U.S. application Ser. No. 13/238,991, filed Sep. 21, 2011, entitled "Methods and Compositions for Treating Neurological Disease," which is a continuation of U.S. application Ser. No. 12/823,917, entitled "Methods and Compositions for Treating Neurological Disease," filed Jun. 25, 2010, which is a continuation of U.S. application Ser. No. 11/506,448, entitled "Methods and Compositions for Treating Neurological Disease," which claims the benefit of U.S. Provisional Patent Application Ser. No. 60/709,985, entitled "Methods and Compositions for Treating Neurological Disease," filed Aug. 18, 2005 and U.S. Provisional Patent Application Ser. No. 60/833,234, entitled "Methods and Compositions for Treating Neurological Disease," filed Jul. 25, 2006. The entire contents of the above-referenced patent applications are hereby incorporated by this reference.

SEQUENCE LISTING

The instant application contains a Sequence Listing, which has been submitted electronically, in ASCII format and is hereby incorporated by reference in its entirety. Said ASCII copy, created on Apr. 27, 2015, is named "565722UMY128CON3_SequenceListing.txt" and is 24,576 bytes in size.

GOVERNMENT SUPPORT

This invention was made with government support under grant number NSO38194 awarded by the National Institutes of Health. The government has certain rights in the invention.

TECHNICAL FIELD

This invention relates to methods and compositions for treating neurological disease, and more particularly to methods of delivering iRNA agents to neural cells for the treatment of neurological diseases.

BACKGROUND

RNA interference or "RNAi" is a term initially coined by Fire and co-workers to describe the observation that double-stranded RNA (dsRNA) can block gene expression when it is introduced into worms (Fire et al., *Nature* 391:806-811, 1998). Short dsRNA directs gene-specific, post-transcriptional silencing in many organisms, including vertebrates, and has provided a new tool for studying gene function.

SUMMARY

Aspects of the invention relate to compositions for treating a neurological disorder, and methods of using those compositions. In one aspect, the invention features a method of treating a subject having, or at risk for developing a neurological disorder by administering an iRNA agent that inhibits expression of a gene expressed in neural cells. In one embodiment, the iRNA agent includes a conjugate to facilitate uptake of the iRNA agent into neural cells. In a preferred embodiment, the conjugate is a lipophilic moiety, e.g., cholesterol. In another embodiment, the iRNA agent inhibits expression of the gene expressed in a neural cell that is involved in a neurological disease or disorder. In yet another embodiment, the iRNA agent is used to treat a patient having or at risk for developing a neurological disorder. In one embodiment, the iRNA agent modified for enhanced uptake into neural cells can inhibit, or decrease, expression of the huntingtin (htt) gene in a human having or at risk for developing Huntington's Disease (HD).

In a preferred embodiment, the subject is a mammal, such as a human, e.g., a subject diagnosed as having, or at risk for developing, a neurological disorder.

In one embodiment the sense strand of the iRNA agent can include at least one mismatch within the antisense strand of the oligonucleotide agent. The mismatch can confer an advantage on the iRNA agent, such as by enhancing antisense strand selection by the RNAi Induced Silencing Complex (RISC). In one embodiment, the mismatch is at least 1, 2, 3, 4, or 5 nucleotides away from the 3'-terminal nucleotide of the sense strand.

In one embodiment, the iRNA agent includes an antisense strand that is substantially complementary to a sequence encoded by a region of the human htt gene including or overlapping a sequence provided in GenBank Accession Number NM_002111 (Aug. 8, 2005).

In certain embodiments, the iRNA agents can target an htt RNA and can include a sense and/or antisense sequence listed in Table 1 or Table 2. In preferred embodiments, the iRNA agent includes at least one modification in addition to the lipophilic moiety for enhanced uptake into neural cells. The at least one additional modification can be, e.g., a phosphorothioate or 2'O-methyl (2'OMe) modification.

TABLE 1 iRNA Agents targeting htt

| iRNA Agent ID | Sequence[a] | Strand[b] | SEQ ID NO: |
|---|---|---|---|
| E1-4 | 5'-CCCUGGAAAAGCUGAUGACGG-chol | S | 1 |
|  | 3'-CUGGGACCUUUUCGACUACUU | as | 2 |
| E1-4-b | 5'-CCCUGGAAAAGCUGAUGACG | S | 3 |
|  | 3'-CUGGGACCUUUUCGACUACUU | as | 4 |
| 7246 | 5'-CCCUCAUCCACUGUGUGCCCU-chol | S | 5 |
|  | 3'-GAGGGAGUAGGUGACACACGU | as | 6 |
| 7246-b | 5'-CCCUCAUCCACUGUGUGCCCU | S | 7 |
|  | 3'-GAGGGAGUAGGUGACACACGU | as | 8 |
| T2886C-6 | 5'-UGUGCUGACUCUGAGGAAAAG-chol | S | 9 |
|  | 3'-CUACACGACUGAGACUCCUUG | as | 10 |
| T2886C-6-b | 5'-UGUGCUGACUCUGAGGAAAAG | S | 11 |
|  | 3'-CUACACGACUGAGACUCCUUG | as | 12 |
| E1-3 | 5'-CCCUGGAAAAGCUGAUGAAGG-chol | S | 13 |
|  | 3'-CUGGGACCUUUUCGACUACUU | as | 14 |
| E1-3-b | 5'-CCCUGGAAAAGCUGAUGAAGG | S | 15 |
|  | 3'-CUGGGACCUUUUCGACUACUU | as | 16 |

[a]"Chol" indicates cholesterol ligand; underlined nucleotides are mismatched with respect to the antisense strand; bold nucleotides represent SNP locations
[b]"s" indicates sense strand; "as" indicates antisense strand
[a]"Chol" indicates cholesterol ligand; underlined nucleotides are mismatched with respect to the antisense strand; bold nucleotides represent SNP locations
[b]"s" indicates sense strand; "as" indicates antisense strand TABLE 2
siRNAs targeting Huntington
Oligonucleotide ligand conjugates
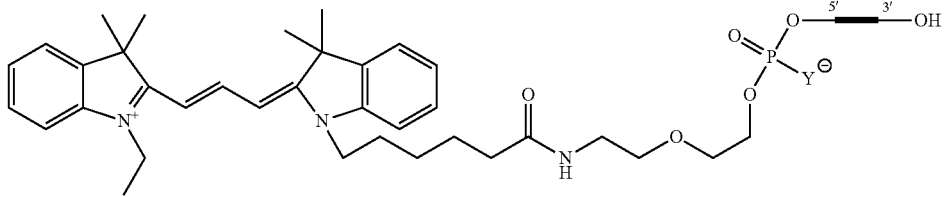
5'-(Cy-3) conjugate
Y = O or S
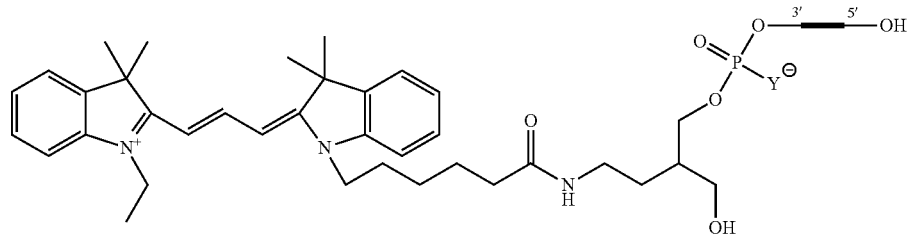
3'-(Cy-3) conjugate
Y = O or S
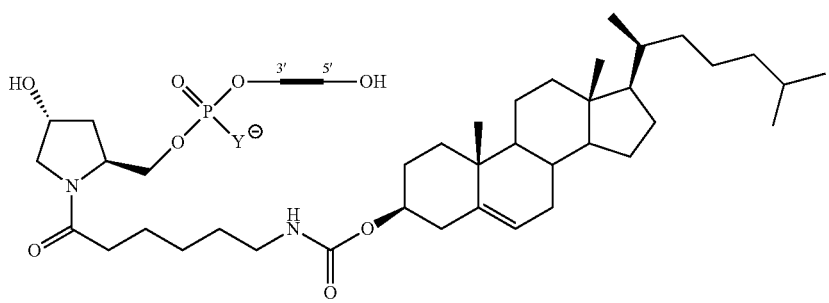
3'-Cholesterol conjugate
Y = O or S TABLE 2-continued
| siRNAs targeting Huntington |
| --- |
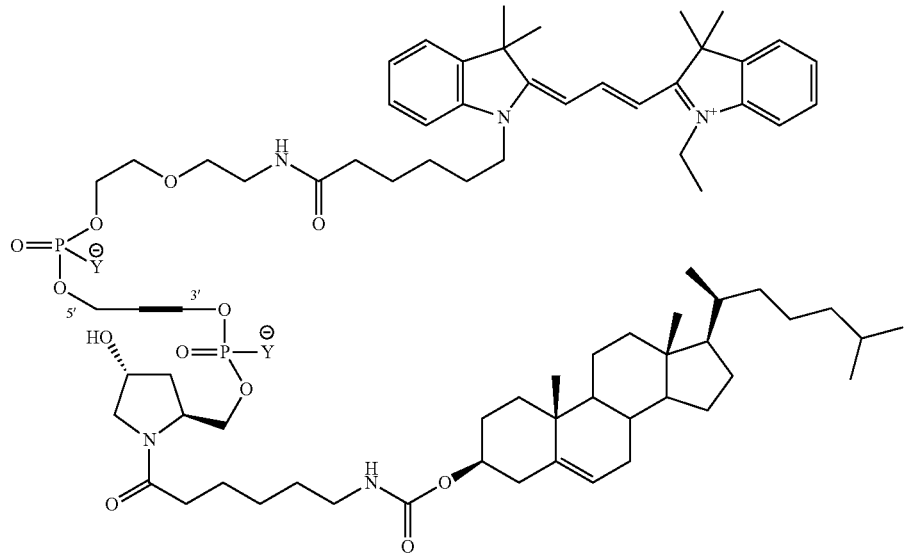
5'-(Cy-3), 3'-Cholesterol Conjugate
Y = O or S
| Ligand building blocks |
| --- |
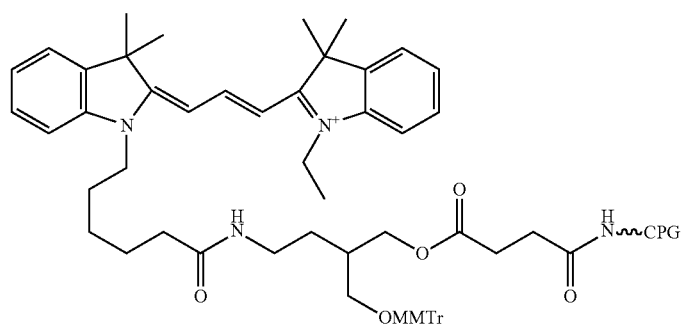
3'-(Cy-3) building block (CPG)
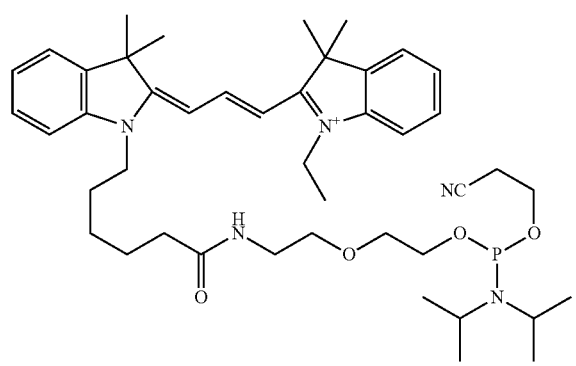
5'-(Cy-3) building block TABLE 2-continued siRNAs targeting Huntington

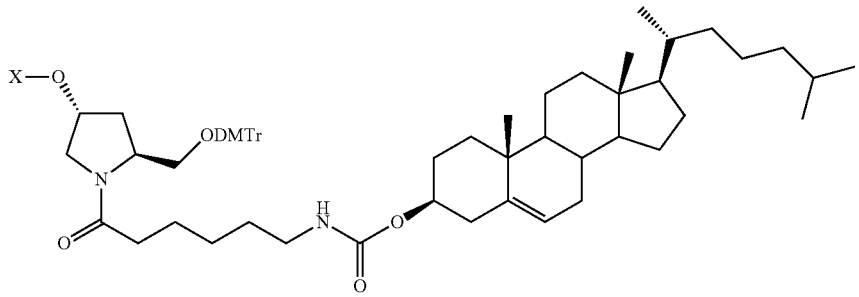

Cholesterol conjugate building blocks

| Project/ Target | SEQ ID NO: | ALN Seq. # | Sequence 5'-3' | Mass Calc | Mass Found | Purity CGE (%) |
|---|---|---|---|---|---|---|
| htt | | 3005 | 5' CsCCUGGAAAAGCUGAUGACsGsG 3' | 6822.3 | 6821.8 | 82.2 |
| | | 3006 | 5' UsUCAUCAGCUUUUCCAGGGsUsC 3' | 6635.08 | 6634.63 | 85.6 |
| htt | | 3007 | 5' CsCsCUGGAAAAGCUGAUGACsGsG 3' | 6854.43 | 6853.89 | 81.1 |
| | | 3008 | 5' UsUsCAUCAGCUUUUCCAGGGsGsUsC 3' | 6667.21 | 6666.59 | 86.4 |
| htt | | 3009 | 5'UsGUGCUGACUCUGAGGAAAsAsG 3' | 6824.27 | 6821.95 | 90.7 |
| | | 3010 | 5' GsUUCCUCAGAGUCAGCACAsUsC 3' | 6680.17 | 6979.8 | 88.2 |
| htt | | 3011 | 5'UsGsUGCUGACUCUGAGGAAsAsAsG 3' | 6856.40 | 6856.13 | 90.2 |
| | | 3012 | 5' GsUsUCCUCAGAGUCAGCACsAUC 3' | 6712.30 | 6712.05 | 89.3 |
| htt | | 3072 | 5' CsCC $U_{2'-OMe}$ GG AAA AGC $U_{2'-OMe}$ GA $U_{2'-OMe}$ GA CsGsG 3' | 6864.38 | 6863.79 | 87.9 |
| | | 3073 | 5' $U_{2'-OMe}$ sG $U_{2'-OMe}$ GC $U_{2'-OMe}$ GAC UC $U_{2'-OMe}$ GAG GAA AsAsG 3' | 6880.38 | 6879.82 | 85.7 |
| htt | | 3076 | 5' CCCUCAUCCACUGUGUGCCCU 3' | 6520.8 | 6520.69 | 88.5 |
| | | 3077 | 5' UGCACACAGUGGAUGAGGGAG 3' | 6854.15 | 6853.92 | 86.3 |
| htt | | 3108 | 5'-CCACAUGAAGCAGCACGACUU-3' | 6678.06 | 6677.93 | 89.1 |
| | | 3109 | 5' AAGUCGUGCUGCUUCAUGUGG$_{2'-OMe}$U$_{2'-OMe}$C 3' | 7345.37 | 7344.25 | 86.2 |
| htt | | 3075 | 5' CsCCUGGAAAAGCUGAUGACsGsGs-Chol 3' | 7542.37 | 7543.06 | 98.7 |
| | | 3112 | 5' Cy-3sCCCUGGAAAAGCUGAUGACsGsGs-Chol 3' | 8363.08 | 8363 & 8179 | 93.78 |
| htt | | 3137 | 5' CsCCUGGAAAAGCUGAUGACGsGs-Chol 3' | 7526.30 | 7526.92 | 84.2 |
| | | 3142 | 5' CsCCCUCAUCCACUGUGUGCCCsUs-Chol 3' | 7273.06 | 7273.91 | 82.0 |
| htt | | 3144 | 5' Cy-3sCsCCUCAUCCACUGUGUGCCCsUs-Chol 3' | 7909.8 | 7961.3 | 89.0 |
| | | 3110 | 5' CCACAUGAAGCAGCACGACUU-Chol 3' | 7382.06 | 7382.91 | 84.73 |
| htt | | 3074 | 5' Cy-3-sCCCUGGAAAAGCUGAUGACsGsG 3' | 7459.08 | 7458.07 | 78.43 |
| | | 3111 | 5' Cy-3-AAGUCGUGCUGCUUCAUGUGG$_{2'-OMe}$ U$_{2'-OMe}$ C 3' | 7981.37 | 7982.74 | 82.0 |
| htt | | 3112 | 5' Cy-3-sCCC UGG AAA AGC UGA UGA CsGsGs Chol 3' | 8363.08 | 8363 & 8179 | 93.78 |
| | | 3139 | 5' Cy-3sCCCUGGAAAAGCUGAUGACsGsGsChol 3' | 8163.1 | 8165.0 | 89.2 |
| htt | | 3143 | 5' UsGCACACAGUGGAUGAGGGAsGs-Cy-3 3' | 7576.4 | 7577.0 | 81.2 |
| | | 3138 | 5' UsUCAUCAGCUUUUCCAGGGUsCs-Cy-3 3' | 7309.1 | 7308.3 | 86.0 |

's' indicates phosphorothioate; 'N$_{2'-OMe}$', where N = A, C, G or U indicates 2'-O-methyl sugar modification; 'Chol' stands for cholesterol conjugate and 'Cy-3' stands for a Cy3 conjugate (Cy3 Quasar building blocks were purchased from Biosearch Technologies, Novato, California).

In a preferred embodiment, the antisense strand of an iRNA agent conjugated to a lipophilic agent has the sequence of an antisense strand listed in Table 1 or Table 2, or differs from an antisense strand listed in Table 1 or Table 2 by no more than 1, 2, 3, 4, or 5 nucleotides. In another preferred embodiment, the sense strand of an iRNA agent conjugated to a lipophilic agent has the sequence of an antisense strand listed in Table 1 or Table 2, or differs from an antisense strand listed in Table 1 or Table 2 by no more than 1, 2, 3, 4, or 5 nucleotides. In another preferred embodiment, the antisense strand of the iRNA agent has at least one modification described in Table 1 or Table 2 (e.g., a cholesterol, 2'-OMe, phosphorothioate, or Cy-3 modification). In another preferred embodiment, the antisense strand will have the modifications shown in Table 1 or Table 2. The antisense strand of an iRNA agent can have one or fewer modifications, e.g., the type shown in Table 1 or Table 2, or can have one or more additional modifications, e.g., the type shown in Table 1 or Table 2. In another preferred embodiment, the sense strand of the iRNA agent has at least one modification described in Table 1 or Table 2 (e.g., a cholesterol, 2'-OMe, phosphorothioate, or Cy-3 modification). In another preferred embodiment, the sense strand will have the modifications shown in Table 1 or Table 2. The sense strand of an iRNA agent can have one or fewer modifications, e.g., the type shown in Table 1 or Table 2, or can have one or more additional modifications, e.g., the type shown in Table 1 or Table 2.

In another embodiment, the iRNA agent targets an htt nucleic acid. In one embodiment, the antisense strand of the iRNA agent includes an antisense sequence described herein, e.g., an antisense sequence listed in Table 1 or Table 2. In another embodiment, the sense strand of the iRNA agent includes the nucleotide sequence of a sense strand described herein, e.g., a sense sequence listed in Table 1 or Table 2. In yet another embodiment, the antisense strand of the iRNA agent overlaps an antisense sequence described herein, e.g., an antisense sequence listed in Table 1 or Table 2, e.g., by at least 1, 5, 10, 11, 12, 13, 14, 15, 16, 17, 18, 19, 20, 21, 22, 23, or 24 nucleotides. Likewise, the sense strand of the iRNA agent overlaps a sense sequence described herein, e.g., a sense sequence listed in Table 1 or Table 2, e.g., by at least 1, 5, 10, 11, 12, 13, 14, 15, 16, 17, 18, 19, 20, 21, 22, 23, or 24 nucleotides.

In a particularly preferred embodiment, the iRNA agent targets a nucleic acid involved in a neurological disease. The iRNA agent has an antisense strand complementary to a nucleotide sequence of the target nucleic acid, and a sense strand sufficiently complementary to hybridize to the antisense strand. The iRNA agent also includes a lipophilic moiety that facilitates its uptake into a neural cell. In a preferred embodiment, the lipophilic moiety is a cholesterol. In another embodiment, the iRNA agent includes a modification that improves the stability or distribution of the iRNA agent in a biological sample. The iRNA agents can further be in isolated form or can be part of a pharmaceutical composition used for the methods described herein, particularly as a pharmaceutical composition formulated for delivery to a neural cell or formulated for parental administration. The pharmaceutical compositions can contain one or more iRNA agents, and in some embodiments, will contain two or more iRNA agents. In one embodiment, the iRNA agent includes a 2'-modified nucleotide, e.g., a 2'-O-methylated nucleotide. In another embodiment, the iRNA agent includes a phosphorothioate.

In another embodiment, the iRNA agent targets a wildtype nucleic acid, e.g., a wildtype htt RNA, involved in the pathogenesis of a neurological disorder, and in yet another embodiment, the iRNA agent targets a polymorphism or mutation of the nucleic acid. In certain embodiments, the iRNA agent can target a sequence in a codon of the open reading frame, the 3'UTR or the 5'UTR of the mRNA transcript of the gene involved in the neurological disorder. In one embodiment, the iRNA agent targets a spliced isoform of mRNA.

In one embodiment, the human carries a form of the huntingtin gene that includes an expanded CAG trinucleotide repeat, i.e., more than 30 CAG trinucleotide repeats (e.g., 35, 40, 50, 60, 70, 80, 90, 100 or more CAG trinucleotide repeats), which results in an abnormal form of the huntingtin polypeptide including an expansion of the polypeptide's normal polyglutamine tract. In another embodiment, the human is diagnosed with Huntington's Disease (HD). In one embodiment, the human carries a polymorphism or mutation in the huntingtin gene. For example, the human can carry a polymorphism at position 171, e.g., an A171C polymorphism, in the huntingtin gene according to the sequence numbering in GenBank Accession No. NM_002111 (Aug. 8, 2005). In another embodiment, the iRNA agent targets a nucleic acid that encodes a polypeptide known to interact with the huntingtin protein. For example, the iRNA agent can target a Huntingtin-associated protein-1 (HAP-1) nucleic acid.

In a preferred embodiment, the iRNA agent modified for enhanced uptake into neural cells does not target an alpha-synuclein (SNCA) RNA.

In another embodiment, the iRNA agent modified for enhanced uptake into neural cells, e.g., conjugated to a cholesterol, is at least 21 nucleotides long and includes a sense RNA strand and an antisense RNA strand, wherein the antisense RNA strand is 25 or fewer nucleotides in length, and the duplex region of the iRNA agent is 18-25 nucleotides in length. The iRNA agent may further include a nucleotide overhang having 1 to 4 unpaired nucleotides, and the unpaired nucleotides may have at least one phosphorothioate dinucleotide linkage. The nucleotide overhang can be, e.g., at the 3' end of the antisense strand of the iRNA agent.

In one aspect, the invention features a method of down regulating expression of a target gene in a neural cell. In one embodiment the method includes contacting an iRNA agent with the neural cell for a time sufficient to allow uptake of the iRNA agent into the cell. In another embodiment, the iRNA agent includes a sense strand and an antisense strand that form an RNA duplex. The iRNA agent also comprises a lipophilic moiety, e.g., a cholesterol, and the antisense strand of the iRNA agent comprises a nucleotide sequence sufficiently complementary to a target sequence of about 18 to 25 nucleotides of an RNA expressed from the target gene. In a preferred embodiment, the lipophilic moiety is conjugated to at least one end of the sense strand, e.g., to the 3' end of the sense strand. In another embodiment, the sense strand and the antisense strand have a sequence selected from the sense and antisense strands listed in Table 1 or Table 2.

In another aspect, the invention features a method of treating a human that includes identifying a human diagnosed as having or at risk for developing a neurological disorder, and administering to the human an iRNA agent that targets a gene expressed in a neural cell. In one embodiment, expression of the gene is associated with symptoms of the neurological disorder. In another embodiment, the iRNA agent includes a sense strand and an antisense strand that form an RNA duplex, and the iRNA agent includes a lipophilic moiety, e.g., a cholesterol. In another embodiment, the antisense strand of the iRNA agent includes a nucleotide sequence sufficiently complementary to a target sequence of about 18 to 25 nucleotides of an RNA expressed from the target gene. In a preferred embodiment, the lipophilic moiety is conjugated to at least one end of the sense strand, e.g., to the 3' end of the sense strand, and in another embodiment, the iRNA agent includes a phosphorothioate or a 2' modification, e.g., a 2'OMe or 2'O-fluoro modification. In one embodiment, the sense and antisense strands include a sequence selected from the sense and antisense strands listed in Table 1 or Table 2.

In one embodiment, the antisense strand of the iRNA agent includes a sequence complementary to a polymorphism of an htt RNA. In another embodiment, the human has or is at risk for developing Huntington's disease. In another embodiment, the human carries a genetic variation in a Parkin gene or a ubiquitin carboxy-terminal hydrolase L1 (UCHL1) gene, and the human has or is at risk for developing Parkinson's disease. In another embodiment, the human has or is at risk for developing Alzheimer's Disease, multiple system atrophy, or Lewy body dementia.

In another aspect, the invention features a pharmaceutical composition including an iRNA agent conjugated to a lipophilic moiety for enhanced uptake into neural cells, e.g., conjugated to a cholesterol molecule, and a pharmaceutically acceptable carrier. Preferably, the iRNA agent targets a nucleic acid involved in a neurological disease or disorder.

In a particularly preferred embodiment, the pharmaceutical composition includes an iRNA agent targeting an htt nucleic acid and a pharmaceutically acceptable carrier. The iRNA agent has an antisense strand complementary to a nucleotide sequence of an htt RNA, and a sense strand sufficiently complementary to hybridize to the antisense strand. In one embodiment, the iRNA agent includes a lipophilic moiety that facilitates its uptake into a neural cell. In one embodiment, the lipophilic moiety is a ligand that includes a cationic group. In another embodiment, the lipophilic moiety is attached to one or both ends of one or both strands of the iRNA agent. In a preferred embodiment, the lipophilic moiety is attached to one end of the sense strand of the iRNA agent, and in another preferred embodiment, the ligand is attached to the 3' end of the sense strand. In certain embodiments, the lipophilic agent is, e.g, cholesterol, vitamin E, vitamin K, vitamin A, folic acid or a cationic dye, such as Cy3. In a preferred embodiment, the lipophilic moiety is a cholesterol.

In another embodiment, the iRNA agent of the pharmaceutical composition includes a modification that improves the stability or distribution of the iRNA agent in a biological sample. The iRNA agents can further be in isolated form or can be part of a pharmaceutical composition used for the methods described herein, particularly as a pharmaceutical composition formulated for delivery to a neural cell or formulated for parental administration. The pharmaceutical compositions can contain one or more iRNA agents, and in some embodiments, will contain two or more iRNA agents. In one embodiment, the iRNA agent includes a 2'-modified nucleotide, e.g., a 2'-O-methylated nucleotide. In another embodiment the iRNA agent includes a phosphorothioate.

In a particularly preferred embodiment, htt RNA levels in a neural cell are reduced by contacting the neural cell of the subject with an iRNA agent modified for enhanced uptake into neural cells. In a preferred embodiment, the ligand is a cholesterol.

In another aspect, the invention features a method of making an iRNA agent that targets a nucleic acid expressed in neural cells and that is modified for enhanced uptake into neural cells. The method includes selecting a nucleotide sequence of between 18 and 25 nucleotides long from the nucleotide sequence of a target mRNA, e.g., an htt mRNA, and synthesizing the iRNA agent. The sense strand of the iRNA agent includes the nucleotide sequence selected from the target RNA, and the antisense strand is sufficiently complementary to hybridize to the sense strand. The method includes incorporating at least one lipophilic moiety into the iRNA agent, e.g., onto at least one end of the sense strand of the iRNA agent. In a preferred embodiment, the lipophilic moiety is incorporated onto the 3' end of the sense strand of the iRNA agent. In one embodiment, a cationic dye, e.g., Cy3, is incorporated into at least one strand of the iRNA agent, e.g., on the 3' or 5' end of the iRNA agent. In one embodiment, more than one lipophilic moiety, e.g., more than one different kind of lipophilic moiety is incorporated into the iRNA agent. In certain embodiments, the iRNA agent includes the ligand conjugates illustrated in Table 1 or Table 2. In other embodiments the method of making the iRNA agent includes use of the building blocks illustrated in Table 1 or Table 2. In yet other embodiments, the methods featured in the invention include methods of making the iRNA agents listed in Table 1 or Table 2, which target htt RNA. In one embodiment, the method further includes administering the iRNA agent to a subject, e.g., a mammalian subject, such as a human subject, such as a human having or at risk for developing a neurological disease or disorder. In one embodiment, the human has or is at risk for developing HD.

In another aspect, the invention features a method of evaluating an iRNA agent, e.g., an iRNA agent conjugated with a lipophilic agent for enhanced uptake into neural cells. The method includes: providing a candidate iRNA agent modified for enhanced uptake into neural cells, e.g., conjugated with a cholesterol molecule and determining whether the iRNA agent is taken up into neural cells. In one embodiment, the iRNA agent is conjugated with a detectable marker, e.g., a fluorescent marker, such as Cy3 or Cy5, and uptake into the cell is assayed by fluorescence. In another embodiment e.g., by the use of one or more of the test systems described herein, if said candidate agent modulates, e.g., inhibits, target gene expression.

In a preferred embodiment the method includes evaluating the iRNA agent in a first test system; and, if a predetermined level of gene expression is observed, evaluating the candidate in a second, preferably different, test system. In a particularly preferred embodiment the second test system includes administering the candidate iRNA agent to a neural cell of an animal and evaluating the effect of the candidate agent on target gene expression in the animal.

A test system can include: contacting the candidate iRNA agent with a target nucleic acid, e.g., a nucleic acid expressed in neural cells, such as an htt RNA. The iRNA is preferably contacted with the target nucleic acid in vitro, and it is determined whether there is an interaction, e.g., binding of the candidate agent to the target. The test system can include contacting the candidate agent with a neural cell and evaluating modulation of neural gene expression, e.g., htt gene expression. For example, this can include contacting the candidate iRNA agent with a neural cell capable of expressing htt RNA (from an endogenous gene or from an exogenous construct) and evaluating the level of htt or htt RNA. In a preferred embodiment, the candidate iRNA agent includes a modification that enhances uptake of the candidate iRNA agent into the neural cell. In a particularly preferred embodiment, the modification is a cholesterol molecule, e.g., a cholesterol attached to the sense strand of the iRNA agent, e.g., to the 3' end of the sense strand. In another embodiment the test system can include contacting the candidate agent with a cell which expresses an RNA or protein from a portion of the neural gene linked to a heterologous sequence, e.g., a marker protein, e.g., a fluorescent protein such as GFP, which construct can be either chromosomal or episomal, and determining the effect on RNA or protein levels. The test system can also include contacting the candidate iRNA agent, in vitro, with a tissue sample, e.g., a brain tissue sample, e.g., a slice or section, an optical tissue sample, or other sample which includes neural tissue, and evaluating the level of neural polypeptide or RNA, e.g., htt polypeptide or RNA. The test system can include administering the candidate iRNA agent, in vivo, to an animal, and evaluating the level of neural polypeptide or neural RNA, e.g., htt polypeptide or htt RNA. In any of these, the effect of the candidate agent on neural gene expression can include comparing gene expression with a predetermined standard, e.g., with control, e.g., an untreated cell, tissue or animal. Gene expression can be compared, e.g., before and after contacting with the candidate iRNA agent. The method allows determining whether the iRNA agent is useful for inhibiting htt gene expression.

A "neural gene" is a gene expressed in neural cells. A neural gene can be expressed exclusively in neural cells, or can be expressed in other cell types in addition to the neural cell.

In one embodiment, neural gene expression can be evaluated by a method to examine neural RNA levels (e.g., Northern blot analysis, RT-PCR, or RNAse protection assay) or neural polypeptide levels (e.g., Western blot, immunohistochemistry, or autofluorescence assays (e.g., to detect GFP or luciferase expression)).

A "neural cell" is a cell of the nervous system, e.g., the peripheral or the central nervous system. A neural cell can be a nerve cell (i.e., a neuron), e.g., a sensory neuron or a motoneuron, or a glial cell. Exemplary neurons include dorsal root ganglia of the spinal cord, spinal motor neurons, retinal bipolar cells, cortical and striatal cells of the brain, hippocampal pyramidal cells, and purkinje cells of the cerebellum. Exemplary glial cells include oligodendrocytes and astrocytes of the central nervous system, and the Schwann cells of the peripheral nervous system.

By "enhanced uptake into neural cells" is meant that higher levels of a modified iRNA agent are incorporated into a neural cell than unmodified iRNA agent when the cells exposed to each type of iRNA agent are treated under similar conditions, in in vitro or in vivo conditions.

In one embodiment, e.g., as a second test, the agent is administered to an animal, e.g., a mammal, such as a mouse, rat, rabbit, human, or non-human primate, and the animal is monitored for an effect of the agent. For example, a tissue of the animal, e.g., a brain tissue, is examined for an effect of the agent on neural gene expression. The tissue can be examined for the presence of neural RNA and/or protein levels, for example. In one embodiment, the animal is observed to monitor an improvement or stabilization of a cognitive symptom. The agent can be administered to the animal by any method, e.g., orally, or by intrathecal or parenchymal injection, such as by stereoscopic injection into the brain.

In a particularly preferred embodiment, the invention features a method of evaluating an iRNA agent, e.g., an iRNA agent described herein, that targets a nucleic acid expressed in neural cells, e.g., an htt nucleic acid. The method includes providing an iRNA agent that targets a nucleic acid expressed in neural cells (e.g., an htt RNA); contacting the iRNA agent with a neural cell containing and capable of expressing the nucleic acid; and evaluating the effect of the iRNA agent on expression of the nucleic acid, e.g., by comparing gene expression with a control, e.g., in the cell. Gene expression can be compared, e.g., before and after contacting the iRNA agent with the cell. The method allows determining whether the iRNA agent is useful for inhibiting gene expression. For example, the iRNA agent can be determined to be useful for inhibiting neural-gene expression if the iRNA agent reduces expression by a predetermined amount, e.g., by 10, 25, 50, 75, or 90%, e.g., as compared with a predetermined reference value, e.g., as compared with the amount of neural RNA or protein prior to contacting the iRNA agent with the cell. The neural gene can be endogenously or exogenously expressed.

The methods and compositions featured in the invention, e.g., the methods and iRNA compositions to treat the neurological disorders described herein, can be used with any dosage and/or formulation described herein, as well as with any route of administration described herein.

Thus, in another aspect, the invention features a method of treating a subject by administering an agent which inhibits the expression of a gene in a neural cell. In a preferred embodiment, the subject is a mammal, such as a human, e.g., a subject diagnosed as having, or at risk for developing a neurological disease or disorder. Agents that inhibit neural gene expression include iRNA agents and antisense molecules that target htt RNA.

A "substantially identical" sequence includes a region of sufficient homology to the target gene, and is of sufficient length in terms of nucleotides, that the iRNA agent (e.g., the iRNA agent conjugated to a lipophilic moiety for enhanced uptake into neural cells), or a fragment thereof, can mediate down regulation of the target gene. A sequence of the iRNA agent that is substantially identical to a target RNA is typically a sequence on the sense strand of a double stranded iRNA agent.

A "substantially complementary" sequence includes a region of sufficient complementarity to the target gene, and is of sufficient length in terms of nucleotides, that the iRNA agent (e.g., the iRNA agent conjugated to a lipophilic moiety for enhanced uptake into neural cells), or a fragment thereof, can mediate down regulation of the target gene. A sequence of the iRNA agent that is substantially complementary to a target RNA is typically a sequence on the antisense strand of a double stranded iRNA agent. Thus, the iRNA agent is or includes a region which is at least partially, and in some embodiments fully, complementary to a target RNA transcript, e.g, an RNA transcript expressed in a neural cell. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA. Complementarity, or degree of homology with the target strand, is most critical in the antisense strand. While perfect complementarity, particularly in the antisense strand, is often desired some embodiments can include, particularly in the antisense strand, one or more but preferably 6, 5, 4, 3, 2, or fewer mismatches (with respect to the target RNA). The mismatches, particularly in the antisense strand, are most tolerated in the terminal regions and if present are preferably in a terminal region or regions, e.g., within 6, 5, 4, or 3 nucleotides of the 5' and/or 3' terminus. The sense strand need only be sufficiently complementary with the antisense strand to maintain the overall double strand character of the molecule.

An "RNA agent" as used herein, is an unmodified RNA, modified RNA, or nucleoside surrogates, which are described herein or are well known in the RNA synthetic art. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5' modification which includes one or more phosphate groups or one or more analogs of a phosphate group.

An "iRNA agent" (abbreviation for "interfering RNA agent") as used herein, is an RNA agent, which can down-regulate the expression of a target gene, preferably an endogenous or pathogen target RNA expressed in a neural cell. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent is preferably a double stranded (ds) iRNA agent.

Further, one aspect of the invention pertains to a method of downregulating expression of a target gene in a neural cell distal to the site of administration, the method comprising contacting an iRNA agent with the neural cell for a time sufficient to allow uptake of the iRNA agent into the cell, wherein (i) the iRNA agent comprises a sense and an antisense strand that form an RNA duplex, and (ii) the sequence of the antisense strand of the iRNA agent comprises a nucleotide sequence sufficiently complementary to a target sequence of about 18 to 25 nucleotides of an RNA expressed from the target gene.

In another aspect, the invention pertains to a method of downregulating expression of a target gene in a neural cell, the method comprising contacting an iRNA agent with the neural cell for a time sufficient to allow uptake of the iRNA agent into the cell, wherein (i) the iRNA agent comprises a sense and an antisense strand that form an RNA duplex, (ii) the iRNA agent comprises a lipophilic moiety, and (iii) the sequence of the antisense strand of the iRNA agent comprises a nucleotide sequence sufficiently complementary to a target sequence of about 18 to 25 nucleotides of an RNA expressed from the target gene.

In one embodiment, the cells are contacted for a time sufficient to allow axonal transport of said iRNA.

In one embodiment, the iRNA agent comprises a lipophilic moiety.

In one embodiment, the lipophilic moiety is a cholesterol.

In one embodiment, the lipophilic moiety is conjugated to the sense strand.

In one embodiment, the lipophilic moiety is conjugated to the 3' end of the sense strand.

In one embodiment, the antisense sequence differs by no more than four nucleotides from an antisense sequence listed in Table 1.

In one embodiment, the antisense strand is selected from an antisense strand listed in Table 1.

In one embodiment, the iRNA agent further comprises a phosphorothioate or a 2'-OMe modification.

In one embodiment, the iRNA agent is provided in a solution that lacks a transfection reagent.

In one embodiment, the iRNA agent is provided in a solution comprising a transfection reagent.

In another aspect, the invention pertains to a method of treating a human comprising identifying a human having or at risk for developing a neurological disorder, the method comprising administering to the human an iRNA agent that targets a gene expressed in a neural cell distal to the site of administration, wherein the expression of the gene is associated with symptoms of the neurological disorder, and wherein (i) the iRNA agent comprises a sense and an antisense strand that form an RNA duplex, and (ii) the antisense strand of the iRNA agent comprises a nucleotide sequence sufficiently complementary to a target sequence of about 18 to 25 nucleotides of an RNA expressed from the target gene.

In another aspect, the invention pertains to a method of treating a human comprising identifying a human having or at risk for developing a neurological disorder, and administering to the human an iRNA agent that targets a gene expressed in a neural cell, wherein the expression of the gene is associated with symptoms of the neurological disorder, and wherein (i) the iRNA agent comprises a sense and an antisense strand that form an RNA duplex, (ii) the iRNA agent comprises a lipophilic moiety, and (iii) the antisense strand of the iRNA agent comprises a nucleotide sequence sufficiently complementary to a target sequence of about 18 to 25 nucleotides of an RNA expressed from the target gene.

In one embodiment, the iRNA agent comprises a lipophilic moiety.

In one embodiment, the lipophilic moiety is a cholesterol.

In one embodiment, the lipophilic moiety is conjugated to the sense strand.

In one embodiment, the lipophilic moiety is conjugated to the 3' end of the sense strand.

In one embodiment, the iRNA agent further comprises a phosphorothioate or a 2'-OMe modification.

In one embodiment, the antisense sequence differs by no more than four nucleotides from an antisense sequence listed in Table 1.

In one embodiment, the antisense strand is selected from an antisense strand listed in Table 1.

In one embodiment, the antisense strand of the iRNA agent comprises a sequence complementary to a sequence comprising a polymorphism of a huntingtin (htt) RNA.

In one embodiment, the human carries a genetic variation in a Parkin gene or a ubiquitin carboxy-terminal hydrolase L1 (UCHL1) gene.

In one embodiment, the neurological disorder is Huntington's disease.

In one embodiment, the neurological disorder is Parkinson's disease.

In one embodiment, the neurological disorder is Alzheimer's Disease, multiple system atrophy, or Lewy body dementia.

In one embodiment, the iRNA agent comprises a nucleotide overhang having 1 to 4 unpaired nucleotides.

In one embodiment, the iRNA agent is provided in a solution that lacks a transfection reagent.

In one embodiment, the iRNA agent is provided in a solution comprising a transfection reagent.

In one embodiment, the iRNA agent is administered as a sustained dose formulation.

In one embodiment, the iRNA agent is administered in multiple doses over a prolonged time period.

In one embodiment, the iRNA agent is administered as a single dose.

In one embodiment, the administration of a second iRNA agent, wherein (i) the second iRNA agent comprises a sense and an antisense strand that form an RNA duplex, and (ii) the antisense strand of the iRNA agent comprises a nucleotide sequence sufficiently complementary to a second target sequence of about 18 to 25 nucleotides of the RNA expressed from the target gene.

In another aspect, the invention pertains to a method of reducing the amount of huntingtin (htt) RNA in a neural cell of a subject, comprising: contacting the neural cell with an iRNA agent, wherein said neural cell is distal to the site of action and the iRNA agent comprises a sense and an antisense strand, wherein the sense and the antisense strands form an RNA duplex, wherein the antisense strand comprises a nucleotide sequence that differs by no more than four nucleotides from an antisense sequence listed in Table 1.

In one embodiment, the iRNA agent further comprises a lipophilic moiety.

In one embodiment, the cells are contacted for a time sufficient to allow uptake of the iRNA agent into the cells and axonal transport of said iRNA In one embodiment, the iRNA agent further comprises a phosphorothioate or a 2'-OMe modification.

In one embodiment, the iRNA agent comprises an antisense strand comprising a sequence selected from the antisense strands listed in Table 1.

In one embodiment, the iRNA agent comprises a sense strand selected from the sense strands listed in Table 1.

In one embodiment, the iRNA agent comprises an antisense strand comprising a sequence complementary to sequence comprising a polymorphism of an htt RNA.

In one embodiment, the polymorphism is an A to C at position 171 according to the sequence of GenBank Accession No. NM_002111.

In one embodiment, the iRNA agent comprises a nucleotide overhang having 1 to 4 unpaired nucleotides.

In another aspect, the invention pertains to an isolated iRNA agent comprising a sense and an antisense strand, wherein the sense and the antisense strands form an RNA duplex, wherein the antisense strand comprises a nucleotide sequence that differs by no more than four nucleotides from an antisense sequence listed in Table 1, and wherein the iRNA agent comprises a lipophilic moiety.

In one embodiment, the lipophilic moiety is a cholesterol molecule.

In one embodiment, the lipophilic moiety is attached to the sense strand.

In one embodiment, the lipophilic moiety is attached to the 3' end of the sense strand.

In one embodiment, the iRNA agent further comprises a phosphorothioate modification, or a 2'-OMe modification.

In one embodiment, the antisense strand comprises a sequence selected from the antisense sequences listed in Table 1.

In one embodiment, the sense strand of the iRNA agent comprises a sequence selected from the sense sequences listed in Table 1.

In one embodiment, the iRNA agent is at least 21 nucleotides in length, and the duplex region of the iRNA agent is about 18-25 nucleotides in length.

In one embodiment, the iRNA agent comprises a nucleotide overhang having 1 to 4 unpaired nucleotides.

In another aspect, the invention pertains to a pharmaceutical composition, comprising (i) an iRNA agent comprising a sense and an antisense strand, wherein the sense and the antisense strands form an RNA duplex, wherein the antisense strand comprises a nucleotide sequence that differs by no more than four nucleotides from an antisense sequence listed in Table 1, and wherein the iRNA agent comprises a lipophilic moiety, and (ii) a pharmaceutically acceptable carrier.

In one embodiment, the iRNA agent further comprises a phosphorothioate or a 2'-OMe modification.

In one embodiment, the antisense strand of the iRNA agent comprises a sequence selected from the antisense sequences listed in Table 1.

In one embodiment, the sense strand of the iRNA agent comprises a sequence from the selected from the sense sequences listed in Table 1.

In one embodiment, the iRNA agent comprises a nucleotide overhang having 1 to 4 unpaired nucleotides.

In another aspect, the invention pertains to a method of evaluating an iRNA agent for enhanced uptake into neural cells comprising: providing a candidate iRNA agent conjugated to a lipophilic agent, wherein the iRNA agent is in a solution that does not contain a transfection reagent, contacting the iRNA agent with a neural cell for a time sufficient for uptake into the neural cell and determining if the iRNA agent is taken up by the neural cell.

In one embodiment, the method includes a step of evaluating the iRNA agent in a cell culture system; and, if a predetermined level of uptake into the neural cell is observed, evaluating the candidate in an animal.

In one embodiment, the iRNA agent comprises an antisense strand that is substantially complementary to a target RNA in the neural cell, and the method further comprises determining whether the candidate iRNA agent decreases expression of a target RNA in the neural cell.

In one embodiment, the lipophilic agent is a cholesterol.

In one embodiment, the target RNA is a huntingtin RNA.

In one embodiment, the iRNA agent comprises an antisense strand that is substantially complementary to a target RNA in the neural cell, and the method further comprises determining whether the candidate iRNA agent decreases expression of the target RNA in a neural cell of the animal.

In one embodiment, the target RNA is a huntingtin RNA.

In one embodiment, the animal is monitored for an effect of the iRNA agent.

In one embodiment, brain tissue from the animal is examined for an effect of the iRNA agent on target gene expression.

In one embodiment, the determining step comprises performing a method selected from the group consisting of Northern blot, Western blot, RT-PCR, and RNAse protection assay.

The details of one or more embodiments of the invention are set forth in the accompanying drawings and the description below. Other features, objects, and advantages of the invention will be apparent from this description, and from the claims. This application incorporates all cited references, patents, and patent applications by references in their entirety for all purposes.

BRIEF DESCRIPTION OF DRAWINGS

FIG. 1A is an in situ stain of striatum tissue. FIGS. 1B, 1C and 1D are in situ stains of the striatum near the globus pallidus. Scale bar=25 µm.

DETAILED DESCRIPTION

Figure 1A:
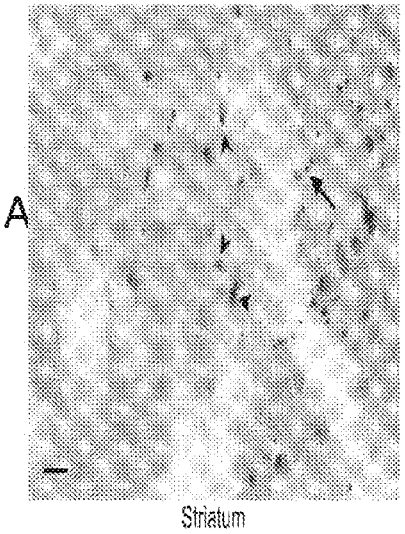
FIGS. 1A-1D are images of in situ staining for pathological hallmarks of Huntington's disease found in mice treated with lentivirus-mut-htt. Staining was by immunohistochemistry against htt protein.
Figure 1B:
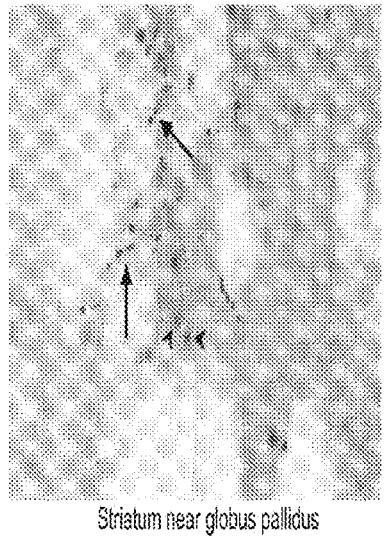
Figure 1C:
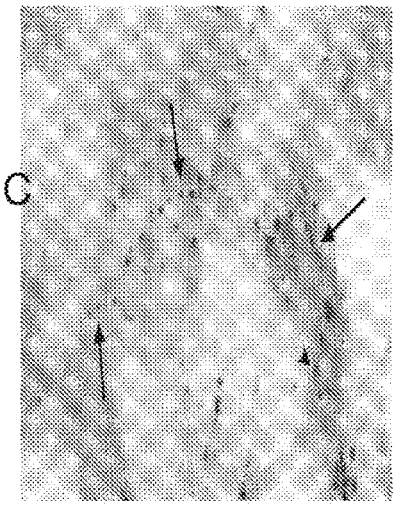
Figure 1D:
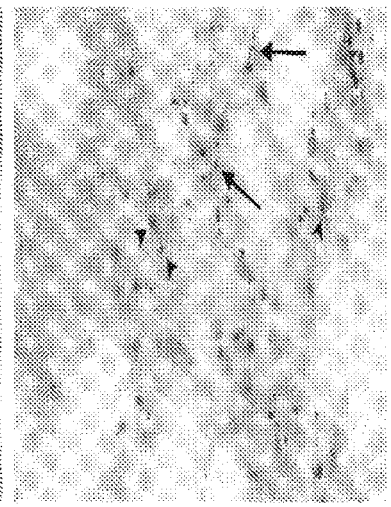

Double-stranded (dsRNA) directs the sequence-specific silencing of mRNA through a process known as RNA interference (RNAi). The process occurs in a wide variety of organisms, including mammals and other vertebrates.

It has been demonstrated that 21-23 nt fragments of dsRNA are sequence-specific mediators of RNA silencing, e.g., by causing RNA degradation. While not wishing to be bound by theory, it may be that a molecular signal, which may be merely the specific length of the fragments, present in these 21-23 nt fragments, recruits cellular factors that mediate RNAi. Described herein are methods for preparing and administering these 21-23 nt fragments, and other iRNA agents, and their use for specifically inactivating gene function in neural cells. The use of iRNA agents (or recombinantly produced or chemically synthesized oligonucleotides of the same or similar nature) enables the targeting of specific mRNAs for silencing in mammalian cells. In addition, longer dsRNA agent fragments can also be used, e.g., as described below.

Although, in mammalian cells, long dsRNAs can induce the interferon response which is frequently deleterious, short dsRNAs (sRNAs) do not trigger the interferon response, at least not to an extent that is deleterious to the cell and host. In particular, the length of the iRNA agent strands in an sRNA agent can be less than 31, 30, 28, 25, or 23 nt, e.g., sufficiently short to avoid inducing a deleterious interferon response. Thus, the administration of a composition of sRNA agent (e.g., formulated as described herein) to a mammalian cell can be used to silence expression of a target gene while circumventing the interferon response. Further, use of a discrete species of iRNA agent can be used to selectively target one allele of a target gene, e.g., in a subject heterozygous for the allele.

Moreover, in one embodiment, a mammalian cell is treated with an iRNA agent that disrupts a component of the interferon response, e.g., dsRNA-activated protein kinase PKR. Such a cell can be treated with a second iRNA agent that includes a sequence complementary to a target RNA and that has a length that might otherwise trigger the interferon response.

In a typical embodiment, the subject is a mammal such as a cow, horse, mouse, rat, dog, pig, goat, or a primate. The subject can be a dairy mammal (e.g., a cow, or goat) or other farmed animal (e.g., a chicken, turkey, sheep, pig, fish, shrimp). In a much preferred embodiment, the subject is a human, e.g., a normal individual or an individual that has, is diagnosed with, or is predicted to have a neurological disease or disorder.

A neurological disease or disorder is any disease or disorder that affects the nervous system (the central or peripheral nervous system). Exemplary neurological diseases and disorders include Huntingtons's Disease (HD), Parkinson's Disease (PD), Amyotropic Lateral Sclerosis (ALS), Alzheimer's Disease, Lewy body dementia, Multiple System Atrophy, spinal and bulbar muscular atrophy (Kennedy's disease), Tourette Syndrome, Autosomal dominant spinocerebellar ataxia (SCA) (e.g., Type 1 SCA1, Type 2 SCA2, Type 3 (Machado-Joseph disease) SCA3/MJD, Type 6 SCA6, Type 7 SCA7, Type 8 SCA8, Friedreich's Ataxia and Dentatorubral pallidoluysian atrophy DRPLA/Haw-River syndrome), schizophrenia, age associated memory impairment, autism, attention-deficit disorder, bipolar disorder, and depression.

Because oligonucleotide agent-mediated modulation persists for several days after administering the oligonucleotide agent composition, in many instances it is possible to administer the composition with a frequency of less than once per day, or, for some instances, only once for the entire therapeutic regimen. For example, treatment of some cancerous neural cells may be mediated by a single bolus administration, whereas a chronic viral infection may require regular administration, e.g., once per week or once per month. For example, treatment of an astrocytoma may be treated with a single bolus administration of an iRNA agent conjugated to a lipophilic agent.

Treatment of Neurological Diseases and Disorders

Any patient having a neurological disease or disorder is a candidate for treatment with a method or composition described herein. Presymptomatic subjects can also be candidates for treatment with an iRNA agent targeted to neural cells. For example, a presymptomatic human determined to be at risk for HD is a candidate for treatment with an anti-htt iRNA agent conjugated to a lipophilic molecule, e.g., a cholesterol molecule, for delivery to neural cells. In one embodiment, a presymptomatic candidate is identified by either or both of risk-factor profiling and functional neuroimaging (e.g., by fluorodopa and positron emission tomography). For example, the candidate subject can be identified by risk-factor profiling followed by functional neuroimaging.

Individuals having a particular genotype are candidates for treatment. In some embodiments the patient will carry a particular genetic mutation that places the patient at increased risk for developing a disorder of the nervous system, e.g., HD. For example, an individual carrying a CAG trinucleotide expansion in htt (e.g., more than 36 repeats) is at increased risk for developing HD and is a candidate for treatment with an iRNA agent featured in the invention, e.g., conjugated to a cholesterol molecule for enhanced uptake into neural cells. The iRNA agent preferably targets the htt gene. In addition, a SNP in the htt gene has been found to be an indicator of the presence of the expanded CAG repeat that triggers HD. The SNP is an A to C polymorphism at position 171, according to the numbering of GenBank Accession No. NM_002111. A human carrying this SNP is therefore a candidate for treatment with an iRNA agent featured in the invention, or is at least a candidate for further genetic studies (such as for testing for the CAG repeat expansion) which will further determine if the human is a candidate for treatment with an iRNA agent targeting htt and modified for enhanced delivery to neurons.

In another example, the non-genetic risk factors for PD include age (e.g., over age 30, 35, 40, 45, or 50 years), gender (men are generally have a higher risk than women), pesticide exposure, heavy metal exposure, and head trauma. In general, exogenous and endogenous factors that disrupt the ubiquitin proteasomal pathway or more specifically inhibit the proteasome, or which disrupt mitochondrial function, or which yield oxidative stress can increase the risk of an individual for developing PD, and can contribute to the pathogenesis of PD. These factors can be considered when evaluating the risk profile of a candidate subject for treatment with an iRNA agent modified for enhanced uptake into a neural cell, e.g., conjugated to a cholesterol molecule.

Design and Selection of iRNA Agents

Candidate iRNA agents can be designed by performing, for example, a gene walk analysis. Overlapping, adjacent, or closely spaced candidate agents corresponding to all or some of the transcribed region can be generated and tested. Each of the iRNA agents can be tested and evaluated for the ability to down regulate target gene expression (see below, "Evaluation of Candidate iRNA agents").

An iRNA agent can be rationally designed based on sequence information and desired characteristics. For example, an iRNA agent can be designed according to the relative melting temperature of the candidate duplex. Generally, the duplex will have a lower melting temperature at the 5' end of the antisense strand than at the 3' end of the antisense strand. This and other elements of rational design are discussed in greater detail below (see, e.g., sections labeled "Palindromes," "Asymmetry," and "Z-X-Y," and "Differential Modification of Terminal Duplex Stability" and "Other-than-Watson-Crick Pairing."

Evaluation of Candidate iRNA Agents

A candidate iRNA agent, e.g., a candidate iRNA agent conjugated to a lipophilic moiety, can be evaluated for its ability to be taken up into neural cells. For example, a candidate iRNA agent conjugated to a lipophilic moiety is provided in a solution that does not contain an additional lipophilic moiety or transfection reagent to facilitate uptake into the cell. "Transfection reagents" include ions or other substances which substantially alter cell permeability to an oligonucleotide agent. Exemplary transfecting agents include Lipofectamine™ (Invitrogen, Carlsbad, Calif.), Lipofectamine 2000™, TransIT TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), or another transfection reagent.

The candidate iRNA agent conjugated to a lipophilic moiety can be evaluated in a cell culture system, such as in a neural cell culture. If a predetermined level of uptake into neural cells is observed, the candidate iRNA agent can be evaluating in an animal, e.g., in a mouse, rat, rabbit, dog, cat, or monkey. The cell cultures can be mammalian cell cultures, such as mouse, rat or human cell cultures. Exemplary neural cell cultures include cortical cell lines, striatal cell lines (e.g., ST14A), pheochromocytoma cell lines (e.g., PC12), neuroblastoma cell lines (e.g., N2a), and the like. The cell cultures can be, for example, non-tumor- or tumor-derived neuronal cell lines, and can be derived from, for example, a glioma, glioblastoma, medulloblastoma, retinoblastoma, or a neuroendocrine cell line. Exemplary cell lines can be provided by the American Type Culture Collection (ATCC) (Manassas, Va.).

A candidate iRNA agent that includes a lipophilic moiety, e.g., a cholesterol, can include an antisense strand that is substantially complementary to a target RNA in the neural cell, e.g., an htt RNA, and the method of evaluating the iRNA agent can include determining whether the agent decreases expression of the target RNA in the cell.

A candidate iRNA agent that can be taken up into neural cells can be further tested for uptake into a neural cell in vivo. For example, following administration of the iRNA agent, such as by direct injection into the animal, e.g., into the brain of the animal, the tissue at the site of injection can be examined for uptake of the iRNA agent. Detection of the iRNA agent can be accomplished by a variety of methods. For example, if the iRNA agent is labeled with a fluorescent molecule, such as Cy3, Cy5, rhodamine or FITC label, uptake of the iRNA agent can be assayed by monitoring for the uptake of the fluorescent label. Detection can also be accomplished by in situ hybridization with an oligonucleotide probe, e.g., to detect the presence of the iRNA. Assays to detect target gene product (target RNA or protein) can also be used to monitor uptake of the candidate iRNA agent into neural cells. Detection can be, for example, by in situ hybridization with an oligonucleotide probe to detect the target RNA or by immunohistochemistry techniques to detect the target polypeptide. Alternatively, target RNA or protein can be isolated from the tissue containing the neural cells, and the RNA detected by, e.g., Northern blot, RT-PCR, or RNAse protection assay, or the target protein detected by Western blot analysis. If a decreased level of RNA or protein is detected, it can be determined that a sufficient amount of iRNA agent is entering the cell to cause the observed decrease in RNA or protein expression.

For example, a candidate iRNA agent conjugated with a lipophilic moiety can be provided, and contacted with a neural cell, e.g., a neural cell that expresses a target gene, such as the htt gene. The level of target gene expression prior to and following contact with the candidate iRNA agent can be compared. The target gene can be an endogenous or exogenous gene within the cell. If it is determined that the amount of RNA or protein expressed from the target gene is lower following contact with the iRNA agent, then it can be concluded that the iRNA agent down regulates target gene expression. The level of target RNA or protein in the cell can be determined by any method desired. For example, the level of target RNA can be determined by Northern blot analysis, reverse transcription coupled with polymerase chain reaction (RT-PCR), or RNAse protection assay. The level of protein an be determined by, for example, Western blot analysis.

The iRNA agent conjugated with a lipophilic moiety, e.g., a cholesterol, can be tested in an in vitro or/and in an in vivo system. For example, the target gene or a fragment thereof can be fused to a reporter gene on a plasmid. The plasmid can be transfected into a cell, e.g., a neural cell, with a candidate iRNA agent. The efficacy of the iRNA agent can be evaluated by monitoring expression of the reporter gene. The reporter gene can be monitored in vivo, such as by fluorescence or in situ hybridization. Exemplary fluorescent reporter genes include but are not limited to green fluorescent protein and luciferase. Expression of the reporter gene can also be monitored by Northern blot, RT-PCR, RNAse-protection assay, or Western blot analysis as described above.

Efficacy of an iRNA agent conjugated to a lipophilic moiety, e.g., cholesterol, can be tested in a mammalian cell line, e.g., a mammalian neural cell line, such as a human neuroblastoma cell line. For example, a cell line useful for testing efficacy of an anti-htt iRNA agent is a striatal cell line, e.g. ST14A cell line. Other mammalian neural cell lines that can take up an iRNA agent conjugated with a lipophilic moiety include, e.g., neuronally differentiated phaeochromocytomas (e.g., PC12 cells), primary neuronal cultures (e.g., isolated from a mouse or rat and cultured immediately), and neuroblastoma cell lines. Neuroblastoma cell lines include BE(2)-M17, SH-SY5Y (both human) and N2a (mouse).

Controls include:
(1) testing the efficacy and specificity of an iRNA agent by assaying for a decrease in expression of the target gene by, for example, comparison to expression of an endogenous or exogenous off-target RNA or protein; and
(2) testing specificity of the effect on target gene expression by administering a "nonfunctional" iRNA agent.

Nonfunctional control iRNA agents can:
(a) target a gene not expressed in the cell;
(b) be of nonsensical sequence (e.g., a scrambled version of the test iRNA); or
(c) have a sequence complementary to the target gene, but be known by previous experiments to lack an ability to silence gene expression.

A candidate iRNA agent conjugated to a lipophilic molecule can include other modifications for nuclease resistance. Resistance to a degradent can be evaluated as follows. A candidate modified iRNA agent (and preferably a control molecule, usually one that does not include the modification believed to be required for nuclease resistance) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein. For example, a modified siRNA homologous to the GFP mRNA can be assayed for the ability to inhibit GFP expression by monitoring for a decrease in cell fluorescence, as compared to a control cell, in which the transfection did not include the candidate siRNA, e.g., controls with no agent added and/or controls with a non-modified RNA added. Efficacy of the candidate agent on gene expression can be assessed by comparing cell fluorescence in the presence of the modified and unmodified iRNA agents.

The effect of the modified iRNA agent on target RNA levels can be verified by Northern blot to assay for a decrease in the level of target mRNA, or by Western blot to assay for a decrease in the level of target protein, as compared to a negative control. Controls can include cells in which no agent is added and/or cells in which a non-modified iRNA agent is added.

Assays can include time course experiments to monitor stability and duration of silencing by an iRNA agent and monitoring in dividing versus nondividing cells. Presumably in dividing cells, the iRNA agent is diluted out over time, thus decreasing the duration of the silencing effect. The implication is that dosage will have to be adjusted in vivo, and/or an iRNA agent will have to be administered more frequently to maintain the silencing effect. To monitor nondividing cells, cells can be arrested by serum withdrawal. Neurons are post-mitotic cells, and thus neural cells are aptly suited for assaying the stability of iRNA agents, such as an anti-htt iRNA agent, for use in therapeutic compositions for the treatment of disorders of the nervous system, e.g., neurological disorders, such as HD.

A candidate iRNA agent can also be evaluated for cross-species reactivity. For example, cell lines derived from different species (e.g., mouse vs. human) or in biological samples (e.g., serum or tissue extracts) isolated from different species can be transfected with a candidate iRNA agent conjugated to a lipophilic moiety, e.g., cholesterol. The efficacy of the iRNA agent can be determined for the cell from the different species.

Stability Testing, Modification, and Retesting of iRNA Agents

A candidate iRNA agent conjugated with a lipophilic agent for enhanced uptake into neural cells can be evaluated with respect to its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject. The component (e.g., an exonuclease or endonuclease) can be specific for a particular area of the body, such as a particular tissue, organ, or bodily fluid (e.g., blood, plasma, or serum). Sites in an iRNA agent that are susceptible to cleavage, either by endonucleolytic or exonucleolytic cleavage, in certain areas of the body, may be resistant to cleavage in other areas of the body. An exemplary method includes:

(1) determining the point or points at which a substance present in the body of a subject, and preferably a component present in a compartment of the body into which a therapeutic dsRNA is to be introduced (this includes compartments into which the therapeutic is directly introduced, e.g., the circulation, as well as in compartments to which the therapeutic is eventually targeted; in some cases, e.g, the eye or the brain the two are the same), cleaves a dsRNA, e.g., an iRNA agent, and (2) identifying one or more points of cleavage, e.g., endonucleolytic, exonucleolytic, or both, in the dsRNA. Optionally, the method further includes providing an RNA modified to inhibit cleavage at such sites.

These steps can be accomplished by using one or more of the following assays:

(i) (a) contacting a candidate dsRNA, e.g., an iRNA agent, with a test agent (e.g., a biological agent),
    (b) using a size-based assay, e.g., gel electrophoresis to determine if the iRNA agent is cleaved. In a preferred embodiment a time course is taken and a number of samples incubated for different times are applied to the size-based assay. In preferred embodiments, the candidate dsRNA is not labeled. The method can be a "stains all" method.

(ii) (a) supplying a candidate dsRNA, e.g., an iRNA agent, which is radiolabeled;
    (b) contacting the candidate dsRNA with a test agent,
    (c) using a size-based assay, e.g., gel electrophoresis to determine if the iRNA agent is cleaved. In a preferred embodiment a time course is taken where a number of samples are incubated for different times and applied to the size-based assay. In preferred embodiments, the determination is made under conditions that allow determination of the number of nucleotides present in a fragment. E.g., an incubated sample is run on a gel having markers that allow assignment of the length of cleavage products. The gel can include a standard that is a "ladder" digestion. Either the sense or antisense strand can be labeled. Preferably only one strand is labeled in a particular experiment. The label can be incorporated at the 5' end, 3' end, or at an internal position. Length of a fragment (and thus the point of cleavage) can be determined from the size of the fragment based on the ladder and mapping using a site-specific endonuclease such as RNAse TI.

(iii) fragments produced by any method, e.g., one of those above, can be analyzed by mass spectrometry. Following contacting the iRNA with the test agent, the iRNA can be purified (e.g., partially purified), such as by phenol-chloroform extraction followed by precipitation. Liquid chromatography can then be used to separate the fragments and mass spectrometry can be used to determine the mass of each fragment. This allows determination of the mechanism of cleavage, e.g., if by direct phosphate cleavage, such as be 5' or 3' exonuclease cleavage, or mediated by the 2'OH via formation of a cyclic phosphate.

More than one iRNA agent, e.g., anti-htt iRNA agent, can be evaluated. The evaluation can be used to select a sequence for use in a therapeutic iRNA agent. For example, it allows the selection of a sequence having an optimal (usually minimized) number of sites that are cleaved by a substance(s), e.g., an enzyme, present in the relevant compartments of a subject's body. Two or more iRNA agent candidates can be evaluated to select a sequence that is optimized. For example, two or more candidates can be evaluated and the one with optimum properties, e.g., fewer cleavage sites, selected.

The information relating to a site of cleavage can be used to select a backbone atom, a sugar or a base, for modification, e.g., a modification to decrease cleavage.

Exemplary modifications include modifications that inhibit endonucleolytic degradation, including the modifications described herein. Particularly favored modifications include: 2' modification, e.g., provision of a 2' OMe moiety on a U in a sense or antisense strand, but especially on a sense strand; modification of the backbone, e.g., with the replacement of an O with an S, in the phosphate backbone, e.g., the provision of a phosphorothioate modification, on the U or the A or both, especially on an antisense strand; replacement of the U with a C5 amino linker; replacement of an A with a G (sequence changes are preferred to be located on the sense strand and not the antisense strand); and modification of the at the 2', 6', 7', or 8' position. Preferred embodiments are those in which one or more of these modifications are present on the sense but not the antisense strand, or embodiments where the antisense strand has fewer of such modifications.

Exemplary modifications also include those that inhibit degradation by exonucleases. Examples of modifications that inhibit exonucleolytic degradation can be found herein. Particularly favored modifications include: 2' modification, e.g., provision of a 2' OMe moiety in a 3' overhang, e.g., at the 3' terminus (3' terminus means at the 3' atom of the molecule or at the most 3' moiety, e.g., the most 3' P or 2' position, as indicated by the context); modification of the backbone, e.g., with the replacement of a P with an S, e.g., the provision of a phosphorothioate modification, or the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrolidine in a 3' overhang, e.g., at the 3' terminus; modification with naproxen, ibuprofen, or other moieties which inhibit degradation at the 3' terminus.

These methods can be used to select and or optimize a therapeutic iRNA agent conjugated with a lipophilic moiety, e.g., cholesterol, for enhanced uptake into neural cells.

The method can be used to evaluate a candidate iRNA agent conjugated with a lipophilic moiety and that also includes a modification that, for example, inhibits degradation, targets the dsRNA molecule, or modulates hybridization. Such modifications are described herein. A cleavage assay can be combined with an assay to determine the ability of a modified or non-modified candidate to silence the target. E.g., one might (optionally) test a candidate to evaluate its ability to silence a target (or off-target sequence), evaluate its susceptibility to cleavage, modify it (e.g., as described herein, e.g., to inhibit degradation) to produce a modified candidate, and test the modified candidate for one or both of the ability to silence and the ability to resist degradation. The procedure can be repeated. Modifications can be introduced one at a time or in groups. A cell-based method can be used to monitor the ability of the iRNA agent to silence. This can be followed by a different method, e.g, a whole animal method, to confirm activity.

A test agent refers to a biological agent, e.g.; biological sample, tissue extract or prep, serum, a known enzyme or other molecule known to modify, e.g., cleave, a dsRNA, e.g., an endonuclease. The test agent can be in a compartment of the body in which the RNAi agent will be exposed. For example, for an iRNA agent that is administered directly in to neural tissue (e.g., into the brain or into the spinal cord) the test agent could be brain tissue extract or spinal fluid. An iRNA agent that is to be supplied directly to the eye can be incubated with an extract of the eye.

In Vivo Testing

An iRNA agent conjugated with a lipophilic moiety and identified as having an enhanced capability of entering neural cells in culture can be tested for functionality in vivo in an animal model (e.g., in a mammal, such as in mouse or rat). For example, the iRNA agent can be administered to an animal, and the iRNA agent evaluated with respect to its biodistribution, e.g., is uptake into neural cells, its stability, and its ability to inhibit expression of a target gene in the neural cells.

The iRNA agent can be administered to the animal model in the same manner that it would be administered to a human. For example, the iRNA agent can be injected directly into a target region of the brain (e.g., into the cortex, the substantia nigra, the globus pallidus, the hippocampus, or the striatum), and after a period of time, the brain can be harvested and tissue slices examined for distribution of the agent.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as Cy3, Cy5, FITC, rhodamine, or fluorescein; a radioactive label, such as $^{32}P$, $^{33}P$, or $^{3}H$; gold particles; or antigen particles for immunohistochemistry).

An iRNA agent useful for monitoring biodistribution can lack gene silencing activity in vivo. For example, the iRNA agent can target a gene not present in the animal (e.g., an iRNA agent injected into mouse can target luciferase), or an iRNA agent can have a non-sense sequence, which does not target any gene, e.g., any endogenous gene). Localization/biodistribution of the iRNA can be monitored by a traceable label attached to the iRNA agent, such as a traceable agent described above The iRNA agent conjugated to a lipophilic moiety can be evaluated with respect to its ability to down regulate target gene expression. Levels of target gene expression in vivo can be measured, for example, by in situ hybridization, or by the isolation of RNA from tissue prior to and following exposure to the iRNA agent. Target RNA can be detected by any desired method, including but not limited to RT-PCR, Northern blot, or RNAase protection assay. Alternatively, or additionally, target gene expression can be monitored by performing Western blot analysis on tissue extracts treated with an iRNA agent.

An iRNA agent conjugated to a lipophilic agent for enhanced uptake into neural cells can be tested in a mouse model for a neurological disease. For example, an iRNA agent conjugated to a lipophilic agent can be tested in a mouse model for HD, such as a mouse carrying a wildtype copy of the human htt gene or in mouse carrying a mutant human htt, e.g., an htt gene carrying an expanded CAG repeat. A treated mouse model can be observed for a decrease in symptoms associated with HD, e.g., a decrease in clasping. The treated mouse can be assessed for other phentypes, e.g., expression of DARPP protein in brain cells, such as in medium spiny neurons of the brain. In one embodiment, such a secondary assay requires dissection of the mouse brain for Western blot analysis or in situ hybridization of brain tissue, including spiny neurons.

iRNA Chemistry

Described herein are isolated iRNA agents, e.g., dsRNA molecules, that mediate RNAi. The iRNA agents are modified for enhanced uptake into neural cells by their attachment to at least one lipophilic moiety, e.g., a cholesterol molecule.

Generally, the iRNA agents featured in the invention should include a region of sufficient homology to a target gene, e.g., a target gene expressed in a neural cell, and be of sufficient length in terms of nucleotides, such that the iRNA agent, or a fragment thereof, can mediate down regulation of the target gene. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA. Therefore, the iRNA agents featured in the instant invention include agents comprising a sense strand and antisense strand each comprising a sequence of at least 16, 17 or 18 nucleotides which is essentially identical, as defined below, to a sequence of a gene expressed in a neural cell, except that not more than 1, 2 or 3 nucleotides per strand, respectively, have been substituted by other nucleotides (e.g., adenosine replaced by uracil), while essentially retaining the ability to inhibit expression of the target gene in a mammalian cell. Exemplary iRNA agents may therefore possess at least 15 nucleotides identical to the target gene sequence, but include 1, 2 or 3 base mismatches with respect to either the target mRNA sequence or between the sense and antisense strand are introduced. Mismatches to the target mRNA sequence particularly in the antisense strand, are most tolerated in the terminal regions and if present are preferably in a terminal region or regions, e.g., within 6, 5, 4, or 3 nucleotides of the 5' and/or 3' terminus, most preferably within 6, 5, 4, of 3 nucleotides of the 5'-terminus of the sense strand or the 3'-terminus of the antisense strand. The sense strand need only be sufficiently complementary with the antisense strand to maintain the over all double strand character of the molecule.

Single stranded regions of an iRNA agent will often be modified or include nucleoside surrogates, e.g., the unpaired region or regions of a hairpin structure, e.g., a region which links two complementary regions, can have modifications or nucleoside surrogates. Modifications to stabilize one or both of the 3'- or 5'-terminus of an iRNA agent, e.g., against exonucleases, or to favor the antisense sRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis. As discussed elsewhere herein, an iRNA agent will often be modified or include an SRMS in addition to the nucleotide surrogate. An SRMS replaces a ribose sugar on a ribonucleotide with another moiety, e.g., a non-carbohydrate (preferably cyclic) carrier. SRMS' are described in greater detail below.

Although, in mammalian cells, long ds iRNA agents can induce the interferon response which is frequently deleterious, short ds iRNA agents do not trigger the interferon response, at least not to an extent that is deleterious to the cell and host. The iRNA agents of the present invention include molecules which are sufficiently short that they do not trigger the interferon response in mammalian cells. Thus, the administration of a composition of an iRNA agent (e.g., formulated as described herein) to a mammalian cell can be used to silence expression of a gene expressed in a neural cell, e.g., the htt gene, while circumventing the interferon response. Molecules that are short enough that they do not trigger an interferon response are termed sRNA agents or shorter iRNA agents herein. "sRNA agent or shorter iRNA agent" as used herein, refers to an iRNA agent, e.g., a double stranded RNA agent or single strand agent, that is sufficiently short that it does not induce a deleterious interferon response in a human cell, e.g., it has a duplexed region of less than 60 but preferably less than 50, 40, or 30 nucleotide pairs.

In addition to homology to target RNA and the ability to down regulate a target gene, an iRNA agent will preferably have one or more of the following properties:

(1) it will be of the Formula 1, 2, 3, or 4 described below;
(2) if single stranded it will have a 5' modification that includes one or more phosphate groups or one or more analogs of a phosphate group;
(3) it will, despite modifications, even to a very large number of bases, specifically base pair and form a duplex structure with a homologous target RNA of sufficient thermodynamic stability to allow modulation of the activity of the targeted RNA;
(4) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, all of the nucleotide sugars can contain e.g., 2'OMe, or 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into hydrogen-bonding which is more characteristic of the 2'-OH moiety of a ribonucleotide than the 2'-H moiety of a deoxyribonucleotide. A preferred iRNA agent will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure. These limitations are particularly preferably in the antisense-strand;

Preferred 2'-modifications with C3'-endo sugar pucker include:

2'-OH, 2'-O-Me, 2'-O-methoxyethyl, 2'-O-aminopropyl, 2'-F, 2'-O—CH2-CO—NHMe, 2'-O—CH2-CH2-O—CH2-CH2-N(Me)2, LNA (5) regardless of the nature of the modification, and even though the oligonucleotide agent can contain deoxynucleotides or modified deoxynucleotides, it is preferred that DNA molecules, or any molecule in which more than 50, 60, or 70% of the nucleotides in the molecule are deoxyribonucleotides, or modified deoxyribonucleotides which are deoxy at the 2' position, are excluded from the definition of oligonucleotide agent.

A "ds iRNA agent" (abbreviation for "double stranded (ds) iRNA agent") as used herein, is an iRNA agent which includes more than one, and preferably two, strands in which interchain hybridization can form a region of duplex structure.

The antisense strand of a double stranded iRNA agent should be equal to or at least, 14, 15, 16 17, 18, 19, 25, 29, 40, or 50 nucleotides in length. It should be equal to or less than 60, 50, 40, or 30 nucleotides in length. Preferred ranges are 15 to 30, 17 to 25, 1.9 to 23, and 19 to 21 nucleotides in length.

The sense strand of a double stranded iRNA agent should be equal to or at least 14, 15, 16 17, 18, 19, 25, 29, 40, or 50 nucleotides in length. It should be equal to or less than 60, 50, 40, or 30 nucleotides in length. Preferred ranges are 17 to 25, 19 to 23, and 19 to 21 nucleotides in length.

The double strand portion of a double stranded iRNA agent should be equal to or at least, 15, 16 17, 18, 19, 20, 21, 22, 23, 24, 25, 29, 40, or 50 nucleotide pairs in length. It should be equal to or less than 60, 50, 40, or 30 nucleotide pairs in length. Preferred ranges are 15 to 30, 17 to 25, 19 to 23, and 19 to 21 nucleotides pairs in length.

It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active iRNA agent/protein or RISC. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional sRNA 5'-end. Antisense strand modifications include 5' phosphorylation as well as any of the other 5' modifications discussed herein.

It is preferred that the sense and antisense strands be chosen such that the ds iRNA agent includes a single strand or unpaired region at one or both ends of the molecule. Thus, a ds iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred iRNA agents will have single-stranded overhangs, preferably 3' overhangs, of 1 to 4, or preferably 2 or 3 nucleotides in length at each end. The overhangs can be the result of one strand being longer than the other, or the result of two strands of the same length being staggered. 5' ends are preferably phosphorylated.

Preferred lengths for the duplexed region is between 15 and 30, most preferably 18, 19, 20, 21, 22, and 23 nucleotides in length, e.g., in the iRNA agent range discussed above. iRNA agents can resemble in length and structure the natural Dicer processed products from long dsRNAs. Embodiments in which the two strands of the sRNA agent are linked, e.g., covalently linked are also included. Hairpin, or other single strand structures which provide the required double stranded region, and preferably a 3' overhang are also within the invention.

As used herein, the phrase "mediates RNAi" refers to the ability of an agent to silence, in a sequence specific manner, a target gene. "Silencing a target gene" means the process whereby a neural cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar neural cell which has not been contacted with the agent. Such product of the target gene can, for example, be a messenger RNA (mRNA), a protein, or a regulatory element While not wishing to be bound by theory, it is believed that silencing by the agents described herein uses the RNAi machinery or process and a guide RNA, e.g., an iRNA agent of 15 to 30 nucleotide pairs.

As used herein, the term "complementary" is used to indicate a sufficient degree of complementarity such that stable and specific binding occurs between a compound of the invention and a target RNA molecule, e.g., an htt mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA (e.g., a target htt mRNA) if the iRNA agent reduces the production of a protein encoded by the target mRNA. The iRNA agent may also be "exactly complementary" (excluding the SRMS containing subunit(s)) to a target RNA, e.g., the target RNA and the iRNA agent can anneal, preferably to form a hybrid made exclusively of Watson-Crick base pairs in the region of exact complementarity. A "sufficiently complementary" target RNA can include a region (e.g., of at least 7 nucleotides) that is exactly complementary to a target RNA, e.g., an htt RNA. Moreover, in some embodiments, the iRNA agent specifically discriminates a single-nucleotide difference.

iRNA agents conjugated with a lipophilic agent for enhanced uptake into neural cells include iRNA agents which have been further modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., *Nucleic Acids Res.* 22: 2183-2196, 1994. Such rare or unusual RNAs, often termed modified RNAs are typically the result of a post transcriptional modification and are within the term unmodified RNA, as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as modified RNAs, they will of course, because of the modification, include molecules that are not, strictly speaking, RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Much of the discussion below refers to single strand molecules. However, it is understood that a ds iRNA agent, e.g., a partially ds iRNA agent, is required or preferred. Thus, it is understood that double stranded structures (e.g. where two separate molecules are contacted to form the double stranded region or where the double stranded region is formed by intramolecular pairing (e.g., a hairpin structure)) made of the single stranded structures described below are within the invention. Preferred lengths are described elsewhere herein.

As nucleic acids are polymers of subunits or monomers, many of the modifications described below occur at a position which is repeated within a nucleic acid, e.g., a modification of a base, or a phosphate moiety, or a non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. The ligand can be at attached at the 3' end, the 5' end, or at an internal position, or at a combination of these positions. For example, the ligand can be at the 3' end and the 5' end; at the 3' end and at one or more internal positions; at the 5' end and at one or more internal positions; or at the 3' end, the 5' end, and at one or more internal positions. For example, a phosphorothioate modification at a non-linking O position may only occur at one or both termini, or may only occur in a terminal region, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both strands. In some cases, the sense and antisense strand will have the same modifications or the same class of modifications, but in other cases the sense and antisense strand will have different modifications, e.g., in some cases it may be desirable to modify only one strand, e.g. the sense strand. The 5' end can be phosphorylated. In a particularly preferred embodiment, the sense strand is modified at the 3' end by the addition of a cholesterol.

In some embodiments it is particularly preferred, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Modifications and nucleotide surrogates are discussed below.

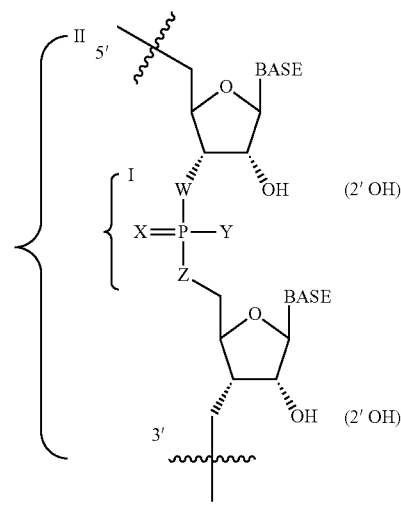

FORMULA 1

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases. Unmodified oligoribonucleotides may also be less than optimal in terms of offering tethering points for attaching ligands or other moieties to an iRNA agent.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein);

(ii) alteration, e.g., replacement, of a constituent of the ribose sugar, e.g., of the 2' hydroxyl on the ribose sugar, or wholesale replacement of the ribose sugar with a structure other than ribose, e.g., as described herein;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g. a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid but rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while hot wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3', and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance.

Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholie acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Preferred modifications include the addition of a methylphosphonate at the 3'-most terminal linkage; a 3' C5-aminoalkyl-dT; 3' cationic group; or another 3' conjugate to inhibit 3'-5' exonucleolytic degradation.

Terminal modifications useful for modulating activity include modification of the 5' end with phosphate or phosphate analogs. E.g., in preferred embodiments iRNA agents, especially antisense strands, are 5' phosphorylated or include a phosphoryl analog at the 5' terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Preferred iRNA Agents

Preferred RNA agents have the following structure (see Formula 2 below):

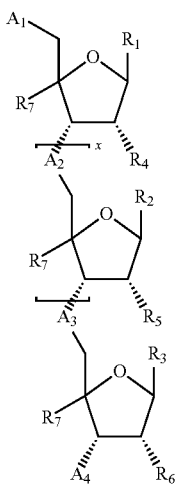

FORMULA 2

Referring to Formula 2 above, $R^1$, $R^2$, and $R^3$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other-alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

$R^4$, $R^5$, and $R^6$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2NHR^9$; $NHC(O)R^8$; cyano; mercapto, $SR^8$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido; or $R^4$, $R^5$, or $R^6$ together combine with $R^7$ to form an [—O—CH$_2$—] covalently bound bridge between the sugar 2' and 4' carbons.

$A^1$ is:

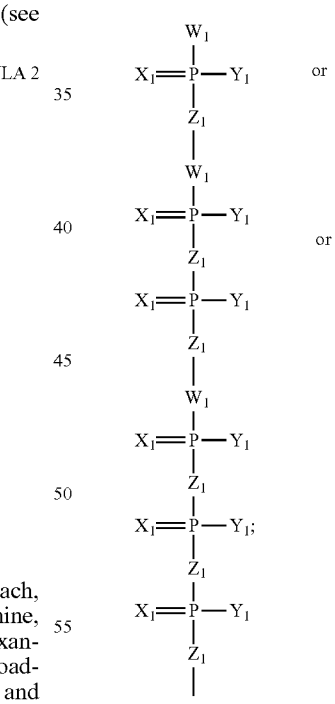

H; OH; $OCH_3$; $W^1$; an abasic nucleotide; or absent;

(a preferred A1, especially with regard to anti-sense strands, is chosen from 5'-monophosphate ((HO)$_2$(O)P—O-5'), 5'-diphosphate ((HO)$_2$(O)P—O—P(HO)(O)—O-5'), 5'-triphosphate ((HO)$_2$(O)P—O—(HO)(O)P—O—P(HO)(O)—O-5'), 5'-guanosine cap (7-methylated or non-methylated) (7m-G-O-5'-(HO)(O)P—O—(HO)(O)P—O—P(HO)(O)—O-5'), 5'-adenosine cap (Appp), and any modified or unmodified nucleotide cap structure (N—O-5'-(HO)(O)P—

O—(HO)(O)P—O—P(HO)(O)—O-5'), 5'-monothiophosphate (phosphorothioate; $(HO)_2(S)P$—O-5'), 5'-monodithiophosphate (phosphorodithioate; (HO)(HS)(S)P—O-5'), 5'-phosphorothiolate $((HO)_2(O)P$—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates $((HO)_2(O)P$—NH-5', $(HO)(NH_2)(O)P$—O-5'), 5'-alkylphosphonates (R=alkyl=methyl, ethyl, isopropyl, propyl, etc., e.g. RP(OH)(O)—O-5'-, $(OH)_2(O)P$-5'-$CH_2$—), 5'-alkyletherphosphonates (R=alkylether=methoxymethyl ($MeOCH_2$—), ethoxymethyl, etc., e.g. RP(OH)(O)—O-5'-)).

$A^2$ is:

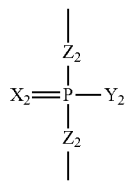

$A^3$ is:

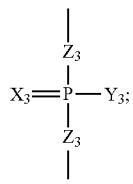

and $A^4$ is:

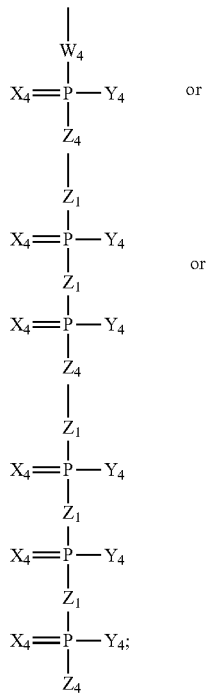

H; $Z^4$; an inverted nucleotide; an abasic nucleotide; or absent.

$W^1$ is OH, $(CH_2)_nR^{10}$, $(CH_2)_nNHR^{10}$, $(CH_2)_nOR^{10}$, $(CH_2)_nSR^{10}$; $O(CH_2)_nR^{10}$; $O(CH_2)_nOR^{10}$, $O(CH_2)_nNR^{10}$, $O(CH_2)_nSR^{10}$, $O(CH_2)_nSS(CH_2)_nOR^{10}$, $O(CH_2)_nC(O)OR^{10}$; $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}O(CH_2CH_2O)_mCH_2CH_2OR^{10}$; $O(CH_2CH_2O)_mCH_2CH_2NHR^{10}$, $NH(CH_2CH_2NH)_mCH_2CH_2NHR^{10}$; $Q-R^{10}$, $O-Q-R^{10}N-Q-R^{10}$, $S-Q-R^{10}$ or —O—. $W^4$ is O, $CH_2$, NH, or S.

$X^1$, $X^2$, $X^3$, and $X^4$ are each, independently, O or S.

$Y^1$, $Y^2$, $Y^3$, and $Y^4$ are each, independently, OH, O⁻, $OR^8$, S, Se, $BH_3^-$, H, $NHR^9$, $N(R^9)_2$ alkyl, cycloalkyl, aralkyl, aryl, or heteroaryl, each of which may be optionally substituted.

$Z^1$, $Z^2$, and $Z^3$ are each independently O, $CH_2$, NH, or S. $Z^4$ is OH, $(CH_2)_nR^{10}$, $(CH_2)_nNHR^{10}$, $(CH_2)_nOR^{10}$, $(CH_2)_nSR^{10}$; $O(CH_2)_nR^{10}$; $O(CH_2)_nOR^{10}$, $O(CH_2)_nNR^{10}$, $O(CH_2)_nSR^{10}$, $O(CH_2)_nSS(CH_2)_nOR^{10}$, $O(CH_2)_nC(O)OR^{10}$; $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}O(CH_2CH_2O)_mCH_2CH_2OR^{10}$, $O(CH_2CH_2O)_mCH_2CH_2NHR^{10}$, $NH(CH_2CH_2NH)_mCH_2CH_2NHR^{10}$; $Q-R^{10}$, $O-Q-R^{10}N-Q-R^{10}$, $S-Q-R^{10}$.

X is 5-100, chosen to comply with a length for an RNA agent described herein.

$R^7$ is H; or is together combined with $R^4$, $R^5$, or $R^6$ to form an [—O—$CH_2$—] covalently bound bridge between the sugar 2' and 4' carbons.

$R^8$ is alkyl, cycloalkyl, aryl, aralkyl, heterocyclyl, heteroaryl, amino acid, or sugar; $R^9$ is $NH_2$, alkylamino, dialkylamino, heterocyclyl, arylamino, diaryl amino, heteroaryl amino, diheteroaryl amino, or amino acid; and $R^{10}$ is H; fluorophore (pyrene, TAMRA, fluorescein, Cy3 or Cy5 dyes); sulfur, silicon, boron or ester protecting group; intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino; alkyl, cycloalkyl, aryl, aralkyl, heteroaryl; radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles); or an RNA agent. m is 0-1,000,000, and n is 0-20. Q is a spacer selected from the group consisting of abasic sugar, amide, carboxy, oxyamine, oxyimine, thioether, disulfide, thiourea, sulfonamide, or morpholino, biotin or fluorescein reagents.

Preferred RNA agents in which the entire phosphate group has been replaced have the following structure (see Formula 3 below):

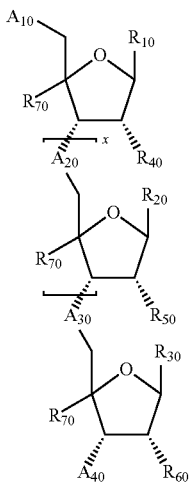

FORMULA 3

Referring to Formula 3, $A^{10}$-$A^{40}$ is L-G-L; $A^{10}$ and/or $A^{40}$ may be absent, in which L is a linker, wherein one or both L may be present or absent and is selected from the group consisting of $CH_2(CH_2)_g$; $N(CH_2)_g$; $O(CH_2)_g$; $S(CH_2)_g$. G is a functional group selected from the group consisting of siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

$R^{10}$, $R^{20}$, and $R^{30}$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6,N6-dimethyladenine, 2,6-diaminopurine, 5-amino-allyl-uracil, N3-methyluracil substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

$R^{40}$, $R^{50}$, and $R^{60}$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2R^9$; $NHC(O)R^8$; cyano; mercapto, $SR^7$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, and ureido groups; or $R^{40}$, $R^{50}$, or $R^{60}$ together combine with $R^{70}$ to form an [—O—$CH_2$—] covalently bound bridge between the sugar 2' and 4' carbons.

x is 5-100 or chosen to comply with a length for an RNA agent described herein.

$R^{70}$ is H; or is together combined with $R^{40}$, $R^{50}$, or $R^{60}$ to form an [—O—$CH_2$—] covalently bound bridge between the sugar 2' and 4' carbons.

$R^8$ is alkyl, cycloalkyl, aryl, aralkyl, heterocyclyl, heteroaryl, amino acid, or sugar; and $R^9$ is $NH_2$, alkylamino, dialkylamino, heterocyclyl, arylamino, diaryl amino, heteroaryl amino, diheteroaryl amino, or amino acid. m is 0-1,000,000, n is 0-20, and g is 0-2.

Preferred nucleoside surrogates have the following structure (see Formula 4 below):

FORMULA 4

S is a nucleoside surrogate selected from the group consisting of mophilino, cyclobutyl, pyrrolidine and peptide nucleic acid. L is a linker and is selected from the group consisting of $CH_2(CH_2)_g$; $N(CH_2)_g$; $O(CH_2)_g$; $S(CH_2)_g$; —C(O)($CH_2)_g$— or may be absent. M is an amide bond; sulfonamide; sulfinate; phosphate group; modified phosphate group as described herein; or may be absent.

$R^{100}$, $R^{200}$, and $R^{300}$ are each, independently, H (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6,N6-dimethyladenine, 2,6-diaminopurine, 5-amino-allyl-uracil, N3-methyluracil substituted 1,2,4,-triazoles, 2-pyridinones, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

x is 5-100, or chosen to comply with a length for an RNA agent described herein; and g is 0-2.

Enhanced Nuclease Resistance

An iRNA agent conjugated to a lipophilic moiety for enhanced uptake into neural cells can have enhanced resistance to nucleases.

For increased nuclease resistance and/or binding affinity to the target, an iRNA agent, e.g., the sense and/or antisense strands of the iRNA agent, can include, for example, 2'-modified ribose units and/or phosphorothioate linkages.

E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$ AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thioalkyl; thioalkoxy; and alkyl, cycloalkyl, aryl, alkenyl and alkynyl, which may be optionally substituted with e.g., an amino functionality.

Preferred substituents are 2'-methoxyethyl, 2'-OCH3, 2'-O-allyl, 2'-C-allyl, and 2'-fluoro.

In certain aspects, nuclease resistance of iRNA agents is enhanced by identifying nuclease-susceptible sites and modifying such sites to inhibit cleavage. For example, the dinucleotides 5'-UA-3', 5' UG 3', 5'-CA-3', 5' UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Generally, these modifications can inhibit hybridization so it is preferable to use them only in terminal regions, and preferable not to use them at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In most cases, the NRM modifications will be distributed differently depending on whether they are included on a sense or antisense strand. If on an antisense strand, modifications which interfere with or inhibit endonuclease cleavage should not be inserted in the region which is subject to RISC mediated cleavage, e.g., the cleavage site or the cleavage region. As used herein cleavage site refers to the nucleotide on either side of the cleavage site, on the target or on the iRNA agent strand which hybridizes to it. Cleavage region means a nucleotide within 1, 2, or 3 nucleotides of the cleavage site, in either direction.

Such modifications can be introduced into the terminal regions, e.g., at the terminal position or with 2, 3, 4, or 5 positions of the terminus.

Ribose Mimics

The monomers and methods described herein can be used to prepare an oligonucleotide agent, that incorporates a ribose mimic.

Thus, an aspect of the invention features an iRNA agent that includes a secondary hydroxyl group, which can increase efficacy and/or confer nuclease resistance to the agent. Nucleases, e.g., cellular nucleases, can hydrolyze nucleic acid phosphodiester bonds, resulting in partial or complete degradation of the nucleic acid. The secondary hydroxy group confers nuclease resistance to an iRNA agent by rendering the iRNA agent less prone to nuclease degradation relative to an iRNA which lacks the modification. While not wishing to be bound by theory, it is believed that the presence of a secondary hydroxyl group on the iRNA agent can act as a structural mimic of a 3' ribose hydroxyl group, thereby causing it to be less susceptible to degradation.

The secondary hydroxyl group refers to an "OH" radical that is attached to a carbon atom substituted by two other carbons and a hydrogen. The secondary hydroxyl group that confers nuclease resistance as described above can be part of any acyclic carbon-containing group. The hydroxyl may also be part of any cyclic carbon-containing group, and preferably one or more of the following conditions is met (1) there is no ribose moiety between the hydroxyl group and the terminal phosphate group or (2) the hydroxyl group is not on a sugar moiety which is coupled to a base. The hydroxyl group is located at least two bonds (e.g., at least three bonds away, at least four bonds away, at least five bonds away, at least six bonds away, at least seven bonds away, at least eight bonds away, at least nine bonds away, at least ten bonds away, etc.) from the terminal phosphate group phosphorus of the iRNA agent. In preferred embodiments, there are five intervening bonds between the terminal phosphate group phosphorus and the secondary hydroxyl group.

Preferred iRNA agent delivery modules with five intervening bonds between the terminal phosphate group phosphorus and the secondary hydroxyl group have the following structure (see formula Y below):

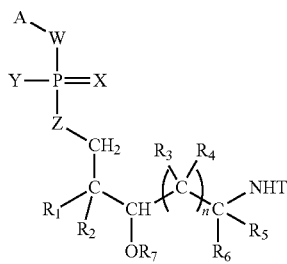

(Y)

Referring to formula Y, A is an iRNA agent, including any iRNA agent described herein. The iRNA agent may be connected directly or indirectly (e.g., through a spacer or linker) to "W" of the phosphate group. These spacers or linkers can include e.g., $-(CH_2)_n-$, $-(CH_2)_nN-$, $-(CH_2)_nO-$, $-(CH_2)_nS-$, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents.

The iRNA agents can have a terminal phosphate group that is unmodified (e.g., W, X, Y, and Z are O) or modified. In a modified phosphate group, W and Z can be independently NH, O, or S; and X and Y can be independently S, Se, $BH_3^-$, $C_1$-$C_6$ alkyl, $C_6$-$C_{10}$ aryl, H, O, $O^-$, alkoxy or amino (including alkylamino, arylamino, etc.). Preferably, W, X and Z are O and Y is S.

$R_1$ and $R_3$ are each, independently, hydrogen; or $C_1$-$C_{100}$ alkyl, optionally substituted with hydroxyl, amino, halo, phosphate or sulfate and/or may be optionally inserted with N, O, S, alkenyl or alkynyl.

$R_2$ is hydrogen; $C_1$-$C_{100}$ alkyl, optionally substituted with hydroxyl, amino, halo, phosphate or sulfate and/or may be optionally inserted with N, O, S, alkenyl or alkynyl; or, when n is 1, $R_2$ may be taken together with $R_4$ or $R_6$ to form a ring of 5-12 atoms.

$R_4$ is hydrogen; $C_1$-$C_{100}$ alkyl, optionally substituted with hydroxyl, amino, halo, phosphate or sulfate and/or may be optionally inserted with N, O, S, alkenyl or alkynyl; or, when n is 1, $R_4$ may be taken together with $R_2$ or $R_5$ to form a ring of 5-12 atoms.

$R_5$ is hydrogen, $C_1$-$C_{100}$ alkyl optionally substituted with hydroxyl, amino, halo, phosphate or sulfate and/or may be optionally inserted with N, O, S, alkenyl or alkynyl; or, when n is 1, $R_5$ may be taken together with $R_4$ to form a ring of 5-12 atoms.

$R_6$ is hydrogen, $C_1$-$C_{100}$ alkyl, optionally substituted with hydroxyl, amino, halo, phosphate or sulfate and/or may be optionally inserted with N, O, S, alkenyl or alkynyl, or, when n is 1, $R_6$ may be taken together with $R_2$ to form a ring of 6-10 atoms;

$R_7$ is hydrogen, $C_1$-$C_{100}$ alkyl, or $C(O)(CH_2)_qC(O)NHR_9$; T is hydrogen or a functional group; n and q are each independently 1-100; $R_8$ is $C_1$-$C_{10}$ alkyl or $C_6$-$C_{10}$ aryl; and R is hydrogen, $C_1$-$C_{10}$ alkyl, $C_6$-$C_{10}$ aryl or a solid support agent.

Preferred embodiments may include one of more of the following subsets of iRNA agent delivery modules.

In one subset of RNAi agent delivery modules, A can be connected directly or indirectly through a terminal 3' or 5' ribose sugar carbon of the RNA agent.

In another subset of RNAi agent delivery modules, X, W, and Z are O and Y is S.

In still yet another subset of RNAi agent delivery modules, n is 1, and $R_2$ and $R_6$ are taken together to form a ring containing six atoms and $R_4$ and $R_5$ are taken together to form a ring containing six atoms. Preferably, the ring system is a trans-decalin. For example, the RNAi agent delivery module of this subset can include a compound of Formula (Y-1):

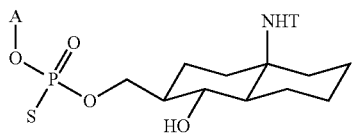

The functional group can be, for example, a targeting group (e.g., a steroid or a carbohydrate), a reporter group (e.g., a fluorophore), or a label (an isotopically labeled moiety). The targeting group can further include protein binding agents, endothelial cell targeting groups (e.g., RGD peptides and mimetics), cancer cell targeting groups (e.g., folate Vitamin B12, Biotin), bone cell targeting groups (e.g., bisphosphonates, polyglutamates, polyaspartates), multivalent mannose (for e.g., macrophage testing), lactose, galactose, N-acetyl-galactosamine, monoclonal antibodies, glycoproteins, lectins, melanotropin, or thyrotropin.

As can be appreciated by the skilled artisan, methods of synthesizing the compounds of the formulae herein will be evident to those of ordinary skill in the art. The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Sugar Replacement Modification Subunit

An iRNA agent modified for enhanced uptake into a neural cell is coupled to a ligand, e.g., a lipophilic ligand. The ligand can be attached to the oligonucleotide agent through a monomer, e.g., a chemically modified monomer that is integrated into the oligonucleotide agent. In a preferred embodiment, the coupling is by a tether or a linker (or both) as described herein, and the complex has the formula represented by:

Ligand-[linker]$_{optional}$-[tether]$_{optional}$-oligonucleotide agent

While, in most cases, embodiments are described with respect to an oligonucleotide agent including a number of nucleotides, the invention includes monomeric subunits having the structure:

Ligand-[linker]$_{optional}$-[tether]$_{optional}$-monomer

Methods of making and incorporating the monomers into the oligonucleotide agents and methods of using of those agents are included in the invention.

In preferred embodiments, the sugar, e.g., the ribose sugar of one or more of the nucleotides, (e.g., ribonucleotide, deoxynucleotide, or modified nucleotide) subunits of an oligonucleotide agent can be replaced with another moiety, e.g., a non-carbohydrate (preferably cyclic) carrier. A nucleotide subunit in which the sugar of the subunit has been so replaced is referred to herein as a sugar replacement modification subunit (SRMS). This is often referred to herein as a "tether." A cyclic carrier may be a carbocyclic ring system, i.e., all ring atoms are carbon atoms or a heterocyclic ring system, i.e., one or more ring atoms may be a heteroatom, e.g., nitrogen, oxygen, or sulfur. The cyclic carrier may be a monocyclic ring system, or may contain two or more rings, e.g. fused rings. The cyclic carrier may be a fully saturated ring system, or it may contain one or more double bonds.

The carriers further include (i) at least two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" as used herein refers to a constituent ring atom of the cyclic carrier, e.g., a carbon atom or a heteroatom (distinct from an atom which provides a backbone attachment point), that connects a selected moiety. The moiety can be, e.g., a ligand, e.g., a targeting or delivery moiety, or a moiety which alters a physical property. One of the most preferred moieties is a moiety which promotes entry into a cell, e.g., a lipophilic moiety, e.g., cholesterol. While not wishing to be bound by theory it is believed the attachment of a lipophilic agent increases the lipophilicity of an oligonucleotide agent. Optionally, the selected moiety is connected by an intervening tether to the cyclic carrier. Thus, it will often include a functional group, e.g., an amino group, or generally, provide a bond, that is suitable for incorporation or tethering of another chemical entity, e.g., a ligand to the constituent ring.

Incorporation of one or more SRMSs described herein into an oligonucleotide agent, particularly when tethered to an appropriate entity, can confer one or more new properties to the oligonucleotide agent and/or alter, enhance or modulate one or more existing properties in the oligonucleotide agent. E.g., it can alter one or more of lipophilicity or nuclease resistance. Incorporation of one or more SRMSs described herein into an oligonucleotide agent can, particularly when the SRMS is tethered to an appropriate entity, modulate, e.g., increase, binding affinity of an oligonucleotide agent to a target RNA, e.g., a pre-mRNA, mRNA, or miRNA of the subject or a pathogen of the subject. Incorporation of one or more SRMSs can alter distribution, target the oligonucleotide agent to a particular part of the body, modify the interaction with nucleic acid binding proteins (e.g., during RISC formation and strand separation), or increase sequence specificity, e.g, to inhibit off-site targeting.

Accordingly, in one aspect, the invention features, an oligonucleotide agent preferably comprising at least one subunit having the structure of formula (I):

wherein:
X is N(CO)R$^7$, NR$^7$ or CH$_2$;
Y is NR$^8$, O, S, CR$^9$R$^{10}$, or absent;
Z is CR$^{11}$R$^{12}$ or absent;
Each of R$^1$, R$^2$, R$^3$, R$^4$, R$^9$, and R$^{10}$ is, independently, H, OR$^a$, OR$^b$, (CH$_2$)$_n$OR$^a$, or (CH$_2$)$_n$OR$^b$, provided that at least one of R$^1$, R$^2$, R$^3$, R$^4$, R$^9$, and R$^{10}$ is OR$^a$ or OR$^b$ and that at least one of R$^1$, R$^2$, R$^3$, R$^4$, R$^9$, and R$^{10}$ is (CH$_2$)$_n$OR$^a$, or (CH$_2$)$_n$OR$^b$ (when the SRMS is terminal, one of R$^1$, R$^2$, R$^3$, R$^4$, R$^9$, and R$^{10}$ will include R$^a$ and one will include R$^b$; when the SRMSS is internal, two of R$^1$, R$^2$, R$^3$, R$^4$, R$^9$, and R$^{10}$ will each include an R$^b$); further provided that preferably OR$^a$ may only be present with (CH$_2$)$_n$OR$^b$ and (CH$_2$)$_n$OR$^a$ may only be present with OR$^b$;
Each of R$^3$, R$^6$, R$^{11}$, and R$^{12}$ is, independently, H, C$_1$-C$_6$ alkyl optionally substituted with 1-3 R$^{13}$, or C(O)NHR$^7$; or R$^5$ and R$^{11}$ together are C$_3$-C$_8$ cycloalkyl optionally substituted with R$^{14}$;
R$^7$ can be a ligand, e.g., R$^7$ can be R$^d$, or R$^7$ can be a ligand tethered indirectly to the carrier, e.g., through a tethering moiety, e.g., C$_1$-C$_{20}$ alkyl substituted with NR$^c$R$^d$; or C$_1$-C$_{20}$ alkyl substituted with NHC(O)R$^d$;
R$^8$ is C$_1$-C$_6$ alkyl;
R$^{13}$ is hydroxy, C$_1$-C$_4$ alkoxy, or halo;
R$^{14}$ is NR$^c$R$^7$;

$R^a$ is:

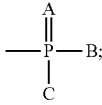

$R^b$ is:

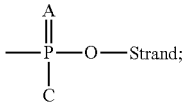

Each of A and C is, independently, O or S;
B is OH, O⁻, or

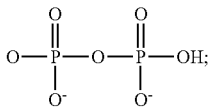

$R^c$ is H or $C_1$-$C_6$ alkyl;
$R^d$ is H or a ligand, e.g., a lipophilic ligand, e.g., cholesterol; and
n is 1-4.

Embodiments can include one or more of the following features:

$R^1$ can be $CH_2OR^a$ and $R^3$ can be $OR^b$; or $R^1$ can be $CH_2OR^a$ and $R^9$ can be $OR^b$; or $R^1$ can be $CH_2OR^a$ and $R^2$ can be $OR^b$.

$R^1$ can be $CH_2OR^b$ and $R^3$ can be $OR^b$; or $R^1$ can be $CH_2OR^b$ and $R^9$ can be $OR^b$; or $R^1$ can be $CH_2OR^b$ and $R^2$ can be $OR^b$; or $R^1$ can be $CH_2OR^b$ and $R^3$ can be $OR^a$; or $R^1$ can be $CH_2OR^b$ and $R^9$ can be $OR^a$; or $R^1$ can be $CH_2OR^b$ and $R^2$ can be $OR^a$.

$R^1$ can be $OR^a$ and $R^3$ can be $CH_2OR^b$; or $R^1$ can be $OR^a$ and $R^9$ can be $CH_2OR^b$; or $R^1$ can be $OR^a$ and $R^2$ can be $CH_2OR^b$.

$R^1$ can be $OR^b$ and $R^3$ can be $CH_2OR^b$; or $R^1$ can be $OR^b$ and $R^9$ can be $CH_2OR^b$; or $R^1$ can be $OR^b$ and $R^2$ can be $CH_2OR^b$; or $R^1$ can be $OR^b$ and $R^3$ can be $CH_2OR^a$; or $R^1$ can be $OR^b$ and $R^9$ can be $CH_2OR^a$; or $R^1$ can be $OR^b$ and $R^2$ can be $CH_2OR^a$.

$R^3$ can be $CH_2OR^a$ and $R^9$ can be $OR^b$; or $R^3$ can be $CH_2OR^a$ and $R^4$ can be $OR^b$.

$R^3$ can be $CH_2OR^b$ and $R^9$ can be $OR^b$; or $R^3$ can be $CH_2OR^b$ and $R^4$ can be $OR^b$; or $R^3$ can be $CH_2OR^b$ and $R^9$ can be $OR^a$; or $R^3$ can be $CH_2OR^b$ and $R^4$ can be $OR^a$.

$R^3$ can be $OR^b$ and $R^9$ can be $CH_2OR^a$; or $R^3$ can be $OR^b$ and $R^4$ can be $CH_2OR^a$; or $R^3$ can be $OR^b$ and $R^9$ can be $CH_2OR^b$; or $R^3$ can be $OR^b$ and $R^4$ can be $CH_2OR^b$.

$R^3$ can be $OR^a$ and $R^9$ can be $CH_2OR^b$; or $R^3$ can be $OR^b$ and $R^4$ can be $CH_2OR^b$.

$R^9$ can be $CH_2OR^a$ and $R^{10}$ can be $OR^b$.

$R^9$ can be $CH_2OR^b$ and $R^{10}$ can be $OR^b$; or $R^9$ can be $CH_2OR^b$ and $R^{10}$ can be $OR^a$.

In a preferred embodiment the ribose is replaced with a pyrroline scaffold or with a 4-hydroxyproline-derived scaffold, and X is $N(CO)R^7$ or $NR^7$, Y is $CR^9R^{10}$, and Z is absent.

$R^1$ and $R^3$ can be cis or $R^1$ and $R^3$ can be trans.

n can be 1.
A can be O or S.
$R^1$ can be $(CH_2)_nOR^b$ and $R^3$ can be $OR^b$; or $R^1$ can be $(CH_2)_nOR^a$ and $R^3$ can be $OR^b$.

$R^7$ can be $(CH_2)_5NHR^d$ or $(CH_2)_5NHR^d$. $R^d$ can be selected from a folic acid radical; a cholesterol radical; a carbohydrate radical; a vitamin A radical; a vitamin E radical; a vitamin K radical. Preferably, $R^d$ is a cholesterol radical.

$R^1$ can be $OR^b$ and $R^3$ can be $(CH_2)_nOR^b$; or $R^1$ can be $OR^b$ and $R^3$ can be $(CH_2)_nOR^a$; or $R^1$ can be $OR^a$ and $R^3$ can be $(CH_2)_nOR^b$; or $R^1$ can be $(CH_2)_nOR^b$ and $R^9$ can be $OR^a$.

$R^1$ and $R^9$ can be cis or $R^1$ and $R^9$ can be trans.

$R^1$ can be $OR^a$ and $R^9$ can be $(CH_2)_nOR^b$; or $R^1$ can be $(CH_2)_nOR^b$ and $R^9$ can be $OR^b$; or $R^1$ can be $(CH_2)_nOR^a$ and $R^9$ can be $OR^b$; or $R^1$ can be $OR^b$ and $R^9$ can be $(CH_2)_nOR^b$; or $R^1$ can be $OR^b$ and $R^9$ can be $(CH_2)_nOR^a$.

$R^3$ can be $(CH_2)_nOR^b$ and $R^9$ can be $OR^a$; or $R^3$ can be $(CH_2)_nOR^b$ and $R^9$ can be $OR^b$; or $R^3$ can be $(CH_2)_nOR^a$ and $R^9$ can be $OR^b$; or $R^3$ can be $OR^a$ and $R^9$ can be $(CH_2)_nOR^b$; $R^3$ can be $OR^b$ and $R^9$ can be $(CH_2)_nOR^b$; or $R^3$ can be $OR^b$ and $R^9$ can be $(CH_2)_nOR^a$.

$R^3$ and $R^9$ can be cis or $R^3$ and $R^9$ can be trans.

In other preferred embodiments the ribose is replaced with a piperidine scaffold, and X is $N(CO)R^7$ or $NR^7$, Y is $CR^9R^{10}$, and Z is $CR^{11}R^{12}$.

$R^9$ can be $(CH_2)_nOR^b$ and $R^{10}$ can be $OR^a$.

n can be 1 or 2.

$R^9$ can be $(CH_2)_nOR^b$ and $R^{10}$ can be $OR^b$; or $R^9$ can be $(CH_2)_nOR^a$ and $R^{10}$ can be $OR^b$.

A can be O or S.

$R^7$ can be $(CH_2)_5NHR^d$ or $(CH_2)_5NHR^d$. $R^d$ can be selected from a folic acid radical; a cholesterol radical; a carbohydrate radical; a vitamin A radical; a vitamin E radical; a vitamin K radical. Preferably, $R^d$ is a cholesterol radical.

$R^3$ can be $(CH_2)_nOR^b$ and $R^4$ can be $OR^a$; or $R^3$ can be $(CH_2)_nOR^b$ and $R^4$ can be $OR^b$; or
$R^3$ can be $(CH_2)_nOR^a$ and $R^4$ can be $OR^b$.

$R^1$ can be $(CH_2)_nOR^b$ and $R^2$ can be $OR^a$; or $R^1$ can be $(CH_2)_nOR^b$ and $R^2$ can be $OR^b$; or $R^1$ can be $(CH_2)_nOR^a$ and $R^2$ can be $OR^b$.

$R^3$ can be $(CH_2)_nOR^b$ and $R^9$ can be $OR^a$.

$R^3$ and $R^9$ can be cis, or $R^3$ and $R^9$ can be trans.

$R^3$ can be $(CH_2)_nOR^b$ and $R^9$ can be $OR^b$; or $R^3$ can be $(CH_2)_nOR^b$ and $R^9$ can be $OR^a$; or $R^3$ can be $(CH_2)_nOR^a$ and $R^9$ can be $OR^b$.

$R^1$ can be $(CH_2)_nOR^b$ and $R^3$ can be $OR^a$.

$R^1$ and $R^3$ can be cis, or $R^1$ and $R^3$ can be trans.

$R^3$ can be $OR^a$ and $R^9$ can be $(CH_2)_nOR^b$.

$R^1$ can be $OR^a$ and $R^3$ can be $(CH_2)_nOR^b$.

In other preferred embodiments the ribose is replaced with a piperazine scaffold, and X is $N(CO)R^7$ or $NR^7$, Y is $NR^8$, and Z is $CR^{11}R^{12}$.

$R^1$ can be $(CH_2)_nOR^b$ and $R^3$ can be $OR^a$.

$R^1$ and $R^3$ can be cis or $R^1$ and $R^3$ can be trans.

n can be 1.

$R^1$ can be $(CH_2)_nOR^b$ and $R^3$ can be $OR^b$; or $R^1$ can be $(CH_2)_nOR^a$ and $R^3$ can be $OR^b$.

A can be O or S, preferably S.

$R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.

$R^8$ can be $CH_3$.

$R^1$ can be $OR^a$ and $R^3$ can be $(CH_2)_nOR^b$.

In other preferred embodiments the ribose is replaced with a morpholino scaffold, and X is N(CO)R$^7$ or NR$^7$, Y is O, and Z is CR$^{11}$R$^{12}$.

R$^1$ can be (CH$_2$)$_n$OR$^b$ and R$^3$ can be OR$^a$.

R$^1$ and R$^3$ can be cis, or R$^1$ and R$^3$ can be trans.

n can be 1.

R$^1$ can be (CH$_2$)$_n$OR$^b$ and R$^3$ can be OR$^b$; of R$^1$ can be (CH$_2$)$_n$OR$^a$ and R$^3$ can be OR$^b$.

A can be O or S.

R$^7$ can be (CH$_2$)$_5$NHR$^d$ or (CH$_2$)$_5$NHR$^d$. R$^d$ can be chosen from the group of a folic acid radical; a cholesterol radical; a carbohydrate radical; a vitamin A radical; a vitamin E radical; a vitamin K radical. Preferably, R$^d$ is a cholesterol radical.

R$^8$ can be CH$_3$.

R$^1$ can be OR$^a$ and R$^3$ can be (CH$_2$)$_n$OR$^b$.

In other preferred embodiments the ribose is replaced with a decalin scaffold, and X is CH$_2$; Y is CR$^9$R$^{10}$; and Z is CR$^{11}$R$^{12}$; and R$^5$ and R$^{11}$ together are C$^6$ cycloalkyl.

R$^6$ can be C(O)NHR$^7$.

R$^{12}$ can be hydrogen.

R$^6$ and R$^{12}$ can be trans.

R$^3$ can be OR$^a$ and R$^9$ can be (CH$_2$)$_n$OR$^b$.

R$^3$ and R$^9$ can be cis, or R$^3$ and R$^9$ can be trans.

n can be 1 or 2.

R$^3$ can be OR$^b$ and R$^9$ can be (CH$_2$)$_n$OR$^b$; or R$^3$ can be OR$^b$ and R$^9$ can be (CH$_2$)$_n$OR$^a$.

A can be O or S.

R$^7$ can be (CH$_2$)$_5$NHR$^d$ or (CH$_2$)$_5$NHR$^d$. R$^d$ can be chosen from the group of a folic acid radical; a cholesterol radical; a carbohydrate radical; a vitamin A radical; a vitamin E radical; a vitamin K radical. Preferably, R$^d$ is a cholesterol radical.

In other preferred embodiments the ribose is replaced with a decalin/indane scaffold, e.g., X is CH$_2$; Y is CR$^9$R$^{10}$; and Z is CR$^{11}$R$^{12}$; and R$^5$ and R$^{11}$ together are C$^5$ cycloalkyl.

R$^6$ can be CH$_3$.

R$^{12}$ can be hydrogen.

R$^6$ and R$^{12}$ can be trans.

R$^3$ can be OR$^a$ and R$^9$ can be (CH$_2$)$_n$OR$^b$.

R$^3$ and R$^9$ can be cis, or R$^3$ and R$^9$ can be trans.

n can be 1 or 2.

R$^3$ can be OR$^b$ and R$^9$ can be (CH$_2$)$_n$OR$^a$; or R$^3$ can be OR$^b$ and R$^9$ can be (CH$_2$)$_n$OR$^a$.

A can be O or S.

R$^{14}$ can be N(CH3)R$^7$. R$^7$ can be (CH$_2$)$_5$NHR$^d$ or (CH$_2$)$_5$NHR$^d$. R$^d$ can be chosen from the group of a folic acid radical; a cholesterol radical; a carbohydrate radical; a vitamin A radical; a vitamin E radical; a vitamin K radical. Preferably, R$^d$ is a cholesterol radical.

In another aspect, this invention features an oligonucleotide agent comprising at least one subunit having a structure of formula (II):

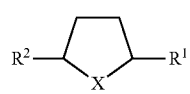

(II)

X is N(CO)R$^7$ or NR$^7$;

Each of R$^1$ and R$^2$ is, independently, OR$^a$, OR$^b$, (CH$_2$)$_n$OR$^a$, or (CH$_2$)$_n$OR$^a$, provided that one of R$^1$ and R$^2$ is OR$^a$ or OR$^b$ and the other is (CH$_2$)$_n$OR$^a$ or (CH$_2$)$_n$OR$^a$ (when the SRMS is terminal, one of R$^1$ or R$^2$ will include R$^a$ and one will include R$^b$; when the SRMSS is internal, both R$^1$ and R$^2$ will each include an R$^b$); further provided that preferably OR$^a$ may only be present with (CH$_2$)$_n$OR$^b$ and (CH$_2$)$_n$OR$^a$ may only be present with OR$^b$;

R$^7$ is C$_1$-C$_{20}$ alkyl substituted with NR$^c$R$^d$;

R$^8$ is C$_1$-C$_6$ alkyl;

R$^{13}$ is hydroxy, C$_1$-C$_4$ alkoxy, or halo;

R$^{14}$ is NR$^c$R$^7$;

R$^a$ is:

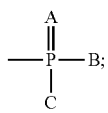

R$^b$ is

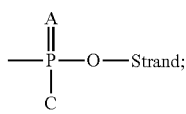

Each of A and C is, independently, O or S;

B is OH, O$^-$, or

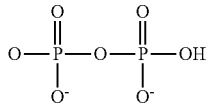

R$^c$ is H or C$_1$-C$_6$ alkyl;

R$^d$ is H or a ligand; and n is 1-4.

The oligonucleotide agent of the conjugate is substantially single-stranded and comprises from about 12 to about 29 subunits, preferably about 15 to about 25 subunits. An oligonucleotide agent that is substantially single-stranded includes at least 60%, 70%, 80%, or 90% or more nucleotides that are not duplexed.

Embodiments can include one or more of the features described above.

In a further aspect, this invention features an oligonucleotide agent having at least one subunit comprising formula (I) or formula (II).

In one aspect, this invention features an oligonucleotide agent having at least two subunits comprising formula (I) and/or formula (II).

In another aspect, this invention provides a method of making an oligonucleotide agent described herein having at least one subunit comprising formula (I) and/or (II). In a further aspect, this invention provides a method of modulating expression of a target gene. The method includes administering an oligonucleotide agent described herein having at least one subunit comprising formula (I) and/or (II) to a subject.

In one aspect, this invention features a pharmaceutical composition having an oligonucleotide agent described herein having at least one subunit comprising formula (I) and/or (II) and a pharmaceutically acceptable carrier.

SRMSs or tethers described herein may be incorporated into any oligonucleotide agent described herein. An oligonucleotide agent may include one or More of the SRMSs described herein. An SRMS can be introduced at one or more points in an oligonucleotide agent. An SRMS can be placed at or near (within 1, 2, or 3 positions) the 3' or 5' end of the oligonucleotide. In some embodiments, it is preferred to not have an SRMS at or near (within 1, 2, or 3 positions of) the 5' end of the oligonucleotide. An SRMS can be internal, and will preferably be positioned in regions not critical for binding to the target.

In an embodiment, an oligonucleotide agent may have an SRMS at (or within 1, 2, or 3 positions of) the 3' end.

In another embodiment, an oligonucleotide agent may have an SRMS at an internal position. In other embodiments, an oligonucleotide agent may have an SRMS at the 3' end and an SRMS at an internal position.

Other modifications to sugars, bases, or backbones described herein can be incorporated into the oligonucleotide agents.

The oligonucleotide agents can take an architecture or structure described herein.

The oligonucleotide agent can be selected to target any of a broad spectrum of genes, including any of the genes described herein.

In a preferred embodiment the oligonucleotide agent has an architecture (architecture refers to one or more of the overall length) described herein. In addition to the SRMS-containing bases of the oligonucleotide agents described herein can include nuclease resistant monomers (NRMs).

In another aspect, the invention features an oligonucleotide agent to which is conjugated a lipophilic moiety, e.g., cholesterol, e.g., by conjugation to an SRMS of an oligonucleotide agent. In a preferred embodiment, the lipophilic moiety enhances entry of the oligonucleotide agent into a cell. In a preferred embodiment, the cell is part of an organism, tissue, or cell line, e.g., a primary cell line, immortalized cell line, or any type of cell line disclosed herein. Thus, the conjugated oligonucleotide agent can be used to inhibit expression of a target gene in an organism, e.g., a mammal, e.g., a human, or to inhibit expression of a target gene in a cell line or in cells which are outside an organism.

The lipophilic moiety can be chosen, for example, from the group consisting of a lipid, cholesterol, oleyl, retinyl, cholesteryl residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. A preferred lipophilic moiety is cholesterol.

The oligonucleotide agent can have at least one subunit having formula (I) or formula (II) incorporated into it. The oligonucleotide agent can have one or more of any of the features described herein. For example, when the subunit is of formula (I), $R^d$ can be cholesterol; X can be N(CO)$R^7$ or N$R^7$, Y can be CR$^9$R$^{10}$, and Z can be absent, and R$^1$ can be (CH$_2$)$_n$OR$^a$ and R$^3$ can be OR$^a$; X can be N(CO)R$^7$ or NR$^7$, Y can be CR$^9$R$^{10}$, and Z can be CR$^{11}$R$^{12}$, and R$^9$ can be (CH$_2$)$_n$OR$^a$ and R$^{10}$ can be OR$^a$; X can be N(CO)R$^7$ or NR$^7$, Y can be NR$^8$, and Z can be CR$^{11}$R$^{12}$, and R$^1$ can be (CH$_2$)$_n$OR$^a$ and R$^3$ can be OR$^a$; X can be CH$_2$; Y can be CR$^9$R$^{10}$; and Z can be CR$^{11}$R$^{12}$, in which R$^6$ can be C(O)NHR$^7$; or X can be CH$_2$; Y can be CR$^9$R$^{10}$; and Z can be CR$^{11}$R$^{12}$, in which R$^{11}$ or R$^{12}$ can be C(O) NHR$^7$ or R$^5$ and R$^{11}$ together can be C$_5$ or C$_6$ cycloalkyl substituted with N(CH3)R$^7$.

Tethered Ligands

A wide variety of entities can be tethered to an oligonucleotide agent, e.g., to the carrier of a ligand-conjugated monomer. Examples are described below in the context of a ligand-conjugated monomer but that is only one preferred embodiment. Entities can be coupled at other points to an oligonucleotide agent.

A ligand tethered to an oligonucleotide agent (e.g., an oligonucleotide agent targeting an miRNA) can have a favorable effect on the agent. For example, the ligand can improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting.

A tethered ligand can include one or more modified bases or sugars that can function as intercalators. These are preferably located in an internal region, such as in a bulge of a miRNA/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand.

In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a miRNA to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage.

A tethered ligand can be an aminoglycoside ligand, which can cause an oligonucleotide agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-S-acridine has an increased affinity for the HIV Rev-response element (RRE). In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent, e.g., an oligonucleotide agent targeting an miRNA or pre-miRNA.

A tethered ligand can be a poly-arginine peptide, peptoid or peptidomimetic, which can enhance the cellular uptake of an oligonucleotide agent.

Preferred moieties are ligands, which are coupled, preferably covalently, either directly or indirectly via an intervening tether, to the ligand-conjugated carrier. In preferred embodiments, the ligand is attached to the carrier via an intervening tether. As discussed above, the ligand or tethered ligand may be present on the monomer when the monomer is incorporated into the growing strand. In some embodiments, the ligand may be incorporated into a "precursor" a ligand-conjugated monomer subunit after a "precursor" a ligand-conjugated monomer has been incorporated into the growing strand. For example, a monomer having, e.g., an amino-terminated tether, e.g., TAP-(CH$_2$)$_n$NH$_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer subunit by coupling the electrophilic group of the ligand with the terminal nucleophilic group of the precursor monomer subunit tether.

In preferred embodiments, a ligand alters the distribution, targeting or lifetime of an oligonucleotide agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Peptides that target markers enriched in proliferating cells can be used. E.g., RGD containing peptides and peptidomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogeneis. Preferred conjugates of this type include an oligonucleotide agent that targets PECAM-1, VEGF, or other cancer gene, e.g., a cancer gene described herein.

The oligonucleotide agents of the invention are particularly useful when targeted to the liver. For example, a single stranded oligonucleotide agent featured in the invention can target an miRNA enriched in the liver, and the oligonucleotide agent can include a ligand for enhanced delivery to the liver. An oligonucleotide agent can be targeted to the liver by incorporation of a monomer derivatized with a ligand which targets to the liver. For example, a liver-targeting agent can be a lipophilic moiety. Preferred lipophilic moieties include lipid, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

An oligonucleotide agent can also be targeted to the liver by association with a low-density lipoprotein (LDL), such as lactosylated LDL. Polymeric carriers complexed with sugar residues can also function to target oligonucleotide agents to the liver.

A targeting agent that incorporates a sugar, e.g., galactose and/or analogues thereof, is particularly useful. These agents target, in particular, the parenchymal cells of the liver. For example, a targeting moiety can include more than one or preferably two or three galactose moieties, spaced about 15 angstroms from each other. The targeting moiety can alternatively be lactose (e.g., three lactose moieties), which is a glucose coupled to a galactose. The targeting moiety can also be N-Acetyl-Galactosamine, N—Ac-Glucosamine. A mannose or mannose-6-phosphate targeting moiety can be used for macrophage targeting.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long (see Table 3, for example).

TABLE 3

Exemplary Cell Permeation Peptides

| Cell Permeation Peptide | Amino acid Sequence | Reference |
|---|---|---|
| Penetratin | RQIKIWFQNRRMKWKK (SEQ ID NO: 31) | Derossi et al., J. Biol. Chem. 269: 10444, 1994 |
| Tat fragment (48-60) | GRKKRRQRRRPPQC (SEQ ID NO: 32) | Vives et al., J. Biol. Chem., 272: 16010, 1997 |
| Signal Sequence-based peptide | GALFLGWLGAAGSTMGAWSQPKKKRKV (SEQ ID NO: 33) | Chaloin et al., Biochem. Biophys. Res. Commun., 243: 601, 1998 |

TABLE 3-continued

Exemplary Cell Permeation Peptides

| Cell Permeation Peptide | Amino acid Sequence | Reference |
|---|---|---|
| PVEC | LLIILRRRIRKQAHAHSK (SEQ ID NO: 34) | Elmquist et al., Exp. Cell Res., 269: 237, 2001 |
| Transportan | GWTLNSAGYLLKINLKALAALAKKIL (SEQ ID NO: 35) | Pooga et al., FASEB J., 12: 67, 1998 |
| Amphiphilic model peptide | KLALKLALKALKAALKLA (SEQ ID NO: 36) | Oehlke et al., Mol. Ther., 2: 339, 2000 |
| Arg$_9$ | RRRRRRRRR (SEQ ID NO: 37) | Mitchell et al., J. Pept. Res., 56: 318, 2000 |
| Bacterial cell wall permeating | KFFKFFKFFK (SEQ ID NO: 38) | |
| LL-37 | LLGDFFRKSKEKIGKEFKRIVQRIKDFLRN LVPRTES (SEQ ID NO: 39) | |
| Cecropin P1 | SWLSKTAKKLENSAKKRISEGIAIAIQGGP R (SEQ ID NO: 40) | |
| α-defensin | ACYCRIPACIAGERRYGTCIYQGRLWAFC C (SEQ ID NO: 41) | |
| b-defensin | DHYNCVSSGGQCLYSACPIFTKIQGTCYR GKAKCCK (SEQ ID NO: 42) | |
| Bactenecin | RKCRIVVIRVCR (SEQ ID NO: 43) | |
| PR-39 | RRRPRPPYLPRPRPPPFFPPRLPPRIPPGFPP RFPPRFPGKR-NH2 (SEQ ID NO: 44) | |
| Indolicidin | ILPWKWPWWPWRR-NH2 (SEQ ID NO: 45) | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:46). An RFGF analogue (e.g., amino acid sequence AALLPVLLAAP (SEQ ID NO:47) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:48) and the Drosophila Antennapedia protein (RQIKIWFQNRRMK-WKK (SEQ ID NO:49) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature 4:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

A "cell permeation peptide" is capable of permeating a cell, e.g., a-mammalian cell, such as a human cell. A cell permeation peptide can also include a nuclear localization signal (NLS). For example, a cell permeation peptide can be a bipartite amphipathic peptide, such as MPG, which is derived from the fusion peptide domain of HIV-1 gp4 and the NLS of SV40 large T antigen (Simeoni et al., Nucl. Acids Res. 31:2717-2724, 2003).

In one embodiment, a targeting peptide tethered to an SRMS can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H$_2$A peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

Methods for Making iRNA Agents iRNA agents conjugate to a lipophilic moiety for enhanced uptake into neural cells can include modified or non-naturally occurring bases, e.g., bases described herein. In addition, iRNA agents can have a modified or non-naturally occurring base and another element described herein.

The synthesis and purification of oligonucleotide peptide conjugates can be performed by established methods. See, for example, Trufert et al., Tetrahedron, 52:3005, 1996; and Manoharan, "Oligonucleotide Conjugates in Antisense Technology," in *Antisense Drug Technology*, ed. S. T. Crooke, Marcel Dekker, Inc., 2001.

In one embodiment of the invention, a peptidomimetic can be modified to create a constrained peptide that adopts a distinct and specific preferred conformation, which can increase the potency and selectivity of the peptide. For example, the constrained peptide can be an azapeptide (Gante, *Synthesis* 405-413, 1989). An azapeptide is synthesized by replacing the α-carbon of an amino acid with a nitrogen atom without changing the structure of the amino acid side chain. For example, the azapeptide can be synthesized by using hydrazine in traditional peptide synthesis coupling methods, such as by reacting hydrazine with a "carbonyl donor," e.g., phenylchloroformate.

In one embodiment of the invention, a peptide or peptidomimetic (e.g., a peptide or peptidomimetic tethered to an SRMS) can be an N-methyl peptide. N-methyl peptides are composed of N-methyl amino acids, which provide an additional methyl group in the peptide backbone, thereby potentially providing additional means of resistance to proteolytic cleavage. N-methyl peptides can by synthesized by methods known in the art (see, for example, Lindgren et al., Trends Pharmacol. Sci. 21:99, 2000; *Cell Penetrating Peptides: Processes and Applications*, Langel, ed., CRC Press, Boca Raton, Fla., 2002; Fische et al., Bioconjugate. Chem. 12: 825, 2001; Wander et al., J. Am. Chem. Soc., 124:13382, 2002). For example, an Ant or Tat peptide can be an N-methyl peptide.

In one embodiment of the invention, a peptide or peptidomimetic (e.g., a peptide or peptidomimetic tethered to an SRMS) can be a β-peptide. β-peptides form stable secondary structures such as helices, pleated sheets, turns and hairpins in solutions. Their cyclic derivatives can fold into nanotubes in the solid state. β-peptides are resistant to degradation by proteolytic enzymes. β-peptides can be synthesized by methods known in the art. For example, an Ant or Tat peptide can be a β-peptide.

In one embodiment of the invention, a peptide or peptidomimetic (e.g., a peptide or peptidomimetic tethered to an SRMS) can be an oligourea conjugate (or an oligothiourea conjugate), in which the amide bond of a peptidomimetic is replaced with a urea moiety. Replacement of the amide bond provides increased resistance to degradation by proteolytic enzymes, e.g., proteolytic enzymes in the gastrointestinal tract. In one embodiment, an oligourea conjugate is tethered to an iRNA agent for use in oral delivery. The backbone in each repeating unit of an oligourea peptidomimetic can be extended by one carbon atom in comparison with the natural amino acid. The single carbon atom extension can increase peptide stability and lipophilicity, for example. An oligourea peptide can therefore be advantageous when an iRNA agent is directed for passage through a bacterial cell wall, or when an iRNA agent must traverse the blood-brain barrier, such as for the treatment of a neurological disorder. In one embodiment, a hydrogen bonding unit is conjugated to the oligourea peptide, such as to create an increased affinity with a receptor. For example, an Ant or Tat peptide can be an oligourea conjugate (or an oligothiourea conjugate).

The dsRNA peptide conjugates of the invention can be affiliated with, e.g., tethered to, SRMSs occurring at various positions on an iRNA agent. For example, a peptide can be terminally conjugated, on either the sense or the antisense strand, or a peptide can be bisconjugated (one peptide tethered to each end, one conjugated to the sense strand, and one conjugated to the antisense strand). In another option, the peptide can be internally conjugated, such as in the loop of a short hairpin iRNA agent. In yet another option, the peptide can be affiliated with a complex, such as a peptide-carrier complex.

A number of exemplary routes of delivery are described that can be used to administer an oligonucleotide agent to a subject. In addition, the oligonucleotide agent can be formulated according to an exemplary method described herein.

An RGD peptide moiety can be used to target a tumor cell, such as an endothelial tumor cell or a breast cancer tumor cell (Zitzmann et al., Cancer Res., 2:5139-43, 2002). An RGD peptide can facilitate targeting of an oligonucleotide agent (e.g., an oligonucleotide agent targeting an miRNA or pre-miRNA) to tumors of a variety of other tissues, including the lung, kidney, spleen, or liver (Aoki et al., *Cancer Gene Therapy* 1:783-787, 2001). Preferably, the RGD peptide will facilitate targeting of an oligonucleotide agent to the kidney. The RGD peptide can be linear or cyclic, and can be modified, e.g., glycosylated or methylated to facilitate targeting to specific tissues. For example, a glycosylated RGD peptide can deliver an oligonucleotide agent to a tumor cell expressing $α_vβ_3$ (Haubner et al., *Jour. Nucl. Med.* 42:326-336, 2001).

Peptides that target markers enriched in proliferating cells can be used. E.g., RGD containing peptides and peptidomimetics can target cancer cells, in particular cells that exhibit an $I_vθ_3$ integrin. Thus, one could use RGD peptides, cyclic peptides containing RGD, RGD peptides that include D-amino acids, as well as synthetic RGD mimics. In addition to RGD, one can use other moieties that target the $I_v$-$θ_3$ integrin ligand. Generally, such ligands can be used to control proliferating cells and angiogeneis. Preferred conjugates of this type include an oligonucleotide agent that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

In one embodiment, a targeting peptide tethered to a ligand-conjugated monomer can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number of helix destabilization residues will be utilized (e.g., proline, or cyclic monomeric units). The capping residue will be considered (for example Gly is an exemplary N-capping residue) and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

In some embodiments, the peptide can have a cationic and/or a hydrophobic moiety.

In some embodiments, the ligand can be any of the nucleobases described herein.

In some embodiments, the ligand can be a substituted amine, e.g. dimethylamino. In some embodiments, the substituted amine can be quaternized, e.g., by protonation or alkylation, rendering it cationic. In some embodiments, the substituted amine can be at the terminal position of a relatively hydrophobic tether, e.g., alkylene.

In some embodiments, the ligand can be one of the following triterpenes:

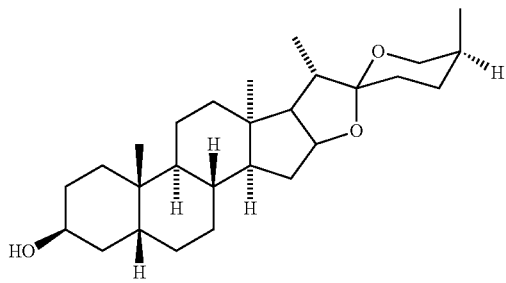

Sarsasapogenin

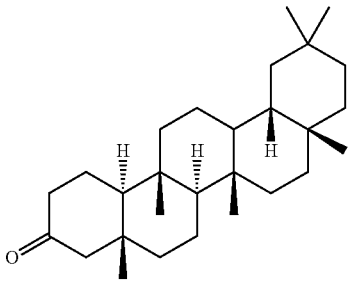

Friedelin

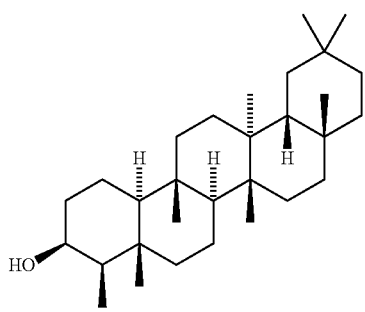

Epifriedelanol

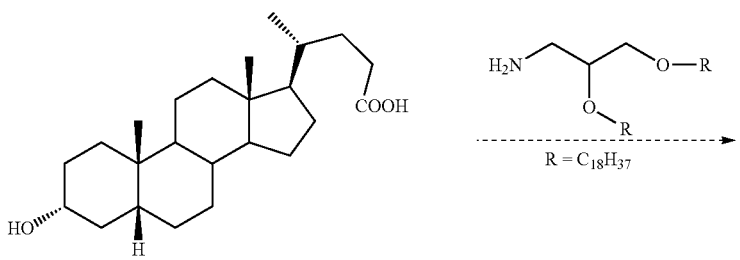

Lithocholic acid $R = C_{18}H_{37}$

-continued

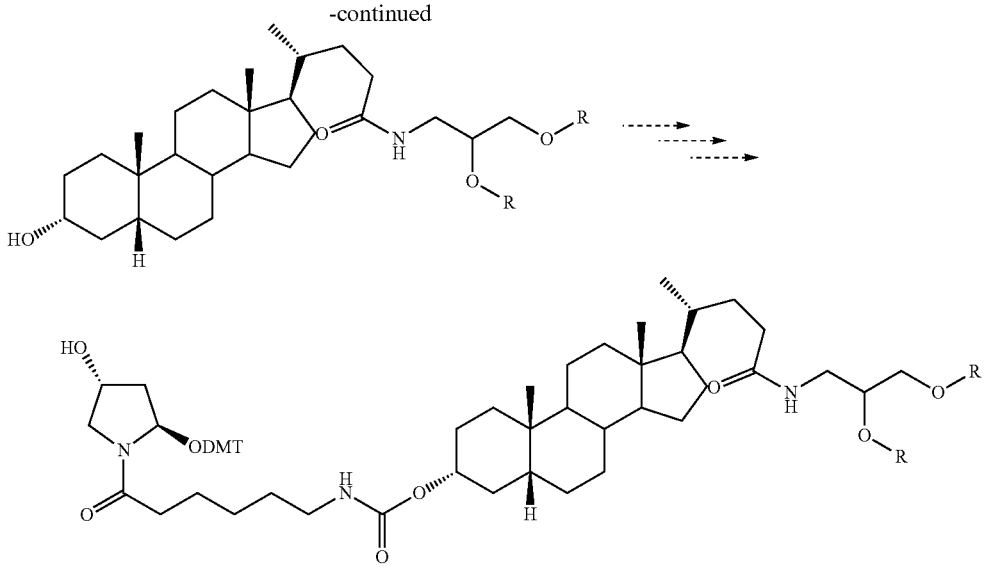

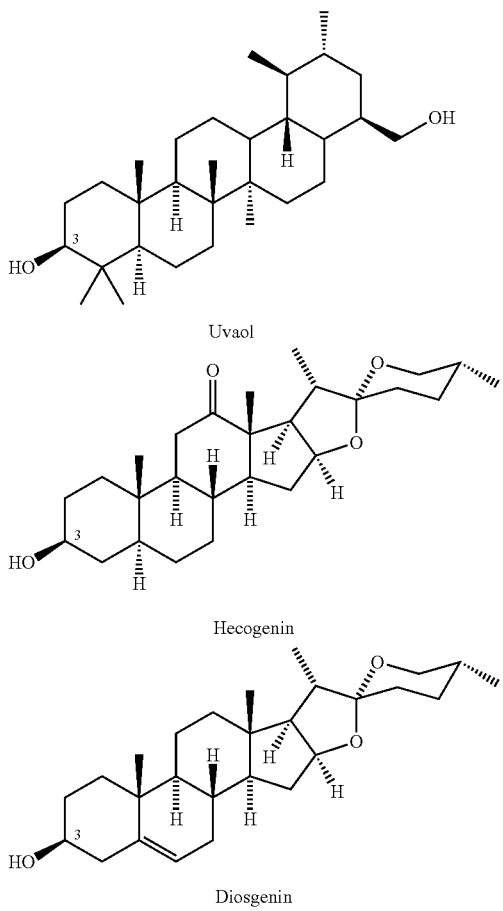

Uvaol

Hecogenin

Diosgenin

In some embodiments, the ligand can be substituted or unsubstituted cholesterol, or a stereoisomer thereof or one of the following steroids:

In some embodiments, a tethered ligand can contain one or more atoms than the corresponding untethered or uncoupled ligand (e.g., one or more protons of a heteroatom-based functional group or an entire heteroatom-based functional group may be displaced from the uncoupled ligand during coupling of a ligand to a carrier or tether). For example, the proton of the 3-hydroxy group of cholesterol can be replaced by a tether (e.g., Chol-3-OH (uncoupled) and Chol-3-O-tether (coupled)) or the entire 3-hydroxy group of cholesterol can be replaced by a sulfur atom (e.g., Chol-3-OH (uncoupled) and Chol-3-S-tether (coupled, e.g., thiocholesterol)).

Methods for Making Oligonucleotide Agents

A listing of ribonucleosides containing the unusual bases described herein are described in "The RNA Modification Database" maintained by Pamela F. Crain, Jef Rozenski and James A. McCloskey; Departments of Medicinal Chemistry and Biochemistry, University of Utah, Salt Lake City, Utah 84112, USA.

The 5' silyl protecting group can be used in conjunction with acid labile orthoesters at the 2' position of ribonucleosides to synthesize oligonucleotides via phosphoramidite chemistry. Final deprotection conditions are known not to significantly degrade RNA products. Functional groups on the unusual and universal bases are blocked during oligonucleotide synthesis with protecting groups that are compatible with the operations being performed that are described herein. All syntheses can be conducted in any automated or manual synthesizer on large, medium, or small scale. The syntheses may also be carried out in multiple well plates or glass slides.

The 5'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion source are tetrabutylammonium fluoride or aminehydrofluorides (e.g., combining aqueous HF with triethylamine in a dipolar aprotic solvent, e.g., dimethylformamide).

The choice of protecting groups for use on the phosphite triesters and phosphotriesters can alter the stability of the triesters towards fluoride. Methyl protection of the phosphotriester or phosphitetriester can stabilize the linkage against fluoride ions and improve process yields.

Since ribonucleosides have a reactive 2' hydroxyl substituent, it can be desirable to protect the reactive 2' position in RNA with a protecting group that is compatible with a 5'-O-silyl protecting group, e.g. one stable to fluoride. Orthoesters meet this criterion and can be readily removed in a final acid deprotection step that can result in minimal RNA degradation.

Tetrazole catalysts can be used in the standard phosphoramidite coupling reaction. Preferred catalysts include e.g. tetrazole, S-ethyl-tetrazole, p-nitrophenyltetrazole.

The general process is as follows. Nucleosides are suitably protected and functionalized for use in solid-phase or solution-phase synthesis of RNA oligonucleotides. The 2'-hydroxyl group in a ribonucleotide can be modified using a tris orthoester reagent. The 2'-hydroxyl can be modified to yield a 2'-O-orthoester nucleoside by reacting the ribonucleoside with the tris orthoester reagent in the presence of an acidic catalyst, e.g., pyridinium p-toluene sulfonate. This reaction is known to those skilled in the art. The product can then be subjected to further protecting group reactions (e.g., 5'-O-silylation) and functionalizations (e.g., 3'-O-phosphitylation) to produce a desired reagent (e.g., nucleoside phosphoramidite) for incorporation within an oligonucleotide or polymer by reactions known to those skilled in the art.

Preferred orthoesters include those comprising ethylene glycol ligands which are protected with acyl or ester protecting groups. Specifically, the preferred acyl group is acetyl. The nucleoside reagents may then be used by those skilled in the art to synthesize RNA oligonucleotides on commercially available synthesizer instruments, e.g., Gene Assembler Plus (Pharmacia), 380B (Applied Biosystems). Following synthesis (either solution-phase or solid-phase) of an oligonucleotide or polymer, the product can be subjected to one or more reactions using non-acidic reagents. One of these reactions may be strong basic conditions, for example, 40% methylamine in water for 10 minutes at 55° C., which will remove the acyl protecting groups from the ethylene glycol ligands but leave the orthoester moiety attached. The resultant orthoester may be left attached when the polymer or oligonucleotide is used in subsequent applications, or it may be removed in a final mildly-acidic reaction, for example, 10 minutes at 55° C. in 50 mM acetic acid, pH 3.0, followed by addition of equal volume of 150 mM TRIS buffer for 10 minutes at 55° C.

Universal bases are described in "Survey and Summary: The Applications of Universal DNA base analogues" Loakes, D., *Nucleic Acid Research* 2001, 29, 2437, which is incorporated by reference in its entirety. Specific examples are described in the following: Liu, D.; Moran, S.; Kool, E. T. *Chem. Biol.*, 1997, 4, 919-926; Morales, J. C.; Kool, E. T. *Biochemistry*, 2000, 39, 2626-2632; Matray, T, J.; Kool, E. T. *J. Am. Chem. Soc.*, 1998, 120, 6191-6192; Moran, S. Ren, R. X.-F.; Rumney I V, S.; Kool, E. T. *J. Am. Chem. Soc.*, 1997, 119, 2056-2057; Guckian, K. M.; Morales, J. C.; Kool, E. T. *J. Org. Chem.*, 1998, 63, 9652-9656; Berger, M.; Wu. Y.; Ogawa, A. K.; McMinn, D. L.; Schultz, P. G.; Romesberg, F. E. *Nucleic Acids Res.*, 2000, 28, 2911-2914; Ogawa, A. K.; Wu, Y.; McMinn, D. L.; Liu, J.; Schultz, P. G.; Romesberg, F. E. *J. Am. Chem. Soc.*, 2000, 122, 3274-3287; Ogawa, A. K.; Wu. Y.; Berger, M.; Schultz, P. G.; Romesberg, F. E. *J. Am. Chem. Soc.*, 2000, 122, 8803-8804; Tae, E. L.; Wu, Y.; Xia, G.; Schultz, P. G.; Romesberg, F. E. *J. Am. Chem. Soc.*, 2001, 123, 7439-7440; Wu, Y.; Ogawa, A. K.; Berger, M.; McMinn, D. L.; Schultz, P. G.; Romesberg, F. E. *J. Am. Chem. Soc.*, 2000, 122, 7621-7632; McMinn, D. L.; Ogawa. A. K.; Wu, Y.; Liu, J.; Schultz, P. G.; Romesberg, F. E. *J. Am. Chem. Soc.*, 1999, 121, 11585-11586; Brotschi, C.; Haberli, A.; Leumann, C, J. *Angew. Chem. Int. Ed.*, 2001, 40, 3012-3014; Weizman, H.; Tor, Y. *J. Am. Chem. Soc.*, 2001, 123, 3375-3376; Lan, T.; McLaughlin, L. W. *J. Am. Chem. Soc.*, 2000, 122, 6512-13.

As discussed above, the monomers and methods described herein can be used in the preparation of modified RNA molecules, or polymeric molecules comprising any combination of monomer compounds described herein and/or natural or modified ribonucleotides in which one or more subunits contain an unusual or universal base. Modified RNA molecules include e.g. those molecules containing a chemically or stereochemically modified nucleoside (e.g., having one or more backbone modifications, e.g., phosphorothioate or P-alkyl; having one or more sugar modifications, e.g., 2'-OCH$_3$ or 2'-F; and/or having one or more base modifications, e.g., 5-alkylamino or 5-allylamino) or a nucleoside surrogate.

Coupling of 5'-hydroxyl groups with phosphoramidites forms phosphite ester intermediates, which in turn are oxidized e.g., with iodine, to the phosphate diester. Alternatively, the phosphites may be treated with, e.g., sulfur, selenium, amino, and boron reagents to form modified phosphate backbones. Linkages between the monomers described herein and a nucleoside or oligonucleotide chain can also be treated with iodine, sulfur, selenium, amino, and boron reagents to form unmodified and modified phosphate backbones respectively. Similarly, the monomers described herein may be coupled with nucleosides or oligonucleotides containing any of the modifications or nucleoside surrogates described herein.

The synthesis and purification of oligonucleotide peptide conjugates can be performed by established methods. See, for example, Trufert et al., Tetrahedron, 52:3005, 1996; and Manoharan, "Oligonucleotide Conjugates in Antisense Technology," in *Antisense Drug Technology*, ed. S. T. Crooke, Marcel Dekker, Inc., 2001.

In one embodiment of the invention, a peptidomimetic can be modified to create a constrained peptide that adopts a distinct and specific preferred conformation, which can increase the potency and selectivity of the peptide. For example, the constrained peptide can be an azapeptide (Gante, *Synthesis*, 1989, 405-413). An azapeptide is synthesized by replacing the α-carbon of an amino acid with a nitrogen atom without changing the structure of the amino acid side chain. For example, the azapeptide can be synthesized by using hydrazine in traditional peptide synthesis coupling methods, such as by reacting hydrazine with a "carbonyl donor," e.g., phenylchloroformate.

In one embodiment of the invention, a peptide or peptidomimetic (e.g., a peptide or peptidomimetic tethered to an ligand-conjugated monomer) can be an N-methyl peptide. N-methyl peptides are composed of N-methyl amino acids, which provide an additional methyl group in the peptide backbone, thereby potentially providing additional means of resistance to proteolytic cleavage. N-methyl peptides can by synthesized by methods known in the art (see, for example, Lindgren et al., Trends Pharmacol. Sci. 21:99, 2000; *Cell Penetrating Peptides: Processes and Applications* Langel, ed., CRC Press, Boca Raton, Fla., 2002; Fische et al., Bioconjugate. Chem. 12: 825, 2001; Wander et al., J. Am. Chem. Soc., 124:13382, 2002). For example, an Ant or Tat peptide can be an N-methyl peptide.

In one embodiment of the invention, a peptide or peptidomimetic (e.g., a peptide or peptidomimetic tethered to a ligand-conjugated monomer) can be a β-peptide. β-peptides form stable secondary structures such as helices, pleated sheets, turns and hairpins in solutions. Their cyclic derivatives can fold into nanotubes in the solid state. β-peptides are resistant to degradation by proteolytic enzymes. β-peptides can be synthesized by methods known in the art. For example, an Ant or Tat peptide can be a β-peptide.

In one embodiment of the invention, a peptide or peptidomimetic (e.g., a peptide or peptidomimetic tethered to a ligand-conjugated monomer) can be a oligocarbamate. Oligocarbamate peptides are internalized into a cell by a transport pathway facilitated by carbamate transporters. For example, an Ant or Tat peptide can be an oligocarbamate.

In one embodiment of the invention, a peptide or peptidomimetic (e.g., a peptide or peptidomimetic tethered to a ligand-conjugated monomer) can be an oligourea conjugate (or an oligothiourea conjugate), in which the amide bond of a peptidomimetic is replaced with a urea moiety. Replacement of the amide bond provides increased resistance to degradation by proteolytic enzymes, e.g., proteolytic enzymes in the gastrointestinal tract. In one embodiment, an oligourea conjugate is tethered to an oligonucleotide agent for use in oral delivery. The backbone in each repeating unit of an oligourea peptidomimetic can be extended by one carbon atom in comparison with the natural amino acid. The single carbon atom extension can increase peptide stability and lipophilicity, for example. An oligourea peptide can therefore be advantageous when an oligonucleotide agent is directed for passage through a bacterial cell wall, or when an oligonucleotide agent must traverse the blood-brain barrier, such as for the treatment of a neurological disorder. In one embodiment, a hydrogen bonding unit is conjugated to the oligourea peptide, such as to create an increased affinity with a receptor. For example, an Ant or Tat peptide can be an oligourea conjugate (or an oligothiourea conjugate).

The siRNA peptide conjugates of the invention can be affiliated with, e.g., tethered to, ligand-conjugated monomers occurring at various positions on an oligonucleotide agent. For example, a peptide can be terminally conjugated, on either the sense or the antisense strand, or a peptide can be bisconjugated (one peptide tethered to each end, one conjugated to the sense strand, and one conjugated to the antisense strand). In another option, the peptide can be internally conjugated, such as in the loop of a short hairpin oligonucleotide agent. In yet another option, the peptide can be affiliated with a complex, such as a peptide-carrier complex.

A peptide-carrier complex consists of at least a carrier molecule, which can encapsulate one or more oligonucleotide agents (such as for delivery to a biological system and/or a cell), and a peptide moiety tethered to the outside of the carrier molecule, such as for targeting the carrier complex to a particular tissue or cell type. A carrier complex can carry additional targeting molecules on the exterior of the complex, or fusogenic agents to aid in cell delivery. The one or more oligonucleotide agents encapsulated within the carrier can be conjugated to lipophilic molecules, which can aid in the delivery of the agents to the interior of the carrier.

A carrier molecule or structure can be, for example, a micelle, a liposome (e.g., a cationic so liposome), a nanoparticle, a microsphere, or a biodegradable polymer. A peptide moiety can be tethered to the carrier molecule by a variety of linkages, such as a disulfide linkage, an acid labile linkage, a peptide-based linkage, an oxyamino linkage or a hydrazine linkage. For example, a peptide-based linkage can be a GFLG peptide. Certain linkages will have particular advantages, and the advantages (or disadvantages) can be considered depending on the tissue target or intended use. For example, peptide based linkages are stable in the blood stream but are susceptible to enzymatic cleavage in the lysosomes.

The protected monomer compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The protected monomer compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds described herein can also contain linkages (e.g., carbon-carbon bonds, carbon-nitrogen bonds, e.g., amides) or substituents that can restrict bond rotation, e.g. restriction resulting from the presence of a ring or double bond. Accordingly, all cis/trans, E/Z isomers, and rotational isomers (rotamers) are expressly included herein. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Representative ligand-conjugated monomers and typical syntheses for preparing ligand-conjugated monomers and related compounds described herein are provided below. As discussed elsewhere, protecting groups for ligand-conjugated monomer hydroxyl groups, e.g., OFG$^1$, include but are not limited to the dimethoxytrityl group (DMT). For example, it can be desirable in some embodiments to use silicon-based protecting groups as a protecting group for OFG$^1$. Silicon-based protecting groups can therefore be used in conjunction with or in place of the DMT group as necessary or desired. Thus, the ligand-conjugated monomers and syntheses delineated below, which feature the DMT protecting group as a protecting group for OFG$^1$, is not to be construed as limiting in any way to the invention.
Synthesis of Pyrroline Carrier
Scheme 1. Synthesis of cis-(-(3S,4R)-pyrrolidine diol
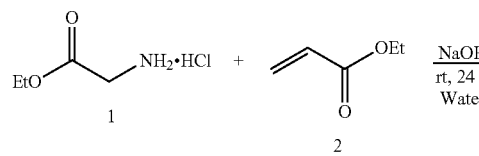
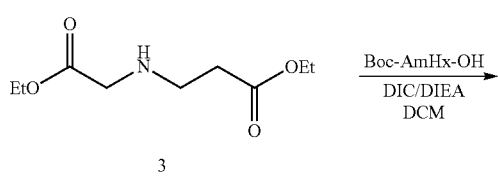
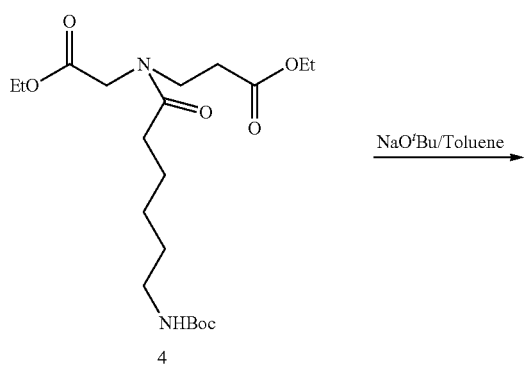
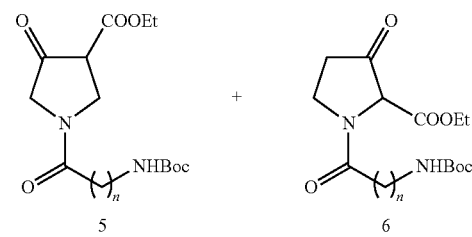
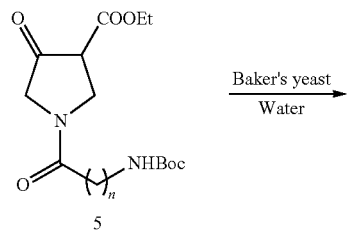
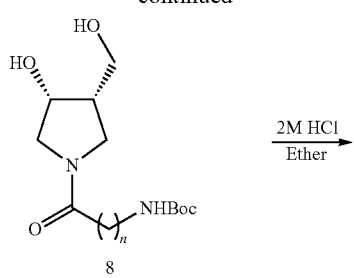
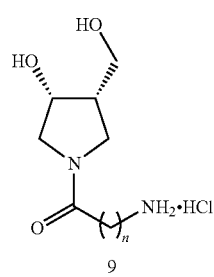
Scheme 2. Synthesis of cis-(-(2R, 3S)-pyrrolidine diol
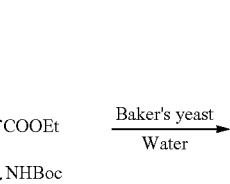
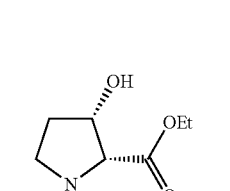
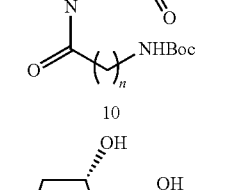
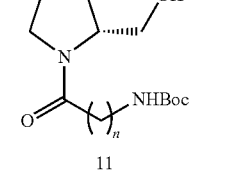

71
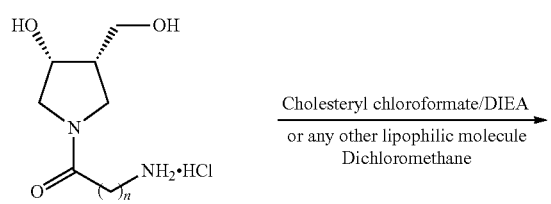
9
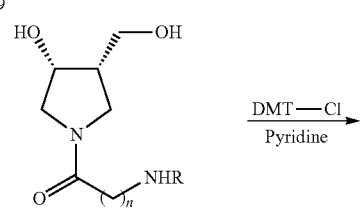
13
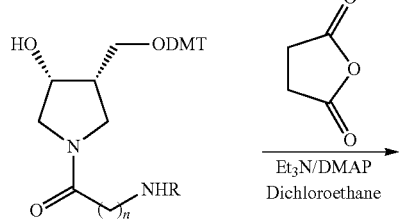
14
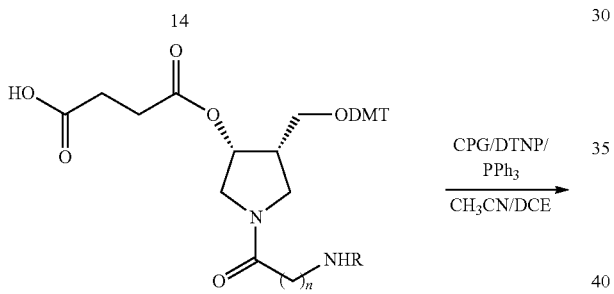
15
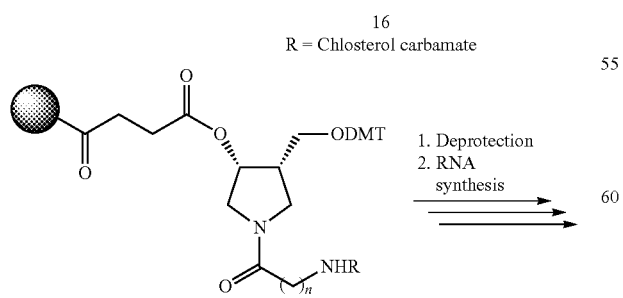
16
R = Chlosterol carbamate
R = Chlosterol carbamate
or any lipophilic molecule
72
-continued
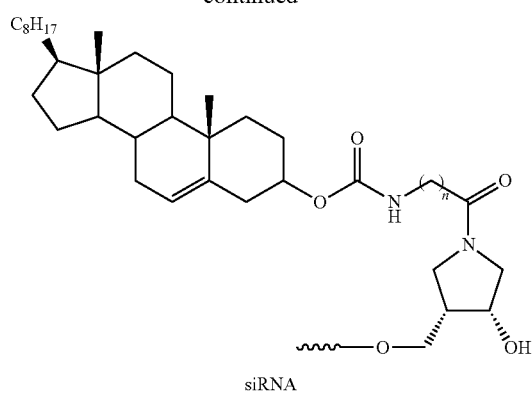
siRNA
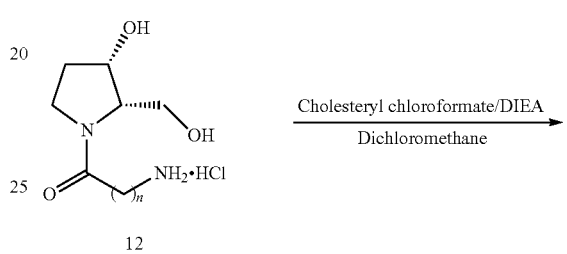
12
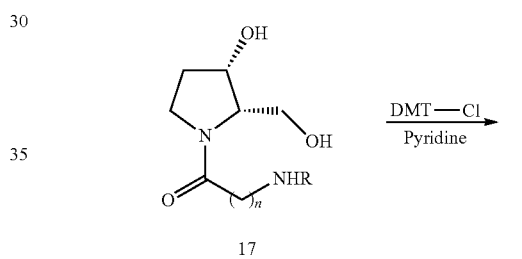
17
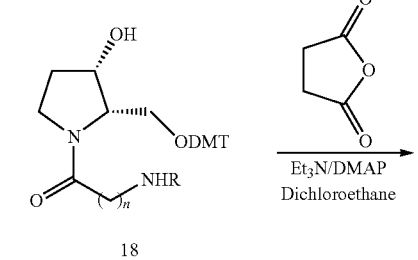
18
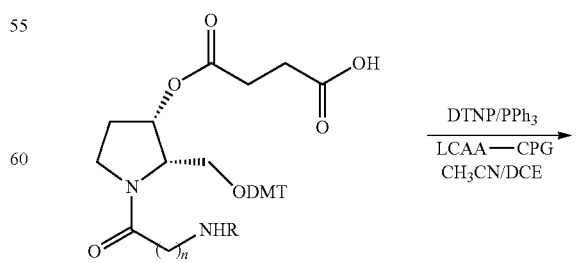
19

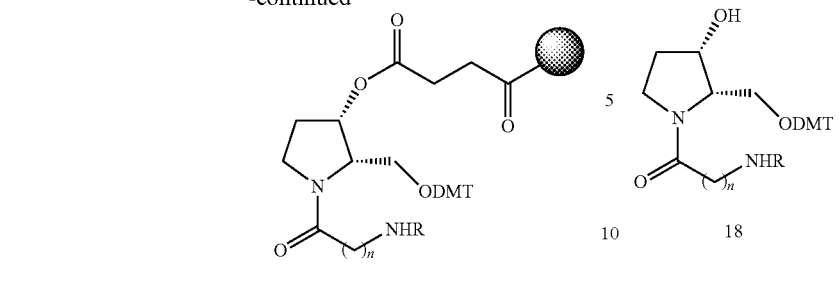
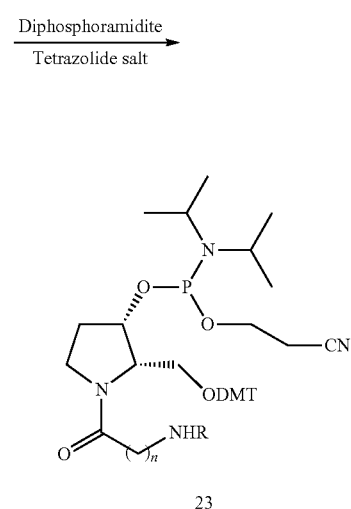
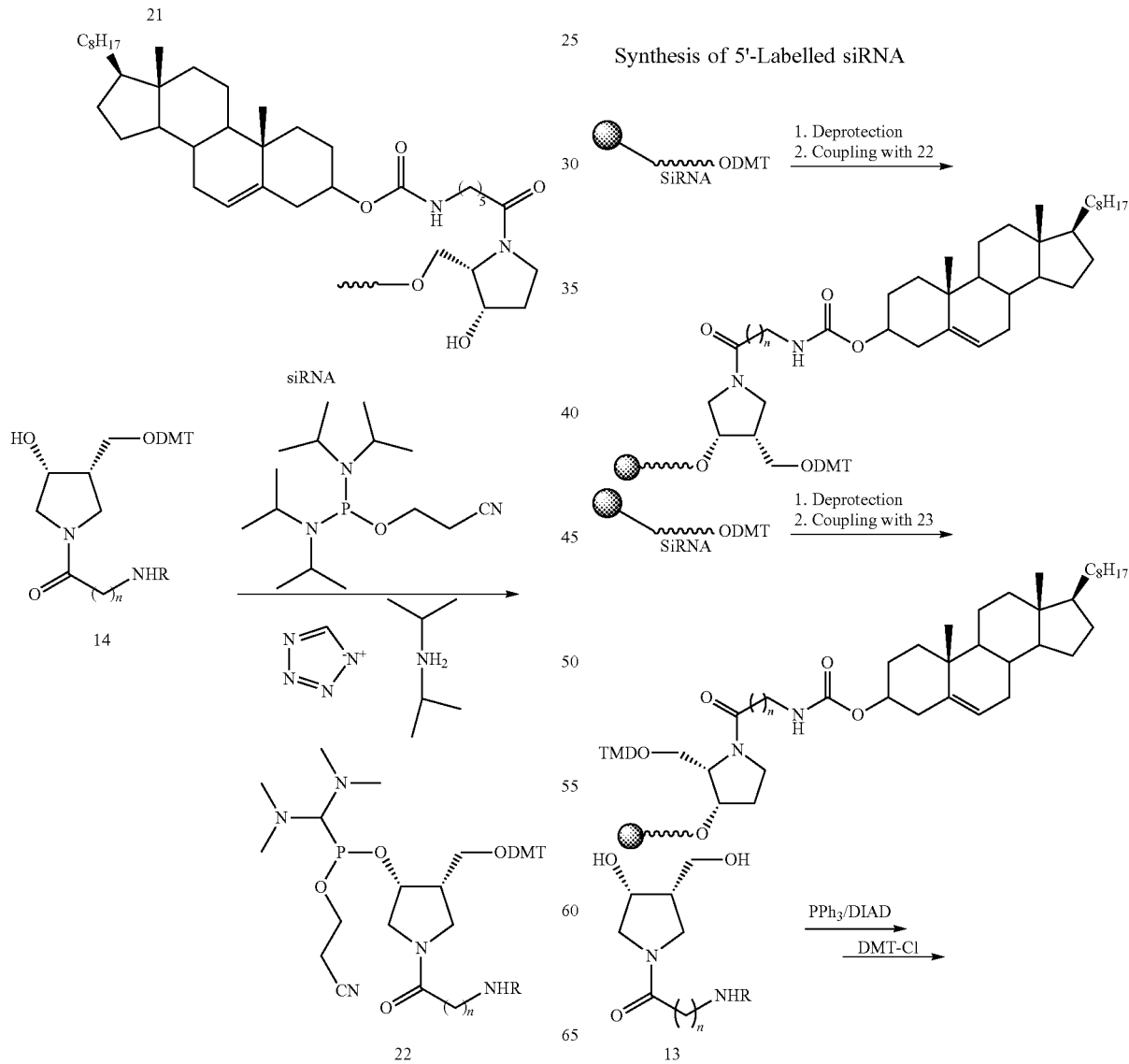
Synthesis of 5'-Labelled siRNA

-continued

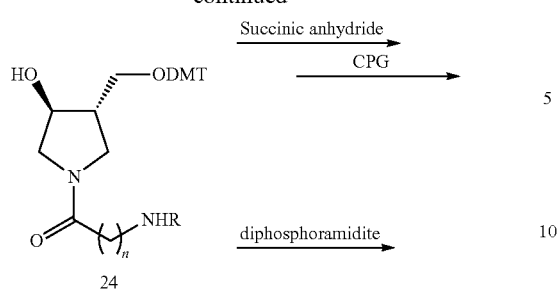
24

Succinic anhydride / CPG → diphosphoramidite →

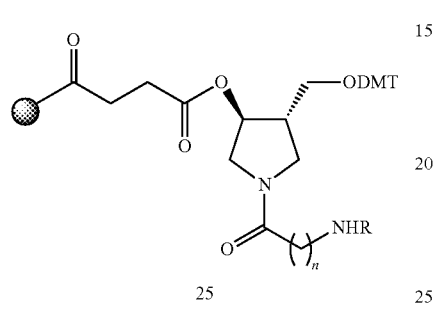
25

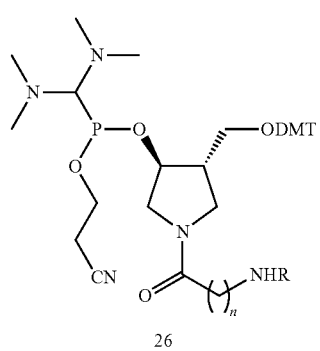
26

25 & 26 can be used for 3',5'-conjugation respectively.

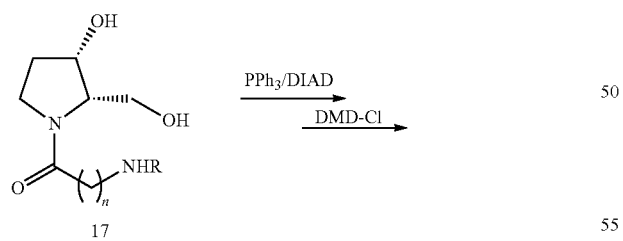
17

PPh₃/DIAD, DMD-Cl →

Succinic anhydride / CPG →

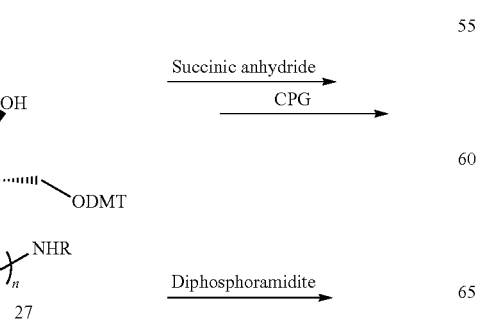
27

Diphosphoramidite →

-continued

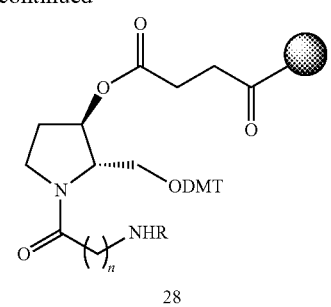
28

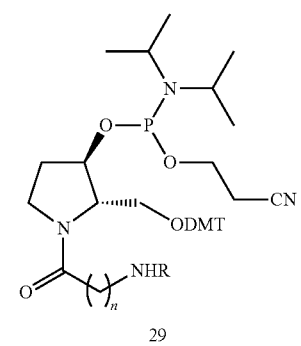
29

Synthesis of Phthalimido Derivative

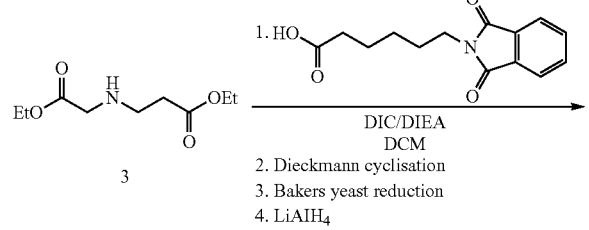
3

1. HO-(CH₂)ₙ-N(phthalimide), DIC/DIEA DCM
2. Dieckmann cyclisation
3. Bakers yeast reduction
4. LiAlH₄

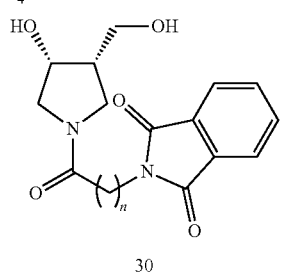
30

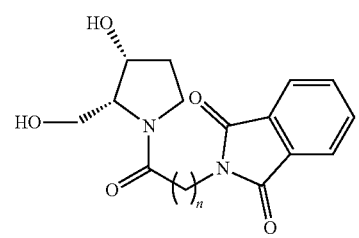
31

30 and 31 can be converted to similar derivatives as shown in schemes 2-4 for 3' and 5' conjugation of siRNA

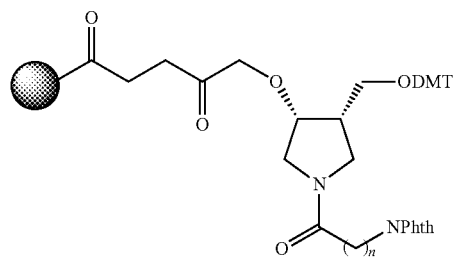
32
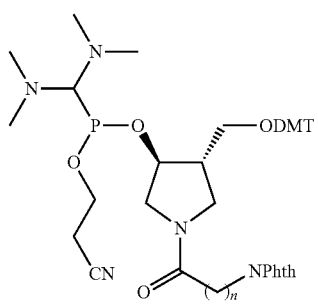
33
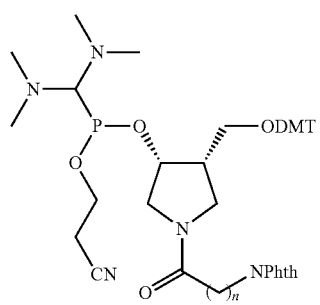
34
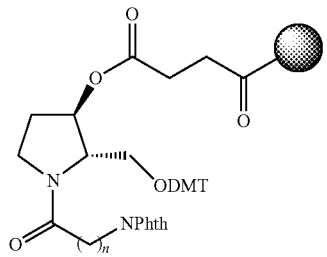
35
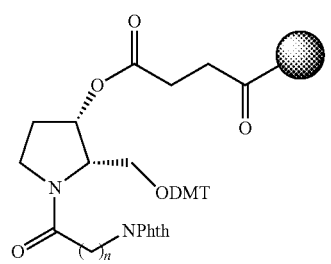
36
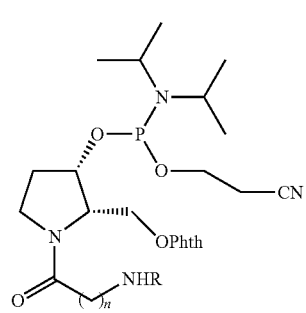
37
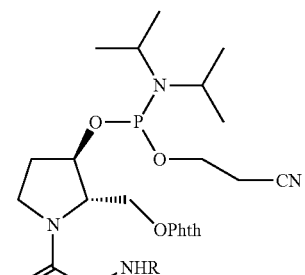
38
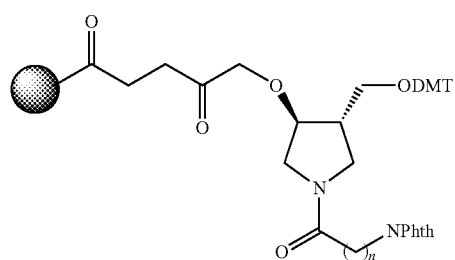
39
Synthesis of Thalimido Derivative
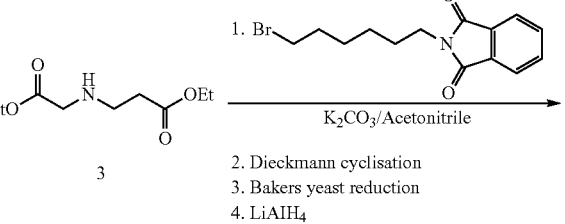
2. Dieckmann cyclisation
3. Bakers yeast reduction
4. LiAlH₄

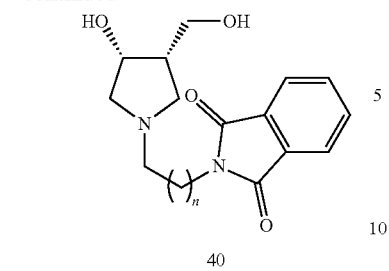
40
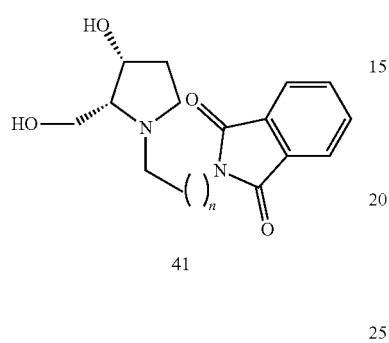
41
40 and 41 can be converted to similar derivatives as shown in schemes 2-4 for 3' and 5' conjugation of siRNA
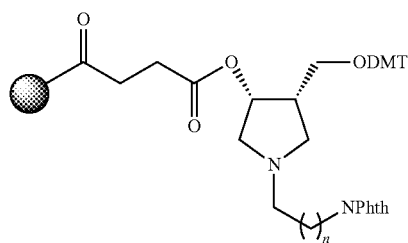
42
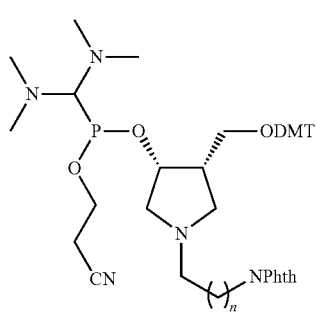
43
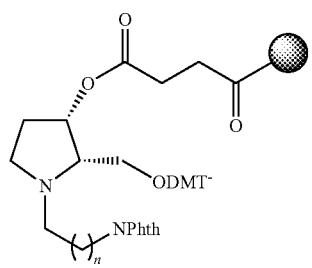
44
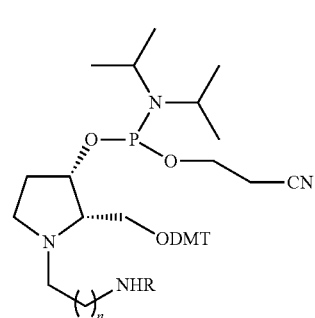
45
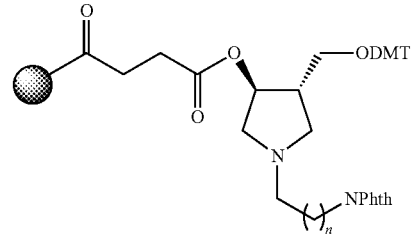
46
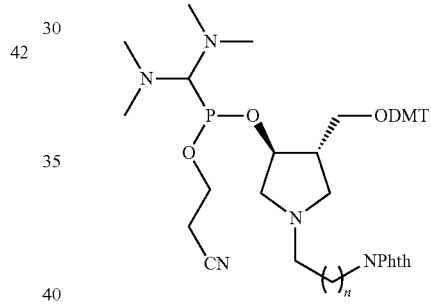
47
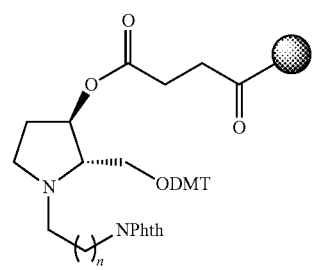
48
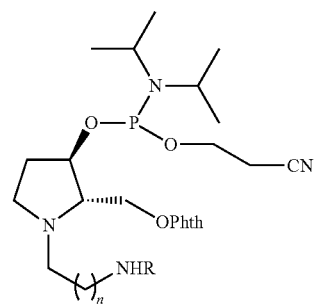
49

Synthesis of N-Alkyl Pyrroline Derivatives
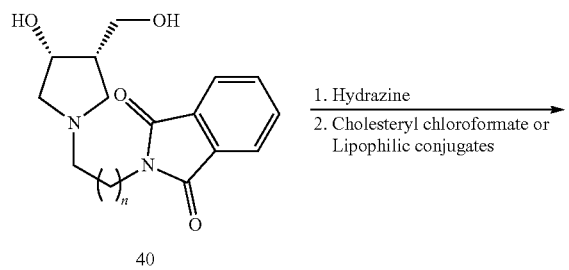
40
1. Hydrazine
2. Cholesteryl chloroformate or Lipophilic conjugates
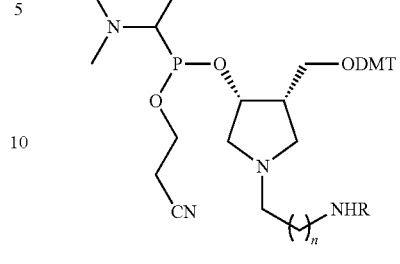
53
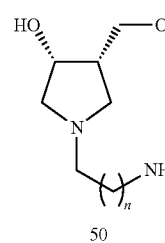
50
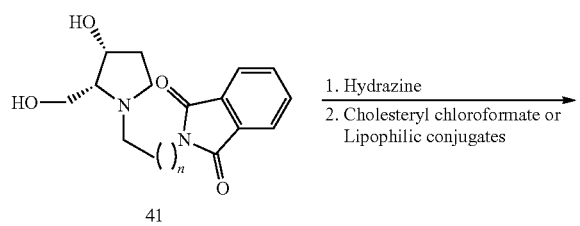
41
1. Hydrazine
2. Cholesteryl chloroformate or Lipophilic conjugates
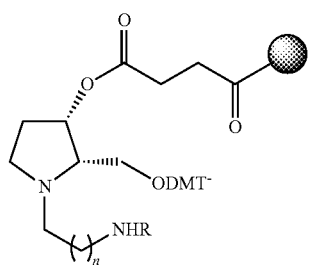
54
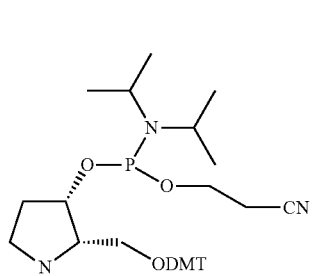
55
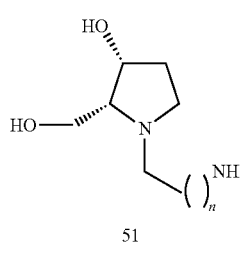
51
Intermediates 50 and 51 can be converted to analogs which could be conjugated with siRNA using similar reactions
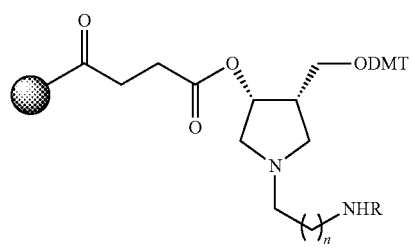
52
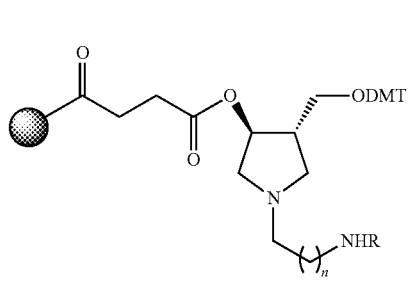
56
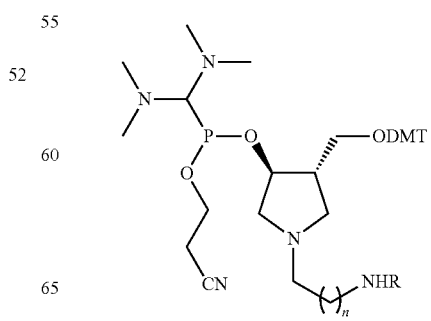
57

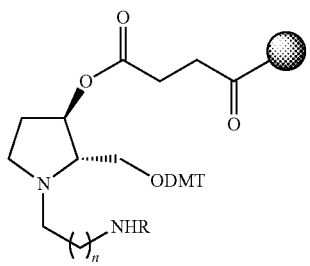
58
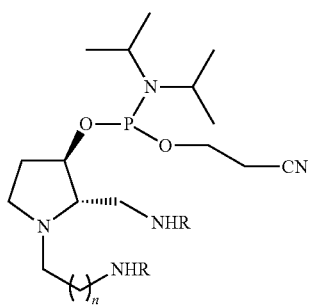
59
Piperidine Series Ligands:
Similar to pyrroline series piperidine series can be synthesised
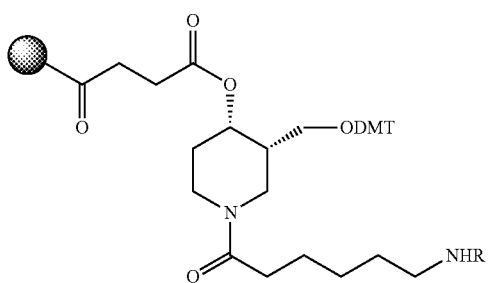
60
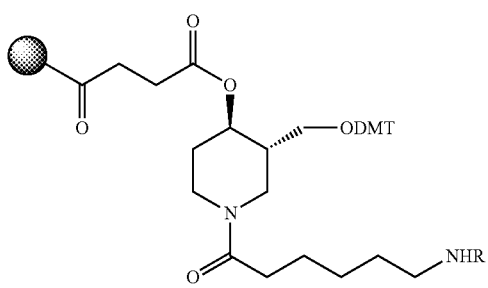
61
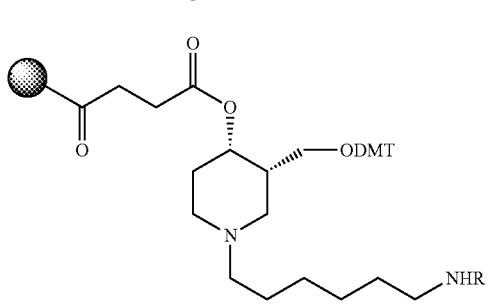
62
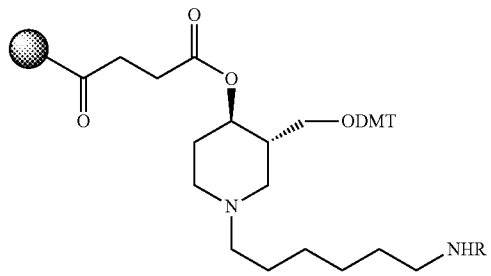
63
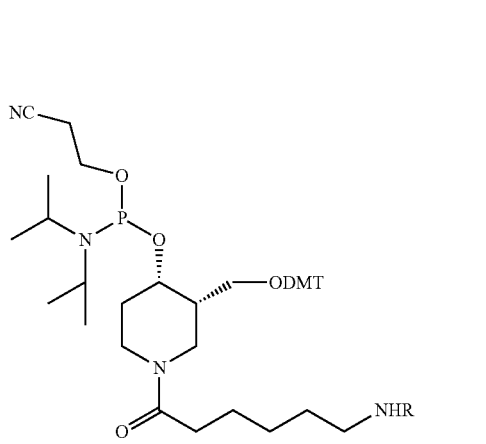
64
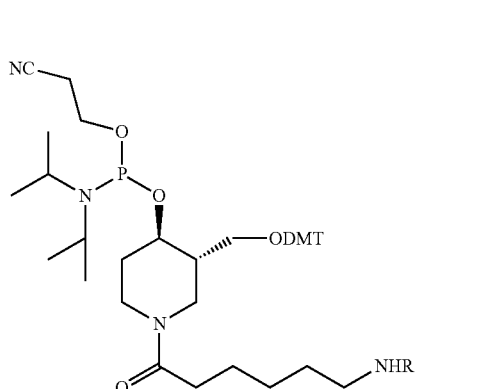
65
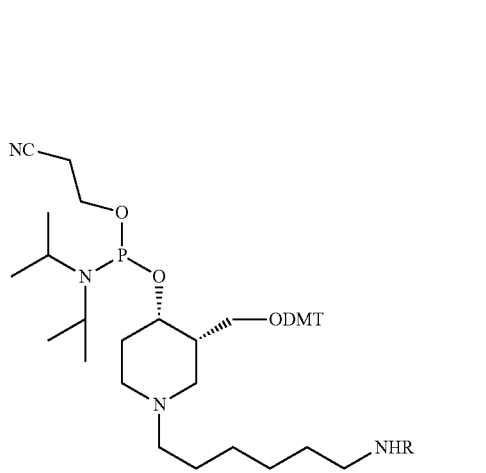
66

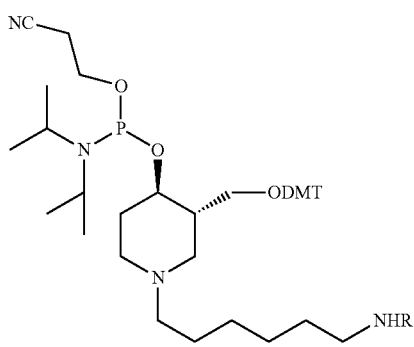
Piperidine Series Ligands:
Similar to pyrroline series piperidine series can be synthesised
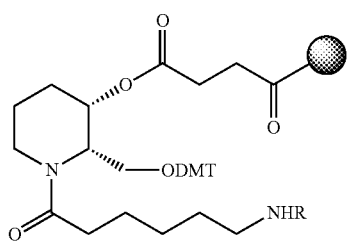
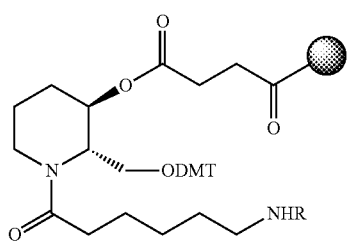
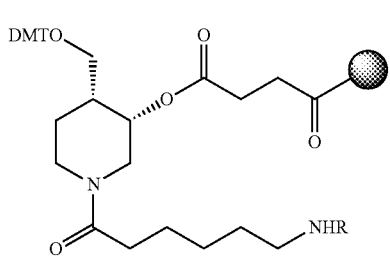
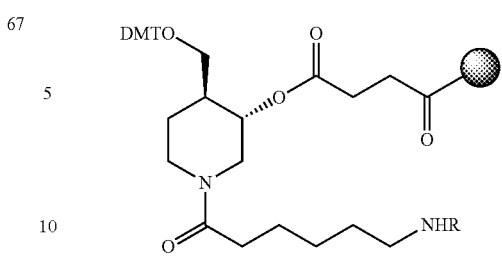
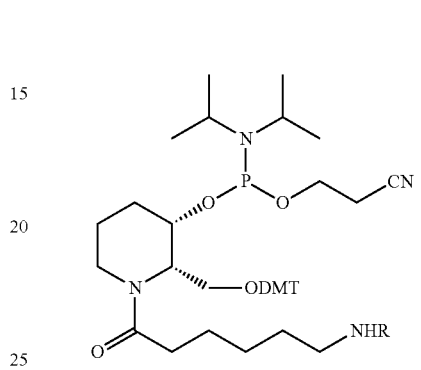
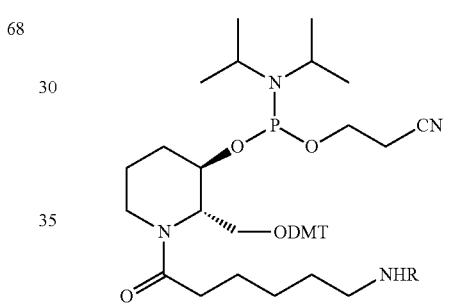
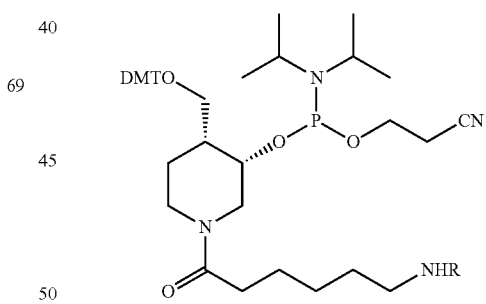
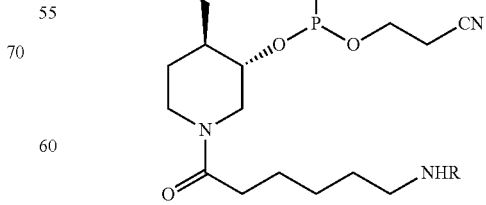
Hydroxy Proline Series Linkers:
From commercially available cis-3-hydroxy proline and (s)-pyrrolidone carboxylate

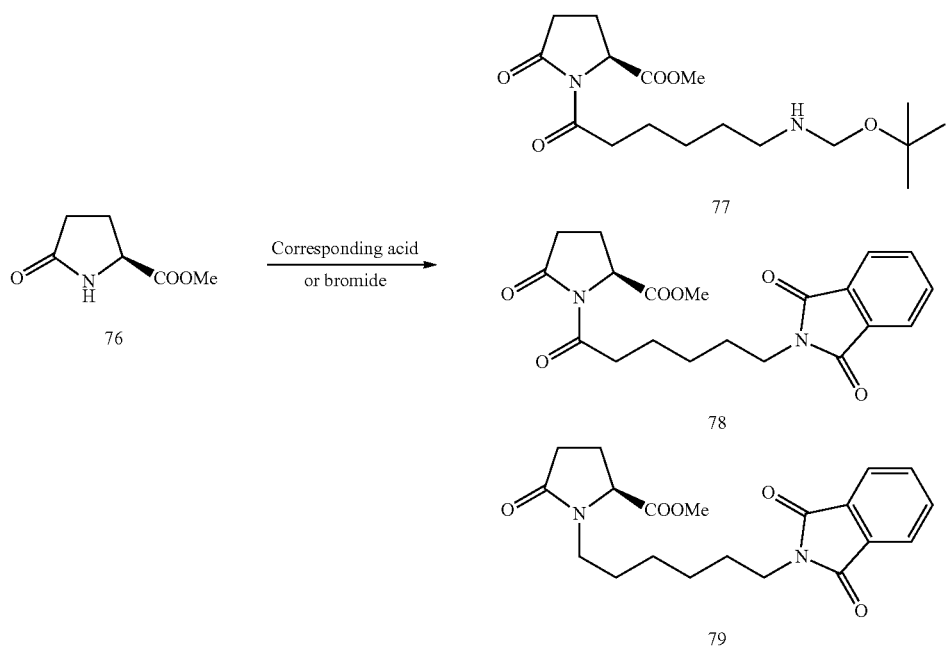
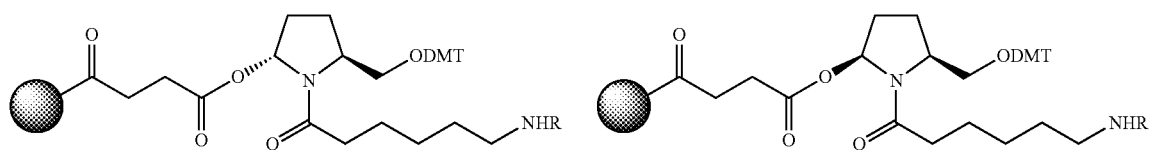
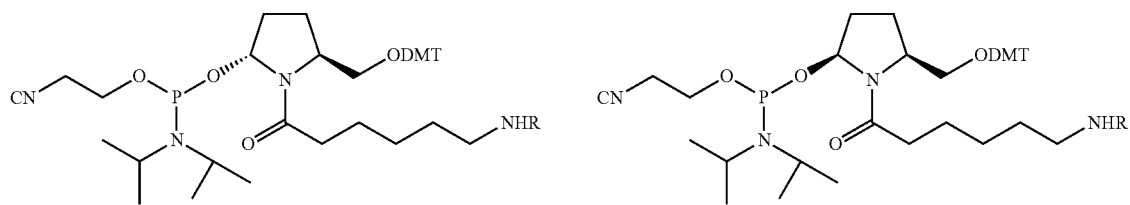
R = Lipophilic conjugates
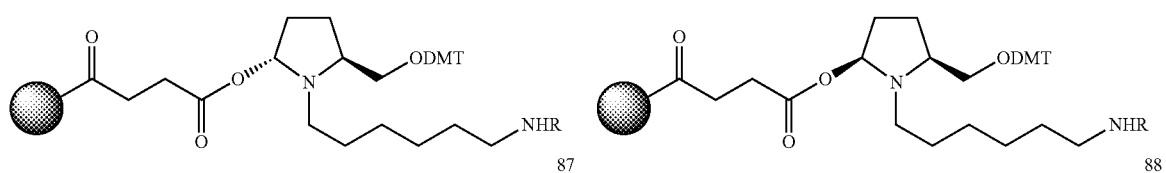
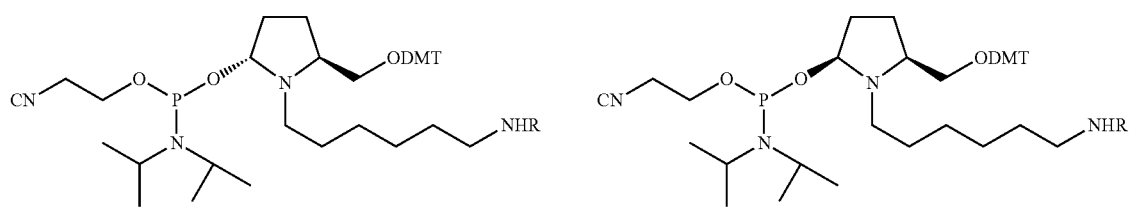
R = Lipophilic conjugates

89
Phthalimide Derivative to Stabilise siRNA
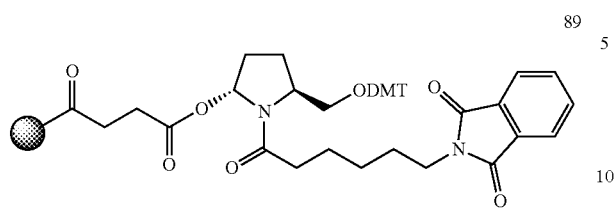
89
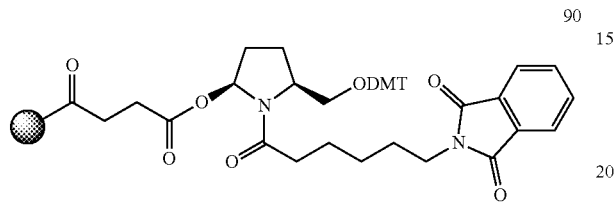
90
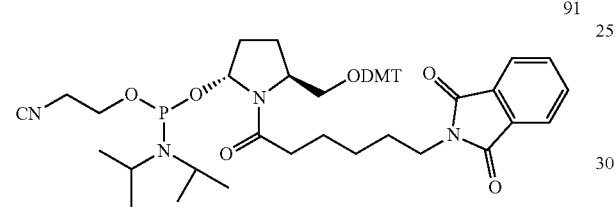
91
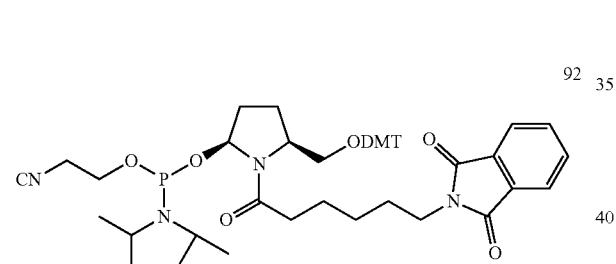
92
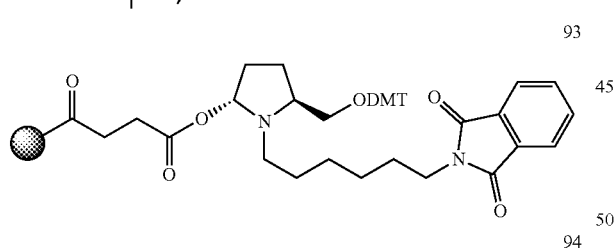
93
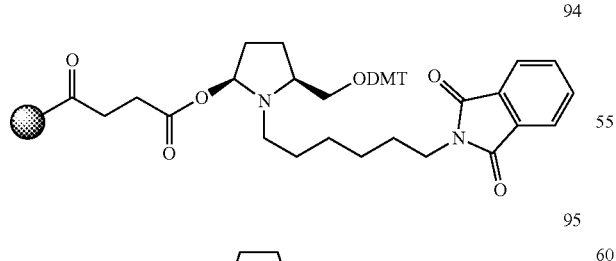
94
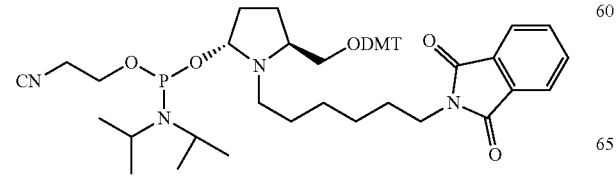
95
90
-continued
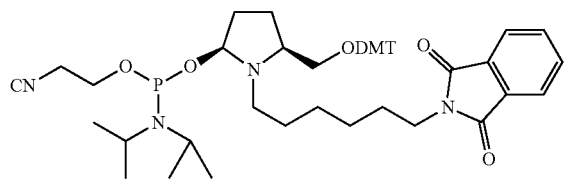
96
4-Hydroxy Proline Derivatives
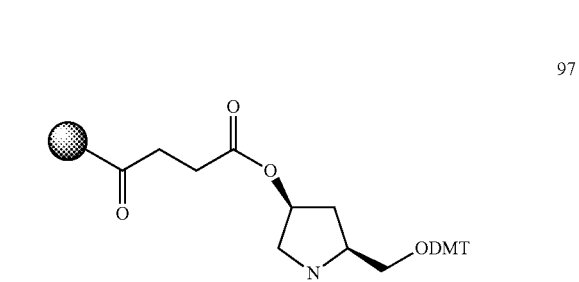
97
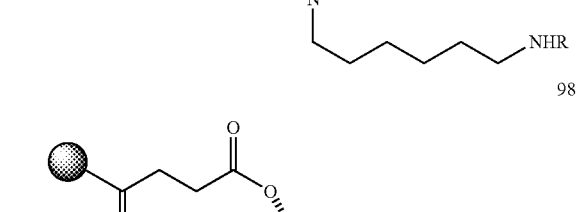
98
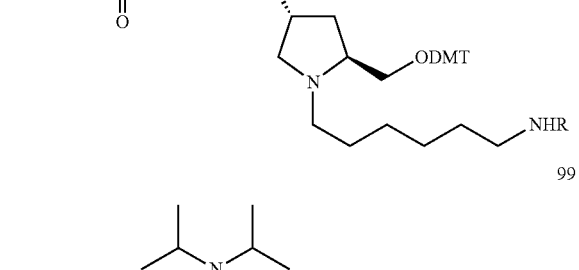
99
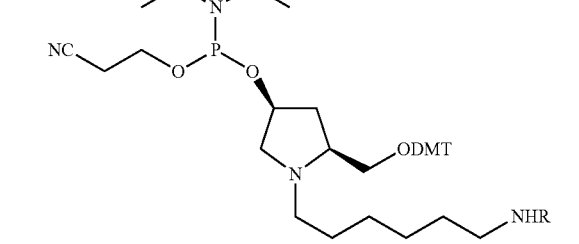
R = Lipophilic conjugates
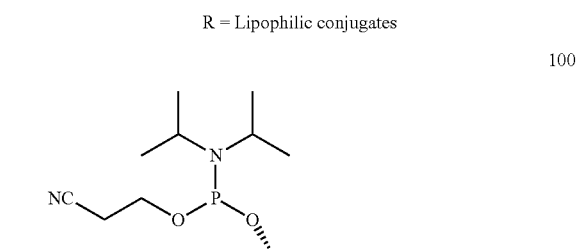
100
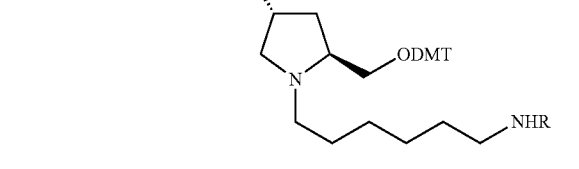

Phthalimido Derivatives
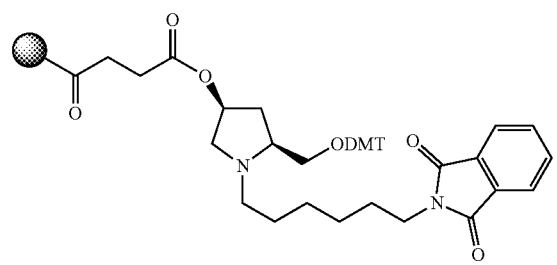
101
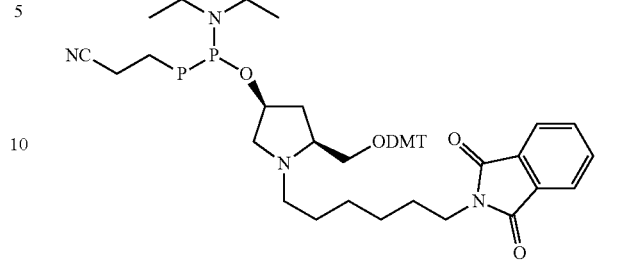
103
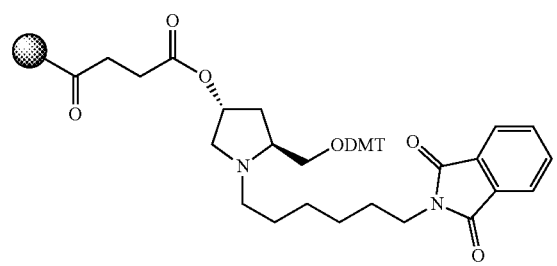
102
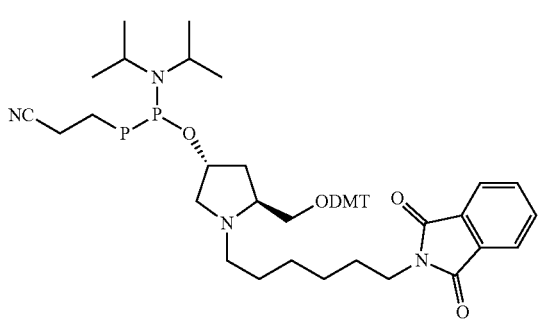
104
Synthesis of 6-Membered Linker
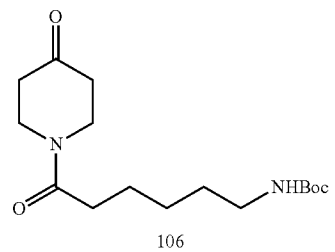
106
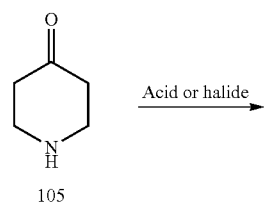
105
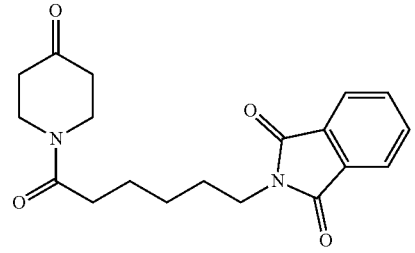
107
Acid or halide
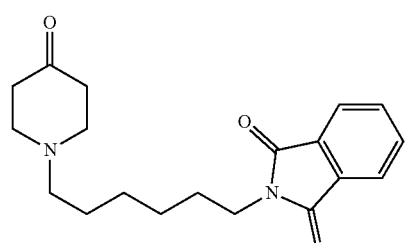
108

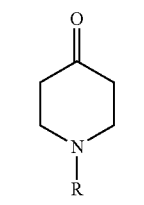
106 or 107 or 108
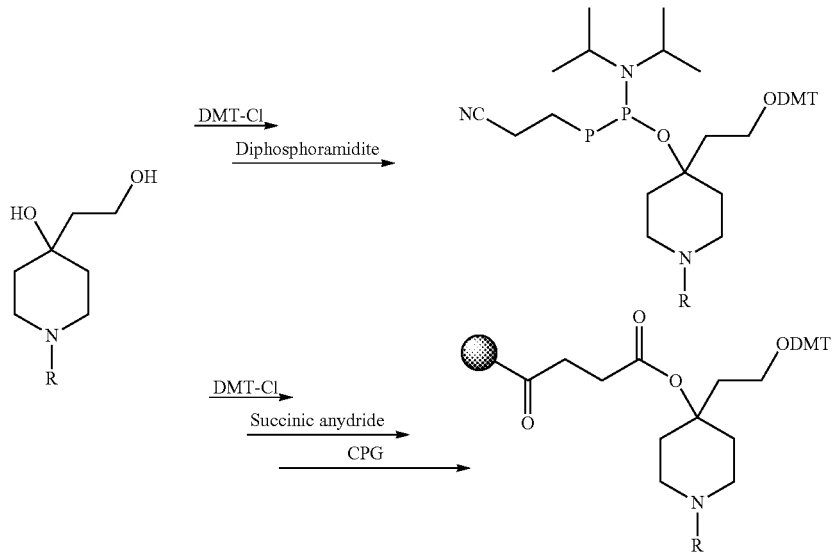
Similar reaction can be carried out with 2-piperidone and 3-piperidone
Linkers from 4-Piperidone
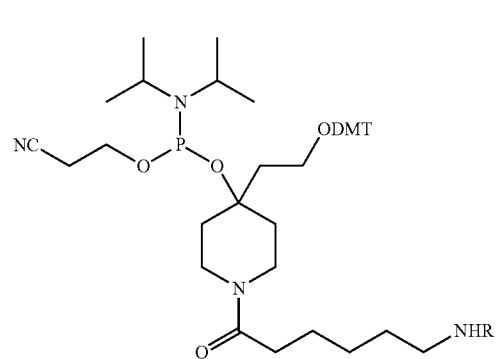
109
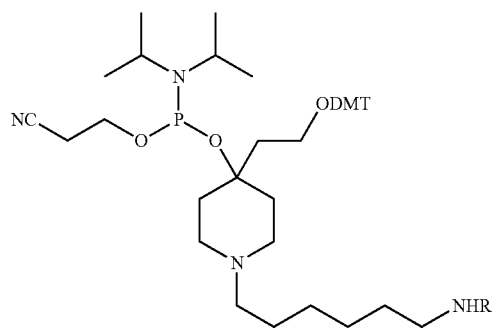
111
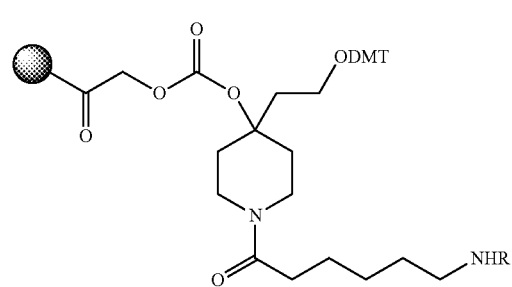
110
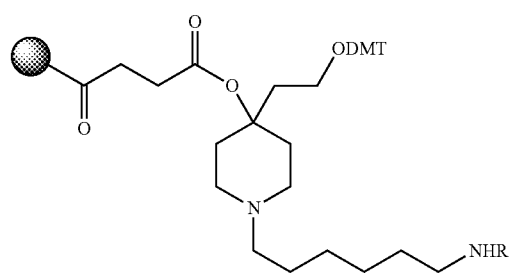
112

96
Linkers from 3-Piperidone
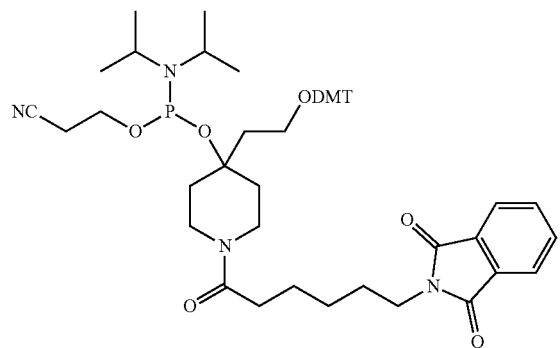
113
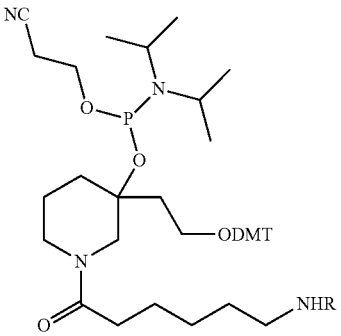
117
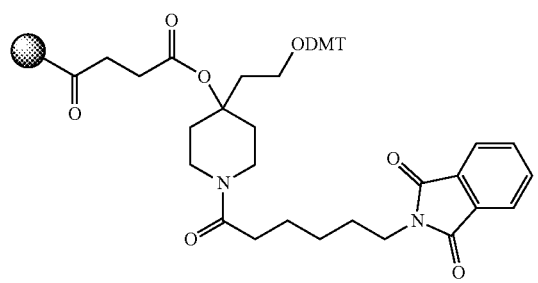
114
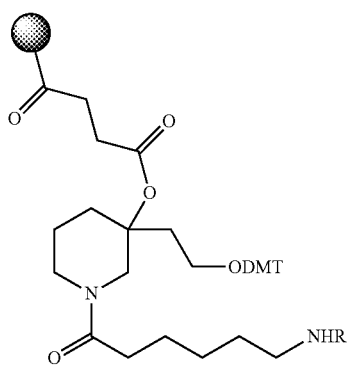
118
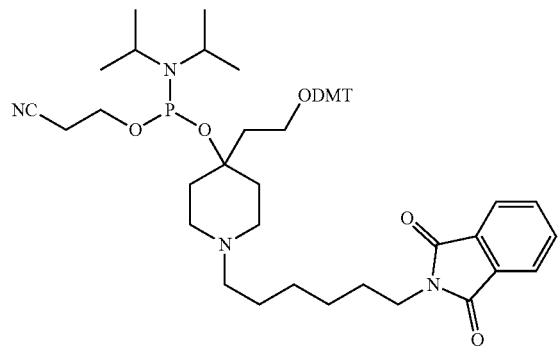
115
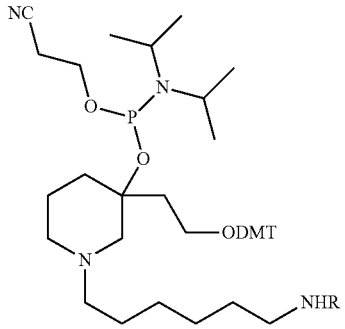
119
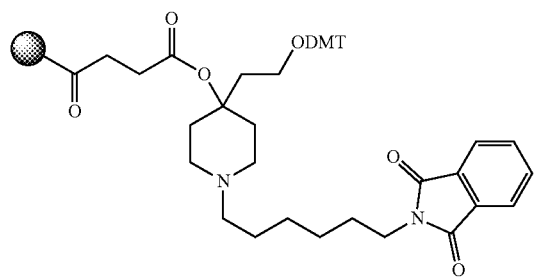
116
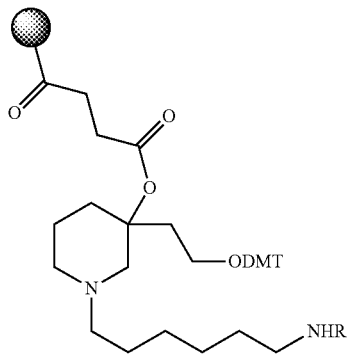
120

98
Linkers from 2-Piperidone
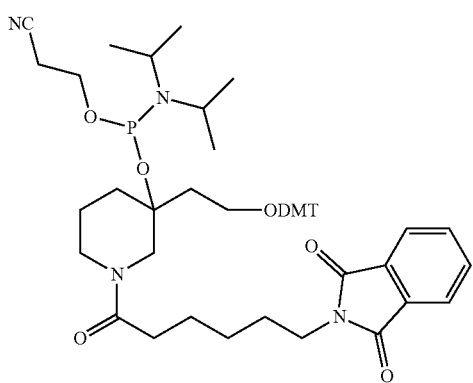
121
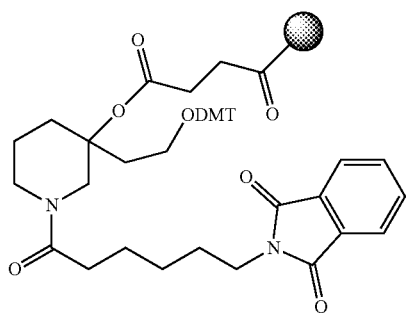
122
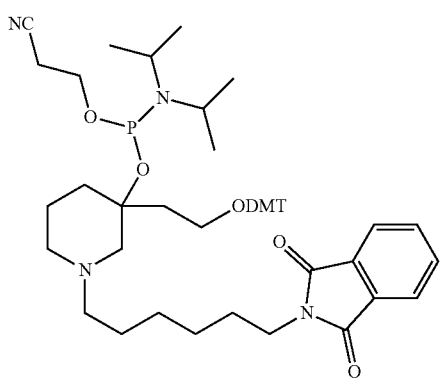
123
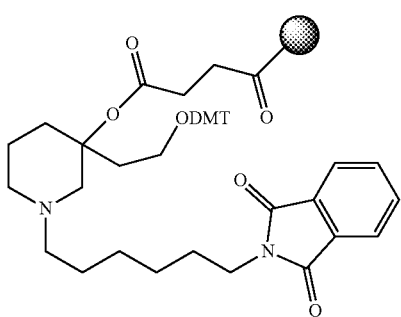
124

-continued
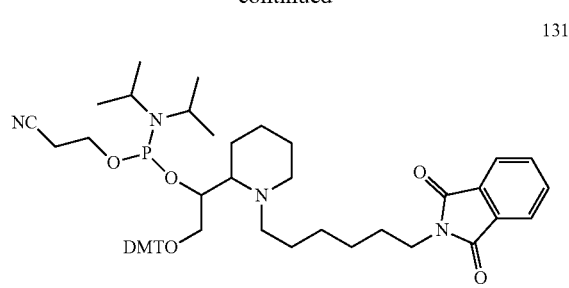
131
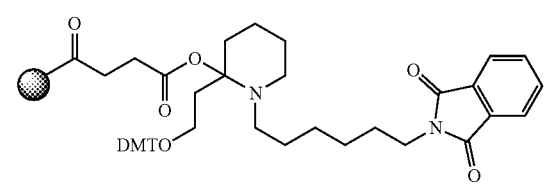
132
Conjugation Through Decalin System
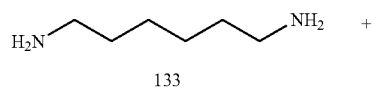
133
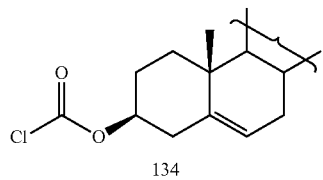
134
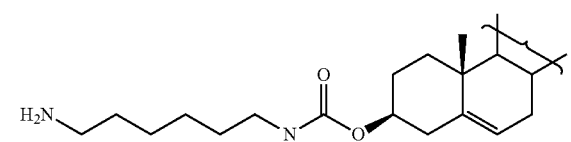
135
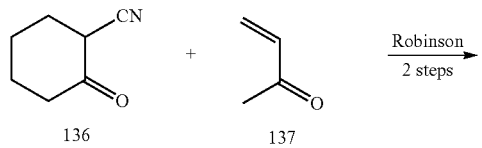
136  137 → Robinson 2 steps
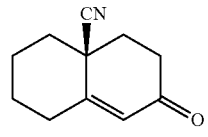
138 → 1. RuH₂(PPh₃)₄ Sealed tube 24 h
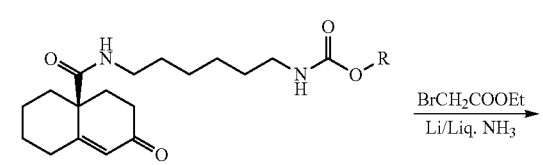
R = Cholesterol
139
→ BrCH₂COOEt Li/Liq. NH₃
-continued
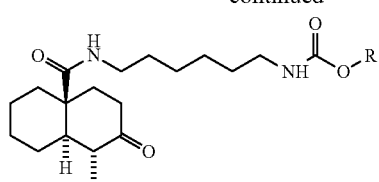
140 → 1. Reduction 2. Protection
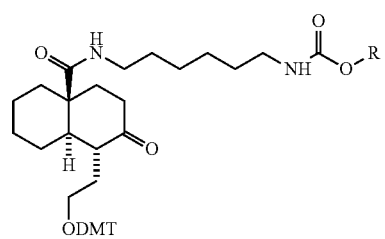 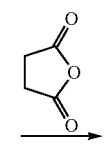
141
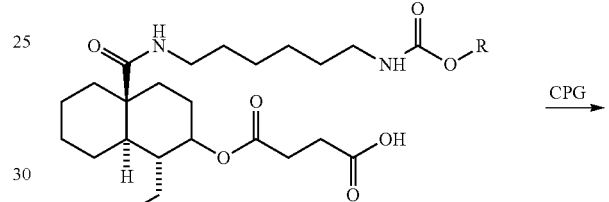 → CPG
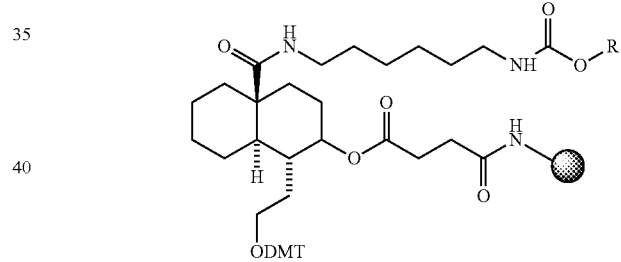
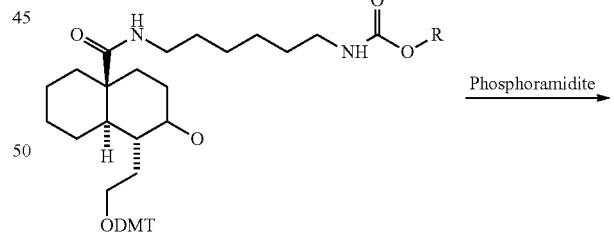 → Phosphoramidite
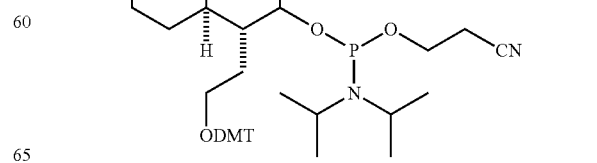

101
Conjugates from Decalin System:
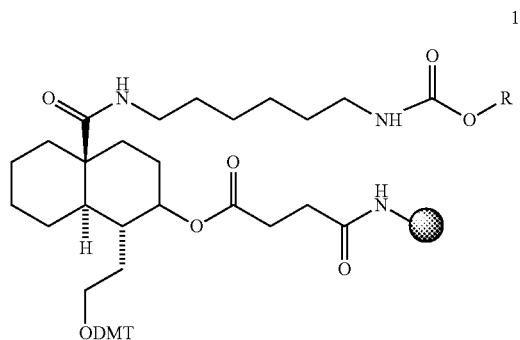
142
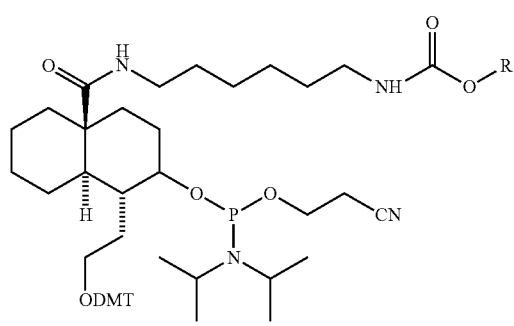
143
102
-continued
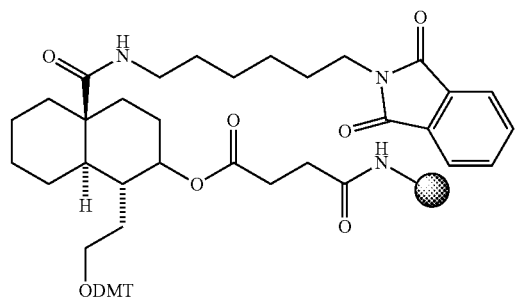
144
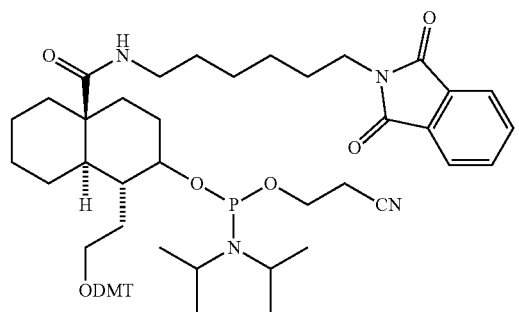
145
R = Lipophilic conjugates
Decalin Linker from Wieland-Miescher Ketone
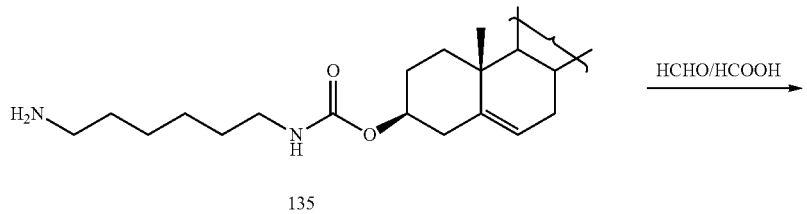
135
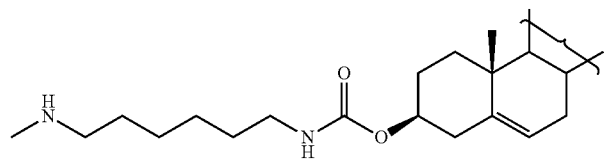
146
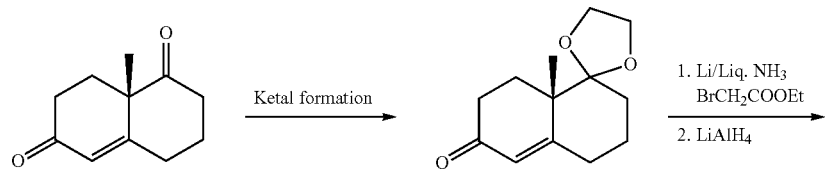
147    148

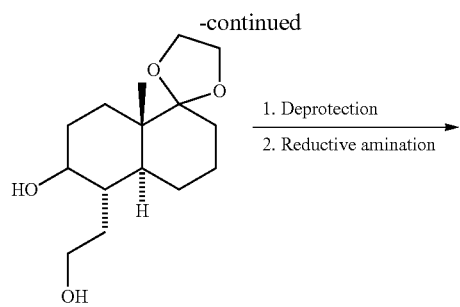
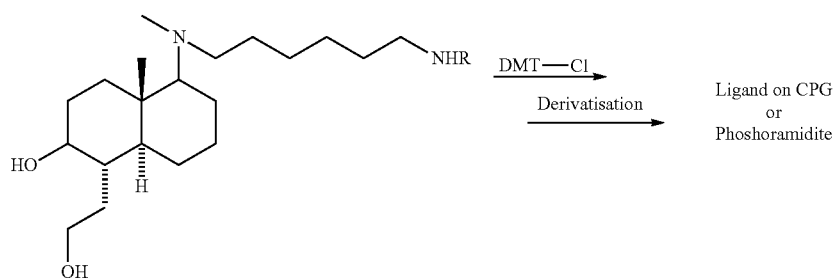
Conjugates from Wieland-Miescher Ketone
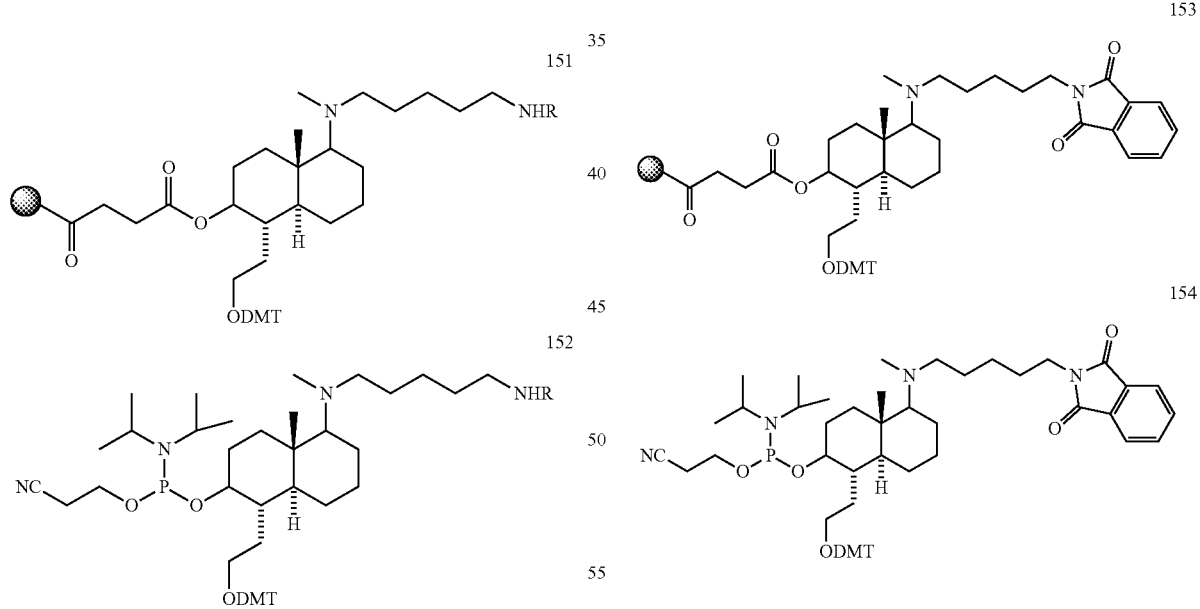
Synthesis of Pyrroline Linker:
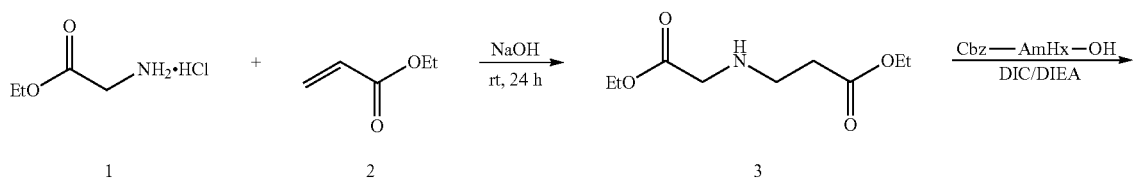

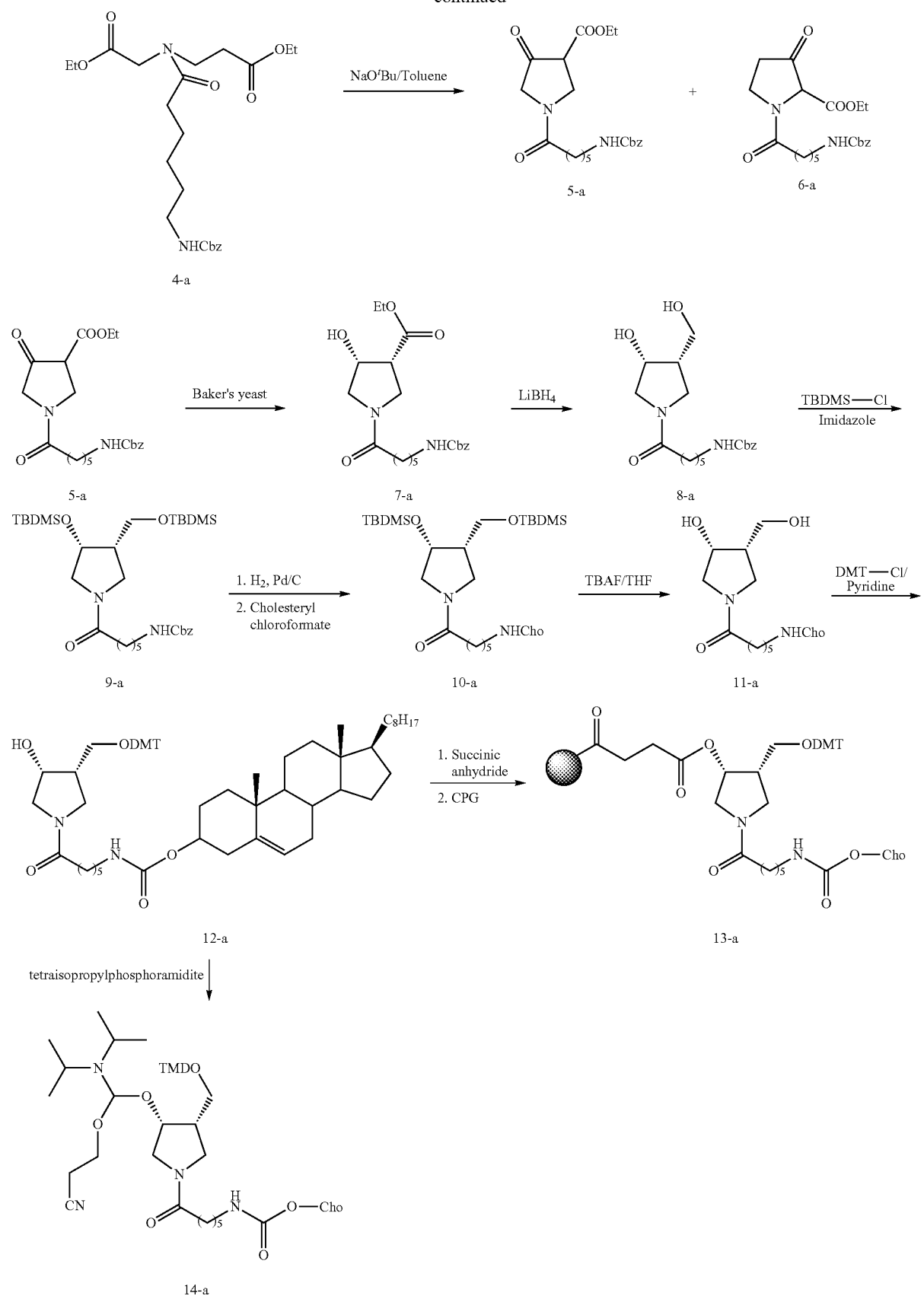

Solid Phase Synthesis and Post-Synthesis Conjugation:
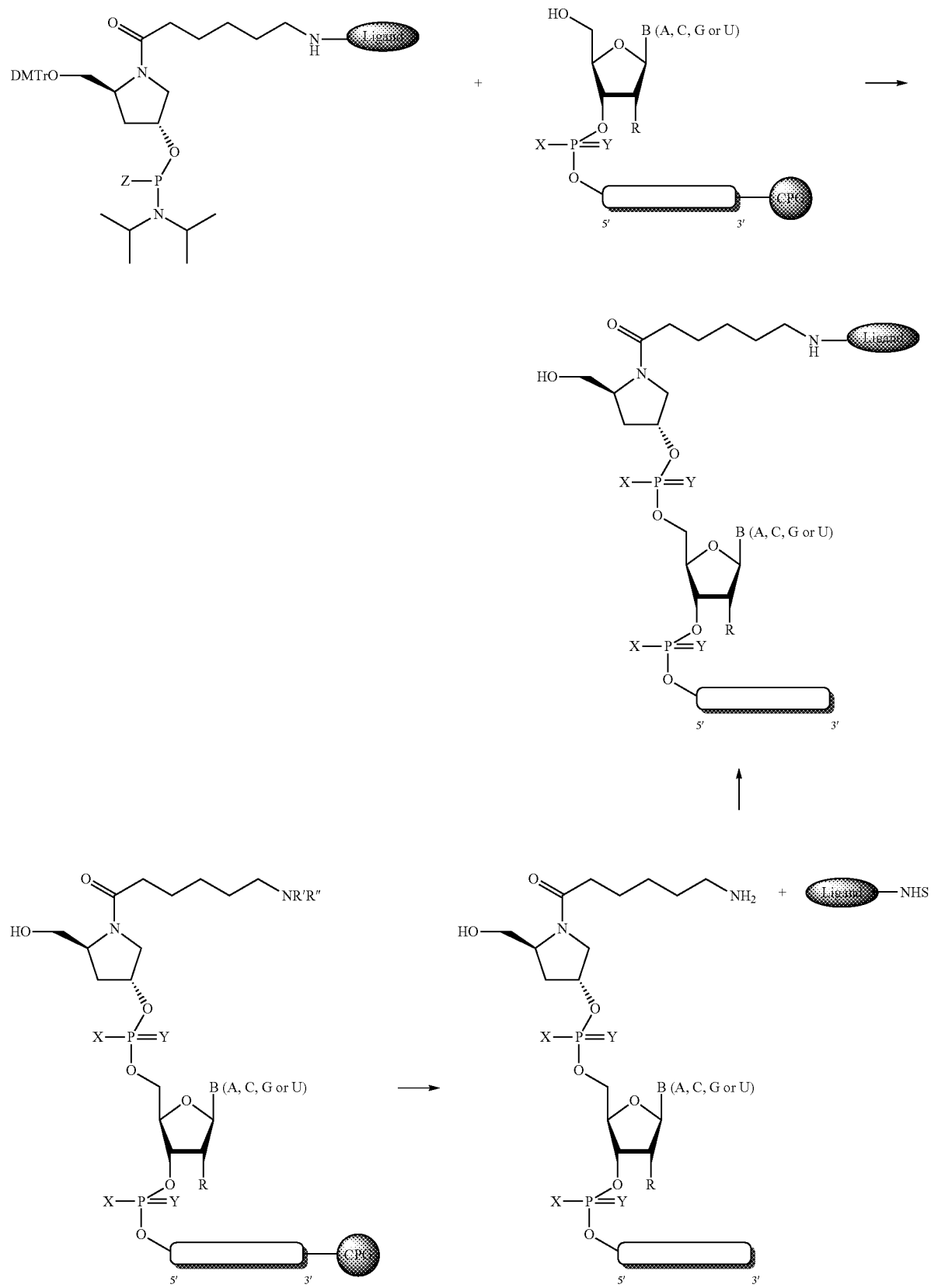

Exemplary Ligand Conjugated Monomers
LCM—E.g.—
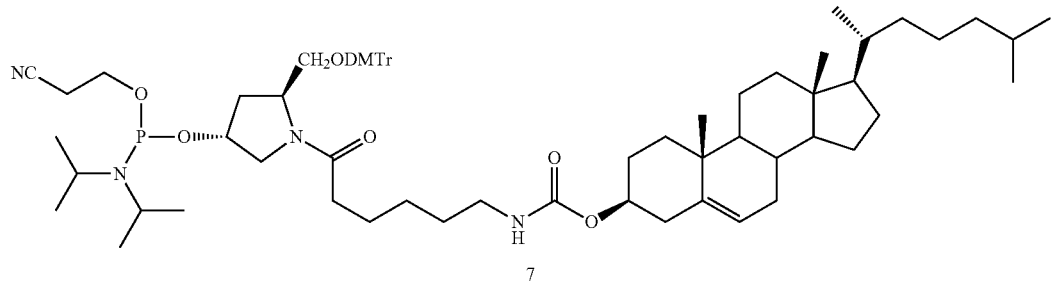
7
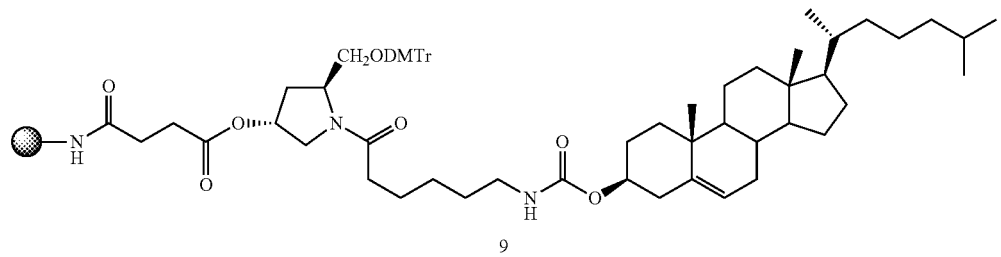
9
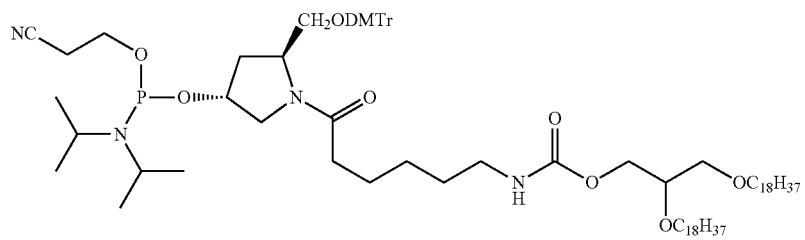
13
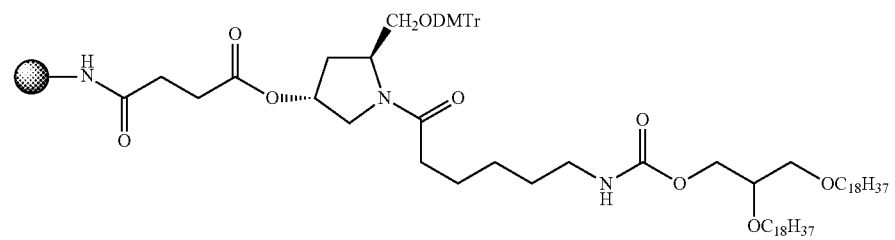
15
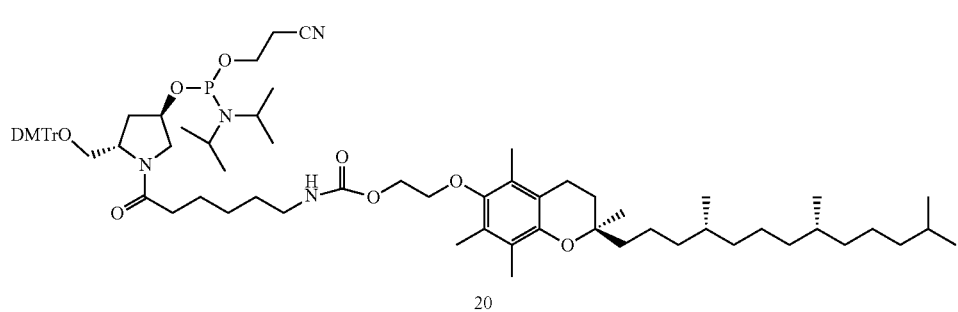
20

-continued
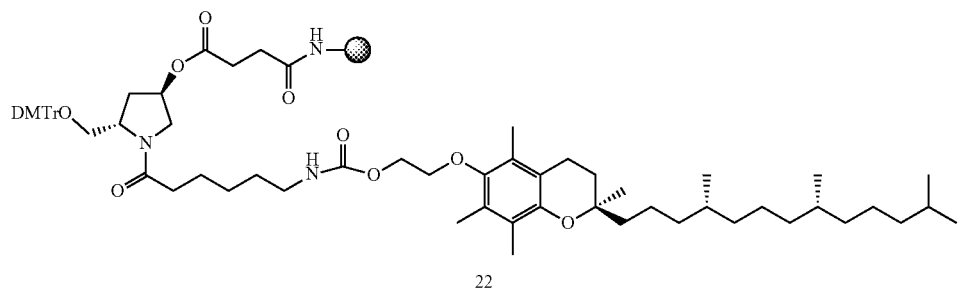
22
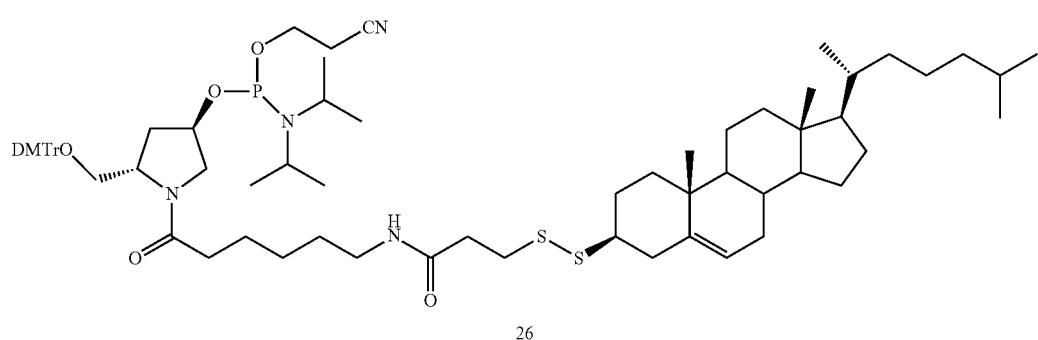
26
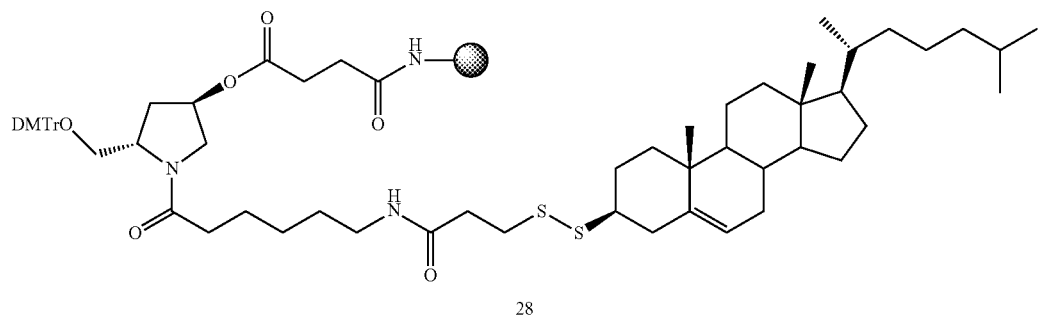
28
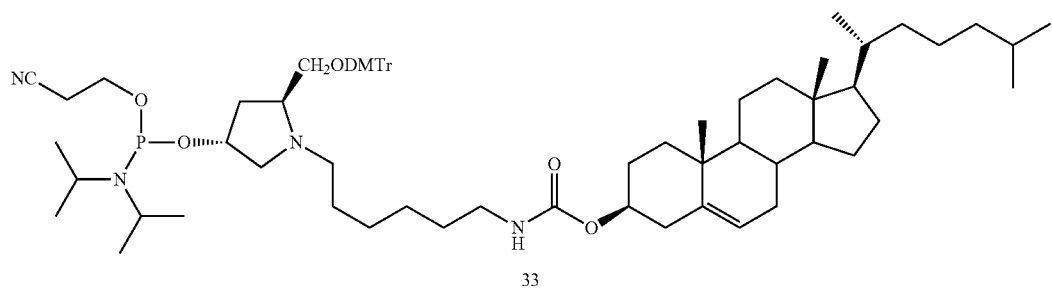
33
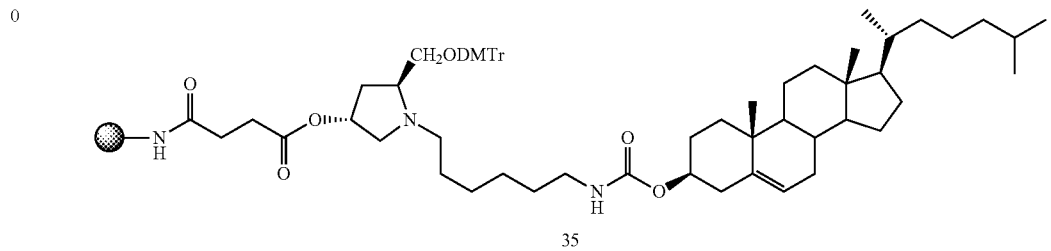
35

1 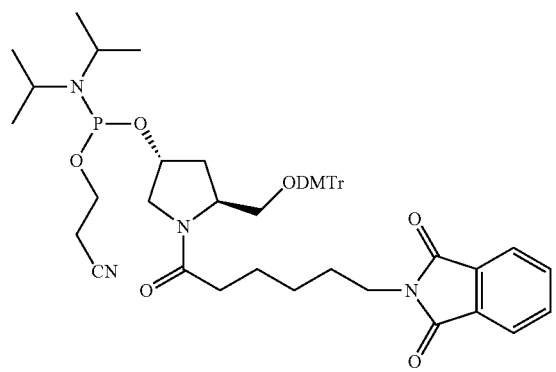
45a
2 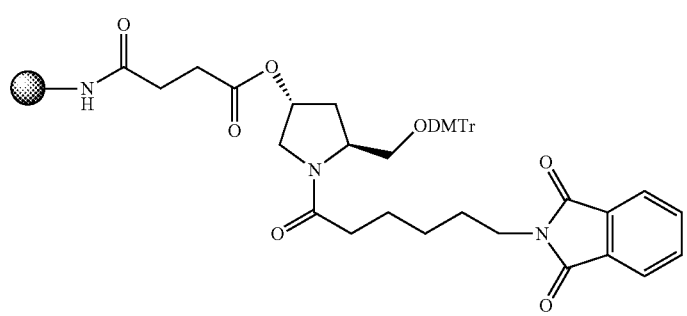
46a
3 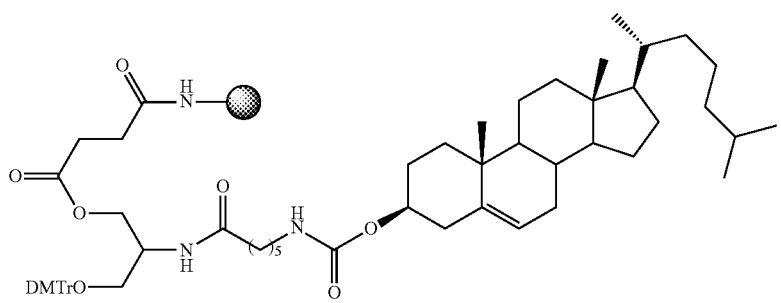
55
4 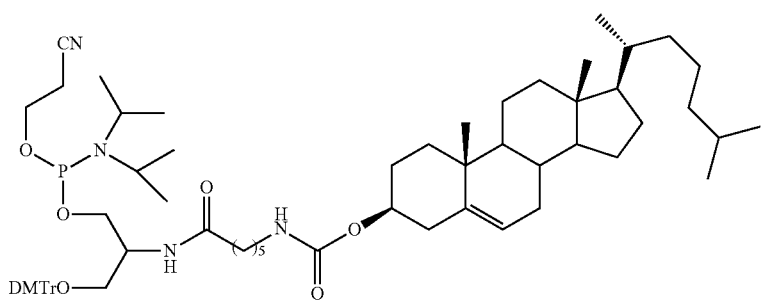
56

-continued
5
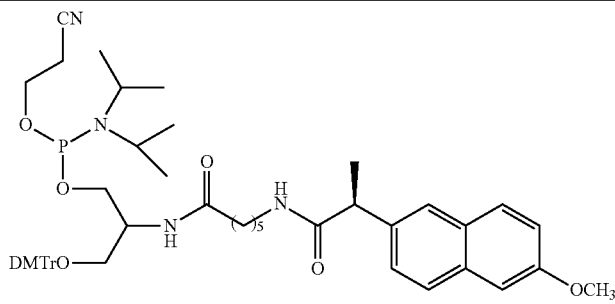
209a
6
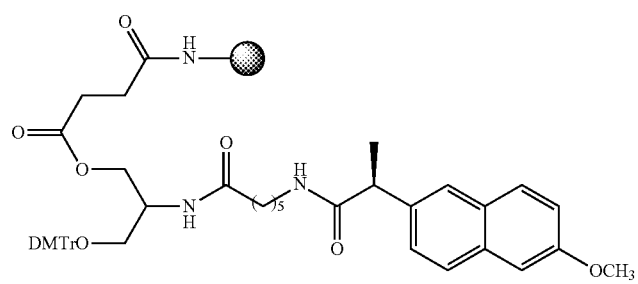
208a
7
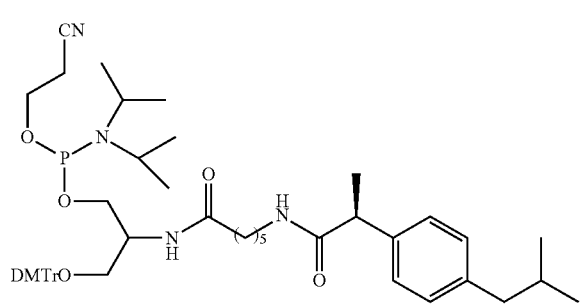
209b
8
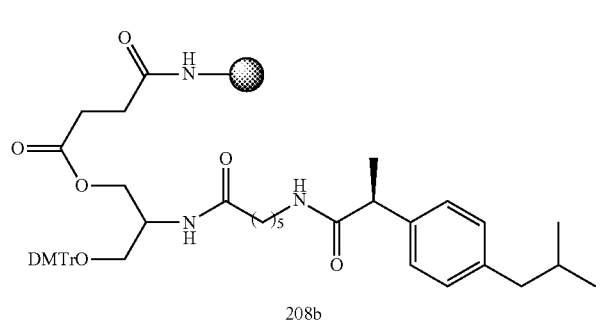
208b
9
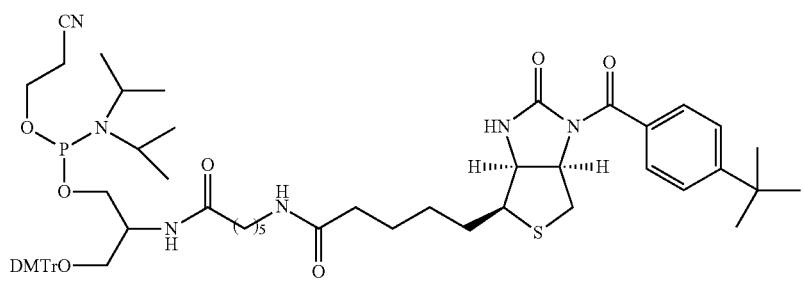
223

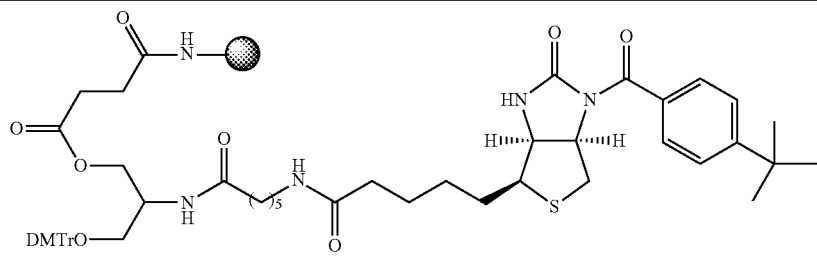
224
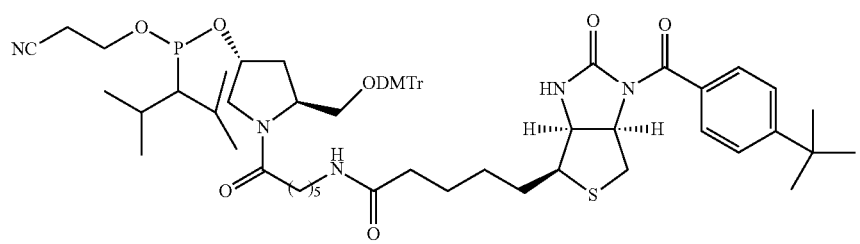
229a
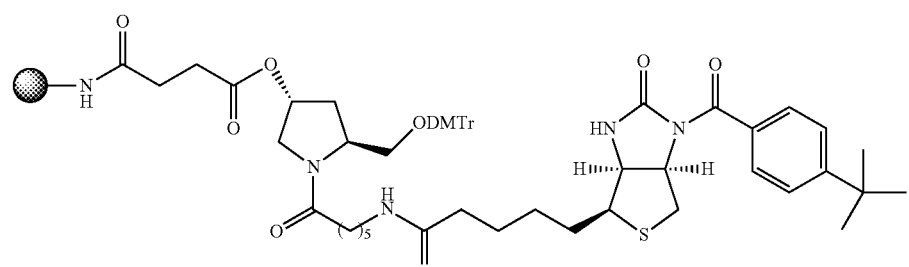
230a
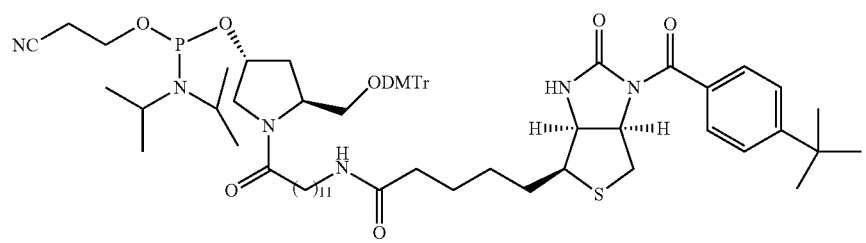
229b
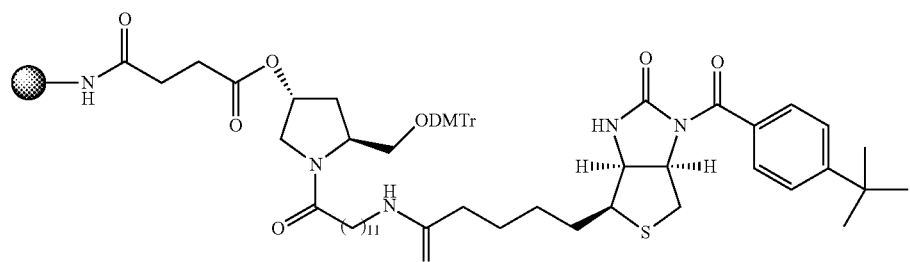
230b 5
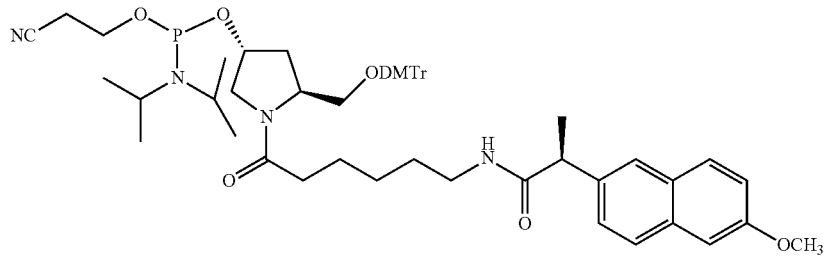
212a
6
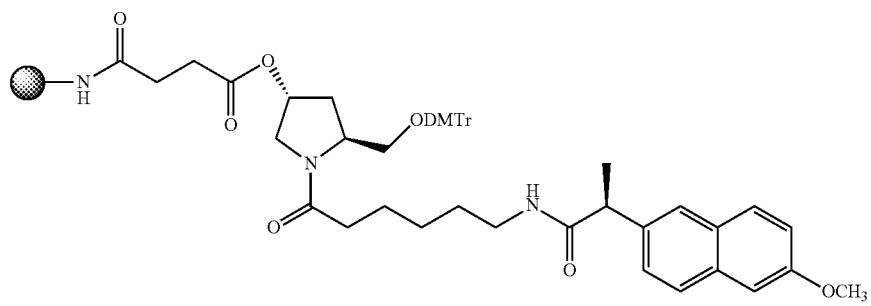
211a
7
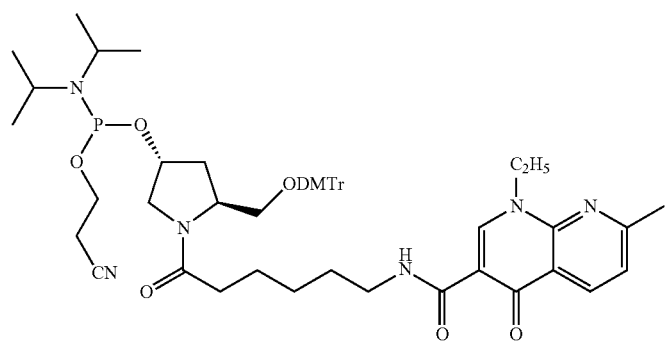
100
8
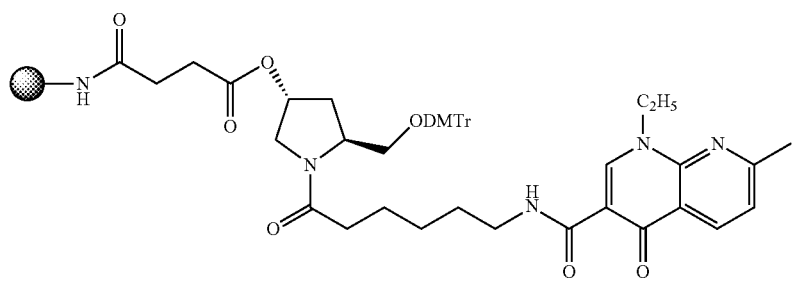
102
9
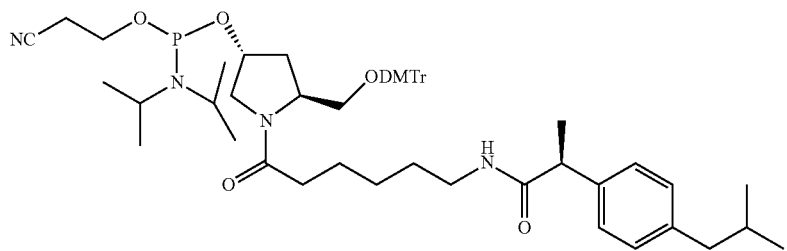
212b

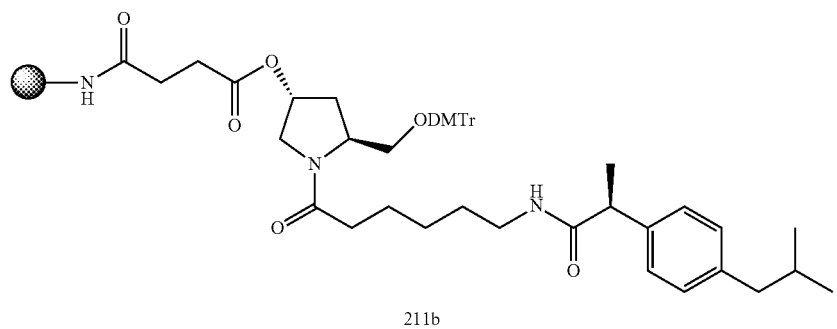
211b
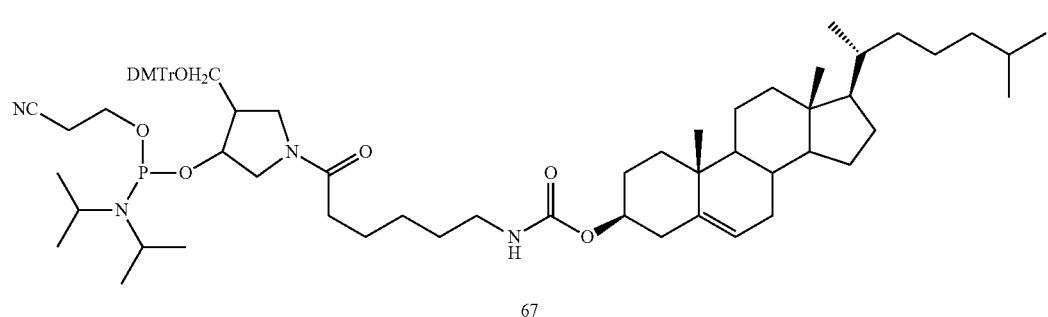
67
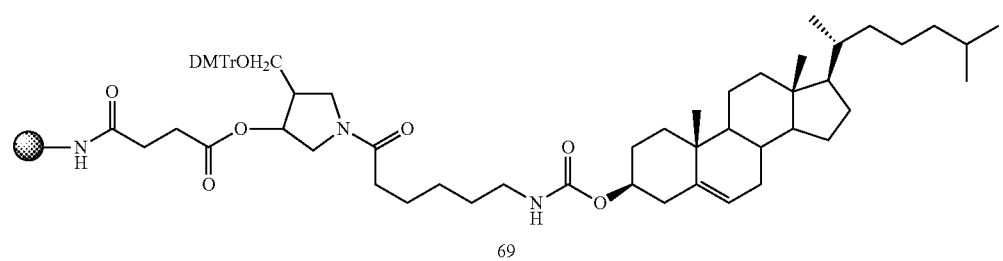
69
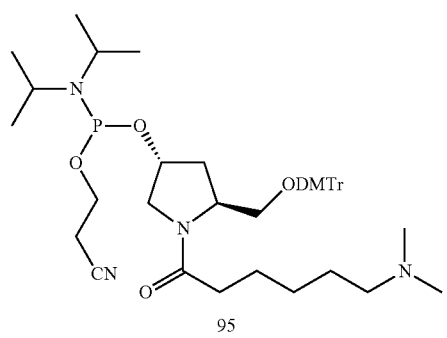
95
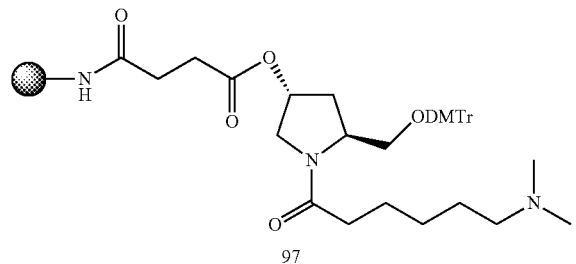
97

5 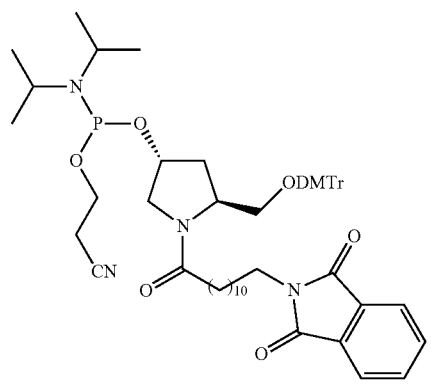
45b
6 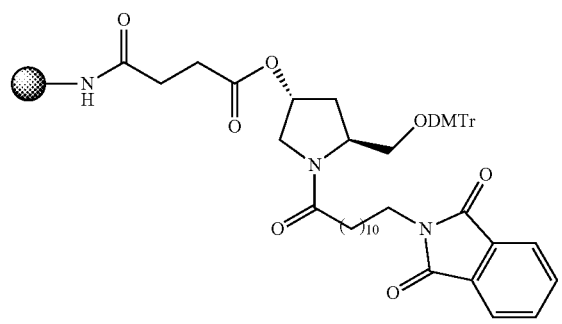
46b
7 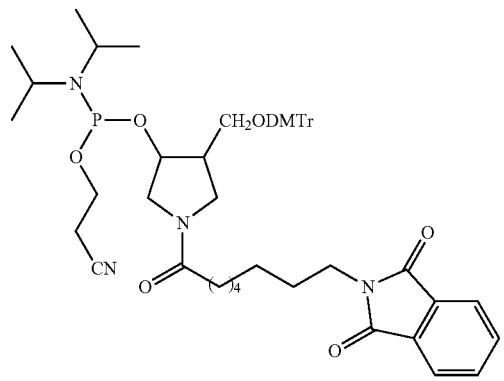
78
8 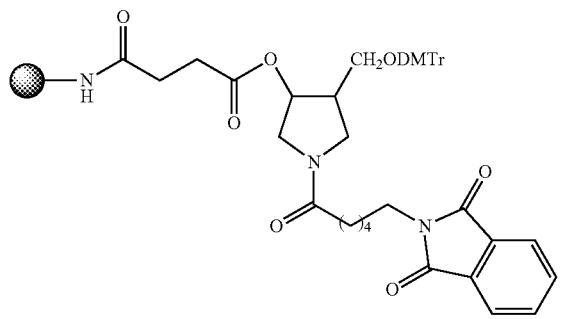
80

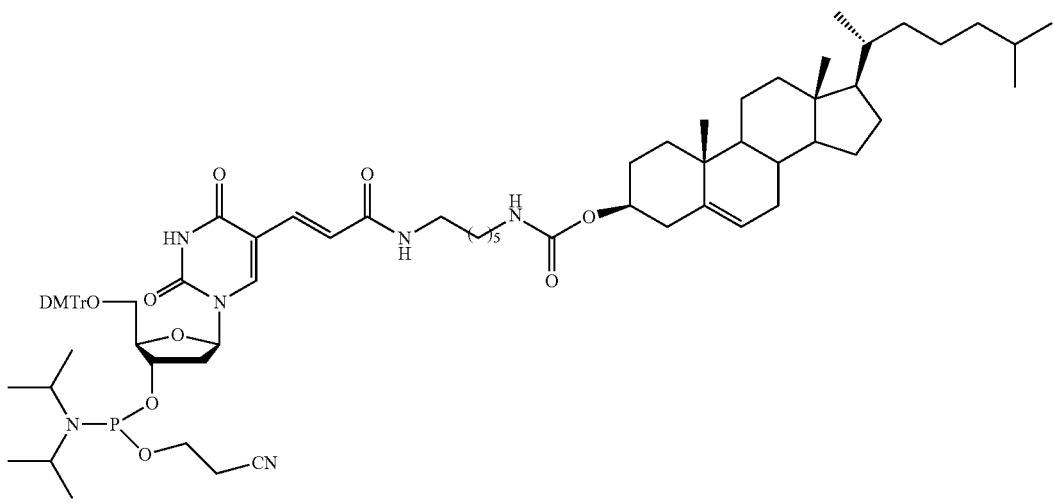
216a
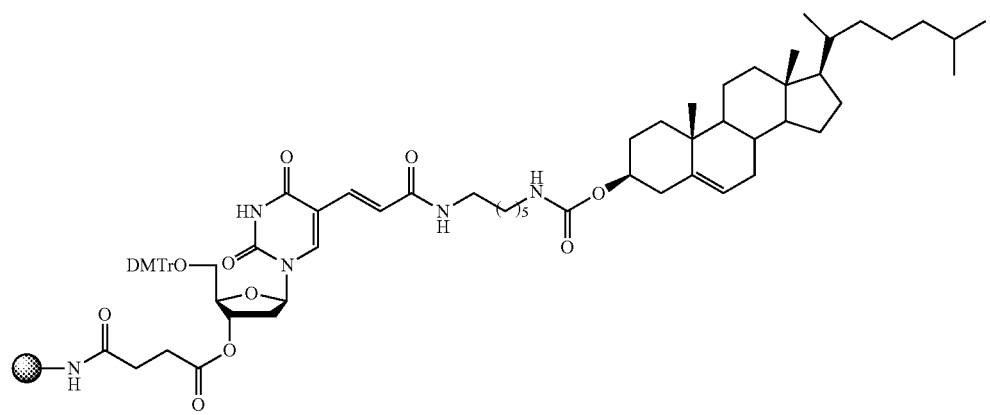
215a
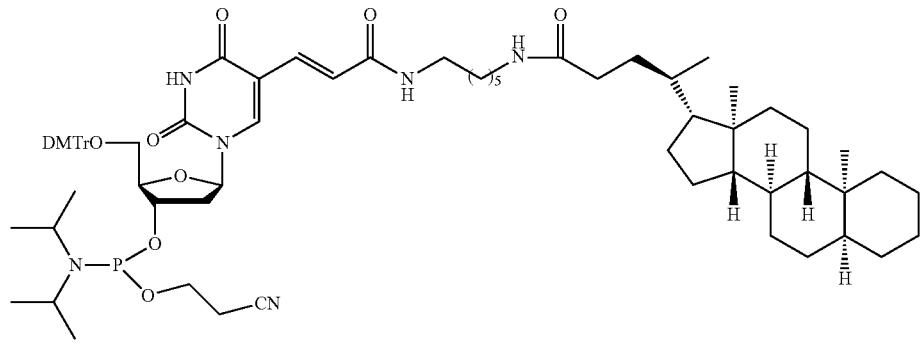
216b

-continued
2
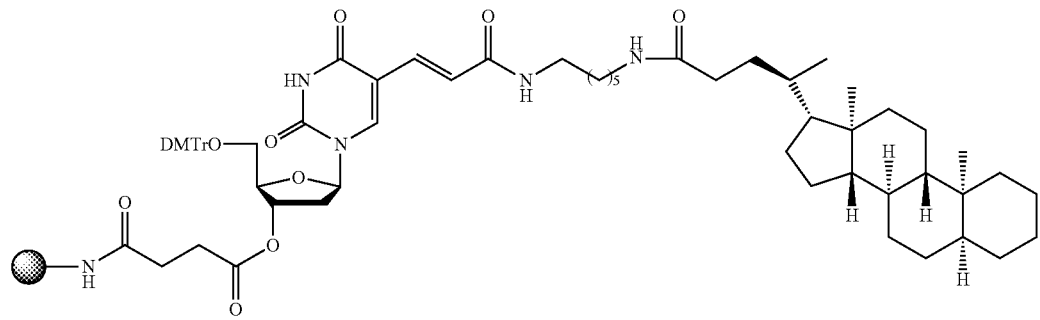
215b
3
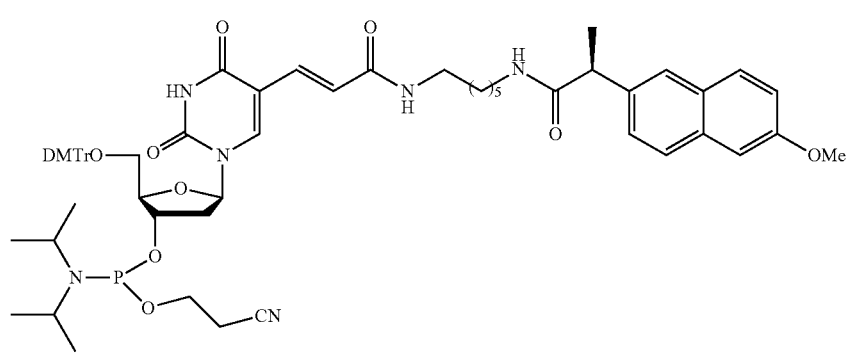
243a
4
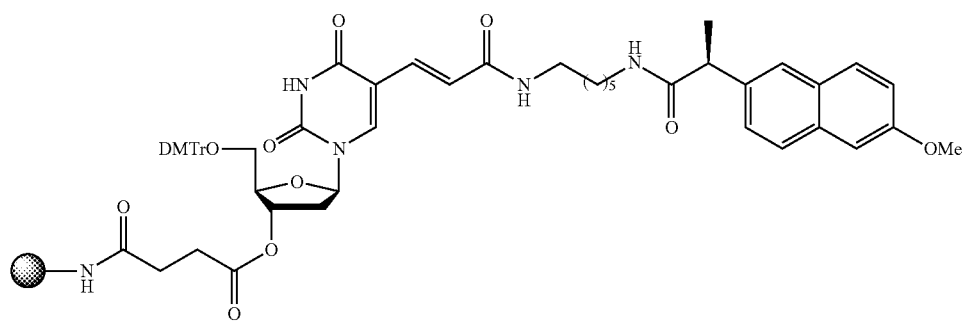
242a
5
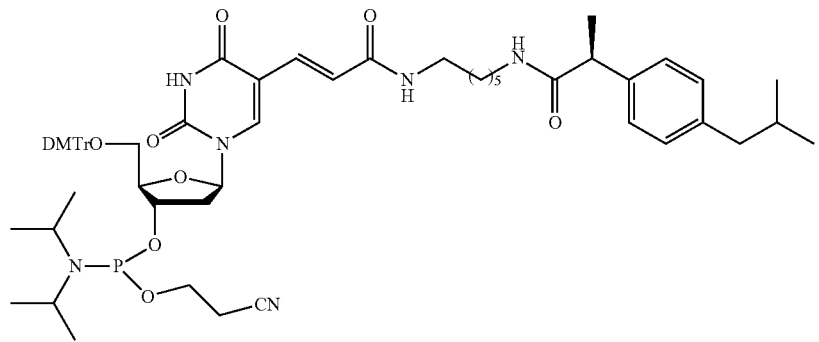
243b 6
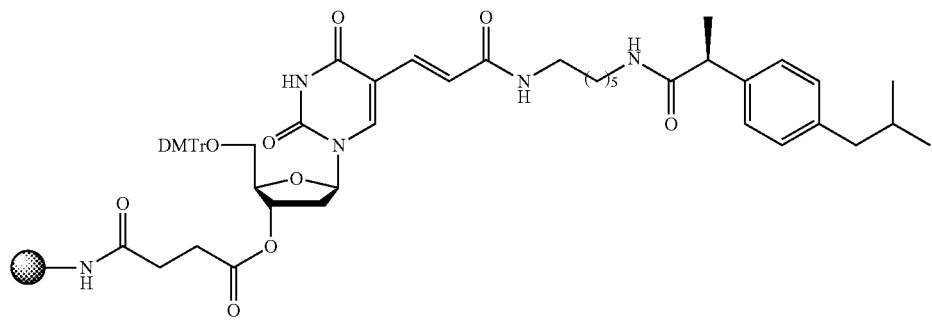
242b
7
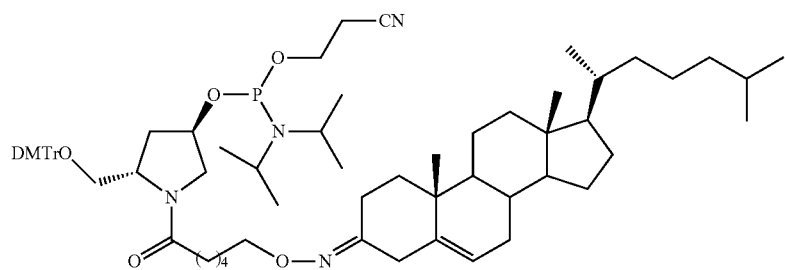
236a
8
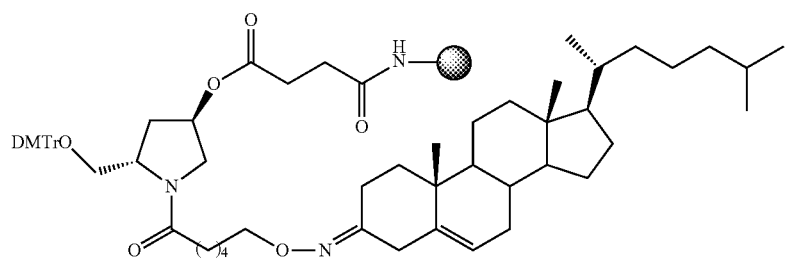
237a
9
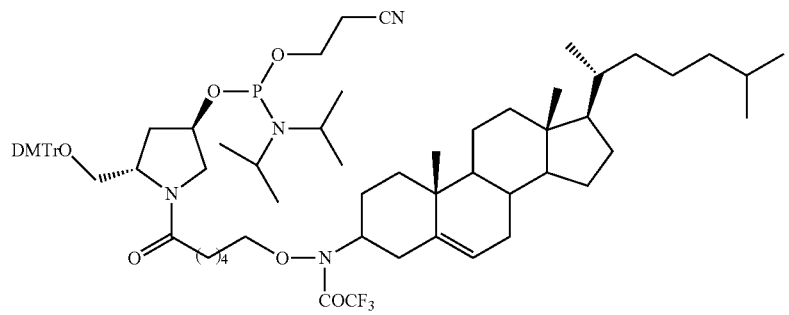
239a

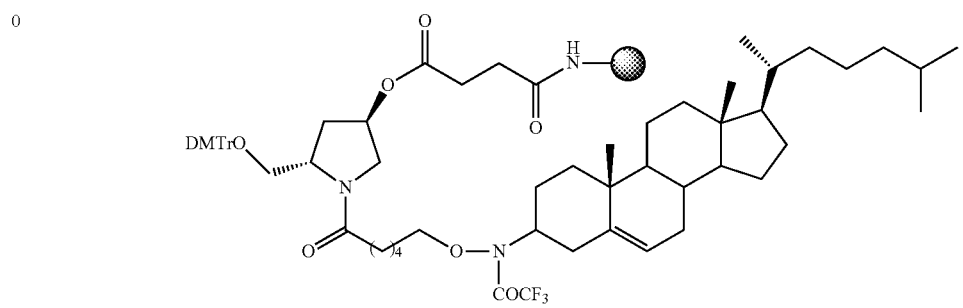
240a
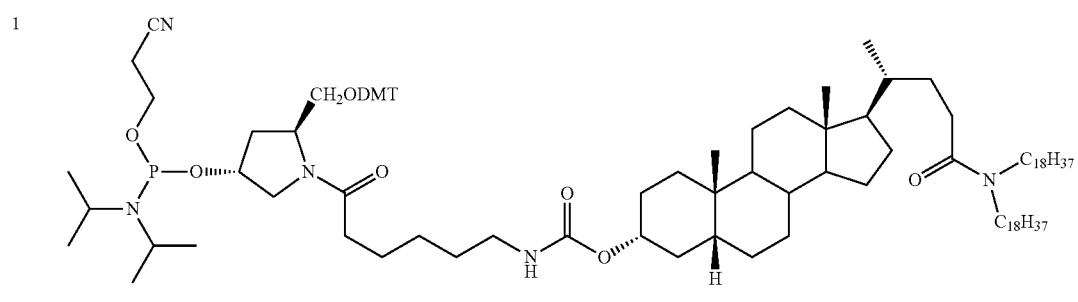
85
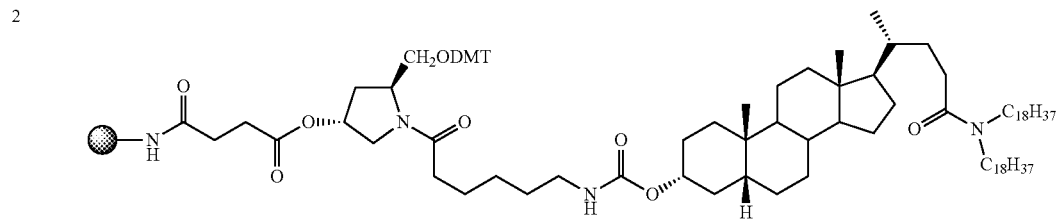
87
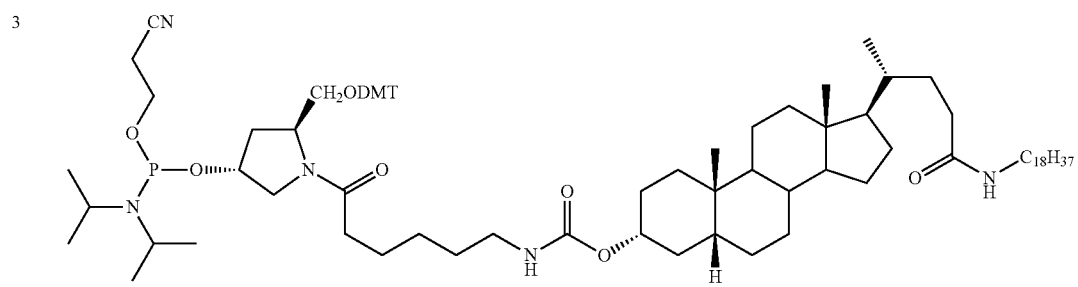
91
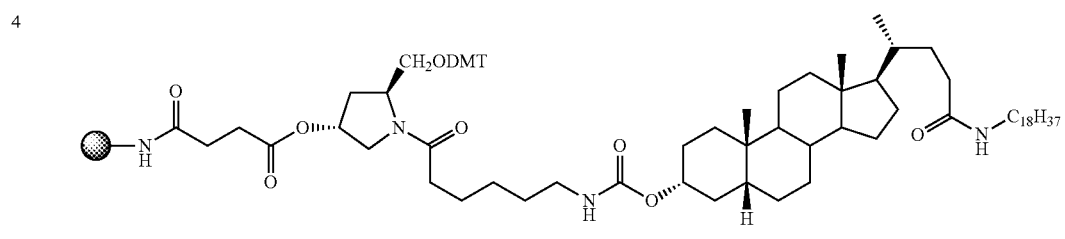
93

5. 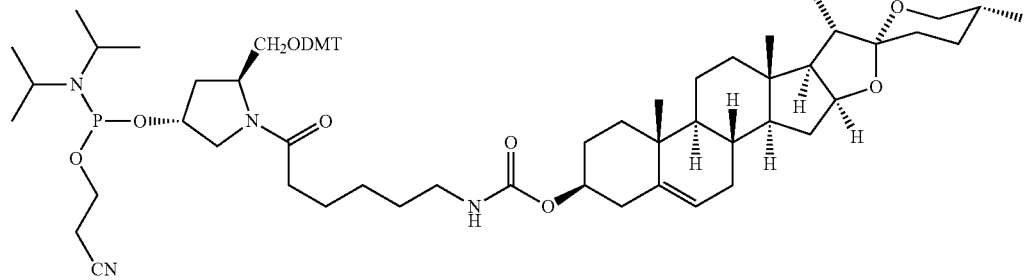
106
Diosgenin
6. 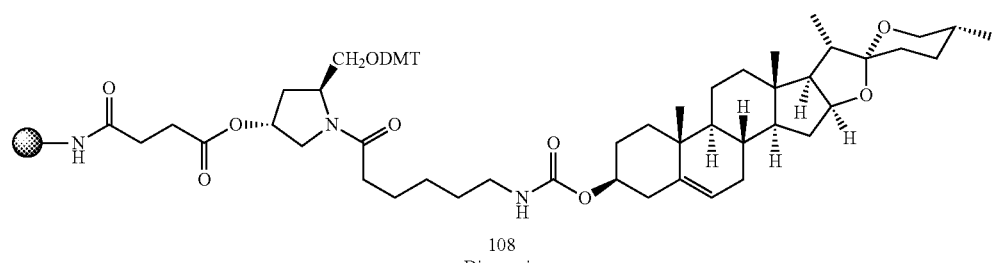
108
Diosgenin
7. 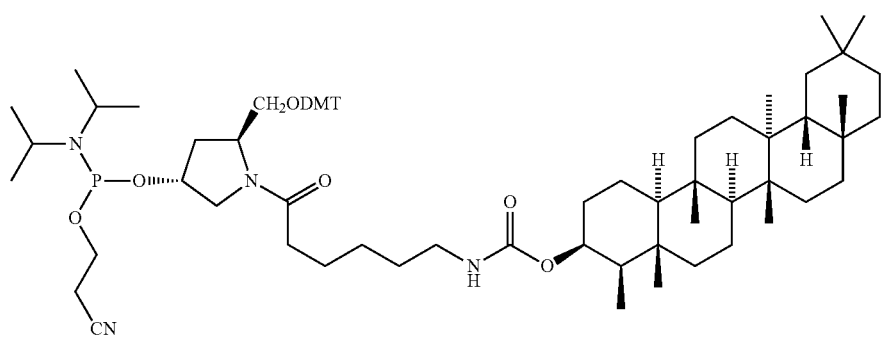
112
Epifriedelanol
8. 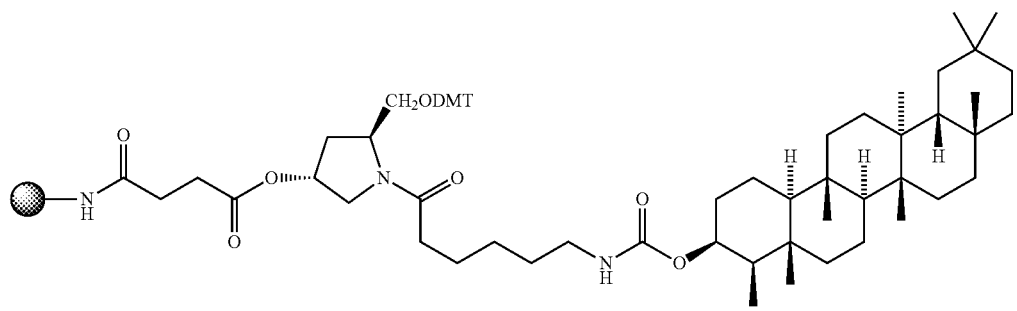
114
Epifriedelanol Conjugation of Ligands to Oligonucleotide Agents The conjugation of a ligand to an oligonucleotide agent, e.g., an oligonucleotide agent that targets an miRNA or pre-miRNA can have a favorable effect on the modulating effect of the agent. For example, the agent can improve pharmacokinetics, stability, and/or tissue specificity.

In some embodiments, an oligonucleotide agent (referred to as "NA" in formula OT-I through OT-IV below, e.g., RNA, DNA, chimeric RNA-DNA, DNA-RNA, RNA-DNA-RNA, or DNA-RNA-DNA) can be chemically modified by conjugating a moiety that includes a ligand having one or more chemical linkages for attachment of the ligand (L) to the oligonucleotide or nucleic acid. The ligand of an oligonucleotide agent can be coupled by one or both of a tether and linker. In the diagram below, exemplary chemical linkages are represented as X, Y, and Z. These can be part of the tether or linker.

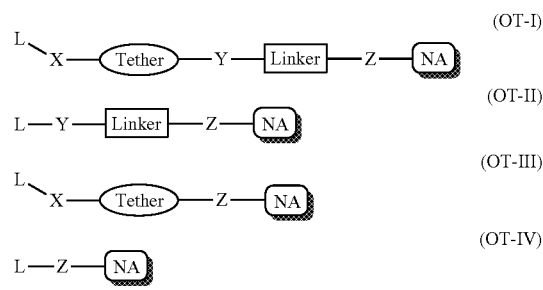

Ligands can be attached at one or both of the 3' end, the 5' end, and internal positions. In certain embodiments, the oligonucleotide agent can be chemically modified by conjugating one or more moieties having formula OT-I. Table 4, shows a variety of conjugates.

TABLE 4

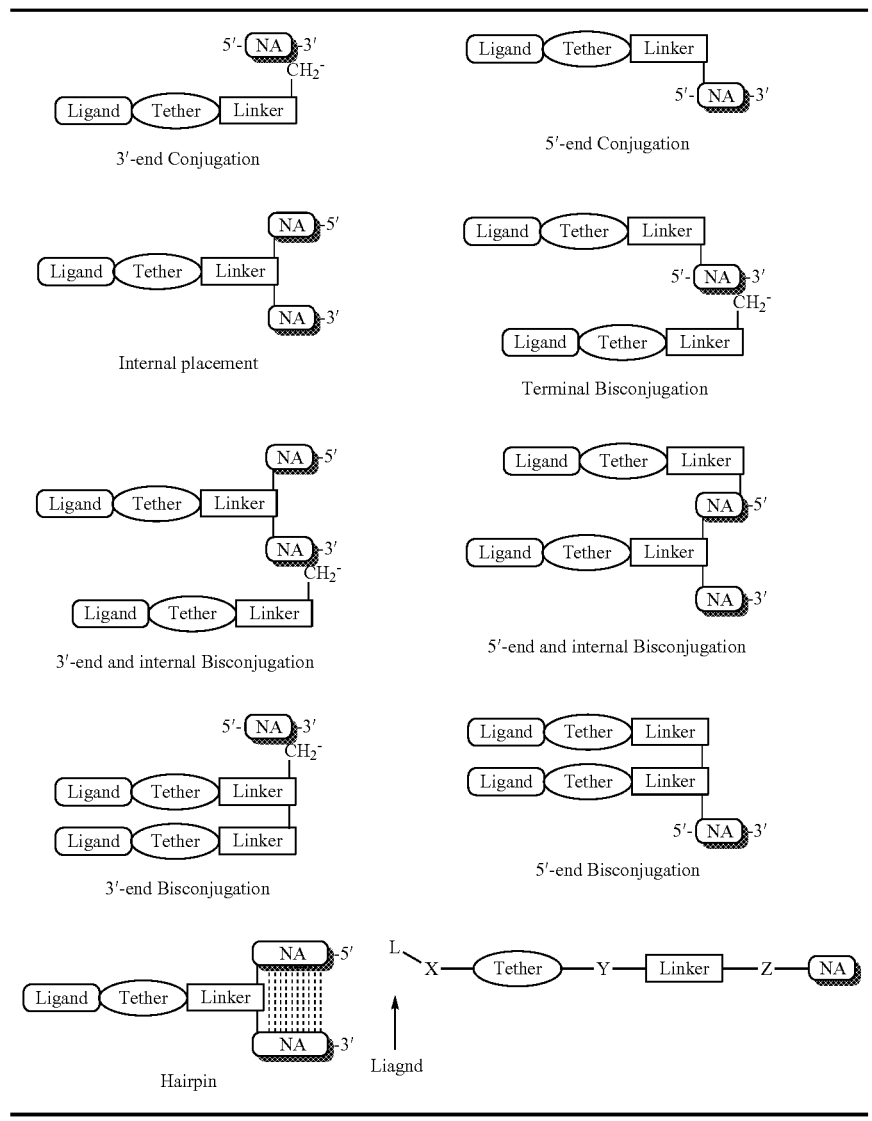

Exemplary ligands are listed in Table 5 and are discussed elsewhere herein. The exemplary ligands (L) shown in Table 5 are preferred.

TABLE 5

L—X—(Tether)—Y—[Linker]—Z—(NA)

L =
Cholesterol
Thiocholesterol
5β-Cholanic Acid
Cholic acid
Lithocholic acid
Biotin
Vitamin E
Naproxen
Ibuprofen
Amines (mono, di, tri, tetraalkyl or aryl)
Folate
Sugar (N-Acetylgalactosamine, galactosamine, galactose, Mannose)
—$(CH_2)_nNQ_1Q_2$, where n = 0-40, $Q_1$, $Q_2$ = H, Me or Et; $Q_1$ = H, $Q_2$ = H, Me, Et or aryl
—$(CH_2)_pCH$=$CH(CH_2)_qNQ_1Q_2$, where p and/or q = 0-40, $Q_1$, $Q_2$ = H, Me or Et; $Q_1$ = H, $Q_2$ = H, Me, Et or aryl with E and/or Z configuration
—$(CH_2)_pCH$≡$CH(CH_2)_qNQ_1Q_2$, where p and/or q = 0-40, $Q_1$, $Q_2$ = H, Me or Et; $Q_1$ = H, $Q_2$ = H, Me, Et or aryl
—$(CH_2)_pCH$=$CH(CH_2)_qCH$=$CH(CH_2)_rNQ_1Q_2$, where p, q and/or r = 0-40, $Q_1$, $Q_2$ = H, Me or Et; $Q_1$ = H, $Q_2$ = H, Me, Et or aryl with E and/or Z configuration
—$O(CH_2)_m(OCH_2CH_2)_n$—OR, where m, n = 0-40 and R = H, Me, $NQ_1Q_2$, —C(O)NR'R" —C(S)NR'R"
—$NH(CH_2)_m(OCH_2CH_2)_n$—OR, where m, n = 0-40 and R = H, Me, $NQ_1Q_2$, —C(O)NR'R" —C(S)NR'R"
—$O(CH_2)_m(NHCH_2CH_2)_n$—R, where m, n = 0-40 and R = H, OH, Me, $NQ_1Q_2$, —C(O)NR'R" —C(S)NR'R"
—$NH(CH_2)_m(NHCH_2CH_2)_n$—R, where m, n = 0-40 and R = H, OH, Me, $NQ_1Q_2$, —C(O)NR'R" —C(S)NR'R"
Dialkylglycerol (sn3, sn1, sn2 and racemic) with number of methylene varies from 0-40
DIacylglycerol (sn3, sn1, sn2 and racemic) with number of methylene varies from 0-40
Dialkylglycerol (sn3, sn1, sn2 and racemic) with number of methylene varies from 0-40 and the alkyl chian contains one or more double bonds with E and/or Z isomers
DIacylglycerol (sn3, sn1, sn2 and racemic) with number of methylene varies from 0-40 and the alkyl chian contains one or more double bonds with E and/or Z isomers
Lipids Exemplary X, Y, and Z moieties are shown in Table 6. The X, Y, and Z moieties can be selected independently of one another.

TABLE 6

L—X—(Tether)—Y—[Linker]—Z—(NA)

| X = | Y = | Z = |
|---|---|---|
| —NHC(O)— | —NHC(O)— | —NHC(O)— |
| —C(O)NH— | —C(O)NH— | —C(O)NH— |
| —OC(O)NH— | —OC(O)NH— | —OC(O)NH— |
| —NHC(O)O— | —NHC(O)O— | —NHC(O)O— |
| —O— | —O— | —O— |
| —S— | —S— | —S— |
| —SS— | —SS— | —SS— |
| —S(O)— | —S(O)— | —S(O)— |
| —S(O$_2$)— | —S(O$_2$)— | —S(O$_2$)— |
| —NHC(O)NH— | —NHC(O)NH— | —NHC(O)NH— |
| —NHC(S)NH— | —NHC(S)NH— | —NHC(S)NH— |
| —C(O)O— | —C(O)O— | —C(O)O— |
| —OC(O)— | —OC(O)— | —OC(O)— |
| —NHC(S)— | —NHC(S)— | —NHC(S)— |
| —NHC(S)O— | —NHC(S)O— | —NHC(S)O— |
| —C(S)NH— | —C(S)NH— | —C(S)NH— |

TABLE 6-continued

L–X–(Tether)–Y–[Linker]–Z–(NA)

| X = | Y = | Z = |
|---|---|---|
| —OC(S)NH— | —OC(S)NH— | —OC(S)NH— |
| —NHC(S)O— | —NHC(S)O— | —NHC(S)O— |
| —CH$_2$— | —CH$_2$— | —CH$_2$— |
| —CH$_2$CH=CH— | —CH$_2$CH=CH— | —CH$_2$CH=CH— |
| —C(O)CH=CH— | —C(O)CH=CH— | —C(O)CH=CH— |
| —NH—CH$_2$CH=CH— | —NH—CH$_2$CH=CH— | —NH—CH$_2$CH=CH— |
| —O—P(O)(OH)—O— | —O—P(O)(OH)—O— | —O—P(O)(OH)—O— |
| —O—P(S)(OH)—O— | —O—P(S)(OH)—O— | —O—P(S)(OH)—O— |
| —O—P(S)(SH)—O— | —O—P(S)(SH)—O— | —O—P(S)(SH)—O— |
| —S—P(O)(OH)—O— | —S—P(O)(OH)—O— | —S—P(O)(OH)—O— |
| —O—P(O)(OH)—S— | —O—P(O)(OH)—S— | —O—P(O)(OH)—S— |
| —S—P(O)(OH)—S— | —S—P(O)(OH)—S— | —S—P(O)(OH)—S— |
| —O—P(S)(OH)—S— | —O—P(S)(OH)—S— | —O—P(S)(OH)—S— |
| —S—P(S)(OH)—O— | —S—P(S)(OH)—O— | —S—P(S)(OH)—O— |
| —O—P(O)(R)—O— | —O—P(O)(R)—O— | —O—P(O)(R)—O— |
| —O—P(S)(R)—O— | —O—P(S)(R)—O— | —O—P(S)(R)—O— |
| —S—P(O)(R)—O— | —S—P(O)(R)—O— | —S—P(O)(R)—O— |
| —S—P(S)(R)—O— | —S—P(S)(R)—O— | —S—P(S)(R)—O— |
| —S—P(O)(R)—S— | —S—P(O)(R)—S— | —S—P(O)(R)—S— |
| —O—P(S)(R)—S— | —O—P(S)(R)—S— | —O—P(S)(R)—S— |

R = Alkyl, fluroalkyl, aryl or aralkyl

Exemplary tethers are shown in Table 7.

L–X–(Tether)–Y–[Linker]–Z–(NA)

Tether:

—(CH$_2$)$_n$—, where n = 1-40

—(CH$_2$—CH$_2$O)$_n$—, where n = 1-20

—O(CH$_2$—CH$_2$O)$_n$—, where n = 1-20

—(CH$_2$—CH$_2$NH)$_n$—, where n = 1-20

—NH(CH$_2$—CH$_2$NH)$_n$—, where n = 1-20

—(CH$_2$)$_l$[(CH=CH)$_m$(CH$_2$)$_n$]$_p$(CH=CH)$_q$(CH$_2$)$_r$—, where l, m, n, p, q and/or r = 0-20

—(CH$_2$)$_l$(C≡C)$_m$(CH$_2$)$_n$]$_p$(C≡C)$_q$(CH$_2$)$_r$—, where l, m, n, p, q and/or r = 0-20

Linker =

| 3'-end | 5'-end | interior |
|---|---|---|

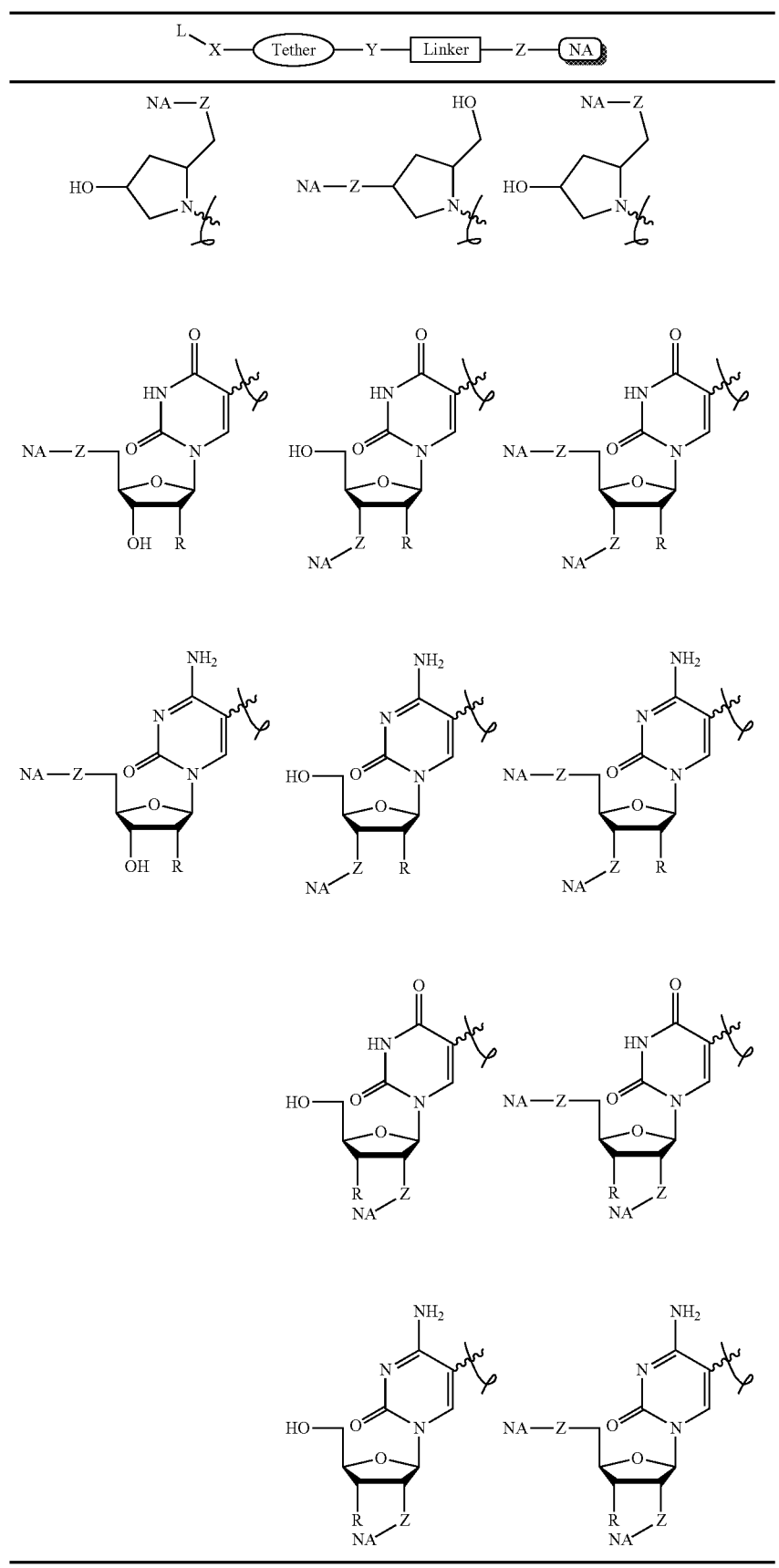

Compounds described herein can be prepared by methods described herein or by conventional methods from commercially available reagents and starting materials.

Compound 1 is prepared as reported by Fraser et al. (Tetrahedron Lett. 41:1523, 2000). Steps (ii), (iii) (a), (iii) (c), (iv), (v) and (vii) are performed according to literature procedure (Fraser et al., Tetrahedron Lett. 41:1523, 2000). Step (iii) (b) and (v) (b) are performed as reported in the literature (Bioorg. Med. Chem. Lett. 13:1713, 2003). Step (iv) is performed as reported in the literature (Corey and Venkateswarlu, J. Am. Chem. Soc. 94:6190, 1972).

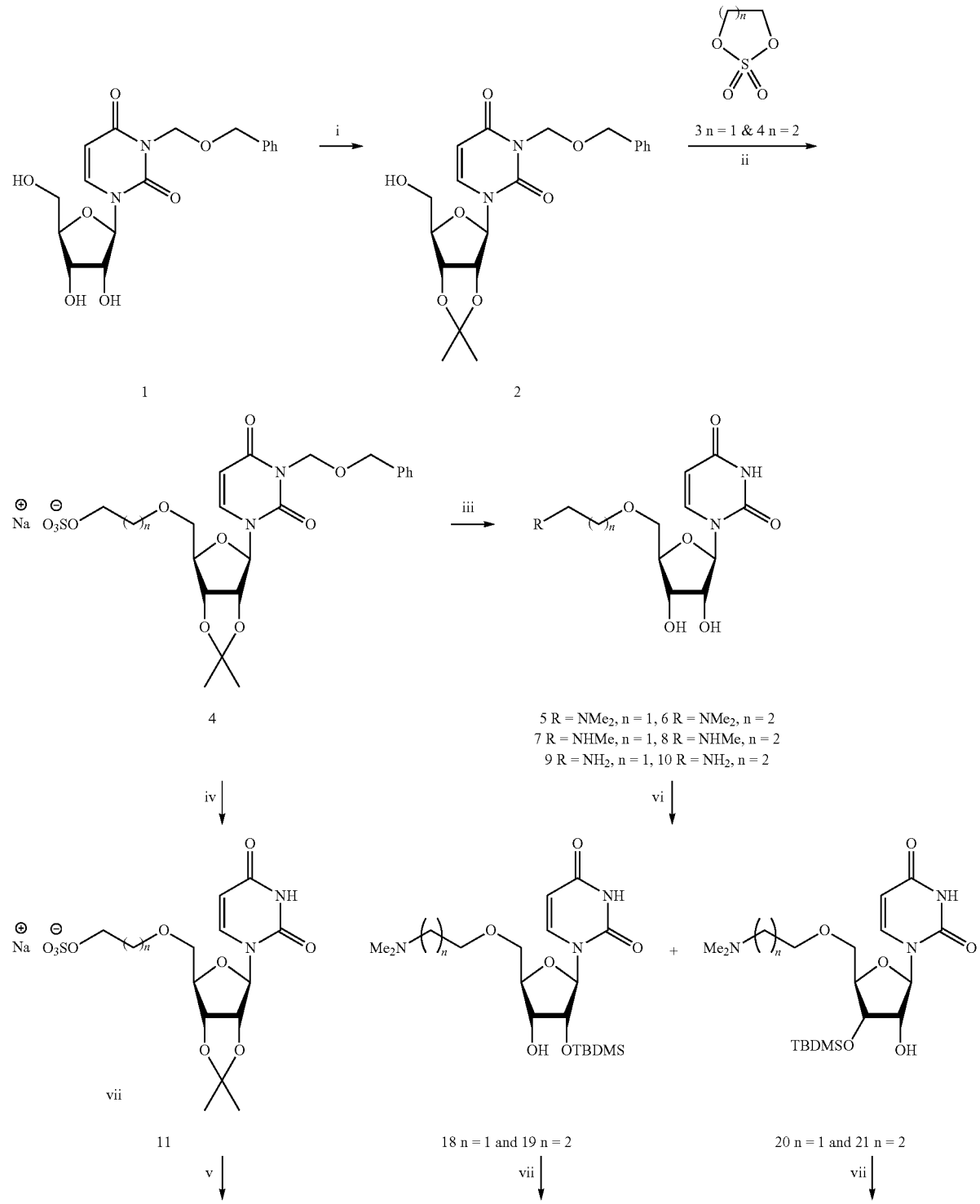

Scheme 1$^a$

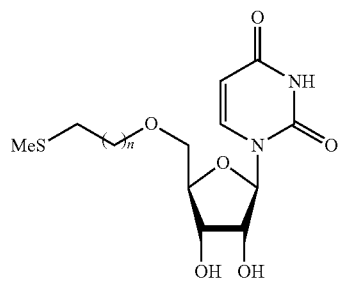
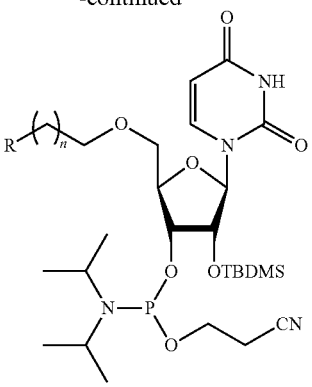
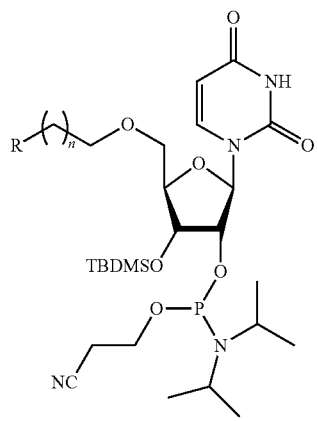

12 n = 1 and 13 n = 2

22 R = SMe, n = 1
23 R = SMe, n = 2
24 R = NMe$_2$, n = 1
25 R = NMe$_2$, n = 2

26 R = SMe, n = 1
27 R = SMe, n = 2
28 R = NMe$_2$, n = 1
29 R = NMe$_2$, n = 2

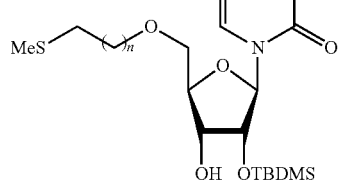
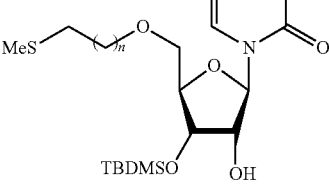

14 n = 1 and 15 n = 2

16 n = 1 and 17 n = 2

$^a$ (i) 2,2-Di-O-methylpropane, PTSA; (ii) NaH/DMF, 3 or 4, -45° C. to rt; (iii) (a) NH$_3$, NH$_2$Me or NHMe$_2$, THF, autoclave, (b) HCOOH—H$_2$O and (c) Pd(OH), EtOH, AcOH, H$_2$ at 55 psi; (iv) Pd(OH), EtOH, AcOH, H$_2$ at 55 psi; (v) NaSMe/DMF, 80° C. and (b) HCOOH—H$_2$O (vi) TBDMS—Cl, Imidazole/Py; (vii) diisopropylamine tetrazolide, 2-cyanoethyl-N,N,N′,N′-tetraisopropylphosphoramidite/CH$_2$Cl$_2$ The synthesis of certain compounds is described in scheme 2, below. Step (i) is performed as reported in Dubowchik and Radia (Tetrahedron Lett., 38:5257, 1997); step (ii) is performed as reported in Corey and Venkateswarlu (J. Am. Chem. Soc. 94:6190, 1972); step (iii) is performed as reported in Fraser et al. (Tetrahedron Lett. 41:1523, 2000) and step (iv) is performed as described in Miller et. al. (Current Protocol in Nucleic Acids Chemistry, 2000, 2.5.1-2.5.36, John Wiley and Sons, Inc.).

Scheme 2$^a$

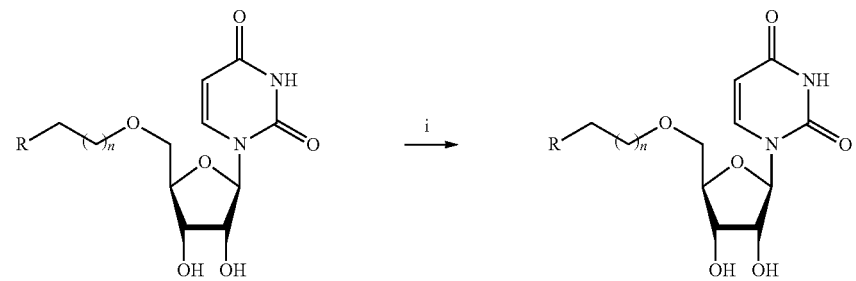

7 R = NHMe, n = 1, 8 R = NHMe, n = 2
9 R = NH$_2$, n = 1, 10 R = NH$_2$, n = 2

30 R′ = NHMMTr, n = 1, 31 R′ = NHMMTr, n = 2
32 R = NMeMMTr, n = 1, 33 R = NMeMMTr, n = 2

147

-continued

148

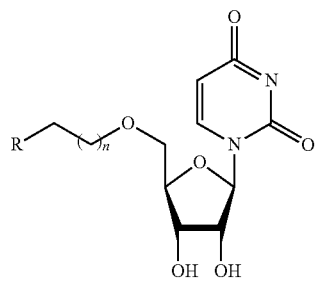

50 R' = NHMMTr, n = 1,
51 R' = NHMMTr, n = 2
52 R = NMeMMTr, n = 1,
53 R = NMeMMTr, n = 2

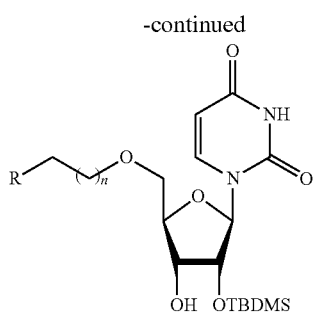

34 R' = NHMMTr, n = 1,
35 R' = NHMMTr, n = 2
36 R = NMeMMTr, n = 1,
37 R = NMeMMTr, n = 2

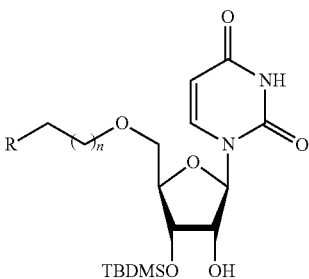

38 R' = NHMMTr, n = 1,
39 R' = NHMMTr, n = 2
40 R = NMeMMTr, n = 1,
41 R = NMeMMTr, n = 2 ii ↓     iii ↓     iii ↓

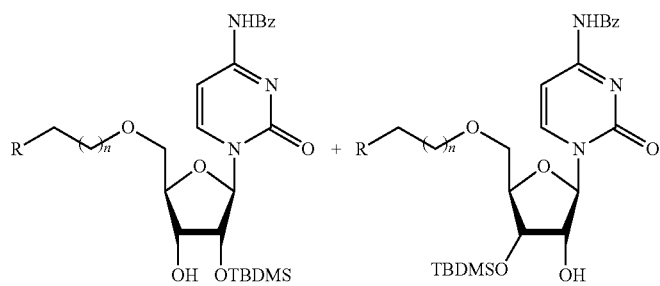

54 R' = NHMMTr, n = 1,
55 R' = NHMMTr, n = 2
56 R = NMeMMTr, n = 1,
57 R = NMeMMTr, n = 2

58 R' = NHMMTr, n = 1,
59 R' = NHMMTr, n = 2
60 R = NMeMMTr, n = 1,
61 R = NMeMMTr, n = 2 iii ↓     iii ↓

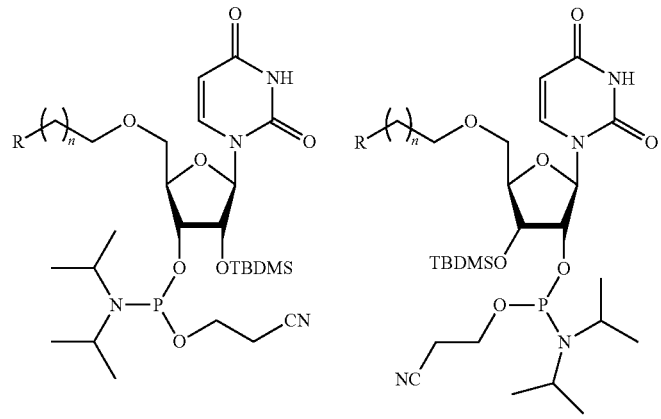

42 R' = NHMMTr, n = 1,
43 R' = NHMMTr, n = 2
44 R = NMeMMTr, n = 1,
45 R = NMeMMTr, n = 2

46 R' = NHMMTr, n = 1,
47 R' = NHMMTr, n = 2
48 R = NMeMMTr, n = 1,
49 R = NMeMMTr, n = 2

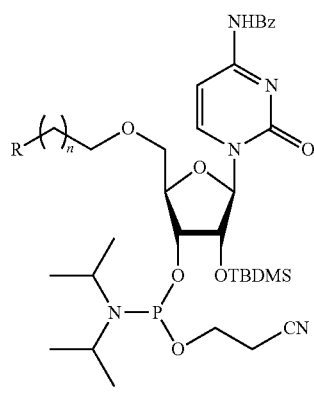

62 R' = NHMMTr, n = 1,
63 R' = NHMMTr, n = 2
64 R = NMeMMTr, n = 1,
65 R = NMeMMTr, n = 2

66 R' = NHMMTr, n = 1,
67 R' = NHMMTr, n = 2
68 R = NMeMMTr, n = 1,
69 R = NMeMMTr, n = 2

[a] (i) MMTr—Cl, TEA/$CH_2Cl_2$; (ii) TBDMS—Cl, Imidazole/Py; (iii) diisopropylamine tetrazolide, 2-cyanoethyl-N,N,N',N'-tetraisopropylphosphoramidite/$CH_2Cl_2$
(iv) (a) $Ac_2O$/Py, (b) Triazole, TEA, 4-chlorophenyl dichlorophosphate/MeCN, (c) $NH_4OH$ and (d) Pentaflurophenyl benzoate/Py The synthesis of certain compounds is performed as described in Scheme 3, below. Step (i) is performed as described in Miller et al. (Current Protocol in Nucleic Acids Chemistry, 2000, 2.5.1-2.5.36, John Wiley and Sons, Inc.); step (ii) is performed as reported in the Corey and Venkateswarlu (J. Am. Chem. Soc. 94:6190, 1972) and step (iii) is performed as reported by Fraser et al. (Tetrahedron Lett. 41:1523, 2000).

Scheme 3[a]

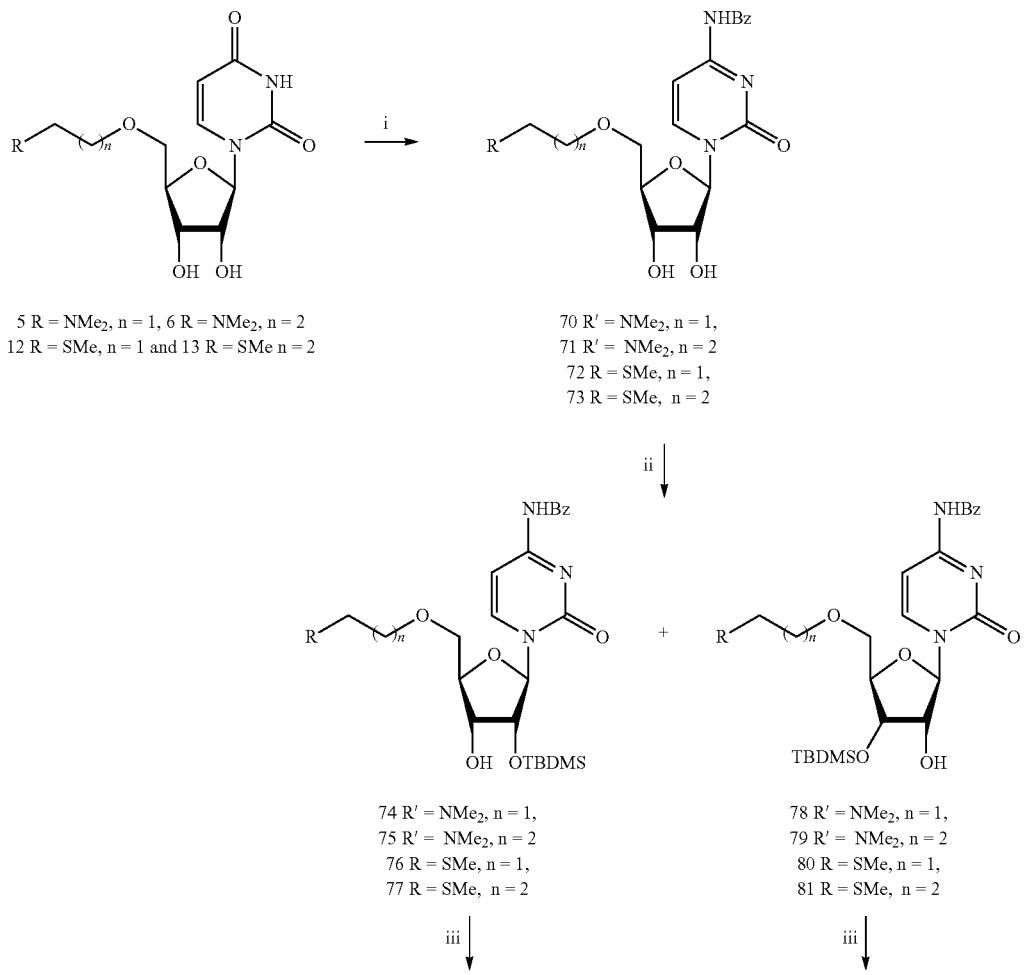

5 R = $NMe_2$, n = 1, 6 R = $NMe_2$, n = 2
12 R = SMe, n = 1 and 13 R = SMe n = 2

70 R' = $NMe_2$, n = 1,
71 R' = $NMe_2$, n = 2
72 R = SMe, n = 1,
73 R = SMe, n = 2

74 R' = $NMe_2$, n = 1,
75 R' = $NMe_2$, n = 2
76 R = SMe, n = 1,
77 R = SMe, n = 2

78 R' = $NMe_2$, n = 1,
79 R' = $NMe_2$, n = 2
80 R = SMe, n = 1,
81 R = SMe, n = 2

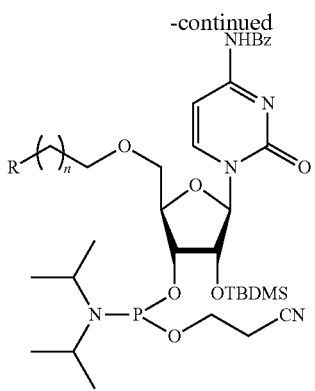
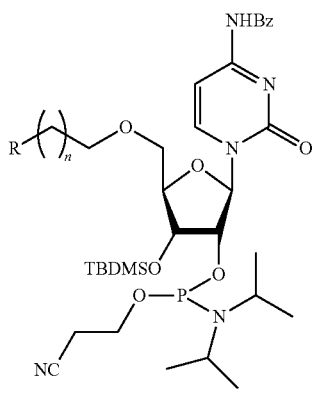

82 R' = NMe₂, n = 1,
83 R' = NMe₂, n = 2
84 R = SMe, n = 1,
85 R = SMe, n = 2

86 R' = NMe₂, n = 1,
87 R' = NMe₂, n = 2
88 R = SMe, n = 1,
89 R = SMe, n = 2

$^a$ (i) (a) Ac₂O/Py, (b) Triazole, TEA, 4-chlorophenyl dichlorophosphate/MeCN, (c) NH₄OH and (d) Pentafluorophenyl benzoate/Py (ii) TBDMS—Cl, Imidazole/Py; (iii) diisopropylamine tetrazolide, 2-cyanoethyl-N,N,N',N'-tetraisopropylphosphoramidite/CH₂Cl₂

The synthesis of certain compounds is performed as described in Scheme 4 below. Step (ii) is performed as reported in Corey and Venkateswarlu (J. Am. Chem. Soc. 94:6190, 1972) and step (iii) is performed as reported by Fraser et al. (Tetrahedron Lett. 41:1523, 2000).

Scheme 4$^a$

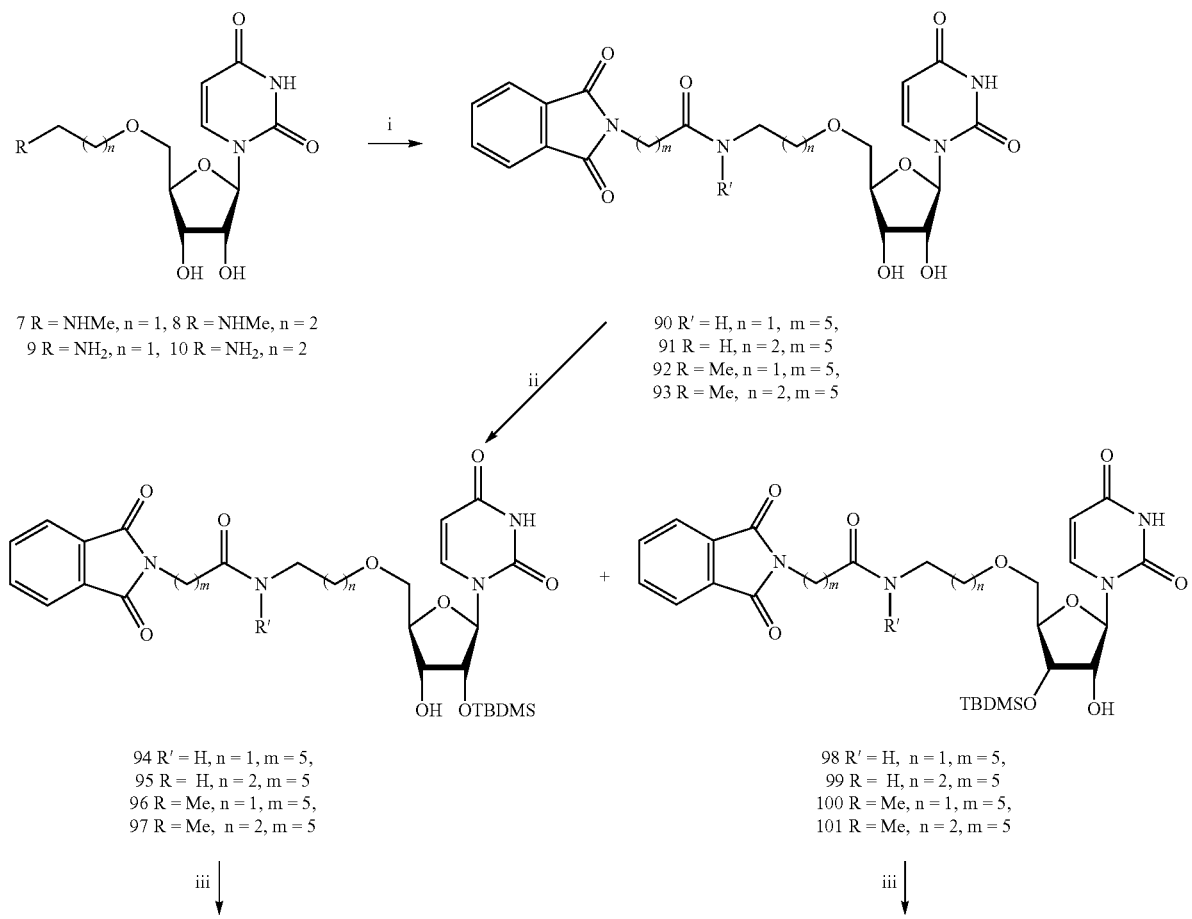

7 R = NHMe, n = 1, 8 R = NHMe, n = 2
9 R = NH₂, n = 1, 10 R = NH₂, n = 2

90 R' = H, n = 1, m = 5,
91 R = H, n = 2, m = 5
92 R = Me, n = 1, m = 5,
93 R = Me, n = 2, m = 5

94 R' = H, n = 1, m = 5,
95 R = H, n = 2, m = 5
96 R = Me, n = 1, m = 5,
97 R = Me, n = 2, m = 5

98 R' = H, n = 1, m = 5,
99 R = H, n = 2, m = 5
100 R = Me, n = 1, m = 5,
101 R = Me, n = 2, m = 5

-continued

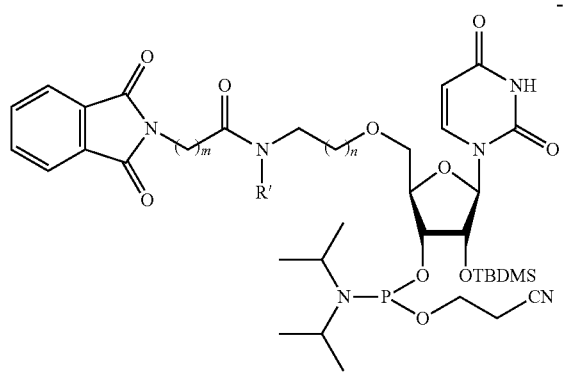

102 R' = H, n = 1, m = 5,
103 R = H, n = 2, m = 5
104 R = Me, n = 1, m = 5,
105 R = Me, n = 2, m = 5

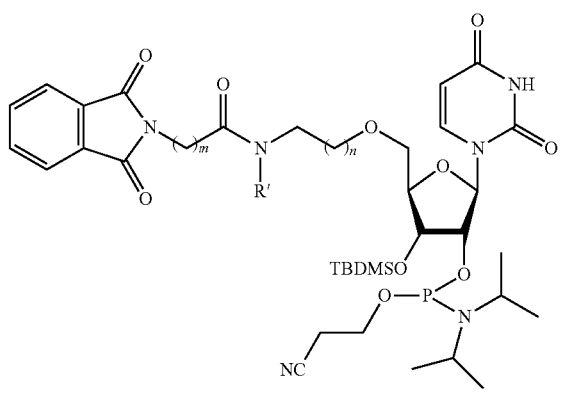

106 R' = H, n = 1, m = 5,
107 R = H, n = 2, m = 5
108 R = Me, n = 1, m = 5,
109 R = Me, n = 2, m = 5

$^a$ (i) N-Phthalimido-6-aminocaproic acid, DCC, DMAP, HOBT; (ii) TBDMS—Cl, Imidazole/Py; (iii) diisopropylamine tetrazolide, 2-cyanoethyl-N,N,N',N'-tetraisopropylphosphoramidite/CH$_2$Cl$_2$ The synthesis of certain compounds is described in Scheme 5, below. Step (i) is performed as described in Miller et al. (Current Protocol in Nucleic Acids Chemistry, 2000, 2.5.1-2.5.36, John Wiley and Sons, Inc.); step (ii) is performed as described in Corey and Venkateswarlu (J. Am. Chem. Soc. 94:6190, 1972) and step (iii) is performed as reported by Fraser et al. (Tetrahedron Lett. 41:1523, 2000).

Scheme 5$^a$

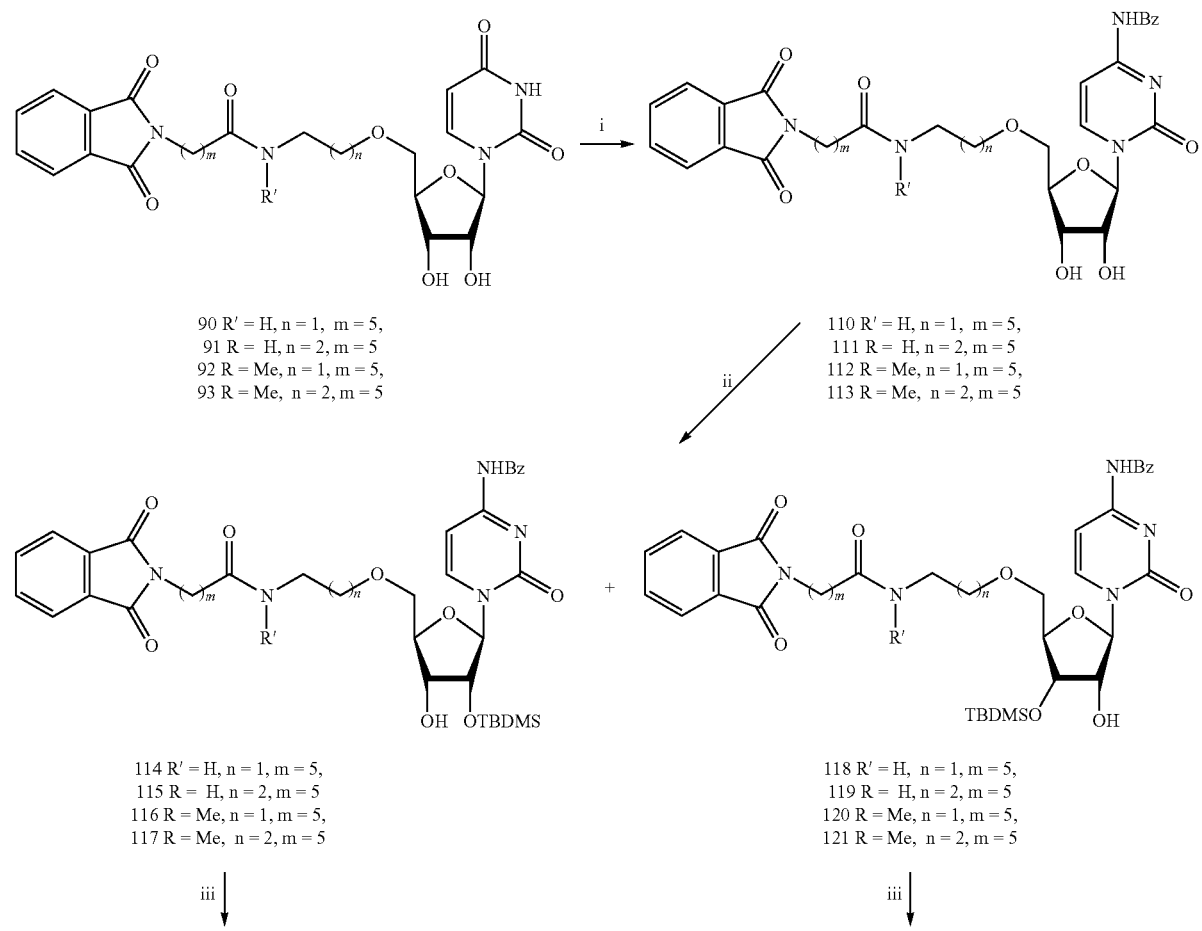

90 R' = H, n = 1, m = 5,
91 R = H, n = 2, m = 5
92 R = Me, n = 1, m = 5,
93 R = Me, n = 2, m = 5

110 R' = H, n = 1, m = 5,
111 R = H, n = 2, m = 5
112 R = Me, n = 1, m = 5,
113 R = Me, n = 2, m = 5

114 R' = H, n = 1, m = 5,
115 R = H, n = 2, m = 5
116 R = Me, n = 1, m = 5,
117 R = Me, n = 2, m = 5

118 R' = H, n = 1, m = 5,
119 R = H, n = 2, m = 5
120 R = Me, n = 1, m = 5,
121 R = Me, n = 2, m = 5

-continued

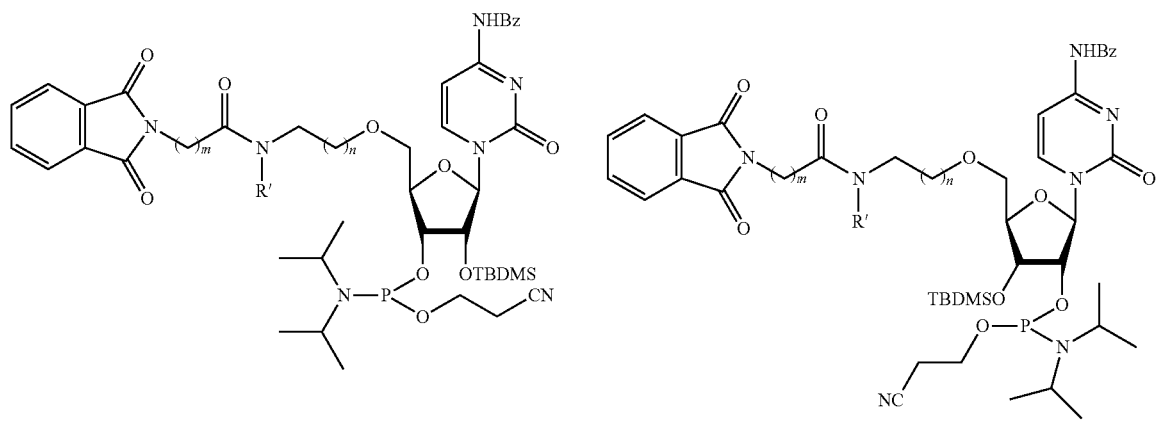

122 R' = H, n = 1, m = 5,
123 R = H, n = 2, m = 5
124 R = Me, n = 1, m = 5,
125 R = Me, n = 2, m = 5

126 R' = H, n = 1, m = 5,
127 R = H, n = 2, m = 5
128 R = Me, n = 1, m = 5,
129 R = Me, n = 2, m = 5

$^a$ (i) (a) Ac$_2$O/Py, (b) Triazole, TEA, 4-chlorophenyl dichlorophosphate/MeCN, (c) NH$_4$OH and (d) Pentaflurophenyl benzoate/Py
(ii) TBDMS—Cl, Imidazole/Py; (iii) diisopropylamine tetrazolide, 2-cyanoethyl-N,N,N',N'-tetraisopropylphosphoramidite/CH$_2$Cl$_2$ The synthesis of certain compounds is described in Scheme 6, below. Compound 130, shown in Scheme 6, is obtained as reported in Liu and Austin, J. Org. Chem. 66:8643, 2001). Step (i) and (iii) (b) are performed as reported in the literature (Chem. Rev., 1954, 54, 1); step (ii) (a) is performed according to literature procedures (J. Org. Chem., 1993, 58, 2334); step (ii) (b), (iii) (a) and (iv) (b) are performed as reported in the literature (Bioorg. Med. Chem. Lett., 2003, 13, 1713); step (iii) (c) is performed as reported in Dubowchik and Radia (Tetrahedron Lett. 38:5257, 1997); step (iv) (a) is performed as reported in the literature (Organic Lett., 2001, 3, 1809); step (v) is performed as reported in Corey and Venkateswarlu (J. Am. Chem. Soc. 94:6190, 1972) and step (vi) is performed as reported by Fraser et al. (Tetrahedron Lett. 41:1523, 2000).

Scheme 6$^a$

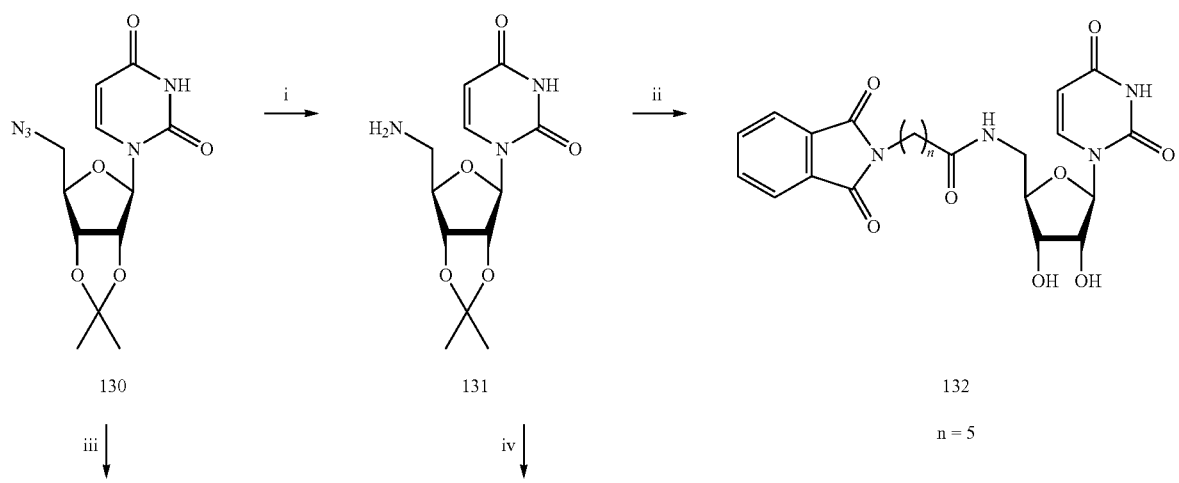

132 n = 5

-continued

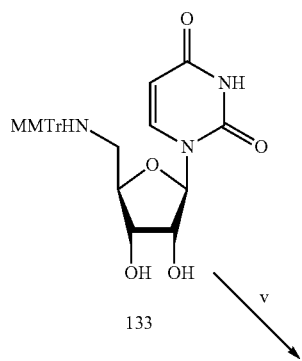

133

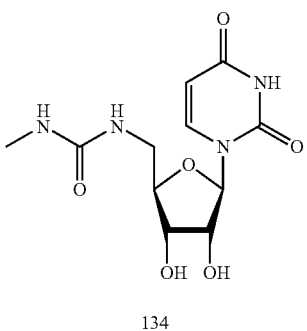

134

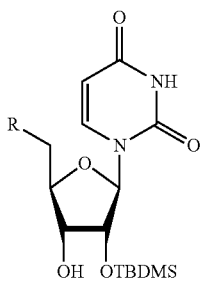

135 R = NHMMTr
136 R = MeNHC(O)NH
137 R = PhthN(CH$_2$)$_5$C(O)NH

+

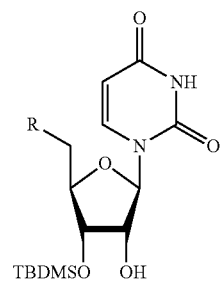

137 R = NHMMTr
138 R = MeNHC(O)NH
139 R = PhthN(CH$_2$)$_5$C(O)NH

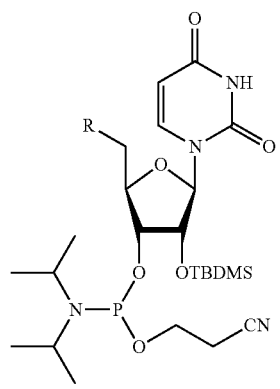

140 R = NHMMTr
141 R = MeNHC(O)NH
142 R = PhthN(CH$_2$)$_5$C(O)NH

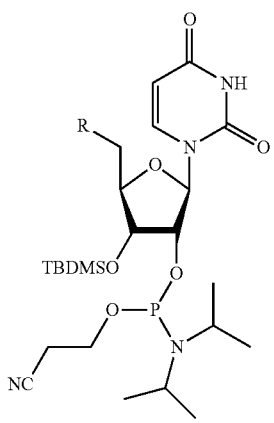

143 R = NHMMTr
144 R = MeNHC(O)NH
145 R = PhthN(CH$_2$)$_5$C(O)NH $^a$ (i) H$_2$, Pd—C (10%)/MeOH 1 atm; (ii) (a) N-Phthalimido-6-aminocaproic acid, DCC, DMAP, HOBT and (b) HCOOH—H$_2$O; (iii) (a) HCOOH—H$_2$O, (b) H$_2$, Pd—C (10%)/MeOH 1 atm and (c) MMTr—Cl, TEA/CH$_2$Cl$_2$; (iv) (a) CDI (carbonyldiimidazole)/THF, MeNH$_2$ or p-Nitrophenylchloroformate, DMAP/Py, MeNH$_2$ and (b) HCOOH—H$_2$O (v) TBDMS—Cl, Imidazole/Py; (vi) diisopropylamine tetrazolide, 2-cyanoethyl-N,N,N′,N′-tetraisopropylphosphoramidite/CH$_2$Cl$_2$ The synthesis of certain compounds is described in Scheme 7, below. Compound 146 is obtained as reported in Liu and Austin (J. Org. Chem., 2001, 66, 8643). Step (i) (b) and (iii) (c) are performed as reported in the literature (Chem. Rev., 1954, 54, 1); step (ii) (a) is performed according to literature procedures (J. Org. Chem., 1993, 58, 2334); step (ii) (b), (iii) (b) and (iv) (b) are performed as reported in the literature (Bioorg. Med. Chem. Lett., 2003, 13, 1713); step (iii) (d) is performed as reported in Dubowchik and Radia (Tetrahedron Lett., 1997, 38, 5257); step (iv) (a) is performed as reported in the literature (Organic Lett., 2001, 3, 1809); step (v) is performed as reported in Corey and Venkateswarlu (J. Am. Chem. Soc., 1972, 94, 6190) and step (vi) is performed as reported by Fraser et al. (Tetrahedron Lett., 2000, 41, 1523)

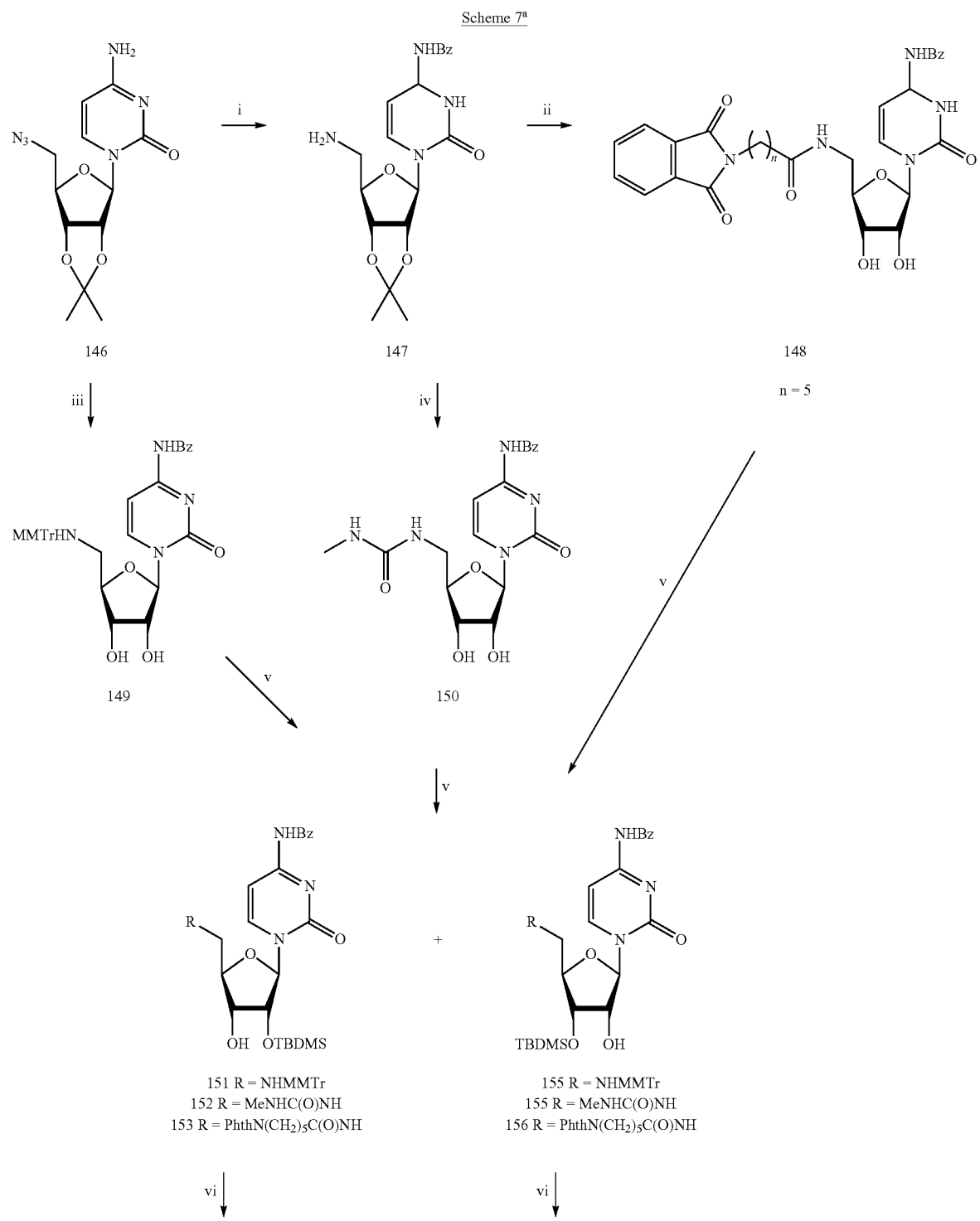

Scheme 7<sup>a</sup>

161

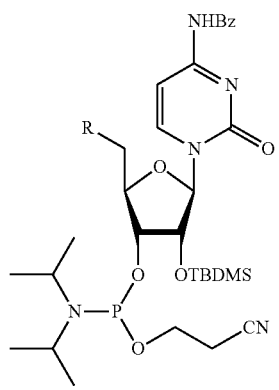

157 R = NHMMTr
158 R = MeNHC(O)NH
159 R = PhthN(CH$_2$)$_5$C(O)NH

162

-continued

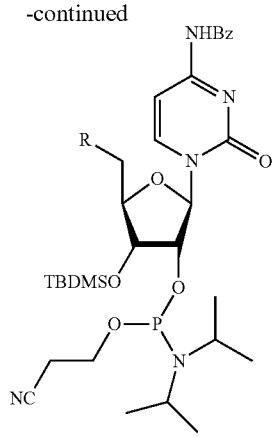

160 R = NHMMTr
161 R = MeNHC(O)NH
162 R = PhthN(CH$_2$)$_5$C(O)NH $^a$ (i) (a)Bz$_2$O/Py and (b) H$_2$Pd—C (10%/MeOH 1 atm; (ii) (a) N-Phthalimido-6-aminocaproic acid, DCC, DMAP, HOBT and (b) HCOOH—H$_2$O; (iii) (a Bz$_2$O/Py, (b) HCOOH—H$_2$O, (c) H$_2$, Pd—C (10%)/MeOH 1 atm and (d) MMTr—Cl/Py; (iv) (a) CDI (carbonyldiimidazole)/THF, MeNH$_2$ or p-Nitrophenylchloroformate, DMAP/Py, MeNH$_2$ and (b) HCOOH—H$_2$O (v) TBDMS—Cl, Imidazole/Py; (vi) diisopropylamine tetrazolide, 2-cyanoethyl-N,N,N',N'-tetraisopropylphosphoramidite/CH$_2$Cl$_2$ The synthesis of certain compounds is described in Scheme 8, below. Compound 163 is obtained as reported in Liu and Austin (J. Org. Chem., 2001, 66, 8643).

Scheme 8$^a$

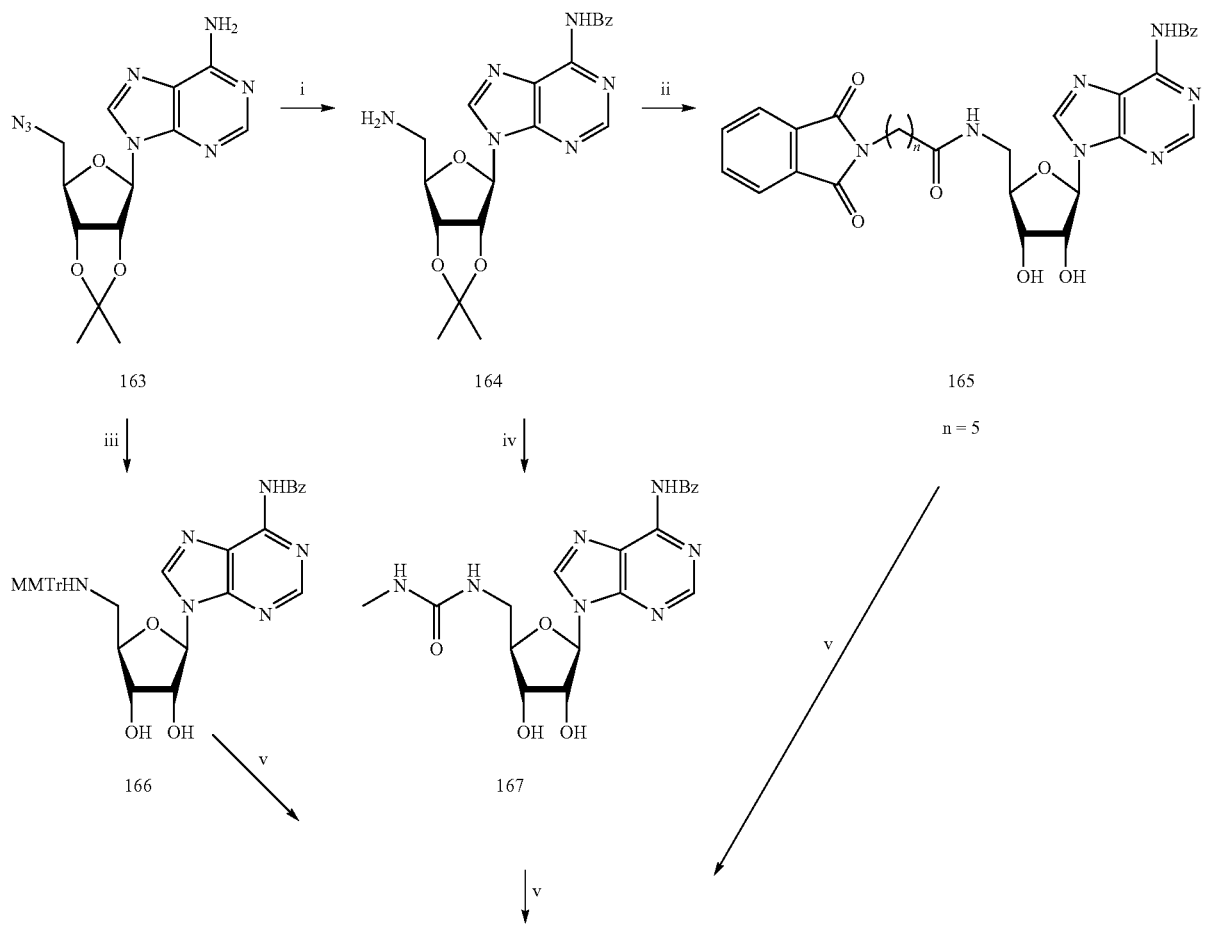

-continued

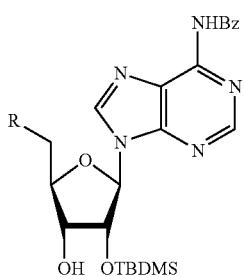 + 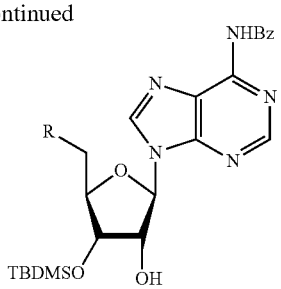

168 R = NHMMTr
169 R = MeNHC(O)NH
170 R = PhthN(CH₂)₅C(O)NH

171 R = NHMMTr
172 R = MeNHC(O)NH
173 R = PhthN(CH₂)₅C(O)NH vi ↓      vi ↓

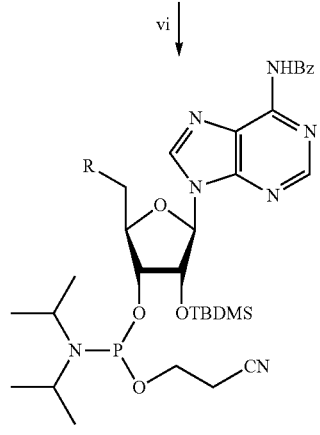 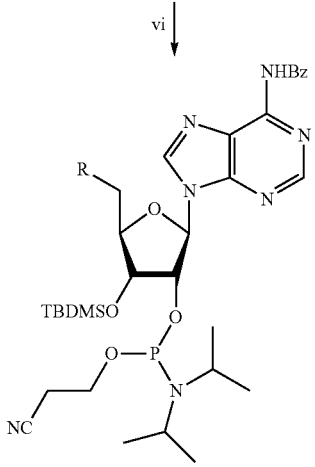

174 R = NHMMTr
175 R = MeNHC(O)NH
176 R = PhthN(CH₂)₅C(O)NH

177 R = NHMMTr
178 R = MeNHC(O)NH
179 R = PhthN(CH₂)₅C(O)NH $^a$ (i) (a) Bz₂O/Py and (b) H₂, Pd——C (10%)/MeOH 1 atm; (ii) (a) N-Phthalimido-6-aminocaproic acid, DCC, DMAP, HOBT and (b)HCOOH——H₂O; (iii) (a) Bz₂O/Py, (b)HCOOH——H₂O, (c) H₂, Pd——C (10%)/MeOH 1 atm and (d) MMTr——Cl/Py; (iv) (a) CDI (carbonyldiimidazole)/THF, MeNH₂ or p-Nitrophenylchloroformate, DMAP/Py, MeNH₂ and (b) HCOOH——H₂O (v) TBDMS——Cl, Imidazole/Py; (vi) diisopropylamine tetrazolide, 2-cyanoethyl-N,N,N',N'-tetraisopropylphosphoramidite/CH₂Cl₂

The synthesis of certain compounds is described in Scheme 9, below. Compound 180 is obtained as reported in Liu and Austin (J. Org. Chem., 2001, 66, 8643).

Scheme 9$^a$

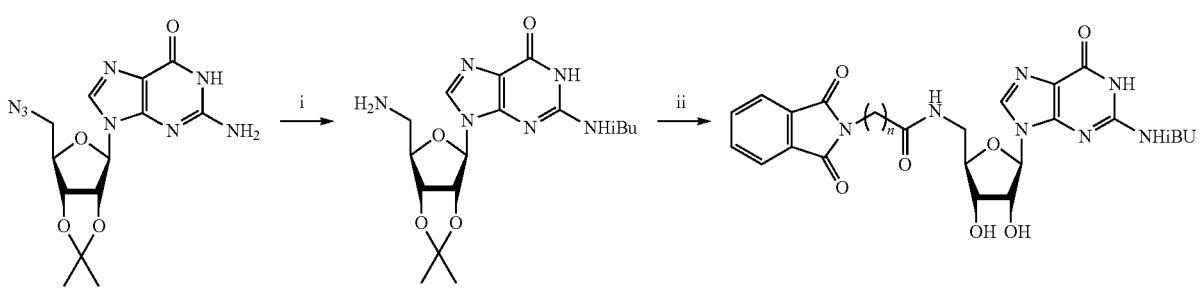

180      181      182 n = 5 iii ↘      iv ↘

-continued

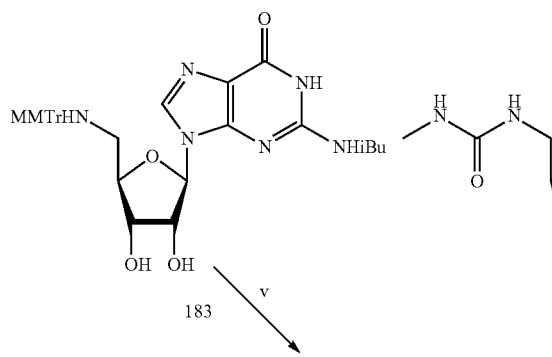

183

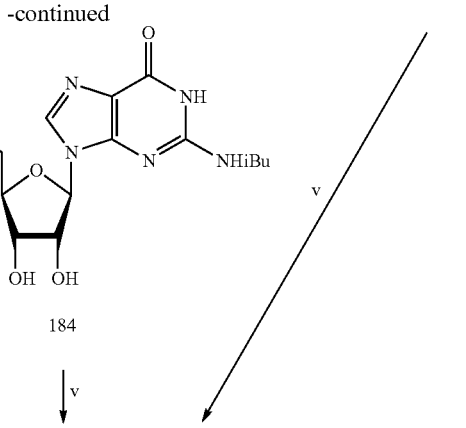

184

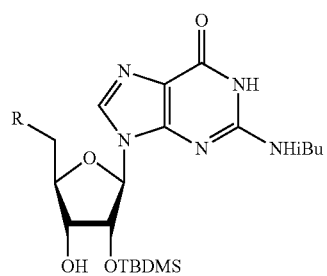

185 R = NHMMTr
186 R = MeNHC(O)NH
187 R = PhthN(CH$_2$)$_5$C(O)NH

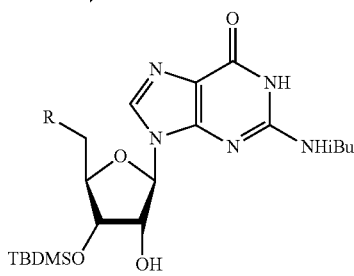

188 R = NHMMTr
189 R = MeNHC(O)NH
190 R = PhthN(CH$_2$)$_5$C(O)NH

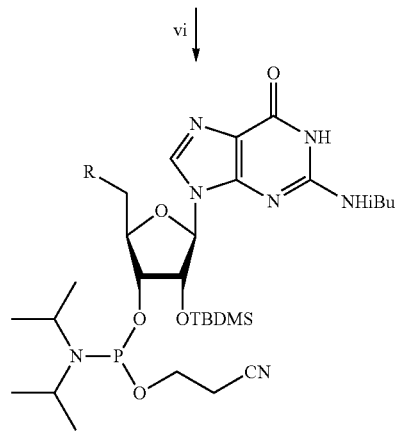

191 R = NHMMTr
192 R = MeNHC(O)NH
193 R = PhthN(CH$_2$)$_5$C(O)NH

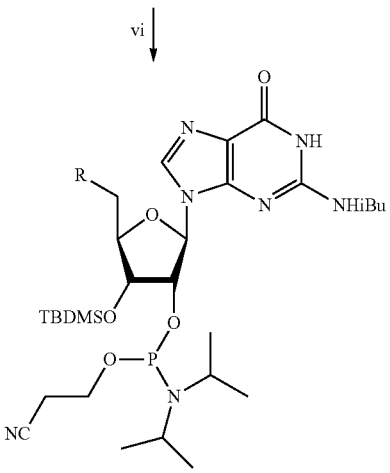

194 R = NHMMTr
195 R = MeNHC(O)NH
196 R = PhthN(CH$_2$)$_5$C(O)NH $^a$ (i) (a) iBuCOCl/Py and (b) H$_2$, Pd——C (10%)/MeOH 1 atm; (ii) (a) N-Phthalimido-6-aminocaproic acid, DCC, DMAP, HOBT and (b)HCOOH——H$_2$O; (iii) (a) iBuCOCl/Py, (b) HCOOH——H$_2$O, (c) H$_2$, Pd——C (10%)/MeOH 1 atm and (d) MMTr——Cl/Py; (iv) (a) CDI (carbonyldiimidazole)/THF, MeNH$_2$ or p-Nitrophenylchloroformate, DMAP/Py, MeNH$_2$ and (b) HCOOH——H$_2$O (v) TBDMS——Cl, Imidazole/Py; (vi) diisopropylamine tetrazolide, 2-cyanoethyl-N,N,N′,N′-tetraisopropylphosphoramidite/CH$_2$Cl$_2$ Ligand-Conjugated Monomer Subunits and Monomers for Oligonucleotide Synthesis Definitions The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —NH(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a $R_3SiO$— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl, and decalin.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, SO$_3$H, sulfate, phosphate, perfluoroalkyl, perfluoroalkoxy, methylenedioxy, ethylenedioxy, carboxyl, oxo, thioxo, imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

As used herein, an "unusual" nucleobase can include any one of the following:

2-methyladeninyl,
N6-methyladeninyl,
2-methylthio-N6-methyladeninyl,
N6-isopentenyladeninyl,
2-methylthio-N6-isopentenyladeninyl,
N6-(cis-hydroxyisopentenyl)adeninyl,
2-methylthio-N6-(cis-hydroxyisopentenyl) adeninyl,
N6-glycinylcarbamoyladeninyl,
N6-threonylcarbamoyladeninyl,
2-methylthio-N6-threonylcarbamoyladeninyl,
N6-methyl-N6-threonylcarbamoyladeninyl,
N6-hydroxynorvalylcarbamoyladeninyl,
2-methylthio-N6-hydroxynorvalylcarbamoyladeninyl,
N6,N6-dimethyladeninyl,
3-methylcytosinyl,
5-methylcytosinyl,
2-thiocytosinyl,
5-formylcytosinyl,

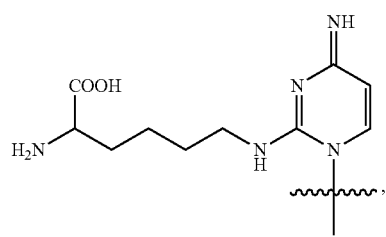 [SMILES: *n1ccc(=N)nc1NCCCCC(N)C(=O)O]

N4-methylcytosinyl,
5-hydroxymethylcytosinyl,
1-methylguaninyl,
N2-methylguaninyl,
7-methylguaninyl,
N2,N2-dimethylguaninyl,

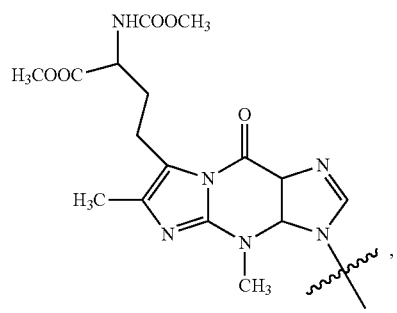

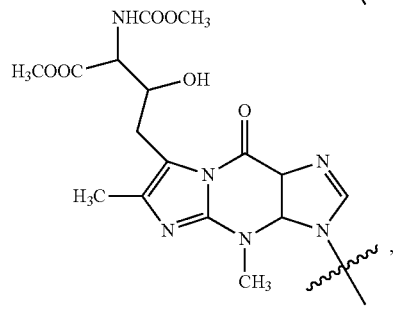

-continued

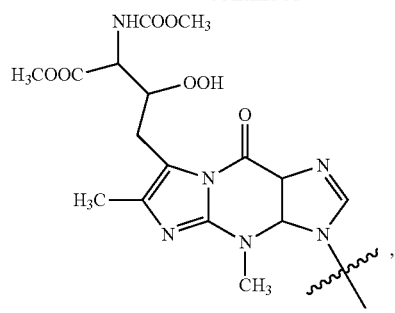

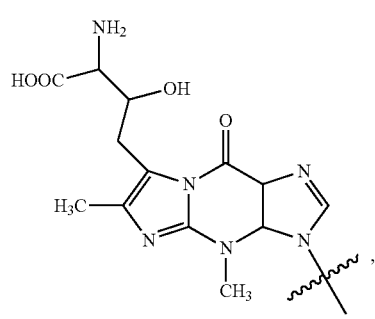

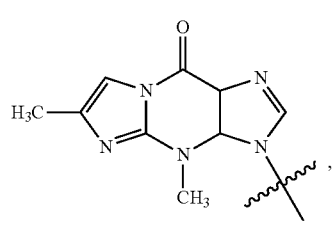

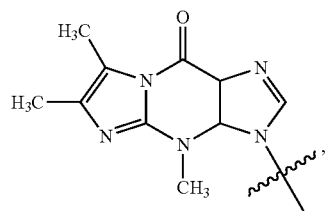

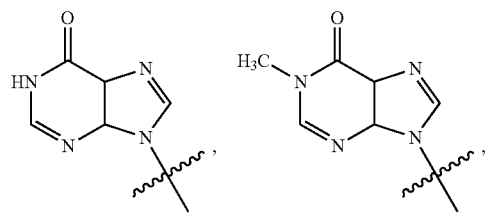

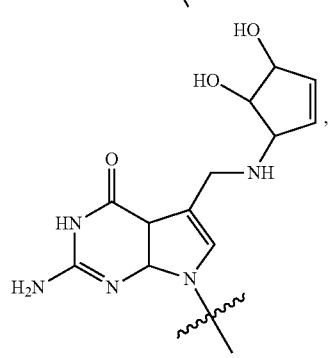

-continued

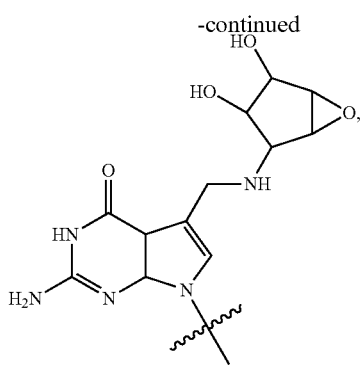

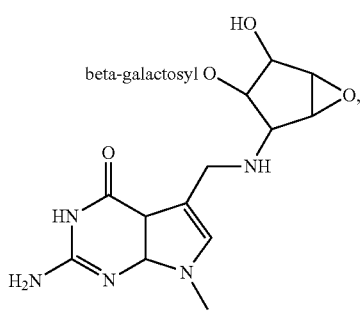

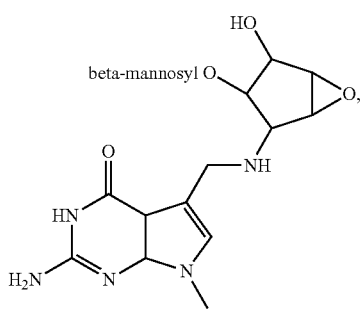

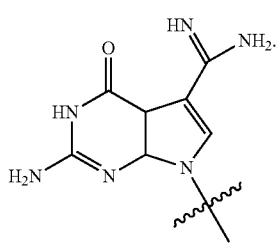

N2,7-dimethylguaninyl,
N2,N2,7-trimethylguaninyl,
1-methylguaninyl,
7-cyano-7-deazaguaninyl,
7-aminomethyl-7-deazaguaninyl,
pseudouracilyl,
dihydrouracilyl,
5-methyluracilyl,
1-methylpseudouracilyl,
2-thiouracilyl,
4-thiouracilyl,
2-thiothyminyl
5-methyl-2-thiouracilyl,
3-(3-amino-3-carboxypropyl)uracilyl,
5-hydroxyuracilyl,
5-methoxyuracilyl,
uracilyl 5-oxyacetic acid,
uracilyl 5-oxyacetic acid methyl ester,
5-(carboxyhydroxymethyl)uracilyl,
5-(carboxyhydroxymethyl)uracilyl methyl ester,
5-methoxycarbonylmethyluracilyl,
5-methoxycarbonylmethyl-2-thiouracilyl,
5-aminomethyl-2-thiouracilyl,
5-methylaminomethyluracilyl,
5-methylaminomethyl-2-thiouracilyl,
5-methylaminomethyl-2-selenouracilyl,
5-carbamoylmethyluracilyl,
5-carboxymethylaminomethyluracilyl,
5-carboxymethylaminomethyl-2-thiouracilyl,
3-methyluracilyl,
1-methyl-3-(3-amino-3-carboxypropyl) pseudouracilyl,
5-carboxymethyluracilyl,
5-methyldihydrouracilyl, or
3-methylpseudouracilyl.

A universal base can form base pairs with each of the natural DNA/RNA bases, exhibiting relatively little discrimination between them. In general, the universal bases are non-hydrogen bonding, hydrophobic, aromatic moieties which can stabilize e.g., duplex RNA or RNA-like molecules, via stacking interactions. A universal base can also include hydrogen bonding substituents.

General

An oligonucleotide agent, e.g., a conjugated oligonucleotide agent, containing a preferred, but nonlimiting ligand-conjugated monomer subunit is presented as formula (II) below. The carrier (also referred to in some embodiments as a "linker") can be a cyclic or acyclic moiety and includes two "backbone attachment points" (e.g., hydroxyl groups) and a ligand. The ligand can be directly attached (e.g., conjugated) to the carrier or indirectly attached (e.g., conjugated) to the carrier by an intervening tether (e.g., an acyclic chain of one or more atoms; or a nucleobase, e.g., a naturally occurring nucleobase optionally having one or more chemical modifications, e.g., an unusual base; or a universal base). The carrier therefore also includes a "ligand or tethering attachment point" for the ligand and tether/tethered ligand, respectively.

The ligand-conjugated monomer subunit may be the 5' or 3' terminal subunit of the RNA molecule, i.e., one of the two "W" groups may be a hydroxyl group, and the other "W" group may be a chain of two or more unmodified or modified ribonucleotides. Alternatively, the ligand-conjugated monomer subunit may occupy an internal position, and both "W" groups may be one or more unmodified or modified ribonucleotides. More than one ligand-conjugated monomer subunit may be present in a RNA molecule, e.g., an oligonucleotide agent. Preferred positions for inclusion of a tethered ligand-conjugated monomer subunit, e.g., one in which a lipophilic moiety, e.g., cholesterol, is tethered to the carrier are at the 3' terminus, the 5' terminus, or at an internal position.

(II)

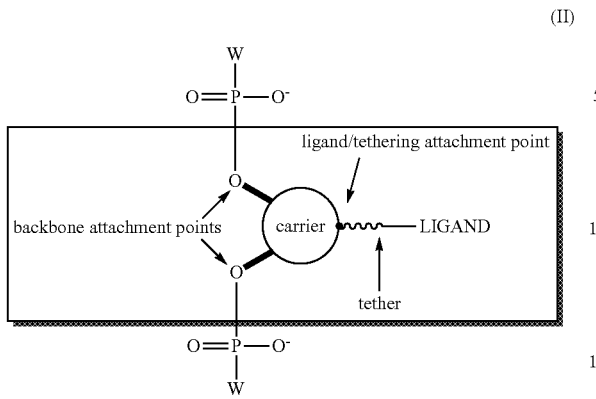

The modified RNA molecule of formula (II) can be obtained using oligonucleotide synthetic methods known in the art. In a preferred embodiment, the modified RNA molecule of formula (II) can be prepared by incorporating one or more of the corresponding monomer compounds (see, e.g., A, B, and C below) into a growing strand, utilizing, e.g., phosphoramidite or H-phosphonate coupling strategies.

The monomers, e.g., a ligand-conjugated monomers, generally include two differently functionalized hydroxyl groups ($OFG^1$ and $OFG^2$), which are linked to the carrier molecule (see A below), and a ligand/tethering attachment point. As used herein, the term "functionalized hydroxyl group" means that the hydroxyl proton has been replaced by another substituent. As shown in representative structures B and C below, one hydroxyl group ($OFG^1$) on the carrier is functionalized with a protecting group (PG). The other hydroxyl group ($OFG^2$) can be functionalized with either (1) a liquid or solid phase synthesis support reagent (solid circle) directly or indirectly through a linker, L, as in B, or (2) a phosphorus-containing moiety, e.g., a phosphoramidite as in C. The tethering attachment point may be connected to a hydrogen atom, a suitable protecting group, a tether, or a tethered ligand at the time that the monomer is incorporated into the growing strand (see variable "R" in A below). Thus, the tethered ligand can be, but need not be attached to the monomer at the time that the monomer is incorporated into the growing strand. In certain embodiments, the tether, the ligand or the tethered ligand may be linked to a "precursor" ligand-conjugated monomer subunit after a "precursor" ligand-conjugated monomer subunit has been incorporated into the strand. The wavy line used below (and elsewhere herein) refers to a connection, and can represent a direct bond between the moiety and the attachment point or a tethering molecule which is interposed between the moiety and the attachment point. Directly tethered means the moiety is bound directly to the attachment point. Indirectly tethered means that there is a tether molecule interposed between the attachment point and the moiety.

A

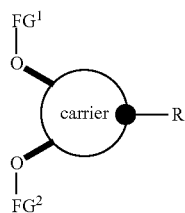

B

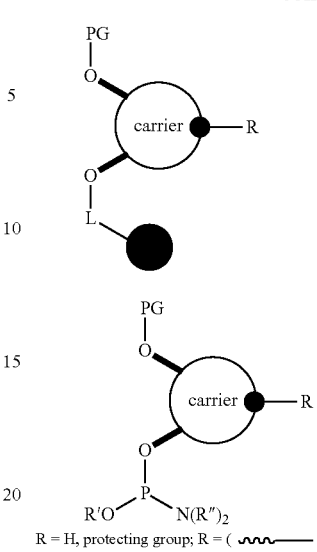

C

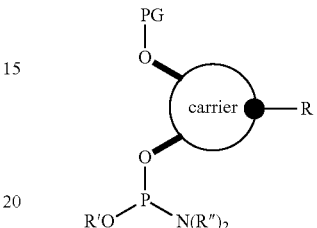

R = H, protecting group; R = ( ~~~ ) R = ( ~~~ ) + (LIGAND)

The ($OFG^1$) protecting group may be selected as desired, e.g., from T. W. Greene and P. G. M. Wuts, *Protective Groups in Organic Synthesis*, 2d. Ed., John Wiley and Sons (1991). The protecting group is preferably stable under amidite synthesis conditions, storage conditions, and oligonucleotide synthesis conditions. Hydroxyl groups, —OH, are nucleophilic groups (i.e., Lewis bases), which react through the oxygen with electrophiles (i.e., Lewis acids). Hydroxyl groups in which the hydrogen has been replaced with a protecting group, e.g., a triarylmethyl group or a trialkylsilyl group, are essentially unreactive as nucleophiles in displacement reactions. Thus, the protected hydroxyl group is useful in preventing e.g., homocoupling of compounds exemplified by structure C during oligonucleotide synthesis. In some embodiments, a preferred protecting group is the dimethoxytrityl group. In other embodiments, a preferred protecting group is a silicon-based protecting group having the formula below:

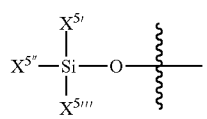

$X^{5'}$, $X^{5''}$, and $X^{5'''}$ can be selected from substituted or unsubstituted alkyl, cycloalkyl, aryl, araklyl, heteroaryl, alkoxy, cycloalkoxy, aralkoxy, aryloxy, heteroaryloxy, or siloxy (i.e., $R_3SiO$—, the three "R" groups can be any combination of the above listed groups). $X^{5'}$, $X^{5''}$, and $X^{5'''}$ may all be the same or different; also contemplated is a combination in which two of $X^{5'}$, $X^{5''}$, and $X^{5'''}$ are identical and the third is different. In certain embodiments $X^{5'}$, $X^{5'}$, and $X^{5'''}$ include at least one alkoxy or siloxy groups. A preferred combination includes $X^{5'}$, $X^{5''}$=trimethylsiloxy and $X^{5'''}$=1,3-(triphenylmethoxy)-2-propoxy or cyclododecyloxy.

Other preferred combinations of $X^{5'}$, $X^{5''}$, and $X^{5'''}$ include those that result in $OFG^1$ groups that meet the deprotection and stability criteria delineated below. The group is preferably stable under amidite synthesis conditions, storage conditions, and oligonucleotide synthesis conditions. Rapid removal, i.e., less than one minute, of the silyl group from e.g., a support-bound oligonucleotide is desirable because it can reduce synthesis times and thereby reduce exposure time of the growing oligonucleotide chain to the reagents. Oligonucleotide synthesis can be improved if the silyl protecting group is visible during deprotection, e.g., from the addition of a chromophore silyl substituent.

Selection of silyl protecting groups can be complicated by the competing demands of the essential characteristics of stability and facile removal, and the need to balance these competitive goals. Most substituents that increase stability can also increase the reaction time-required for removal of the silyl group, potentially increasing the level of difficulty in removal of the group.

The addition of alkoxy and siloxy substituents to $OFG^1$ silicon-containing protecting groups increases the susceptibility of the protecting groups to fluoride cleavage of the silylether bonds. Increasing the steric bulk of the substituents preserves stability while not decreasing fluoride lability to an equal extent. An appropriate balance of substituents on the silyl group makes a silyl ether a viable nucleoside protecting group.

Candidate $OFG^1$ silicon-containing protecting groups may be tested by exposing a tetrahydrofuran solution of a preferred carrier bearing the candidate $OFG^1$ group to five molar equivalents of tetrahydrofuran at room temperature. The reaction time may be determined by monitoring the disappearance of the starting material by thin layer chromatography.

When the $OFG^2$ in B includes a linker, e.g., a relatively long organic linker, connected to a soluble or insoluble support reagent, solution or solid phase synthesis techniques can be employed to build up a chain of natural and/or modified ribonucleotides once $OFG^1$ is deprotected and free to react as a nucleophile with another nucleoside or monomer containing an electrophilic group (e.g., an amidite group). Alternatively, a natural or modified ribonucleotide or oligoribonucleotide chain can be coupled to monomer C via an amidite group or H-phosphonate group at $OFG^2$. Subsequent to this operation, $OFG^1$ can be deblocked, and the restored nucleophilic hydroxyl group can react with another nucleoside or monomer containing an electrophilic group. R' can be substituted or unsubstituted alkyl or alkenyl. In preferred embodiments, R' is methyl, allyl or 2-cyanoethyl. R" may a $C_1$-$C_{10}$ alkyl group, preferably it is a branched group containing three or more carbons, e.g., isopropyl.

$OFG^2$ in B can be hydroxyl functionalized with a linker, which in turn contains a liquid or solid phase synthesis support reagent at the other linker terminus. The support reagent can be any support medium that can support the monomers described herein. The monomer can be attached to an insoluble support via a linker, L, which allows the monomer (and the growing chain) to be solubilized in the solvent in which the support is placed. The solubilized, yet immobilized, monomer can react with reagents in the surrounding solvent; unreacted reagents and soluble by-products can be readily washed away from the solid support to which the monomer or monomer-derived products is attached. Alternatively, the monomer can be attached to a soluble support moiety, e.g., polyethylene glycol (PEG) and liquid phase synthesis techniques can be used to build up the chain. Linker and support medium selection is within skill of the art. Generally the linker may be —C(O)(CH$_2$)$_q$C(O)—, or —C(O)(CH$_2$)$_q$S—, in which q can be 0, 1, 2, 3, or 4; preferably, it is oxalyl, succinyl or thioglycolyl. Standard control pore glass solid phase synthesis supports can not be used in conjunction with fluoride labile 5' silyl protecting groups because the glass is degraded by fluoride with a significant reduction in the amount of full-length product. Fluoride-stable polystyrene based supports or PEG are preferred.

The ligand/tethering attachment point can be any divalent, trivalent, tetravalent, pentavalent or hexavalent atom. In some embodiments, ligand/tethering attachment point can be a carbon, oxygen, nitrogen or sulfur atom. For example, a ligand/tethering attachment point precursor functional group can have a nucleophilic heteroatom, e.g., —SH, —NH$_2$, secondary amino, ONH$_2$, or NH$_2$NH$_2$. As another example, the ligand/tethering attachment point precursor functional group can be an olefin, e.g., —CH=CH$_2$ or a Diels-Alder diene or dienophile and the precursor functional group can be attached to a ligand, a tether, or tethered ligand using, e.g., transition metal catalyzed carbon-carbon (for example olefin metathesis) processes or cycloadditions (e.g., Diels-Alder). As a further example, the ligand/tethering attachment point precursor functional group can be an electrophilic moiety, e.g., an aldehyde. When the carrier is a cyclic carrier, the ligand/tethering attachment point can be an endocyclic atom (i.e., a constituent atom in the cyclic moiety, e.g., a nitrogen atom) or an exocyclic atom (i.e., an atom or group of atoms attached to a constituent atom in the cyclic moiety).

The carrier can be any organic molecule containing attachment points for $OFG^1$, $OFG^2$, and the ligand. In certain embodiments, carrier is a cyclic molecule and may contain heteroatoms (e.g., O, N or S). E.g., carrier molecules may include aryl (e.g., benzene, biphenyl, etc.), cycloalkyl (e.g., cyclohexane, cis or trans decalin, etc.), or heterocyclyl (piperazine, pyrrolidine, etc.). In other embodiments, the carrier can be an acyclic moiety, e.g., based on serinol. Any of the above cyclic systems may include substituents in addition to $OFG^1$, $OFG^2$, and the ligand.

Sugar-Based Monomers

In some embodiments, the carrier molecule is an oxygen containing heterocycle. Preferably the carrier is a ribose sugar as shown in structure LCM-I. In this embodiment, the ligand-conjugated monomer is a nucleoside.

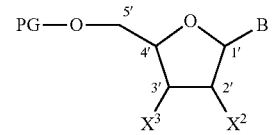

LCM-I

"B" represents a nucleobase, e.g., a naturally occurring nucleobase optionally having one or more chemical modifications, e.g., and unusual base; or a universal base.

As used herein, an "unusual" nucleobase can include any one of the following:
2-methyladeninyl,
N6-methyladeninyl,
2-methylthio-N6-methyladeninyl,
N6-isopentenyladeninyl,
2-methylthio-N6-isopentenyladeninyl,
N6-(cis-hydroxyisopentenyl)adeninyl,
2-methylthio-N6-(cis-hydroxyisopentenyl)adeninyl,
N6-glycinylcarbamoyladeninyl,
N6-threonylcarbamoyladeninyl,
2-methylthio-N6-threonylcarbamoyladeninyl,
N6-methyl-N6-threonylcarbamoyladeninyl,
N6-hydroxynorvalylcarbamoyladeninyl, 2-methylthio-N6-hydroxynorvalylcarbamoyladeninyl,
N6,N6-dimethyladeninyl,
3-methylcytosinyl,
5-methylcytosinyl,
2-thiocytosinyl,
5-formylcytosinyl,
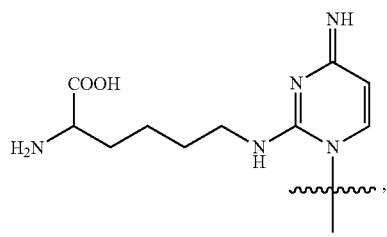
N4-methylcytosinyl,
5-hydroxymethylcytosinyl,
1-methylguaninyl,
N2-methylguaninyl,
7-methylguaninyl,
N2,N2-dimethylguaninyl,
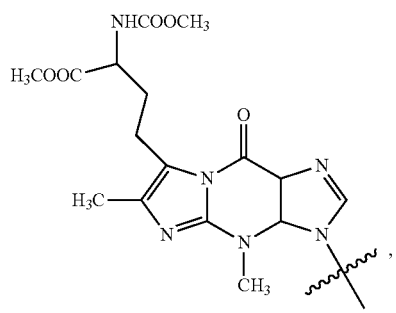
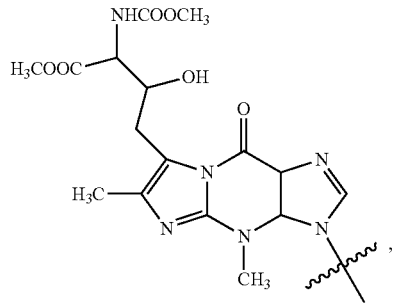
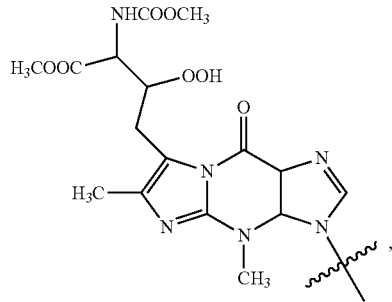
-continued
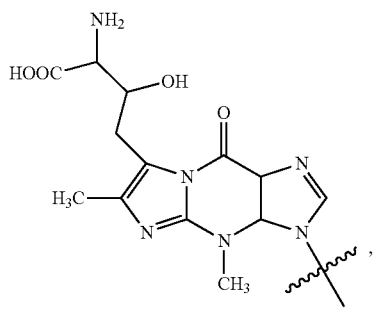
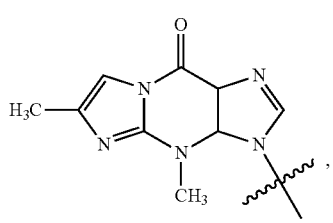
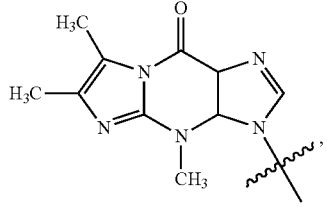
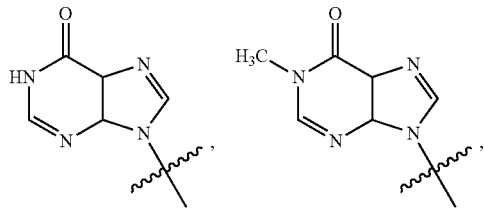
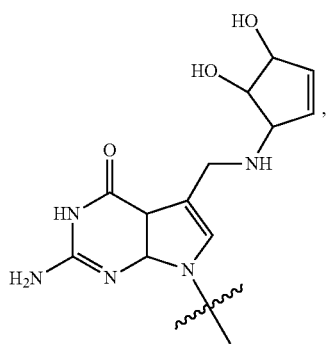
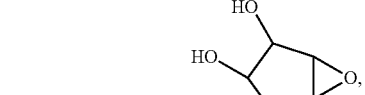
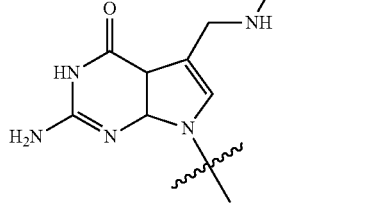

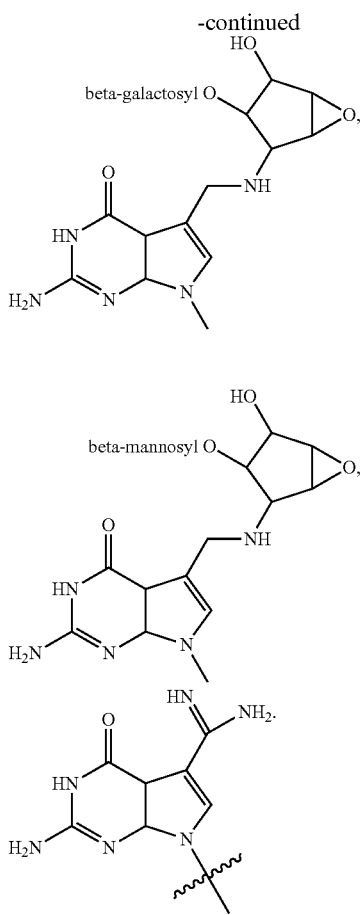

N2,7-dimethylguaninyl,
N2,N2,7-trimethylguaninyl,
1-methylguaninyl,
7-cyano-7-deazaguaninyl,
7-aminomethyl-7-deazaguaninyl,
pseudouracilyl,
dihydrouracilyl,
5-methyluracilyl,
1-methylpseudouracilyl,
2-thiouracilyl,
4-thiouracilyl,
2-thiothyminyl
5-methyl-2-thiouracilyl,
3-(3-amino-3-carboxypropyl)uracilyl,
5-hydroxyuracilyl,
5-methoxyuracilyl,
uracilyl 5-oxyacetic acid,
uracilyl 5-oxyacetic acid methyl ester,
5-(carboxyhydroxymethyl)uracilyl,
5-(carboxyhydroxymethyl)uracilyl methyl ester,
5-methoxycarbonylmethyluracilyl,
5-methoxycarbonylmethyl-2-thiouracilyl,
5-aminomethyl-2-thiouracilyl,
5-methylaminomethyluracilyl,
5-methylaminomethyl-2-thiouracilyl,
5-methylaminomethyl-2-selenouracilyl,
5-carbamoylmethyluracilyl,
5-carboxymethylaminomethyluracilyl,
5-carboxymethylaminomethyl-2-thiouracilyl,
3-methyluracilyl,
1-methyl-3-(3-amino-3-carboxypropyl)pseudouracilyl,
5-carboxymethyluracilyl,
5-methyldihydrouracilyl, or
3-methylpseudouracilyl.

A universal base can form base pairs with each of the natural DNA/RNA bases, exhibiting relatively little discrimination between them. In general, the universal bases are non-hydrogen bonding, hydrophobic, aromatic moieties which can stabilize e.g., duplex RNA or RNA-like molecules, via stacking interactions. A universal base can also include hydrogen bonding substituents.

As used herein, a "universal base" can include anthracenes, pyrenes or any one of the following:

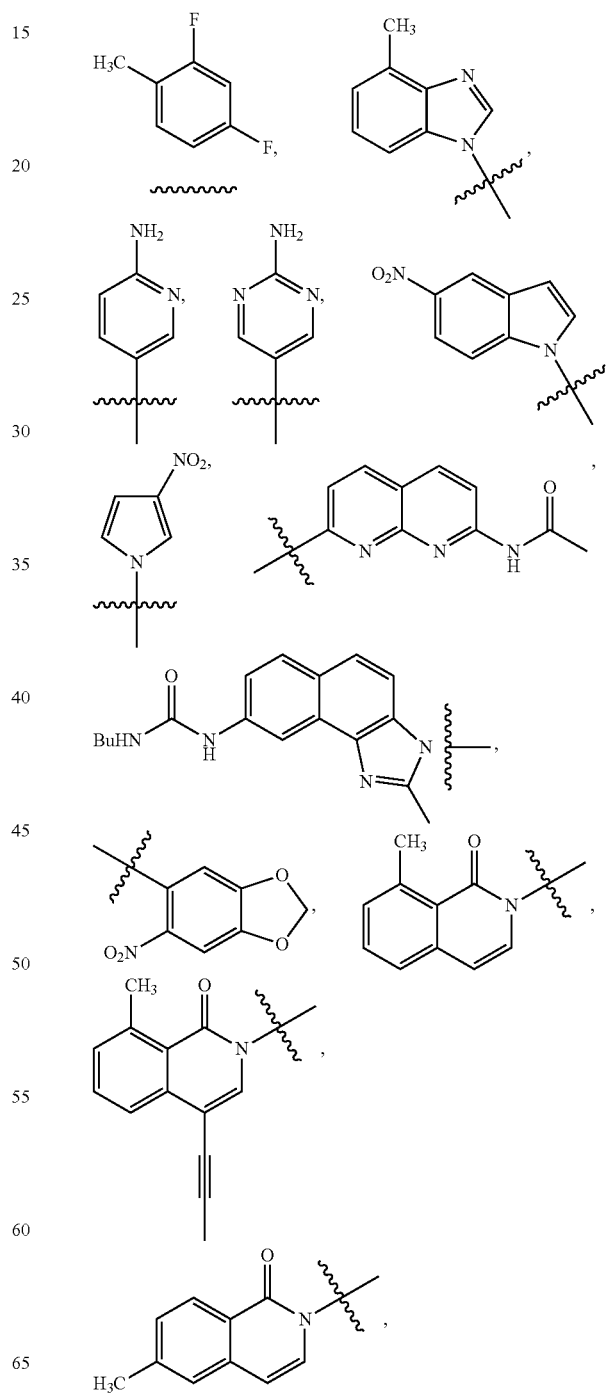

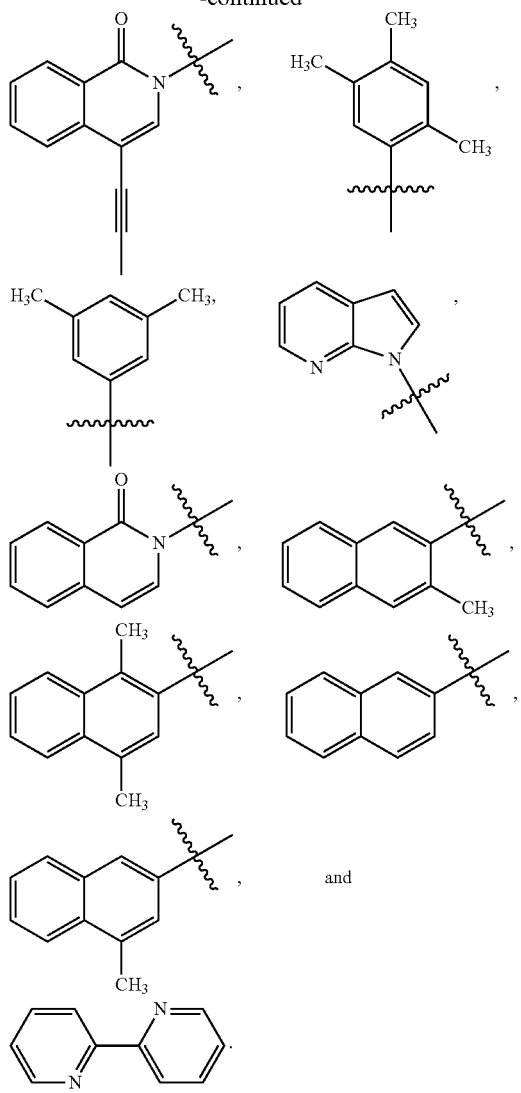

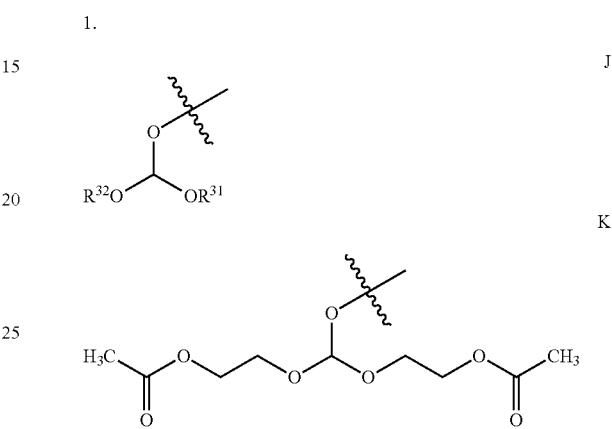

In some embodiments, B can form part of a tether that connects a ligand to the carrier. For example, the tether can be B—CH═CH—C(O)NH—(CH$_2$)$_5$—NHC(O)-LIGAND. In a preferred embodiment, the double bond is trans, and the ligand is a substituted or unsubstituted cholesterolyl radical (e.g., attached through the D-ring side chain or the C-3 hydroxyl); an aralkyl moiety having at least one sterogenic center and at least one substituent on the aryl portion of the aralkyl group; or a nucleobase. In certain embodiments, B, in the tether described above, is uracilyl or a universal base, e.g., an aryl moiety, e.g., phenyl, optionally having additional substituents, e.g., one or more fluoro groups. B can be substituted at any atom with the remainder of the tether.

$X^2$ can include "oxy" or "deoxy" substituents in place of the 2'-OH or be a ligand or a tethered ligand.

Examples of "oxy"-substituents include alkoxy or aryloxy (OR, e.g., R═H, alkyl, cycloalkyl, aryl, aralkyl, heteroaryl, sugar, or protecting group); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-PROTECTED AMINE (AMINE═NH$_2$; alkylamino, dialkylamino, heterocyclyl, arylamino, diaryl amino, heteroaryl amino, or diheteroaryl amino, ethylene diamine, polyamino) and aminoalkoxy, O(CH$_2$)$_n$PROTECTED AMINE, (e.g., AMINE═NH$_2$; alkylamino, dialkylamino, heterocyclyl, arylamino, diaryl amino, heteroaryl amino, or diheteroaryl amino, ethylene diamine, polyamino), and orthoester. Amine protecting groups can include formyl, amido, benzyl, allyl, etc.

Preferred-orthoesters have the general formula J. The groups $R^{31}$ and $R^{32}$ may be the same or different. A preferred orthoester is the "ACE" group, shown below as structure K.

1.

J $$R^{32}O\overset{O-}{\underset{}{\diagup}}OR^{31}$$

K

[structure K: H$_3$C—C(═O)—O—CH$_2$CH$_2$—O—CH(—O—)—O—CH$_2$CH$_2$—O—C(═O)—CH$_3$]

"Deoxy" substituents include hydrogen (i.e. deoxyribose sugars); halo (e.g., fluoro); protected amino (e.g. NH$_2$; alkylamino, dialkylamino, heterocyclyl, arylamino, diaryl amino, heteroaryl amino, diheteroaryl amino, or amino acid in which all amino are protected); fully protected polyamino, (e.g., NH(CH$_2$CH$_2$NH)$_n$CH$_2$CH$_2$-AMINE, wherein AMINE═NH$_2$; alkylamino, dialkylamino, heterocyclyl, arylamino, diaryl amino, heteroaryl amino, or diheteroaryl amino and all amino groups are protected), —NHC(O)R (R═alkyl, cycloalkyl, aryl, aralkyl, heteroaryl or sugar), cyano; alkyl-thio-alkyl; thioalkoxy; and alkyl, cycloalkyl, aryl, alkenyl and alkynyl, which may be optionally substituted with e.g., a protected amino functionality. Preferred substitutents are 2'-methoxyethyl, 2'-OCH3, 2'-O-allyl, 2'-C— allyl, and 2'-fluoro.

$X^3$ is as described for OFG$^2$ above.

PG can be a triarylmethyl group (e.g., a dimethoxytrityl group) or Si(X$^{5'}$)(X$^{5''}$)(X$^{5'''}$) in which (X$^{5'}$), (X$^{5''}$), and (X$^{5'''}$) are as described elsewhere.

Sugar Replacement-Based Monomers

Cyclic sugar replacement-based monomers, e.g., sugar replacement-based ligand-conjugated monomers, are also referred to herein as sugar replacement monomer subunit (SRMS) monomer compounds. Preferred carriers have the general formula (LCM-2) provided below. (In that structure preferred backbone attachment points can be chosen from $R^1$ or $R^2$; $R^3$ or $R^4$; or $R^9$ and $R^{10}$ if Y is CR$^9$R$^{10}$ (two positions are chosen to give two backbone attachment points, e.g., $R^1$ and $R^4$, or $R^4$ and $R^9$). Preferred tethering attachment points include $R^7$; $R^5$ or $R^6$ when X is CH$_2$. The carriers are described below as an entity, which can be incorporated into a strand. Thus, it is understood that the structures also encompass the situations wherein one (in the case of a terminal position) or two (in the case of an internal position) of the attachment points, e.g., $R^1$ or $R^2$; $R^3$ or $R^4$; or $R^9$ or $R^{10}$ (when Y is CR$^9$R$^{10}$), is connected to the phosphate, or modified phosphate, e.g., sulfur containing, backbone. E.g., one of the above-named R groups can be —CH$_2$—, wherein one bond is connected to the carrier and one to a backbone atom, e.g., a linking oxygen or a central phosphorus atom.

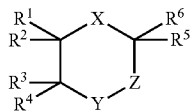
(LCM-2)

in which,

X is N(CO)R$^7$, NR$^7$ or CH$_2$;

Y is NR$^8$, O, S, CR$^9$R$^{10}$;

Z is CR$^{11}$R$^{12}$ or absent;

Each of R$^1$, R$^2$, R$^3$, R$^4$, R$^9$, and R$^{10}$ is, independently, H, OR$^a$, or (CH$_2$)$_n$OR$^b$, provided that at least two of R$^1$, R$^2$, R$^3$, R$^4$, R$^9$, and R$^{10}$ are OR$^a$ and/or (CH$_2$)$_n$OR$^b$;

Each of R$^5$, R$^6$, R$^{11}$, and R$^{12}$ is, independently, a ligand, H, C$_1$-C$_6$ alkyl optionally substituted with 1-3 R$^{13}$, or C(O)NHR$^7$; or R$^5$ and R$^{11}$ together are C$_3$-C$_8$ cycloalkyl optionally substituted with R$^{14}$;

R$^7$ can be a ligand, e.g., R$^7$ can be R$^d$, or R$^7$ can be a ligand tethered indirectly to the carrier, e.g., through a tethering moiety, e.g., C$_1$-C$_{20}$ alkyl substituted with NR$^c$R$^d$; or C$_1$-C$_{20}$ alkyl substituted with NHC(O)R$^d$;

R$^8$ is H or C$_1$-C$_6$ alkyl;

R$^{13}$ is hydroxy, C$_1$-C$_4$ alkoxy, or halo;

R$^{14}$ is NR$^c$R$^7$;

R$^{15}$ is C$_1$-C$_6$ alkyl optionally substituted with cyano, or C$_2$-C$_6$ alkenyl;

R$^{16}$ is C$_1$-C$_{10}$ alkyl;

R$^{17}$ is a liquid or solid phase support reagent;

L is —C(O)(CH$_2$)$_q$C(O)—, or —C(O)(CH$_2$)$_q$S—;

R$^a$ is a protecting group, e.g., CAr$_3$; (e.g., a dimethoxytrityl group) or Si(X$^{5'}$)(X$^{5''}$)(X$^{5'''}$) in which (X$^{5'}$), (X$^{5''}$), and (X$^{5'''}$) are as described elsewhere.

R$^b$ is P(O)(O$^-$)H, P(OR$^{15}$)N(R$^{16}$)$_2$ or L-R$^{17}$;

R$^c$ is H or C$_1$-C$_6$ alkyl;

R$^d$ is H or a ligand;

Each Ar is, independently, C$_6$-C$_{10}$ aryl optionally substituted with C$_1$-C$_4$ alkoxy;

n is 1-4; and q is 0-4.

Exemplary carriers include those in which, e.g., X is N(CO)R$^7$ or NR$^7$, Y is CR$^9$R$^{10}$, and Z is absent; or X is N(CO)R$^7$ or NR$^7$, Y is CR$^9$R$^{10}$, and Z is CR$^{11}$R$^{12}$; or X is N(CO)R$^7$ or NR$^7$, Y is NR$^8$, and Z is CR$^{11}$R$^{12}$; or X is N(CO)R$^7$ or NR$^7$, Y is O, and Z is CR$^{11}$R$^{12}$; or X is CH$_2$; Y is CR$^9$R$^{10}$; Z is CR$^{11}$R$^{12}$, and R$^5$ and R$^{11}$ together form C$_6$ cycloalkyl (H, z=2), or the indane ring system, e.g., X is CH$_2$; Y is CR$^9$R$^{10}$, Z is CR$^{11}$R$^{12}$, and R$^5$ and R$^{11}$ together form C$_5$ cycloalkyl (H, z=1).

In certain embodiments, the carrier may be based on the pyrroline ring system or the 4-hydroxyproline ring system, e.g., X is N(CO)R$^7$ or NR$^7$, Y is CR$^9$R$^{10}$, and Z is absent (D). OFG$^1$ is preferably attached to a primary carbon, e.g., an exocyclic alkylene

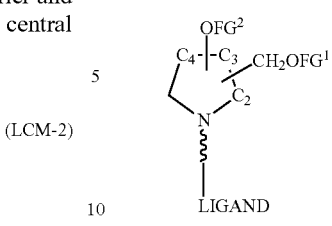
D group, e.g., a methylene group, connected to one of the carbons in the five-membered ring (—CH$_2$OFG$^1$ in D). OFG$^2$ is preferably attached directly to one of the carbons in the five-membered ring (—OFG$^2$ in D). For the pyrroline-based carriers, —CH$_2$OFG$^1$ may be attached to C-2 and OFG$^2$ may be attached to C-3; or —CH$_2$OFG$^1$ may be attached to C-3 and OFG$^2$ may be attached to C-4. In certain embodiments, CH$_2$OFG$^1$ and OFG$^2$ may be geminally substituted to one of the above-referenced carbons. For the 3-hydroxyproline-based carriers, —CH$_2$OFG$^1$ may be attached to C-2 and OFG$^2$ may be attached to C-4. The pyrroline- and 4-hydroxyproline-based monomers may therefore contain linkages (e.g., carbon-carbon bonds) wherein bond rotation is restricted about that particular linkage, e.g. restriction resulting from the presence of a ring. Thus, CH$_2$OFG$^1$ and OFG$^2$ may be cis or trans with respect to one another in any of the pairings delineated above Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen. Preferred examples of carrier D include the following:

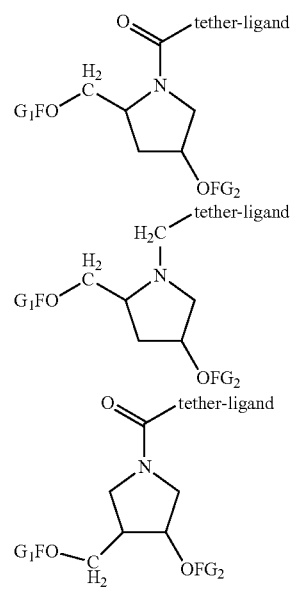

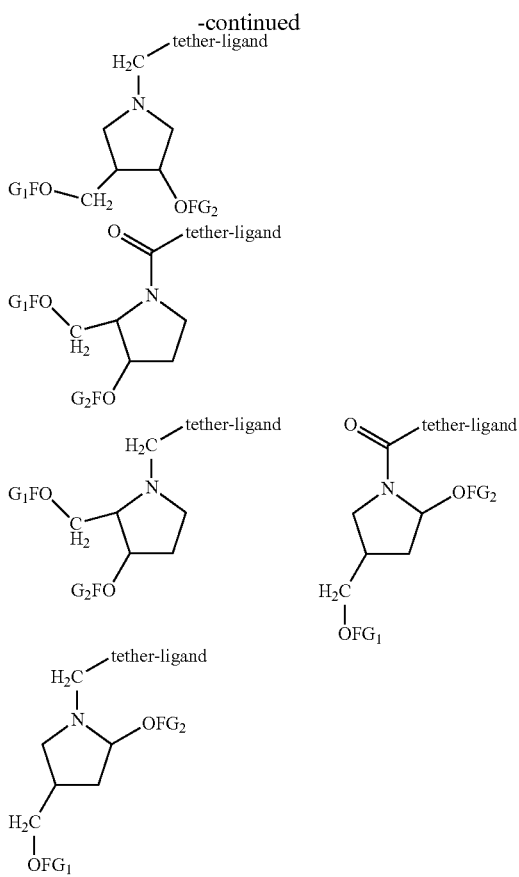

In certain embodiments, the carrier may be based on the piperidine ring system (E), e.g., X is N(CO)R$^7$ or NR$^7$, Y is CR$^9$R$^{10}$, and Z is CR$^{11}$R$^{12}$. OFG$^1$ is preferably

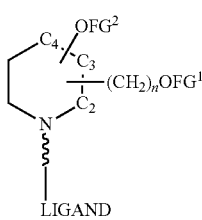

attached to a primary carbon, e.g., an exocyclic alkylene group, e.g., a methylene group (n=1) or ethylene group (n=2), connected to one of the carbons in the six-membered ring [—(CH$_2$)$_n$OFG$^1$ in E]. OFG$^2$ is preferably attached directly to one of the carbons in the six-membered ring (—OFG$^2$ in E). —(CH$_2$)$_n$OFG$^1$ and OFG$^2$ may be disposed in a geminal manner on the ring, i.e., both groups may be attached to the same carbon, e.g., at C-2, C-3, or C-4. Alternatively, —(CH$_2$)$_n$OFG$^1$ and OFG$^2$ may be disposed in a vicinal manner on the ring, i.e., both groups may be attached to adjacent ring carbon atoms, e.g., —(CH$_2$)$_n$OFG$^1$ may be attached to C-2 and OFG$^2$ may be attached to C-3; —(CH$_2$)$_n$OFG$^1$ may be attached to C-3 and OFG$^2$ may be attached to C-2; —(CH$_2$)$_n$OFG$^1$ may be attached to C-3 and OFG$^2$ may be attached to C-4; or —(CH$_2$)$_n$OFG$^1$ may be attached to C-4 and OFG$^2$ may be attached to C-3. The piperidine-based monomers may therefore contain linkages (e.g., carbon-carbon bonds) wherein bond rotation is restricted about that particular linkage, e.g. restriction resulting from the presence of a ring. Thus, —(CH$_2$)$_n$OFG$^1$ and OFG$^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen.

In certain embodiments, the carrier may be based on the piperazine ring system (F), e.g., X is N(CO)R$^7$ or NR$^7$, Y is NR$^8$, and Z is CR$^{11}$R$^{12}$, or the morpholine ring system (G), e.g., X is N(CO)R$^7$ or NR$^7$, Y is O, and Z is CR$^{11}$R$^{12}$. OFG$^1$ is preferably

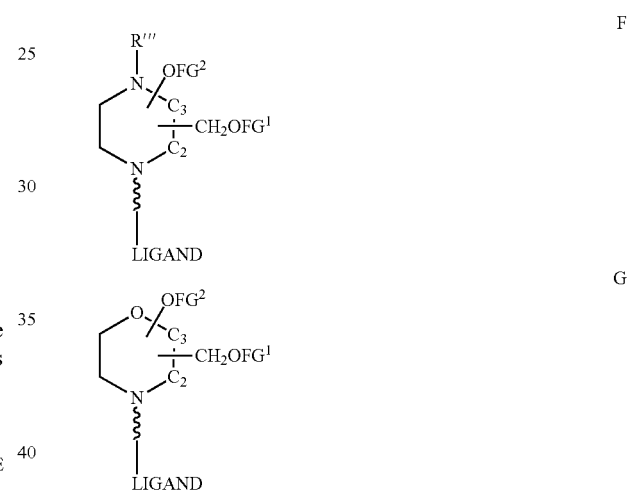

attached to a primary carbon, e.g., an exocyclic alkylene group, e.g., a methylene group, connected to one of the carbons in the six-membered ring (—CH$_2$OFG$^1$ in F or G). OFG$^2$ is preferably attached directly to one of the carbons in the six-membered rings (—OFG$^2$ in F or G). For both F and G, —CH$_2$OFG$^1$ may be attached to C-2 and OFG$^2$ may be attached to C-3; or vice versa. In certain embodiments, CH$_2$OFG$^1$ and OFG$^2$ may be geminally substituted to one of the above-referenced carbons. The piperazine- and morpholine-based monomers may therefore contain linkages (e.g., carbon-carbon bonds) wherein bond rotation is restricted about that particular linkage, e.g. restriction resulting from the presence of a ring. Thus, CH$_2$OFG$^1$ and OFG$^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa); R''' can be, e.g., $C_1$-$C_6$ alkyl, preferably $CH_3$. The tethering attachment point is preferably nitrogen in both F and G.

In certain embodiments, the carrier may be based on the decalin ring system, e.g., X is $CH_2$; Y is $CR^9R^{10}$; Z is $CR^{11}R^{12}$, and $R^5$ and $R^{11}$ together form $C_6$ cycloalkyl (H, z=2), or the indane ring system, e.g., X is $CH_2$; Y is $CR^9R^{10}$; Z is $CR^{11}R^{12}$, and $R^5$ and $R^{11}$ together form $C_5$ cycloalkyl (H, z=1). $OFG^1$ is preferably attached to a primary carbon,

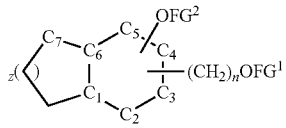

H e.g., an exocyclic methylene group (n=1) or ethylene group (n=2) connected to one of C-2, C-3, C-4, or C-5 [—$(CH_2)_n OFG^1$ in H]. $OFG^2$ is preferably attached directly to one of C-2, C-3, C-4, or C-5 (—$OFG^2$ in H). —$(CH_2)_n OFG^1$ and $OFG^2$ may be disposed in a geminal manner on the ring, i.e., both groups may be attached to the same carbon, e.g., at C-2, C-3, C-4, or C-5. Alternatively, —$(CH_2)_n OFG^1$ and $OFG^2$ may be disposed in a vicinal manner on the ring, i.e., both groups may be attached to adjacent ring carbon atoms, e.g., —$(CH_2)_n OFG^1$ may be attached to C-2 and $OFG^2$ may be attached to C-3; —$(CH_2)_n OFG^1$ may be attached to C-3 and $OFG^2$ may be attached to C-2; —$(CH_2)_n OFG^1$ may be attached to C-3 and $OFG^2$ may be attached to C-4; or —$(CH_2)_n OFG^1$ may be attached to C-4 and $OFG^2$ may be attached to C-3; —$(CH_2)_n OFG^1$ may be attached to C-4 and $OFG^2$ may be attached to C-5; or —$(CH_2)_n OFG^1$ may be attached to C-5 and $OFG^2$ may be attached to C-4. The decalin or indane-based monomers may therefore contain linkages (e.g., carbon-carbon bonds) wherein bond rotation is restricted about that particular linkage, e.g. restriction resulting from the presence of a ring. Thus, —$(CH_2)_n OFG^1$ and $OFG^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing $CH_2 OFG^1$ and $OFG^2$ can both have the R configuration; or both have the S configuration; or one center can have the R configuration and the other center can have the S configuration and vice versa). In a preferred embodiment, the substituents at C-1 and C-6 are trans with respect to one another. The tethering attachment point is preferably C-6 or C-7.

Other carriers may include those based on 3-hydroxyproline (J). Thus, —$(CH_2)_n OFG^1$ and $OFG^2$ may be cis or trans with respect to one another. Accordingly, all cis/trans isomers are expressly included. The monomers may also contain one or more asymmetric centers

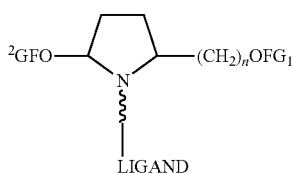

J and thus occur as racemates and racemic mixtures, single enantiomers, individual diastereomers and diastereomeric mixtures. All such isomeric forms of the monomers are expressly included (e.g., the centers bearing $CH_2 OFG^1$ and $OFG^2$ can both have the R configuration; or both have the S configuration; or one center can have the R configuration and the other center can have the S configuration and vice versa). The tethering attachment point is preferably nitrogen.

Sugar Replacement-Based Monomers (Acyclic)

Acyclic sugar replacement-based monomers, e.g., sugar replacement-based ligand-conjugated monomers, are also referred to herein as sugar replacement monomer subunit (SRMS) monomer compounds. Preferred acyclic carriers can have formula LCM-3 or LCM-4 below.

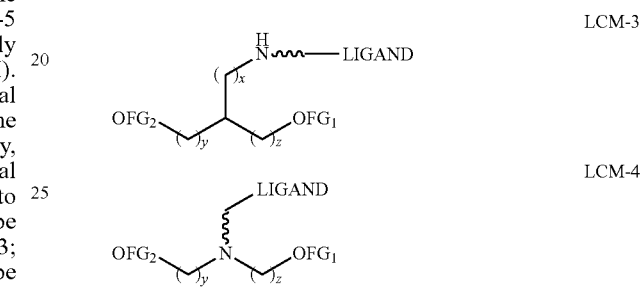

In some embodiments, each of x, y, and z can be, independently of one another, 0, 1, 2, or 3. In formula LCM-3, when y and z are different, then the tertiary carbon can have either the R or S configuration. In preferred embodiments, x is zero and y and z are each 1 in formula LCM-3 (e.g., based on serinol), and y and z are each 1 in formula LCM-3. Each of formula LCM-3 or LCM-4 below can optionally be substituted, e.g., with hydroxy, alkoxy, perhaloalkyl.

Tethers

In certain embodiments, a moiety, e.g., a ligand may be connected indirectly to the carrier via the intermediacy of an intervening tether. Tethers are connected to the carrier at a tethering attachment point (TAP) and may include any $C_1$-$C_{100}$ carbon-containing moiety, (e.g. $C_1$-$C_{75}$, $C_1$-$C_{50}$, $C_1$-$C_{20}$, $C_1$-$C_{10}$; $C_1$, $C_2$, $C_3$, $C_4$, $C_5$, $C_6$, $C_7$, $C_8$, $C_9$, or $C_{10}$), preferably having at least one nitrogen atom. In preferred embodiments, the nitrogen atom forms part of a terminal amino or amido (NHC(O)—) group on the tether, which may serve as a connection point for the ligand. Preferred tethers (underlined) include TAP-$\underline{(CH_2)_n NH}$—; TAP-$\underline{C(O)(CH_2)_n NH}$—; TAP-$\underline{NR''''(CH_2)_n NH}$—, TAP-$\underline{C(O)-(CH_2)_n-C(O)}$—; TAP-$\underline{C(O)-(CH_2)_n-C(O)O}$—; TAP-$\underline{C(O)-O}$—; TAP-$\underline{C(O)-(CH_2)_n-NH-C(O)}$—; TAP-$\underline{C(O)-(CH_2)_n}$—; TAP-$\underline{C(O)-NH}$—; TAP-$\underline{C(O)}$—; TAP-$\underline{(CH_2)_n-C(O)}$—; TAP-$\underline{(CH_2)_n-C(O)O}$—; TAP-$\underline{(CH_2)_n}$—; or TAP-$\underline{(CH_2)_n-NH-C(O)}$—; in which n is 1-20 (e.g., 1, 2, 3, 4, 5, 6, 7, 8, 9, 10, 11, 12, 13, 14, 15, 16, 17, 18, 19, or 20) and R'''' is $C_1$-$C_6$ alkyl. Preferably, n is 5, 6, or 11. In other embodiments, the nitrogen may form part of a terminal oxyamino group, e.g., —$ONH_2$, or hydrazino group, —$NHNH_2$. The tether may optionally be substituted, e.g., with hydroxy, alkoxy, perhaloalkyl, and/or optionally inserted with one or more additional heteroatoms, e.g., N, O, or S. Preferred tethered ligands may include, e.g., TAP-(CH₂)ₙNH(LIGAND); TAP-C(O)(CH₂)ₙNH(LIGAND); TAP-NR""(CH₂)ₙNH(LIGAND); TAP-(CH₂)ₙONH(LIGAND); TAP-C(O)(CH₂)ₙONH(LIGAND); TAP-NR""(CH₂)ₙONH(LIGAND); TAP-(CH₂)ₙNHNH₂(LIGAND), TAP-C(O)(CH₂)ₙNHNH₂(LIGAND); TAP-NR""(CH₂)ₙNHNH₂(LIGAND); TAP-C(O)—(CH₂)ₙ—C(O)(LIGAND); TAP-C(O)—(CH₂)ₙ—C(O)O(LIGAND); TAP-C(O)—O(LIGAND); TAP-C(O)—(CH₂)ₙ—NH—C(O)(LIGAND); TAP-C(O)—(CH₂)ₙ(LIGAND); TAP-C(O)—NH(LIGAND); TAP-C(O)(LIGAND); TAP-(CH₂)ₙ—C(O)(LIGAND); TAP-(CH₂)ₙ—C(O)O(LIGAND); TAP-(CH₂)ₙ(LIGAND); or TAP-(CH₂)ₙ—NH—C(O)(LIGAND). In some embodiments, amino terminated tethers (e.g., NH₂, ONH₂, NH₂NH₂) can form an imino bond (i.e., C═N) with the ligand. In some embodiments, amino terminated tethers (e.g., NH₂, ONH₂, NH₂NH₂) can acylated, e.g., with C(O)CF₃.

In some embodiments, the tether can terminate with a mercapto group (i.e., SH) or an olefin (e.g., CH═CH₂). For example, the tether can be TAP-(CH₂)ₙ—SH, TAP-C(O)(CH₂)ₙSH, TAP-(CH₂)ₙ—(CH═CH₂), or TAP-C(O)(CH₂)ₙ(CH═CH₂), in which n can be as described elsewhere. In certain embodiments, the olefin can be a Diels-Alder diene or dienophile. The tether may optionally be substituted, e.g., with hydroxy, alkoxy, perhaloalkyl, and/or optionally inserted with one or more additional heteroatoms, e.g., N, O, or S. The double bond can be cis or trans or E or Z.

In other embodiments the tether may include an electrophilic moiety, preferably at the terminal position of the tether. Preferred electrophilic moieties include, e.g., an aldehyde, alkyl halide, mesylate, tosylate, nosylate, or brosylate, or an activated carboxylic acid ester, e.g. an NHS ester, or a pentafluorophenyl ester. Preferred tethers (underlined) include TAP-(CH₂)ₙCHO; TAP-C(O)(CH₂)ₙCHO; or TAP-NR""(CH₂)ₙCHO, in which n is 1-6 and R"" is C₁-C₆ alkyl; or TAP-(CH₂)ₙC(O)ONHS; TAP-C(O)(CH₂)ₙC(O)ONHS; or TAP-NR""(CH₂)ₙC(O)ONHS, in which n is 1-6 and R"" is C₁-C₆ alkyl; TAP-(CH₂)ₙC(O)OC₆F₅; TAP-C(O)(CH₂)ₙC(O)OC₆F₅; or TAP-NR""(CH₂)ₙC(O)OC₆F₅, in which n is 1-11 and R"" is C₁-C₆ alkyl; or —(CH₂)ₙCH₂LG; TAP-C(O)(CH₂)ₙCH₂LG; or TAP-NR""(CH₂)ₙCH₂LG, in which n can be as described elsewhere and R"" is C₁-C₆ alkyl (LG can be a leaving group, e.g., halide, mesylate, tosylate, nosylate, brosylate). Tethering can be carried out by coupling a nucleophilic group of a ligand, e.g., a thiol or amino group with an electrophilic group on the tether.

In other embodiments, it can be desirable for the ligand-conjugated monomer or a ligand-conjugated monomer to include a phthalimido group (K) at the terminal position of the tether.

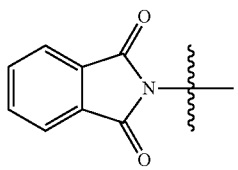

K

In other embodiments, other protected amino groups can be at the terminal position of the tether, e.g., alloc, monomethoxy trityl (MMT), trifluoroacetyl, Fmoc, or aryl sulfonyl (e.g., the aryl portion can be ortho-nitrophenyl or ortho, para-dinitrophenyl).

Any of the tethers described herein may further include one or more additional linking groups, e.g., —O—(CH₂)ₙ—, —(CH₂)ₙ—SS—, —(CH₂)ₙ—, or —(CH═CH)—.

Asymmetrical Modifications

An RNA, e.g., an iRNA agent, can be asymmetrically modified as described herein, and as described in International Application Serial No. PCT/US04/07070, filed Mar. 8, 2004, which is hereby incorporated by reference.

An asymmetrically modified iRNA agent is one in which a strand has a modification which is not present on the other strand. An asymmetrical modification is a modification found on one strand but not on the other strand. Any modification, e.g., any modification described herein, can be present as an asymmetrical modification. An asymmetrical modification can confer any of the desired properties associated with a modification, e.g., those properties discussed herein. E.g., an asymmetrical modification can: confer resistance to degradation, an alteration in half life; target the iRNA agent to a particular target, e.g., to a particular tissue; modulate, e.g., increase or decrease, the affinity of a strand for its complement or target sequence; or hinder or promote modification of a terminal moiety, e.g., modification by a kinase or other enzymes involved in the RISC mechanism pathway. The designation of a modification as having one property does not mean that it has no other property, e.g., a modification referred to as one which promotes stabilization might also enhance targeting.

While not wishing to be bound by theory or any particular mechanistic model, it is believed that asymmetrical modification allows an iRNA agent to be optimized in view of the different or "asymmetrical" functions of the sense and antisense strands. For example, both strands can be modified to increase nuclease resistance, however, since some changes can inhibit RISC activity, these changes can be chosen for the sense stand. In addition, since some modifications, e.g., targeting moieties, can add large bulky groups that, e.g., can interfere with the cleavage activity of the RISC complex, such modifications are preferably placed on the sense strand. Thus, targeting moieties, especially bulky ones (e.g. cholesterol), are preferentially added to the sense strand. In one embodiment, an asymmetrical modification in which a phosphate of the backbone is substituted with S, e.g., a phosphorothioate modification, is present in the antisense strand, and a 2' modification, e.g., 2' OMe is present in the sense strand. A targeting moiety can be present at either (or both) the 5' or 3' end of the sense strand of the iRNA agent. In a preferred example, a P of the backbone is replaced with S in the antisense strand, 2'OMe is present in the sense strand, and a targeting moiety is added to either the 5' or 3' end of the sense strand of the iRNA agent.

In a preferred embodiment an asymmetrically modified iRNA agent has a modification on the sense strand which modification is not found on the antisense strand and the antisense strand has a modification which is not found on the sense strand.

Each strand can include one or more asymmetrical modifications. By way of example: one strand can include a first asymmetrical modification which confers a first property on the iRNA agent and the other strand can have a second asymmetrical modification which confers a second property on the iRNA. E.g., one strand, e.g., the sense strand can have a modification which targets the iRNA agent to a tissue, and the other strand, e.g., the antisense strand, has a modification which promotes hybridization with the target gene sequence.

In some embodiments both strands can be modified to optimize the same property, e.g., to increase resistance to nucleolytic degradation, but different modifications are chosen for the sense and the antisense strands, e.g., because the modifications affect other properties as well. E.g., since some changes can affect RISC activity these modifications are chosen for the sense strand.

In one embodiment, one strand has an asymmetrical 2' modification, e.g., a 2' OMe modification, and the other strand has an asymmetrical modification of the phosphate backbone, e.g., a phosphorothioate modification. So, in one embodiment the antisense strand has an asymmetrical 2' OMe modification and the sense strand has an asymmetrical phosphorothioate modification (or vice versa). In a particularly preferred embodiment, the RNAi agent will have asymmetrical 2'-O alkyl, preferably, 2'-OMe modifications on the sense strand and asymmetrical backbone P modification, preferably a phosphorothioate modification in the antisense strand. There can be one or multiple 2'-OMe modifications, e.g., at least 2, 3, 4, 5, or 6, of the subunits of the sense strand can be so modified. There can be one or multiple phosphorothioate modifications, e.g., at least 2, 3, 4, 5, or 6, of the subunits of the antisense strand can be so modified. It is preferable to have an iRNA agent wherein there are multiple 2'-OMe modifications on the sense strand and multiple phosphorothioate modifications on the antisense strand. All of the subunits on one or both strands can be so modified. A particularly preferred embodiment of multiple asymmetric modifications on both strands has a duplex region about 20-21, and preferably 19, subunits in length and one or two 3' overhangs of about 2 subunits in length.

Asymmetrical modifications are useful for promoting resistance to degradation by nucleases, e.g., endonucleases. iRNA agents can include one or more asymmetrical modifications which promote resistance to degradation. In preferred embodiments the modification on the antisense strand is one which will not interfere with silencing of the target, e.g., one which will not interfere with cleavage of the target. Most if not all sites on a strand are vulnerable, to some degree, to degradation by endonucleases. One can determine sites which are relatively vulnerable and insert asymmetrical modifications which inhibit degradation. It is often desirable to provide asymmetrical modification of a UA site in an iRNA agent, and in some cases it is desirable to provide the UA sequence on both strands with asymmetrical modification. Examples of modifications which inhibit endonucleolytic degradation can be found herein. Particularly favored modifications include: 2' modification, e.g., provision of a 2' OMe moiety on the U, especially on a sense strand; modification of the backbone, e.g., with the replacement of an O with an S, in the phosphate backbone, e.g., the provision of a phosphorothioate, modification, on the U or the A or both, especially on an antisense strand; replacement of the U with a C5 amino linker; replacement of the A with a G (sequence changes are preferred to be located on the sense strand and not the antisense strand); and modification of the at the 2', 6', 7', or 8' position. Preferred embodiments are those in which one or more of these modifications are present on the sense but not the antisense strand, or embodiments where the antisense strand has fewer of such modifications.

Asymmetrical modification can be used to inhibit degradation by exonucleases. Asymmetrical modifications can include those in which only one strand is modified as well as those in which both are modified. In preferred embodiments the modification on the antisense strand is one which will not interfere with silencing of the target, e.g., one which will not interfere with cleavage of the target. Some embodiments will have an asymmetrical modification on the sense strand, e.g., in a 3' overhang, e.g., at the 3' terminus, and on the antisense strand, e.g., in a 3' overhang, e.g., at the 3' terminus. If the modifications introduce moieties of different size it is preferable that the larger be on the sense strand. If the modifications introduce moieties of different charge it is preferable that the one with greater charge be on the sense strand.

Examples of modifications which inhibit exonucleolytic degradation can be found herein. Particularly favored modifications include: 2' modification, e.g., provision of a 2' OMe moiety in a 3' overhang, e.g., at the 3' terminus (3' terminus means at the 3' atom of the molecule or at the most 3' moiety, e.g., the most 3' P or 2' position, as indicated by the context); modification of the backbone, e.g., with the replacement of a P with an S, e.g., the provision of a phosphorothioate modification, or the use of a methylated P in a 3' overhang, e.g., at the 3' terminus; combination of a 2' modification, e.g., provision of a 2' OMe moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrolidine in a 3' overhang, e.g., at the 3' terminus; modification with naproxene, ibuprofen, or other moieties which inhibit degradation at the 3' terminus. Preferred embodiments are those in which one or more of these modifications are present on the sense but not the antisense strand, or embodiments where the antisense strand has fewer of such modifications.

Modifications, e.g., those described herein, which affect targeting can be provided as asymmetrical modifications. Targeting modifications which can inhibit silencing, e.g., by inhibiting cleavage of a target, can be provided as asymmetrical modifications of the sense strand. A biodistribution altering moiety, e.g., cholesterol, can be provided in one or more, e.g., two, asymmetrical modifications of the sense strand. Targeting modifications which introduce moieties having a relatively large molecular weight, e.g., a molecular weight of more than 400, 500, or 1000 daltons, or which introduce a charged moiety (e.g., having more than one positive charge or one negative charge) can be placed on the sense strand.

Modifications, e.g., those described herein, which modulate, e.g., increase or decrease, the affinity of a strand for its compliment or target, can be provided as asymmetrical modifications. These include: 5 methyl U; 5 methyl C; pseudouridine, Locked nucleic acids include: 2 thio U and 2-amino-A. In some embodiments one or more of these is provided on the antisense strand.

iRNA agents have a defined structure, with a sense strand and an antisense strand, and in many cases short single strand overhangs, e.g., of 2 or 3 nucleotides are present at one or both 3' ends. Asymmetrical modification can be used to optimize the activity of such a structure, e.g., by being placed selectively within the iRNA. E.g., the end region of the iRNA agent defined by the 5' end of the sense strand and the 3' end of the antisense strand is important for function. This region can include the terminal 2, 3, or 4 paired nucleotides and any 3' overhang. In preferred embodiments asymmetrical modifications which result in one or more of the following are used: modifications of the 5' end of the sense strand which inhibit kinase activation of the sense strand, including, e.g., attachments of conjugates which target the molecule or the use modifications which protect against 5' exonucleolytic degradation; or modifications of either strand, but preferably the sense strand, which enhance binding between the sense and antisense strand and thereby promote a "tight" structure at this end of the molecule.

The end region of the iRNA agent defined by the 3' end of the sense strand and the 5' end of the antisense strand is also important for function. This region can include the terminal 2, 3, or 4 paired nucleotides and any 3' overhang. Preferred embodiments include asymmetrical modifications of either strand, but preferably the sense strand, which decrease binding between the sense and antisense strand and thereby promote an "open" structure at this end of the molecule. Such modifications include placing conjugates which target the molecule or modifications which promote nuclease resistance on the sense strand in this region. Modification of the antisense strand which inhibit kinase activation are avoided in preferred embodiments.

Exemplary modifications for asymmetrical placement in the sense strand include the following:

(a) backbone modifications, e.g., modification of a backbone P, including replacement of P with S, or P substituted with alkyl or allyl, e.g., Me, and dithioates (S—P=S); these modifications can be used to promote nuclease resistance;

(b) 2'-O alkyl, e.g., 2'-OMe, 3'-O alkyl, e.g., 3'-OMe (at terminal and/or internal positions); these modifications can be used to promote nuclease resistance or to enhance binding of the sense to the antisense strand, the 3' modifications can be used at the 5' end of the sense strand to avoid sense strand activation by RISC;

(c) 2'-5' linkages (with 2'-H, 2'-OH and 2'-OMe and with P=O or P=S) these modifications can be used to promote nuclease resistance or to inhibit binding of the sense to the antisense strand, or can be used at the 5' end of the sense strand to avoid sense strand activation by RISC;

(d) L sugars (e.g., L ribose, L-arabinose with 2'-H, 2'-OH and 2'-OMe); these modifications can be used to promote nuclease resistance or to inhibit binding of the sense to the antisense strand, or can be used at the 5' end of the sense strand to avoid sense strand activation by RISC;

(e) modified sugars (e.g., locked nucleic acids (LNA's), hexose nucleic acids (HNA's) and cyclohexene nucleic acids (CeNA's)); these modifications can be used to promote nuclease resistance or to inhibit binding of the sense to the antisense strand, or can be used at the 5' end of the sense strand to avoid sense strand activation by RISC;

(f) nucleobase modifications (e.g., C-5 modified pyrimidines, N-2 modified purines, N-7 modified purines, N-6 modified purines), these modifications can be used to promote nuclease resistance or to enhance binding of the sense to the antisense strand;

(g) cationic groups and Zwitterionic groups (preferably at a terminus), these modifications can be used to promote nuclease resistance;

(h) conjugate groups (preferably at terminal positions), e.g., naproxen, biotin, cholesterol, ibuprofen, folic acid, peptides, and carbohydrates; these modifications can be used to promote nuclease resistance or to target the molecule, or can be used at the 5' end of the sense strand to avoid sense strand activation by RISC.

Exemplary modifications for asymmetrical placement in the antisense strand include the following:

(a) backbone modifications, e.g., modification of a backbone P, including replacement of P with S, or P substituted with alkyl or allyl, e.g., Me, and dithioates (S—P=S);

(b) 2'-O alkyl, e.g., 2'-OMe, (at terminal positions);

(c) 2'-5' linkages (with 2'-H, 2'-OH and 2'-OMe) e.g., terminal at the 3' end); e.g., with P=O or P=S preferably at the 3'-end, these modifications are preferably excluded from the 5' end region as they may interfere with RISC enzyme activity such as kinase activity;

(d) L sugars (e.g, L ribose, L-arabinose with 2'-H, 2'-OH and 2'-OMe); e.g., terminal at the 3' end; e.g., with P=O or P=S preferably at the 3'-end, these modifications are preferably excluded from the 5' end region as they may interfere with kinase activity;

(e) modified sugars (e.g., LNA's, HNA's and CeNA's); these modifications are preferably excluded from the 5' end region as they may contribute to unwanted enhancements of paring between the sense and antisense strands, it is often preferred to have a "loose" structure in the 5' region, additionally, they may interfere with kinase activity;

(f) nucleobase modifications (e.g., C-5 modified pyrimidines, N-2 modified purines, N-7 modified purines, N-6 modified purines);

(g) cationic groups and Zwitterionic groups (preferably at a terminus);

cationic groups and Zwitterionic groups at 2'-position of sugar; 3'-position of the sugar; as nucleobase modifications (e.g., C-5 modified pyrimidines, N-2 modified purines, N-7 modified purines, N-6 modified purines);

conjugate groups (preferably at terminal positions), e.g., naproxen, biotin, cholesterol, ibuprofen, folic acid, peptides, and carbohydrates, but bulky groups or generally groups which inhibit RISC activity should are less preferred.

The 5'-OH of the antisense strand should be kept free to promote activity. In some preferred embodiments modifications that promote nuclease resistance should be included at the 3' end, particularly in the 3' overhang.

In another aspect, the invention features a method of optimizing, e.g., stabilizing, an iRNA agent. The method includes selecting a sequence having activity, introducing one or more asymmetric modifications into the sequence, wherein the introduction of the asymmetric modification optimizes a property of the iRNA agent but does not result in a decrease in activity.

The decrease in activity can be less than a preselected level of decrease. In preferred embodiments decrease in activity means a decrease of less than 5, 10, 20, 40, or 50% activity, as compared with an otherwise similar iRNA lacking the introduced modification. Activity can, e.g., be measured in vivo, or in vitro, with a result in either being sufficient to demonstrate the required maintenance of activity.

The optimized property can be any property described herein and in particular the properties discussed in the section on asymmetrical modifications provided herein. The modification can be any asymmetrical modification, e.g., an asymmetric modification described in the section on asymmetrical modifications described herein. Particularly preferred asymmetric modifications are 2'-O alkyl modifications, e.g., 2'-OMe modifications, particularly in the sense sequence, and modifications of a backbone O, particularly phosphorothioate modifications, in the antisense sequence.

In a preferred embodiment a sense sequence is selected and provided with an asymmetrical modification, while in other embodiments an antisense sequence is selected and provided with an asymmetrical modification. In some embodiments both sense and antisense sequences are selected and each provided with one or more asymmetrical modifications.

Multiple asymmetric modifications can be introduced into either or both of the sense and antisense sequence. A sequence can have at least 2, 4, 6, 8, or more modifications and all or substantially all of the monomers of a sequence can be modified.

Differential Modification of Terminal Duplex Stability

In one aspect, the invention features an iRNA agent which can have differential modification of terminal duplex stability (DMTDS).

In addition, the invention includes iRNA agents having DMTDS and another element described herein. E.g., the invention includes an iRNA agent described herein, e.g., a palindromic iRNA agent, an iRNA agent having a non canonical pairing, an iRNA agent which targets a gene described herein, e.g., an htt gene, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates DMTDS.

iRNA agents can be optimized by increasing the propensity of the duplex to disassociate or melt (decreasing the free energy of duplex association), in the region of the 5' end of the antisense strand duplex. This can be accomplished, e.g., by the inclusion of subunits, which increase the propensity of the duplex to disassociate or melt in the region of the 5' end of the antisense strand. This can also be accomplished by the attachment of a ligand that increases the propensity of the duplex to disassociate of melt in the region of the 5' end. While not wishing to be bound by theory, the effect may be due to promoting the effect of an enzyme such as a helicase, for example, promoting the effect of the enzyme in the proximity of the 5' end of the antisense strand.

The inventors have also discovered that iRNA agents can be optimized by decreasing the propensity of the duplex to disassociate or melt (increasing the free energy of duplex association), in the region of the 3' end of the antisense strand duplex. This can be accomplished, e.g., by the inclusion of subunits which decrease the propensity of the duplex to disassociate or melt in the region of the 3' end of the antisense strand. It can also be accomplished by the attachment of ligand that decreases the propensity of the duplex to disassociate or melt in the region of the 5' end.

Modifications which increase the tendency of the 5' end of the duplex to dissociate can be used alone or in combination with other modifications described herein, e.g., with modifications which decrease the tendency of the 3' end of the duplex to dissociate. Likewise, modifications which decrease the tendency of the 3' end of the duplex to dissociate can be used alone or in combination with other modifications described herein, e.g., with modifications which increase the tendency of the 5' end of the duplex to dissociate.

Decreasing the Stability of the AS 5' End of the Duplex

Subunit pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation:

A:U is preferred over G:C;
G:U is preferred over G:C;
I:C is preferred over G:C (I=inosine);
mismatches, e.g., non-canonical or other than canonical pairings (as described elsewhere herein) are preferred over canonical (A:T, A:U, G:C) pairings;
pairings which include a universal base are preferred over canonical pairings.

A typical ds iRNA agent can be diagrammed as follows:

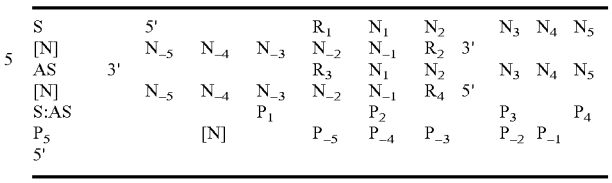

S indicates the sense strand; AS indicates antisense strand; $R_1$ indicates an optional (and nonpreferred) 5' sense strand overhang; $R_2$ indicates an optional (though preferred) 3' sense overhang; $R_3$ indicates an optional (though preferred) 3' antisense sense overhang; $R_4$ indicates an optional (and nonpreferred) 5' antisense overhang; N indicates subunits; [N] indicates that additional subunit pairs may be present; and $P_x$, indicates a paring of sense $N_x$ and antisense $N_x$. Overhangs are not shown in the P diagram. In some embodiments a 3' AS overhang corresponds to region Z, the duplex region corresponds to region X, and the 3'S strand overhang corresponds to region Y, as described elsewhere herein. (The diagram is not meant to imply maximum or minimum lengths, on which guidance is provided elsewhere herein.)

It is preferred that pairings which decrease the propensity to form a duplex are used at 1 or more of the positions in the duplex at the 5' end of the AS strand. The terminal pair (the most 5' pair in terms of the AS strand) is designated as $P_{-1}$, and the subsequent pairing positions (going in the 3' direction in terms of the AS strand) in the duplex are designated, $P_{-2}$, $P_{-3}$, $P_{-4}$, $P_{-5}$, and so on. The preferred region in which to modify or modulate duplex formation is at $P_{-5}$ through $P_{-1}$, more preferably $P_{-4}$ through $P_{-1}$, more preferably $P_{-3}$ through $P_{-1}$. Modification at $P_{-1}$, is particularly preferred, alone or with modification(s) other position(s), e.g., any of the positions just identified. It is preferred that at least 1, and more preferably 2, 3, 4, or 5 of the pairs of one of the recited regions be chosen independently from the group of:

A:U
G:U
I:C
mismatched pairs, e.g., non-canonical or other than canonical pairings or pairings which include a universal base.

In preferred embodiments the change in subunit needed to achieve a pairing which promotes dissociation will be made in the sense strand, though in some embodiments the change will be made in the antisense strand.

In a preferred embodiment the at least 2, or 3, of the pairs in $P_{-1}$, through $R_{-4}$, are pairs which promote dissociation.

In a preferred embodiment the at least 2, or 3, of the pairs in $P_{-1}$, through $P_{-4}$, are A:U.

In a preferred embodiment the at least 2, or 3, of the pairs in $P_{-1}$, through $P_{-4}$, are G:U.

In a preferred embodiment the at least 2, or 3, of the pairs in $P_{-1}$, through $P_{-4}$, are I:C.

In a preferred embodiment the at least 2, or 3, of the pairs in $P_{-1}$, through $P_{-4}$, are mismatched pairs, e.g., non-canonical or other than canonical pairings.

In a preferred embodiment the at least 2, or 3, of the pairs in $P_{-1}$, through $P_{-4}$, are pairings which include a universal base.

Increasing the Stability of the AS 3' End of the Duplex

Subunit pairs can be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability:

G:C is preferred over A:U

Watson-Crick matches (A:T, A:U, G:C) are preferred over non-canonical or other than canonical pairings analogs that increase stability are preferred over Watson-Crick matches (A:T, A:U, G:C)

2-amino-A:U is preferred over A:U 2-thio U or 5 Me-thio-U:A are preferred over U:A G-clamp (an analog of C having 4 hydrogen bonds):G is preferred over C:G guanadinium-G-clamp:G is preferred over C:G pseudo uridine:A is preferred over U:A sugar modifications, e.g., 2' modifications, e.g., 2'F, ENA, or LNA, which enhance binding are preferred over non-modified moieties and can be present on one or both strands to enhance stability of the duplex. It is preferred that pairings which increase the propensity to form a duplex are used at 1 or more of the positions in the duplex at the 3' end of the AS strand. The terminal pair (the most 3' pair in terms of the AS strand) is designated as $P_1$, and the subsequent pairing positions (going in the 5' direction in terms of the AS strand) in the duplex are designated, $P_2$, $P_3$, $P_4$, $P_5$, and so on. The preferred region in which to modify to modulate duplex formation is at $P_5$ through $P_1$, more preferably $P_4$ through $P_1$, more preferably $P_3$ through $P_1$. Modification at $P_1$, is particularly preferred, alone or with modification(s) at other position(s), e.g., any of the positions just identified. It is preferred that at least 1, and more preferably 2, 3, 4, or 5 of the pairs of the recited regions be chosen independently from the group of:

G:C a pair having an analog that increases stability over Watson-Crick matches (A:T, A:U, G:C)

2-amino-A:U 2-thio U or 5 Me-thio-U:A

G-clamp (an analog of C having 4 hydrogen bonds):G guanadinium-G-clamp:G pseudo uridine:A a pair in which one or both subunits has a sugar modification, e.g., a 2' modification, e.g., 2'F, ENA, or LNA, which enhance binding.

In a preferred embodiment the at least 2, or 3, of the pairs in $P_{-1}$, through $P_{-4}$, are pairs which promote duplex stability.

In a preferred embodiment the at least 2, or 3, of the pairs in $P_1$, through $P_4$, are G:C.

In a preferred embodiment the at least 2, or 3, of the pairs in $P_1$, through $P_4$, are a pair having an analog that increases stability over Watson-Crick matches.

In a preferred embodiment the at least 2, or 3, of the pairs in $P_1$, through $P_4$, are 2-amino-A:U.

In a preferred embodiment the at least 2, or 3, of the pairs in $P_1$, through $P_4$, are 2-thio U or 5 Me-thio-U:A.

In a preferred embodiment the at least 2, or 3, of the pairs in $P_1$, through $P_4$, are G-clamp:G.

In a preferred embodiment the at least 2, or 3, of the pairs in $P_1$, through $P_4$, are guanidinium-G-clamp:G.

In a preferred embodiment the at least 2, or 3, of the pairs in $P_1$, through $P_4$, are pseudo uridine:A.

In a preferred embodiment the at least 2, or 3, of the pairs in $P_1$, through $P_4$, are a pair in which one or both subunits has a sugar modification, e.g., a 2' modification, e.g., 2'F, ENA, or LNA, which enhances binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

Simultaneously Decreasing the Stability of the AS 5'End of the Duplex and Increasing the Stability of the AS 3' End of the Duplex As is discussed above, an iRNA agent can be modified to both decrease the stability of the AS 5' end of the duplex and increase the stability of the AS 3' end of the duplex. This can be effected by combining one or more of the stability decreasing modifications in the AS 5' end of the duplex with one or more of the stability increasing modifications in the AS 3' end of the duplex. Accordingly a preferred embodiment includes modification in $R_{-5}$ through $P_{-1}$, more preferably $R_{-4}$ through $P_{-1}$ and more preferably $P_{-3}$ through $P_{-1}$. Modification at $P_{-1}$, is particularly preferred, alone or with other position, e.g., the positions just identified. It is preferred that at least 1, and more preferably 2, 3, 4, or 5 of the pairs of one of the recited regions of the AS 5' end of the duplex region 1:16 chosen independently from the group of:

A:U

G:U

I:C mismatched pairs, e.g., non-canonical or other than canonical pairings which include a universal base; and a modification in $P_5$ through $P_1$, more preferably $P_4$ through $P_1$ and more preferably $P_3$ through $P_1$. Modification at $P_1$, is particularly preferred, alone or with other position, e.g., the positions just identified. It is preferred that at least 1, and more preferably 2, 3, 4, or 5 of the pairs of one of the recited regions of the AS 3' end of the duplex region be chosen independently from the group of:

G:C a pair having an analog that increases stability over Watson-Crick matches (A:T, A:U, G:C)

2-amino-A:U 2-thio U or 5 Me-thio-U:A

G-clamp (an analog of C having 4 hydrogen bonds):G guanadinium-G-clamp:G pseudo uridine:A a pair in which one or both subunits has a sugar modification, e.g., a 2' modification, e.g., 2'F, ENA, or LNA, which enhance binding.

The invention also includes methods of selecting and making iRNA agents having DMTDS. E.g., when screening a target sequence for candidate sequences for use as iRNA agents one can select sequences having a DMTDS property described herein or one which can be modified, preferably with as few changes as possible, especially to the AS strand, to provide a desired level of DMTDS.

The invention also includes, providing a candidate iRNA agent sequence, and modifying at least one P in $P_{-5}$ through $P_{-1}$ and/or at least one P in $P_5$ through $P_1$ to provide a DMTDS iRNA agent.

DMTDS iRNA agents can be used in any method described herein, e.g., to silence an htt RNA, to treat any disorder described herein, e.g., a neurological disorder, in any formulation described herein, and generally in and/or with the methods and compositions described elsewhere herein. DMTDS iRNA agents can incorporate other modifications described herein, e.g., the attachment of targeting agents or the inclusion of modifications which enhance stability, e.g., the inclusion of nuclease resistant monomers or the inclusion of single strand overhangs (e.g., 3' AS overhangs and/or 3'S strand overhangs) which self associate to form intrastrand duplex structure.

Preferably these iRNA agents will have an architecture described herein.

Other Embodiments

An RNA, e.g., an iRNA agent, can be produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of an iRNA agent and one that produces a transcript that includes the bottom strand of an iRNA agent. When the templates are transcribed, the iRNA agent is produced, and processed into sRNA agent fragments that mediate gene silencing.

Physiological Effects

The iRNA agents described herein can be designed such that determining therapeutic toxicity is made easier by the complementarity of the iRNA agent with both a human and a non-human animal sequence. By these methods, an iRNA agent can consist of a sequence that is fully complementary to a nucleic acid sequence from a human and a nucleic acid sequence from at least one non-human animal, e.g.; a non-human mammal, such as a rodent, ruminant or primate. For example, the non-human mammal can be a mouse, rat, dog, pig, goat, sheep, cow, monkey, Pan paniscus, Pan troglodytes, Macaca mulatto, or Cynomolgus monkey. The sequence of the iRNA agent could be complementary to sequences within homologous genes, e.g., oncogenes or tumor suppressor genes, of the non-human mammal and the human. By determining the toxicity of the iRNA agent in the non-human mammal, one can extrapolate the toxicity of the iRNA agent in a human. For a more strenuous toxicity test, the iRNA agent can be complementary to a human and more than one, e.g., two or three or more, non-human animals.

The methods described herein can be used to correlate any physiological effect of an iRNA agent on a human, e.g., any unwanted effect, such as a toxic effect, or any positive, or desired effect.

Amphipathic Delivery Agents

An iRNA agent, described herein can be used with an amphipathic delivery conjugate or module, such as those described herein.

An amphipathic molecule is a molecule having a hydrophobic and a hydrophilic region. Such molecules can interact with (e.g., penetrate or disrupt) lipids, e.g., a lipid bilayer of a cell. As such, they can serve as delivery agent for an associated (e.g., bound) iRNA (e.g., an iRNA or sRNA described herein). A preferred amphipathic molecule to be used in the compositions described herein (e.g., the amphipathic iRNA constructs described herein) is a polymer. The polymer may have a secondary structure, e.g., a repeating secondary structure.

One example of an amphipathic polymer is an amphipathic polypeptide, e.g., a polypeptide having a secondary structure such that the polypeptide has a hydrophilic and a hydrophobic face. The design of amphipathic peptide structures (e.g., alpha-helical polypeptides) is routine to one of skill in the art. For example, the following references provide guidance: Grell et al. (2001) *J Pept Sci* 7(3):146-51; Chen et al. (2002) *J Pept Res* 59(1):18-33; Iwata et al. (1994) *J Biol Chem* 269(7):4928-33; Cornut et al. (1994) *FEBS Lett* 349(1):29-33; Negrete et al. (1998) *Protein Sci* 7(6):1368-79.

Another example of an amphipathic polymer is a polymer made up of two or more amphipathic subunits, e.g., two or more subunits containing cyclic moieties (e.g., a cyclic moiety having one or more hydrophilic groups and one or more hydrophobic groups). For example, the subunit may contain a steroid, e.g., cholic acid; or a aromatic moiety. Such moieties preferably can exhibit atropisomerism, such that they can form opposing hydrophobic and hydrophilic faces when in a polymer structure.

The ability of a putative amphipathic molecule to interact with a lipid membrane, e.g., a cell membrane, can be tested by routine methods, e.g., in a cell free or cellular assay. For example, a test compound is combined or contacted with a synthetic lipid bilayer, a cellular membrane fraction, or a cell, and the test compound is evaluated for its ability to interact with, penetrate, or disrupt the lipid bilayer, cell membrane or cell. The test compound can be labeled in order to detect the interaction with the lipid bilayer, cell membrane, or cell. In another type of assay, the test compound is linked to a reporter molecule or an iRNA agent (e.g., an iRNA or sRNA described herein), and the ability of the reporter molecule or iRNA agent to penetrate the lipid bilayer, cell membrane or cell is evaluated. A two-step assay can also be performed, wherein a first assay evaluates the ability of a test compound alone to interact with a lipid bilayer, cell membrane or cell; and a second assay evaluates the ability of a construct (e.g., a construct described herein) that includes the test compound and a reporter or iRNA agent to interact with a lipid bilayer, cell membrane or cell.

An amphipathic polymer useful in the compositions described herein has at least 2, preferably at least 5, more preferably at least 10, 25, 50, 100, 200, 500, 1000, 2000, 50000 or more subunits (e.g., amino acids or cyclic subunits). A single amphipathic polymer can be linked to one or more, e.g., 2, 3, 5, 10 or more iRNA agents (e.g., iRNA or sRNA agents described herein). In some embodiments, an amphipathic polymer can contain both amino acid and cyclic subunits, e.g., aromatic subunits.

The invention features a composition that includes an iRNA agent (e.g., an iRNA or sRNA described herein) in association with an amphipathic molecule. Such compositions may be referred to herein as "amphipathic iRNA constructs." Such compositions and constructs are useful in the delivery or targeting of iRNA agents, e.g., delivery or targeting of iRNA agents to a cell. While not wanting to be bound by theory, such compositions and constructs can increase the porosity of, e.g., can penetrate or disrupt, a lipid (e.g., a lipid bilayer of a cell), e.g., to allow entry of the iRNA agent into a cell.

In one aspect, the invention relates to a composition comprising an iRNA agent (e.g., an iRNA or sRNA agent described herein) linked to an amphipathic molecule. The iRNA agent and the amphipathic molecule may be held in continuous contact with one another by either covalent or noncovalent linkages.

The amphipathic molecule of the composition or construct is preferably other than a phospholipid, e.g., other than a micelle, membrane or membrane fragment.

The amphipathic molecule of the composition or construct is preferably a polymer. The polymer may include two or more amphipathic subunits. One or more hydrophilic groups and one or more hydrophobic groups may be present on the polymer. The polymer may have a repeating secondary structure as well as a first face and a second face. The distribution of the hydrophilic groups and the hydrophobic groups along the repeating secondary structure can be such that one face of the polymer is a hydrophilic face and the other face of the polymer is a hydrophobic face.

The amphipathic molecule can be a polypeptide, e.g., a polypeptide comprising an α-helical conformation as its secondary structure.

In one embodiment, the amphipathic polymer includes one or more subunits containing one or more cyclic moiety (e.g., a cyclic moiety having one or more hydrophilic groups and/or one or more hydrophobic groups). In one embodiment, the polymer is a polymer of cyclic moieties such that the moieties have alternating hydrophobic and hydrophilic groups. For example, the subunit may contain a steroid, e.g., cholic acid. In another example, the subunit may contain an aromatic moiety. The aromatic moiety may be one that can exhibit atropisomerism, e.g., a 2,2'-bis(substituted)-1-1'-binaphthyl or a 2,2'-bis(substituted) biphenyl. A subunit may include an aromatic moiety of Formula (M):

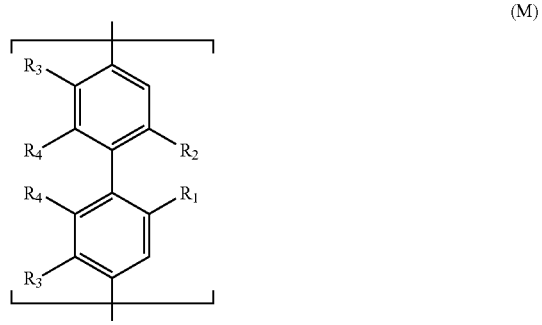

(M)

The invention features a composition that includes an iRNA agent (e.g., an iRNA or sRNA described herein) in association with an amphipathic molecule. Such compositions may be referred to herein as "amphipathic iRNA constructs." Such compositions and constructs are useful in the delivery or targeting of iRNA agents, e.g., delivery or targeting of iRNA agents to a cell. While not wanting to be bound by theory, such compositions and constructs can increase the porosity of, e.g., can penetrate or disrupt, a lipid (e.g., a lipid bilayer of a cell), e.g., to allow entry of the iRNA agent into a cell.

Referring to Formula M, $R_1$ is $C_1$-$C_{100}$ alkyl optionally substituted with aryl, alkenyl, alkynyl, alkoxy or halo and/or optionally inserted with O, S, alkenyl or alkynyl; $C_1$-$C_{100}$ perfluoroalkyl; or $OR_5$.

$R_2$ is hydroxy; nitro; sulfate; phosphate; phosphate ester; sulfonic acid; $OR_6$; or $C_1$-$C_{100}$ alkyl optionally substituted with hydroxy, halo, nitro, aryl or alkyl sulfinyl, aryl or alkyl sulfonyl, sulfate, sulfonic acid, phosphate, phosphate ester, substituted or unsubstituted aryl, carboxyl, carboxylate, amino carbonyl, or alkoxycarbonyl, and/or optionally inserted with O, NH, S, S(O), $SO_2$, alkenyl, or alkynyl.

$R_3$ is hydrogen, or when taken together with $R_4$ forms a fused phenyl ring.

$R_4$ is hydrogen, or when taken together with $R_3$ forms a fused phenyl ring.

$R_5$ is $C_1$-$C_{100}$ alkyl optionally substituted with aryl, alkenyl, alkynyl, alkoxy or halo and/or optionally inserted with O, S, alkenyl or alkynyl; or $C_1$-$C_{100}$ perfluoroalkyl; and $R_6$ is $C_1$-$C_{100}$ alkyl optionally substituted with hydroxy, halo, nitro, aryl or alkyl sulfinyl, aryl or alkyl sulfonyl, sulfate, sulfonic acid, phosphate, phosphate ester, substituted or unsubstituted aryl, carboxyl, carboxylate, amino carbonyl, or alkoxycarbonyl, and/or optionally inserted with O, NH, S, S(O), $SO_2$, alkenyl, or alkynyl.

An iRNA agent can have a ZXY structure, such as is described in co-owned PCT Application No. PCT/US2004/07070 filed on Mar. 8, 2004.

The sense and antisense sequences of an iRNA agent can be palindromic. Exemplary features of palindromic iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Increasing Cellular Uptake of dsRNAs

A method of the invention that can include the administration of an iRNA agent and a drug that affects the uptake of the iRNA agent into the cell. The drug can be administered before, after, or at the same time that the iRNA agent is administered. The drug can be covalently linked to the iRNA agent. The drug can have a transient effect on the cell.

The drug can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

iRNA Conjugates

An iRNA agent conjugated to lipophilic agent for enhanced uptake into a neural cell can be coupled, e.g., covalently coupled, to a second agent. For example, an iRNA agent used to treat a particular neurological disorder can be coupled to a second therapeutic agent, e.g., an agent other than the iRNA agent. The second therapeutic agent can be one which is directed to the treatment of the same neurological disorder. For example, in the case of an iRNA used to treat a HD, the iRNA agent can be coupled to a second agent which is known to be useful for the treatment of HD.

iRNA Production

An iRNA can be produced, e.g., in bulk, by a variety of methods. Exemplary methods include: organic synthesis and RNA cleavage, e.g., in vitro cleavage.

Organic Synthesis.

An iRNA can be made by separately synthesizing each respective strand of a double-stranded RNA molecule. The component strands can then be annealed.

A large bioreactor, e.g., the OligoPilot II from Pharmacia Biotec AB (Uppsala Sweden), can be used to produce a large amount of a particular RNA strand for a given iRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the 21 to 23 nucleotide strand for the iRNA. Typically, the two complementary strands are produced separately and then annealed, e.g., after release from the solid support and deprotection.

Organic synthesis can be used to produce a discrete iRNA species. The complementary of the species to a particular target gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

dsRNA Cleavage.

iRNAs can also be made by cleaving a larger ds iRNA. The cleavage can be mediated in vitro or in vivo. For example, to produce iRNAs by cleavage in vitro, the following method can be used:

In vitro transcription. dsRNA is produced by transcribing a nucleic acid (DNA) segment in both directions. For example, the HiScribe™ RNAi transcription kit (New England Biolabs) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used. In one embodiment, RNA generated by this method is carefully purified to remove endotoxins that may contaminate preparations of the recombinant enzymes.

In vitro cleavage. dsRNA is cleaved in vitro into iRNAs, for example, using a Dicer or comparable RNAse III-based activity. For example, the dsRNA can be incubated in an in vitro extract from *Drosophila* or using purified components, e.g. a purified RNAse or RISC complex (RNA-induced silencing complex). See, e.g., Ketting et al. *Genes Dev* 2001 Oct. 15; 15(20):2654-9. and Hammond *Science* 2001 Aug. 10; 293(5532):1146-50.

dsRNA cleavage generally produces a plurality of iRNA species, each being a particular 21 to 23 nt fragment of a source dsRNA molecule. For example, iRNAs that include sequences complementary to overlapping regions and adjacent regions of a source dsRNA molecule may be present.

Regardless of the method of synthesis, the iRNA preparation can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Synthesis of modified and nucleotide surrogate iRNA agents is discussed below.

Formulation

The iRNA agents described herein can be formulated for administration to a subject.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA that can mediated RNAi with respect to a second gene, or with respect to the same gene. Still other preparation can include at least three, five, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than an RNA or a DNA). For example, a iRNA composition for the treatment of a neurological disease, e.g., neurodegenerative disease, such as PD, might include a known PD therapeutic (e.g., levadopa or depronil)

Targeting

For ease of exposition the formulations, compositions and methods in this section are discussed largely with regard to unmodified iRNAs. It should be understood, however, that these formulations, compositions and methods can be practiced with other iRNA agents, e.g., modified iRNA agents, and such practice is within the invention.

In some embodiments, an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) is targeted to a particular cell. For example, a liposome or particle or other structure that includes a iRNA can also include a targeting moiety that recognizes a specific molecule on a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell.

An antigen, can be used to target an iRNA to a neural cell in the brain.

In one embodiment, the targeting moiety is attached to a liposome. For example, U.S. Pat. No. 6,245,427 describes a method for targeting a liposome using a protein or peptide. In another example, a cationic lipid component of the liposome is derivatized with a targeting moiety. For example, WO 96/37194 describes converting N-glutaryldioleoylphosphatidyl ethanolamine to a N-hydroxysuccinimide activated ester. The product was then coupled to an RGD peptide.

Treatment Methods and Routes of Delivery

A composition that includes an iRNA agent targeting a gene expressed in neural cells, can be delivered to a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the iRNA agents to peripheral neurons. A preferred route of delivery is directly to the brain, e.g., into the ventricles or the hypothalamus of the brain, or into the lateral or dorsal areas of the brain. The iRNA agents for neural cell delivery can be incorporated into pharmaceutical compositions suitable for administration. For example, compositions can include one or more species of an iRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. A pharmaceutically acceptable carrier does not include a transfection reagent or a reagent to facilitate uptake in a neural cell that is in addition to the lipophilic moiety conjugated to the iRNA agent featured in the invention. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration.

The route of delivery can be dependent on the disorder of the patient. For example, a subject diagnosed with HD can be administered an anti-htt iRNA agent conjugated to a lipophilic agent directly into the brain (e.g., into the globus pallidus or the corpus striatum of the basal ganglia, and near the medium spiny neurons of the corpus striatum). A subject diagnosed with multiple system atrophy can be administered an iRNA agent directly into the brain, e.g., into the striatum and substantia nigra regions of the brain, and into the spinal cord. A subject diagnosed with Lewy body dementia can be administered an iRNA agent directly into the brain, e.g., directly into the cortex of the brain, and administration can be diffuse. In addition to an iRNA agent modified for enhanced delivery to neural cells, a patient can be administered a second therapy, e.g., a palliative therapy and/or disease-specific therapy. The secondary therapy can be, for example, symptomatic, (e.g., for alleviating symptoms), neuroprotective (e.g., for slowing or halting disease progression), or restorative (e.g., for reversing the disease process). Preferable, the subject is not administered an anti-SNCA iRNA.

For the treatment of HD, for example, symptomatic therapies can include the drugs haloperidol, carbamazepine, or valproate. Other therapies can include psychotherapy, physiotherapy, speech therapy, communicative and memory aids, social support services, and dietary advice.

For the treatment of Parkinson's Disease, symptomatic therapies can include the drugs carbidopa/levodopa, entacapone, tolcapone, pramipexole, ropinerole, pergolide, bromocriptine, selegeline, amantadine, and several anticholingergic agents. Deep brain stimulation surgery as well as stereotactic brain lesioning may also provide symptomatic relief. Neuroprotective therapies include, for example, carbidopa/levodopa, selegeline, vitamin E, amantadine, pramipexole, ropinerole, coenzyme Q10, and GDNF. Restorative therapies can include, for example, surgical transplantation of stem cells.

An iRNA agent conjugated with a lipophilic moiety can be delivered to neural cells of the brain. Delivery methods that do not require passage of the composition across the blood-brain barrier can be utilized. For example, a pharmaceutical composition containing an iRNA agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The iRNA agent can be delivered into multiple regions of the central nervous system (e.g., into multiple regions of the brain, and/or into the spinal cord). The iRNA agent can be delivered into diffuse regions of the brain (e.g., diffuse delivery to the cortex of the brain).

In one embodiment, the iRNA agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of iRNA agent. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An iRNA agent conjugated to a lipophilic moiety, e.g., cholesterol, can be further modified such that it is capable of traversing the blood brain barrier. For example, the iRNA agent can be conjugated to a molecule that enables the agent to traverse the barrier. Such modified iRNA agents can be administered by any desired method, such as by intraventricular or intramuscular injection, or by pulmonary delivery, for example.

The iRNA agent conjugated to a lipophilic moiety for enhanced uptake into neural cells can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the iRNA agent can also be applied via an ocular patch.

Administration can be provided by the subject or by another person, e.g., a another caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The subject can be monitored for reactions to the treatment, such as edema or hemorrhaging. For example, the patient can be monitored by MRI, such as daily or weekly following injection, and at periodic time intervals following injection.

The subject can also be monitored for an improvement or stabilization of disease symptoms. Such monitoring can be achieved, for example, by serial clinical assessments (e.g., using the United Parkinson's Disease Rating Scale) or functional neuroimaging. Monitoring can also include serial quantitative measures of striatal dopaminergic function (e.g., fluorodopa and positron emission tomography) comparing treated subjects to normative data collected from untreated subjects. Additional outcome measures can include survival and survival free of palliative therapy and nursing home placement. Statistically significant differences in these measurements and outcomes for treated and untreated subjects is evidence of the efficacy of the treatment.

A pharmaceutical composition containing an iRNA agent conjugated to a lipophilic moiety for enhanced uptake into neural cells can be administered to any patient diagnosed as having or at risk for developing a neurological disorder, such as HD. In one embodiment, the patient is diagnosed as having a neurological disorder, and the patient is otherwise in general good health. For example, the patient is not terminally ill, and the patient is likely to live at least 2, 3, 5, or 10 years or longer following diagnosis. The patient can be treated immediately following diagnosis, or treatment can be delayed until the patient is experiencing more debilitating symptoms, such as motor fluctuations and dyskinesis in PD patients. In another embodiment, the patient has not reached an advanced stage of the disease, e.g., the patient has not reached Hoehn and Yahr stage 5 of PD (Hoehn and Yahr, *Neurology* 17:427-442, 1967). In general, an iRNA agent conjugated to a lipophilic moiety can be administered by any suitable method. As used herein, topical delivery can refer to the direct application of an iRNA agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the iRNA agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration preferably do not include a transfection reagent or an additional lipophilic moiety besides the lipophilic moiety attached to the iRNA agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An iRNA agent conjugated to a lipophilic agent for enhanced uptake into neural cells can be administered to a subject by pulmonary delivery. Pulmonary delivery compositions can be delivered by inhalation by the patient of a dispersion so that the composition, preferably iRNA, within the dispersion can reach the lung where it can be readily absorbed through the alveolar region directly into blood circulation. Pulmonary delivery can be effective both for systemic delivery and for localized delivery to treat diseases of the lungs. In one embodiment, an iRNA agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An iRNA agent conjugated to a lipophilic moiety for enhanced uptake into neural cells can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an iRNA agent administered by oral or nasal delivery has been modified to be capable of traversing the blood-brain barrier.

In one embodiment, unit doses or measured doses of a composition that include iRNA are dispensed by an implanted device. The device can include a sensor that monitors a parameter within a subject. For example, the device can include a pump, such as an osmotic pump and, optionally, associated electronics.

An iRNA agent can be packaged in a viral natural capsid or in a chemically or enzymatically produced artificial capsid or structure derived therefrom.

Dosage.

An iRNA agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an iRNA agent directly to an organ (e.g., directly to the brain) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a neurological disease or disorder, e.g., HD.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has PD and the modality is a therapeutic agent other than an iRNA agent, e.g., other than a double-stranded iRNA agent, or sRNA agent. The therapeutic modality can be, for example, levadopa or depronil.

In one embodiment, a subject is administered an initial dose, and one or more maintenance doses of an iRNA agent, e.g., a double-stranded iRNA agent, or sRNA agent, (e.g., a precursor, e.g., a larger iRNA agent which can be processed into an sRNA agent, or a DNA which encodes an iRNA agent, e.g., a double-stranded iRNA agent, or sRNA agent, or precursor thereof). The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g.; a pump, semi-permanent stent (e.g., intravenous, intraperitoneal, intracisternal or intracapsular), or reservoir may be advisable.

In one embodiment, the iRNA agent pharmaceutical composition includes a plurality of iRNA agent species. In another embodiment, the iRNA agent species has sequences that are non-overlapping and non-adjacent to another species with respect to a naturally occurring target sequence. In another embodiment, the plurality of iRNA agent species is specific for different naturally occurring target genes. In another embodiment, the iRNA agent is allele specific.

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent, e.g., a double-stranded iRNA agent, or sRNA agent (e.g., a precursor, e.g., a larger iRNA agent which can be processed into a sRNA agent, or a DNA which encodes an iRNA agent, e.g., a double-stranded iRNA agent, or sRNA agent, or precursor thereof) can include a single treatment or, preferably, can include a series of treatments. It will also be appreciated that the effective dosage of an iRNA agent such as an sRNA agent used for treatment may increase or decrease over the course of a particular treatment. Changes in dosage may result and become apparent from the results of diagnostic assays as described herein. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an iRNA agent that is complementary, at least in an internal region, to a sequence that is conserved between the target RNA in the animal model and the target RNA in a human.

Kits.

In certain other aspects, the invention provides kits that include a suitable container containing a pharmaceutical formulation of an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an iRNA agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The invention is further illustrated by the following examples, which should not be construed as further limiting.

EXAMPLES

Example 1: Cholesterol Conjugated siRNAs are Taken Up into Primary Striatal Neurons Primary striatal neurons were isolated from mouse fetal tissue at day 15.5 gestation. The isolated cells were cultured in NeuroBasal™ medium (Gibco) for 7 days. An siRNA conjugated with cholesterol and Cy3 (called Chol-siRNA-Cy3) targeting against GFP, in a solution of PBS, was introduced to a culture of primary striatal neurons isolated from mouse (final concentration=50 nM). The cells were incubated with chol-siRNA-Cy3 for 6-12 hours and then the medium was changed, washing away any chol-siRNA-Cy3 that was not taken up into the cell. No transfection agents were used. Nearly all primary neurons were observed to contain the chol-siRNA-Cy3 in the cytoplasm of neurons. An siRNA-Cy3 (without a cholesterol conjugate) was found to be taken up by primary neurons to a much lesser extent then the cholesterol-conjugated siRNA when the cells were cultured under the same conditions.

Example 2: Cholesterol-Conjugated siRNAs were Administered to Neurons In Vivo

We administered chol-siRNA-Cy3 against GFP in mouse striatum by a single direct injection and by Alzet® pump (DURECT Corporation, Cupertino, Calif.) over 7 days. The direct injection contained 50 µM in 1 µl solution with PBS, and the Alzet pump delivered 50 µM in 1 µl per day. We compared the chol-siRNA with high dose unconjugated siRNA-Cy3, at the same doses. By fluorescence microscopy, we found that both sets of siRNAs entered many brain cells. The chol-siRNA-Cy3 had a higher frequency of cell entry than the unconjugated siRNA in administration with Alzet pump by observation. Direct injection of chol-siRNA-Cy3 showed presence of Cy3 siRNA one week later, whereas direct injection of unconjugated siRNA showed very little Cy3 labeling after one week.

In separate experiments, 2 µl of 50 µM chol-siRNA-Cy3 in PBS was injected into the striatum of mice. Three days later, mice were perfused and striatal sections prepared for immunofluorescence (FITC) for DARRP 32. DARRP 32 serves as a marker for medium spiny neurons, a neuronal type affected in Huntington's disease. The data indicated that the chol-siRNA at the volume tested spreads throughout the extent of the striatum and enters medium size spiny neurons. The sections were studied under 60X oil, to ensure that the Cy3 labeling resides inside the neurons, not on the surface. Sections at each of the three striatal regions were counted (1113 cells in all). 98% of the cells in each striatal region had colocalization of FITC (DARRP 32) and Cy3 (chol-siRNA). These pilot studies provide support that modified siRNA can be delivered to brain, to enter neurons.

To investigate whether cholesterol conjugated siRNAs were toxic to the striatal cells in vivo, the cells were stained with fluorojade, a marker for apoptotic cell death. Fluorojade staining was observed along the injection site, but not in the surrounding cells. In a positive control experiment, fluorojade staining was observed in striatal cells in vivo following injection of the NMDA receptor agonist quinolinic acid, which is known to induce neuronal cell death. These experiments indicated that chol-siRNA is not toxic to striatal cells in vivo.

Example 3. GFP Expression was Inhibited in PC12 Cells Stably Transfected with GFP-Htt We tested whether chol-siRNA targeting GFP could knockdown GFP expression, and also examined the duration of this RNAi activity. We added chol-siRNA versus GFP (50 nM final concentration) to PC12 cells stably transfected with GFP fused to human mut-htt carrying about a 100 Q expansion (Qin et al., *Hum Mol Genet.* 12:3231-44, 2003, Epub 2003 Oct. 21). Treatment with pronasterone increases expression of a because of promoter GFP-htt protein, but significantly reduces GFP fluorescence in the stably transfected cells. A control pronasterone-treated PC12 culture was treated with chol-siRNA in PBS (final concentration=100 nM) targeting luciferase; and a test pronasterone-treated PC12 cell culture was treated with chol-siRNA (final concentration 100 nM) targeting GFP. No transfection reagents were used. The chol-siRNA was kept in the culture medium for 6-12 hours and then the medium was refreshed, therefore washing out an chol-siRNA not incorporated into the cells. Images were taken one week later to assess the effect on cell fluorescence. GFP fluorescence was decreased to a much greater extent in cells treated with chol-siRNA targeting GFP, than in cells treated with chol-siRNA targeting luciferase.

Example 4. siRNA Protects Against Huntingtin-Induced Neuronal Dysfunction

With evidence that chol-siRNA can enter brain cells and knockdown target gene expression (see above), we tested chol-siRNA against human mut-htt carrying about a 100-Q expansion expression in vivo. In a mouse model of Huntington's Disease, introduction of lentivirus-mut-htt (1 µl, $1 \times 10^{10}$ particles) leads to clasping 5 days later. We injected lentivirus-mut-htt into the cortex and striatum of 4 mice. In two of the mice, we co-injected chol-siRNA against htt mRNA. In one mouse, we co-injected chol-siRNA targeting luciferase, and in the other mouse, we co-injected vehicle. The two mice that received chol-siRNA against htt showed no clasping at 7 days. The control mice clasped, as expected. The results are shown in Table 8.

TABLE 8

Study Testing Cholesterol siRNA in Vivo

| Treatment | Animal | | | |
|---|---|---|---|---|
| | 1 | 2 | 3 | 4 |
| Lentivirus-mut-htt | + | + | + | + |
| Chol-siRNA targeting mut-htt | + | + | − | − |
| Chol-siRNA targeting GFP | − | − | + | − |
| No siRNA | − | − | − | + |
| Behavior: Clasping | No | No | Yes | Yes |

Example 5. Hallmarks of Huntington's Disease are Found in Mice Treated with Lentivirus-Mut-Htt Mice continue to have clasping for seven months after lentivirus-mut-htt administration into a unilateral striatum. In other respects, the mice grew and moved as expected. Furthermore, mice treated with lentivirus-WT-htt (CAG repeat of 18) show no evidence of clasping over the course of the experimental protocol, which was to three weeks post-injection. The images in FIGS. 1A-1D are taken from the striatum of a mouse seven months after injection with lentivirus-mut-htt. The tissue was treated with an antiserum against the N-terminus of huntingtin (Ab1) for immunohistochemical analysis. Notable phenotypes include nuclear inclusions (arrowheads) and dystrophic neurites (arrows) similar to those found in adult-onset human HD (see DiFiglia et al, *Science* 277:1990-3, 1997). Use of the lentivirus model is convenient for use with co-injection of siRNA. Coinjection allows for reduced discrepancies in time and space that may complicate delivery of siRNA in transgenic mouse models.

Figure 2:
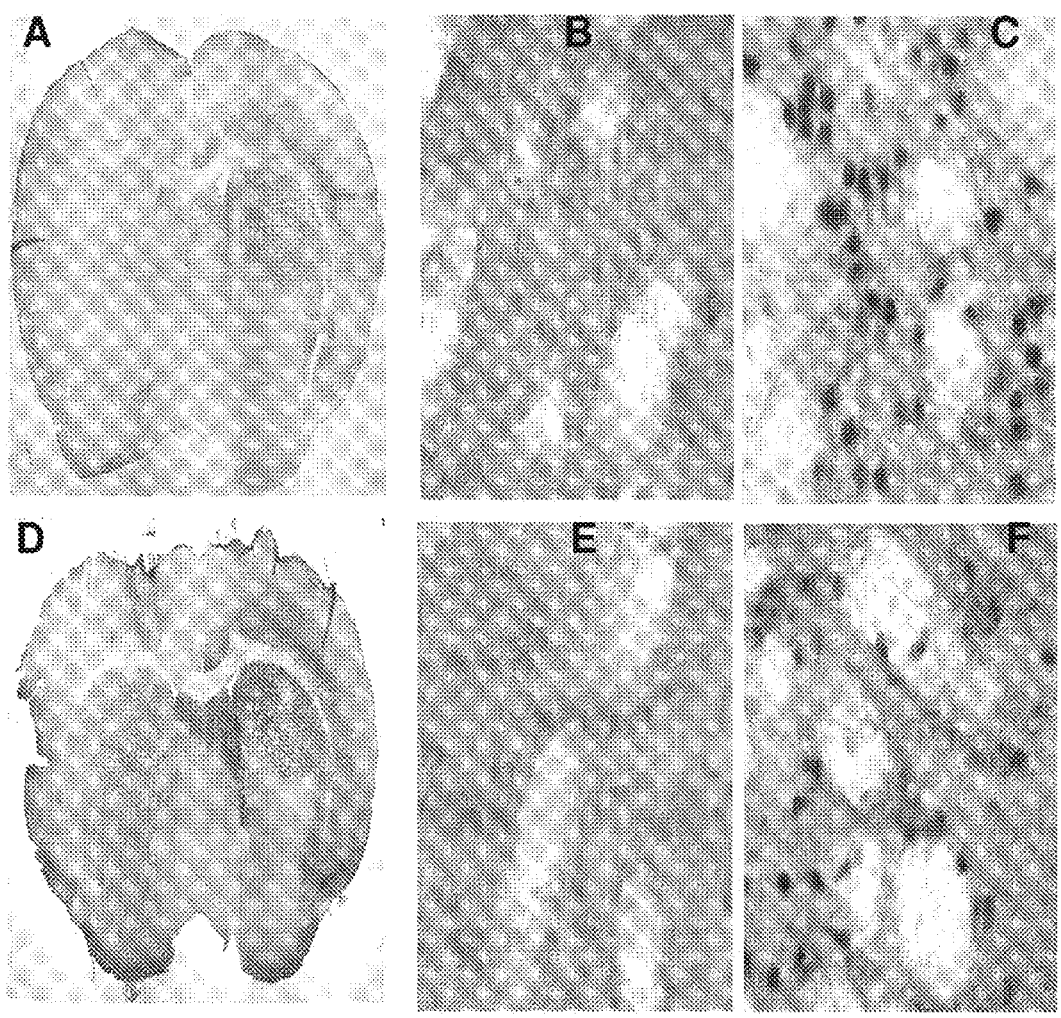
FIG. 2. Intrastriatal injection of cholesterol-conjugated dsRNA AL-DP-1799 targeting huntingtin changes pattern of cellular huntingtin-immunoreactivity in a mouse model of Huntington's disease.
Figure 3:
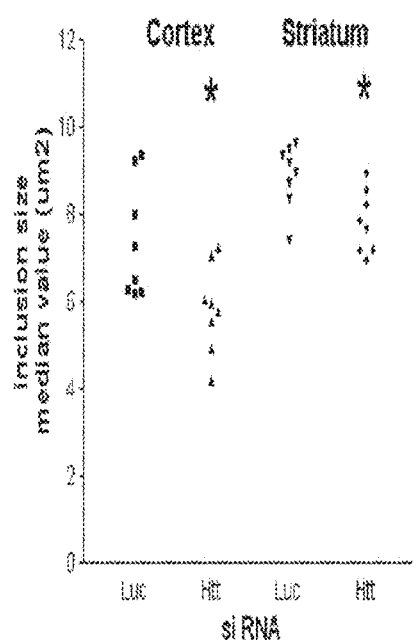
FIG. 3. Intrastriatal injection of cholesterol-conjugated dsRNA AL-DP-1799 targeting huntingtin reduces size of huntingtin-immunoreactive inclusions in cortex and striatum, and reduces neuropil aggregates in a mouse model of Huntington's disease.
Figure 3:
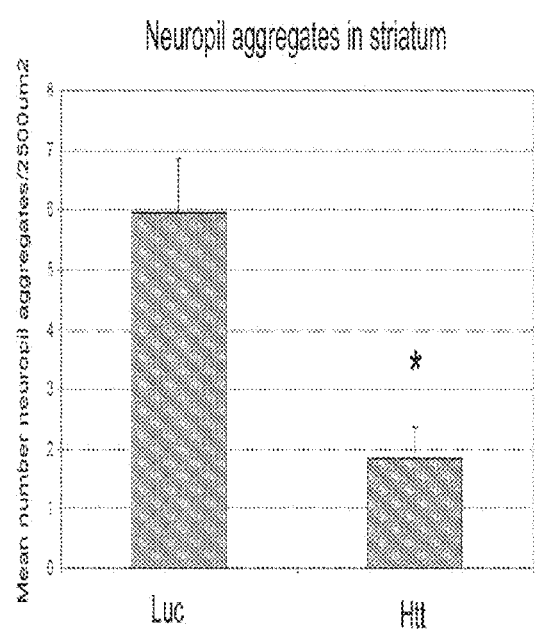

Example 6. A Single Intrastriatal Administration of siRNA Targeting Huntingtin Reduces Neuropathology in a Mouse Model of Huntington's Disease The effect of an siRNA targeting huntingtin was evaluated in an AAV mouse model of Huntington's disease. In this mouse model of Huntington's disease, a portion of the mutant human huntingtin gene with a polyglutamine expansion comprising 100 CAG repeats is introduced into the brain by viral (AAV) delivery. When a single intrastriatal injection of 0.5 nmoles (7.5 ug) siRNA was administered, the cholesterol-conjugated siRNA, AL-DP-1799 (E1-4), targeting huntingtin reduced inclusion size in striatum (FIGS. 2, 3) and cortex (FIG. 3A), and reduced neuropil aggregates in striatum (FIG. 3B), compared with a non-physiological siRNA, AL-DP-1956, targeting luciferase. In addition, the number of huntingtin-immunoreactive cells in the striatum was significantly increased, consistent with an increase in survival of striatal neurons after a single intrastriatal injection of AL-DP-1799 (FIG. 3).

Adult female SJL/B6 mice, 6 months of age, received an injection of 3 uL of $1.1 \times 10^{13}$ titer units of AAV-htt-100Q, together with 0.5 nmoles (7.5 ug) siRNA. AAV-htt-100Q comprised AAV serotype 8, for delivery of the portion of the human huntingtin gene encoding amino acids 1-400, with a 100 CAG repeat (100Q). The siRNA tested was either a cholesterol-conjugated siRNA targeting huntingtin (AL-DP-1799, below) or an irrelevant cholesterol-conjugated siRNA targeting luciferase (AL-DP-1956). For each mouse, 0.5 uL of 1 mM siRNA was injected unilaterally into the striatum at a rate of 100 nL/minute. The injection coordinates were AP+1.0 mm, Lateral+1.8 mm, Ventral 2.3 mm. For immunohistochemical analysis, mice were sacrificed 14 days after siRNA injection, and perfused intracardially with 4% paraformaldehyde. Brains were removed and vibratome frozen sections of 30 or 40 µm thickness were cut. The primary antibody against huntingtin, Ab1, that recognizes both human and mouse huntingtin, was made as described previously (DiFiglia M, Sapp E, Chase K, Schwarz C, Meloni A, Young C, Martin E, Vonsattel J-P, Carraway R, Reeves S A, Boyce F M, Carraway R, and Aronin N: Huntingtin is a cytoplasmic protein associated with vesicles in human and rat brain neurons. *Neuron* 14:1075-1081; 1995; Aronin N, Chase K, Young C, Sapp E, Schwarcz C, Matta N, Kornreich R, Sheth A, Landwehrmeyer B, Bird E, Vonsattel J-P, Smith T, Carraway R, Boyce F M, Beal M F, Young A B, Penney J B, and DiFiglia M: CAG expansion affects the expression of mutant huntingtin in the Huntington's disease brain. *Neuron* 15:1193-1201, 1995). Immunoabsorbed antiserum Ab1 was used at a concentration of 1 µg/ml. The secondary antibody was a goat anti-rabbit antibody (Vector Laboratories, California) and used at 1:10,000. For DAB histological processing, a kit was used (Pierce Laboratory, Illinois).
Sequence of Cholesterol-Conjugated dsRNA AL-DP-1799

| AL-DP-Number | sense: 5'-3' | antisense: 5'-3' |
|---|---|---|
| AL-DP-1799 | CsCCUGGAAAAGCUGAUGACGsGsChol | UsUCAUCAGCUUUUCCAGGGsUsC |

Note:
's' represents a phosphorothioate bound inbetween neighboring bases, 'Chol' represents cholesterol-conjugate Mice that received AAV-htt-100Q exhibited huntingtin-immunoreactivity in the ipsilateral striatum and cortex, whether they received cholesterol-conjugated siRNA targeting luciferase (AL-DP-1956; FIG. 2A) or cholesterol-conjugated siRNA targeting huntingtin (AL-DP-1799; FIG. 2D). However, the appearance of intracellular staining for huntingtin in mice that received AAV-htt-100Q was clearly different, in that the size of the inclusions appeared smaller in the ipsilateral striatum of mice treated with AL-DP-1799 (cholesterol-conjugated siRNA targeting huntingtin, FIG. 2F) than in the ipsilateral striatum of mice treated with AL-DP-1956 (cholesterol-conjugated siRNA targeting luciferase, FIG. 2C). The contralateral striatum exhibited faint staining for huntingtin in mice that received AAV-htt-100Q, whether they received cholesterol-conjugated siRNA targeting luciferase (AL-DP-1956; FIG. 2B) or cholesterol-conjugated siRNA targeting huntingtin (AL-DP-1799; FIG. 2E). When ipsilateral striatal and cortical inclusion sizes were quantified (70-100 inclusions measured per mouse) in mice treated with AL-DP-1956 (n=8) and mice treated with AL-DP-1799 (n=8), inclusion size was significantly ($p<0.02$) reduced in mice treated with AL-DP-1799 compared to mice treated with AL-DP-1956. Median inclusion sizes for ipsilateral cortex and striatum are shown as scatter plots in FIG. 3A. Therefore, a single intrastriatal injection of cholesterol-conjugated siRNA targeting huntingtin results in reduced striatal and cortical pathology, and represents a novel approach to providing effective treatment of Huntington's disease.

Moreover, when the same mice were evaluated for neuropil aggregates in the striatum (FIG. 3B), mice that received AAV-htt-100Q and AL-DP-1799 (cholesterol-conjugated siRNA targeting huntingtin) exhibited an approximately two-thirds reduction ($p<0.02$) in the number of neuropil aggregates compared with mice that received AAV-htt-100Q and AL-DP-1956 (cholesterol-conjugated siRNA targeting luciferase). Total neuropil aggregates were counted in a 2500 $um^2$ area, using 6 sections per mouse. These data provide additional evidence that a single intrastriatal injection of cholesterol-conjugated siRNA targeting huntingtin results in reduced neuropathology, and represents a novel approach to providing effective treatment of Huntington's disease.

Figure 4:
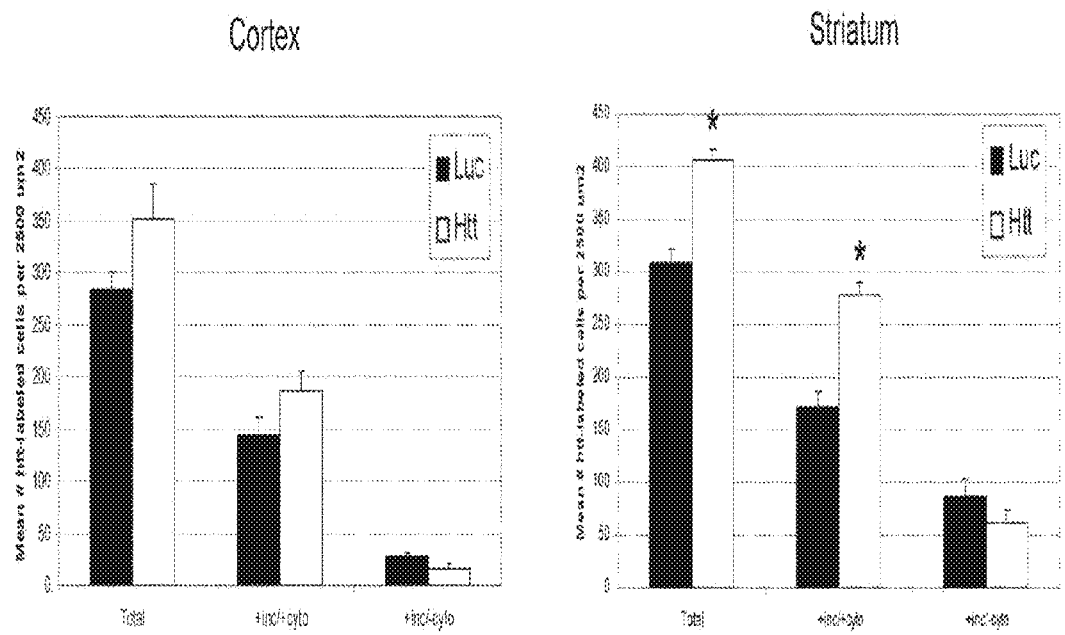
FIG. 4. Intrastriatal injection of cholesterol-conjugated dsRNA AL-DP-1799 targeting huntingtin increases the number of huntingtin-immunoreactive cells in striatum in a mouse model of Huntington's disease.

The number of huntingtin-immunoreactive cells was scored in cortex and striatum of 8 mice that received AAV-htt-100Q and AL-DP-1799 (cholesterol-conjugated siRNA targeting huntingtin, 'Htt') and 8 mice that received AAV-htt-100Q and AL-DP-1956 (cholesterol-conjugated siRNA targeting luciferase, 'luc'). In the striatum (FIG. 4), a statistically significant increase ($p<0.001$) was found in the mean number of total huntingtin-immunoreactive cells per 2500 $um^2$ area in mice treated with AL-DP-1799 (cholesterol-conjugated siRNA targeting huntingtin) compared to mice treated with AL-DP-1956 (cholesterol-conjugated siRNA targeting luciferase). In the cortex (FIG. 4), there was a trend towards an increased mean number of total huntingtin-immunoreactive cells per 2500 $um^2$ area in mice treated with AL-DP-1799 (cholesterol-conjugated siRNA targeting huntingtin) compared to mice treated with AL-DP-1956 (cholesterol-conjugated siRNA targeting luciferase). When cells with nuclear inclusions and cytoplasmic aggregates ('+inc/+cyto') were scored separately from cells with nuclear inclusions and no cytoplasmic aggregates ('+inc/−cyto'), there was a statistically significant increase ($p<0.001$) in the number of cells with nuclear inclusions and cytoplasmic aggregates in striatum. One explanation for this result is that mice that received AAV-htt-100Q and were treated with AL-DP-1799 (cholesterol-conjugated siRNA targeting huntingtin) have more surviving striatal neurons. These data imply that a single intrastriatal injection of cholesterol-conjugated siRNA targeting huntingtin results in protection of striatal neurons, and represents a novel approach to providing effective treatment of Huntington's disease.

Figure 5:
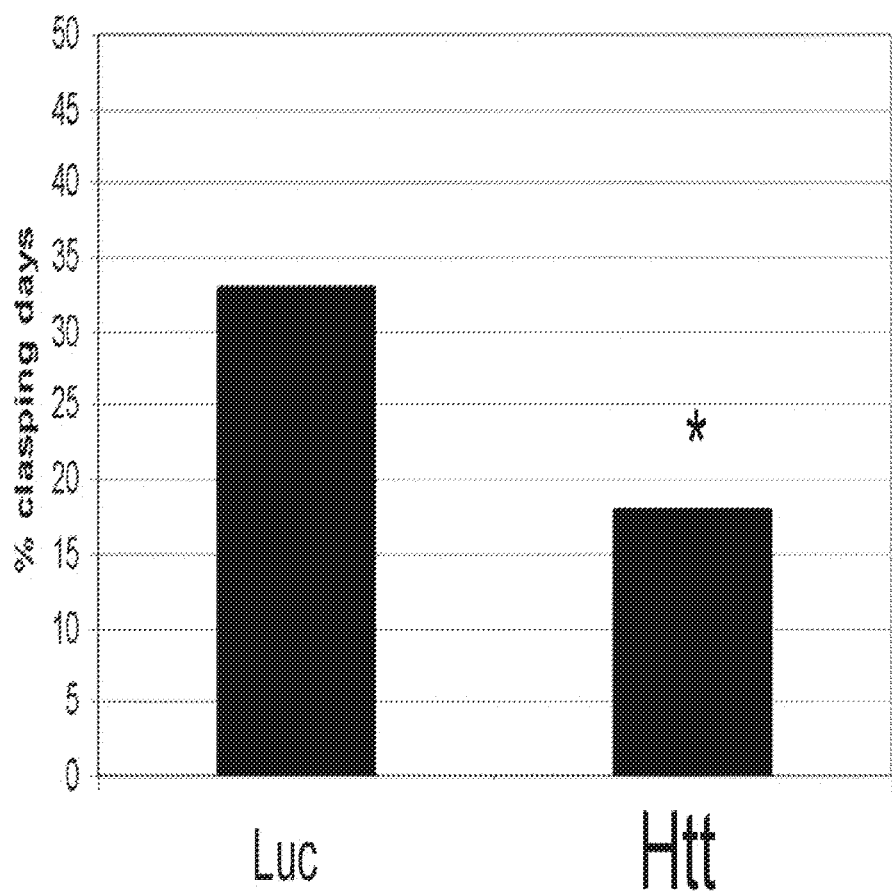
FIG. 5. Intrastriatal injection of cholesterol-conjugated dsRNA AL-DP-1799 targeting huntingtin reduces abnormal clasping behavior in a mouse model of Huntington's disease.

Example 7. A Single Intrastriatal Administration of siRNA Targeting Huntingtin Reduces Abnormal Clasping Behavior in a Mouse Model of Huntington's Disease The effect of the siRNA targeting huntingtin was further evaluated in the AAV mouse model of Huntington's disease by assessing clasping behavior, a stereotypical and abnormal behavior characteristic of animal models of Huntington's disease. In the same mice where pathology was subsequently evaluated, clasping was scored as a binary yes/no daily assessment over a period of 14 days, and then the percentage of days that clasping was observed was determined for each mouse. The average percentage of clasping days was reduced by approximately half ($p<0.01$) in mice treated with the cholesterol-conjugated siRNA targeting huntingtin, AL-DP-1799 ('Htt', FIG. 4), as compared to mice that received a non-physiological siRNA targeting luciferase, AL-DP-1956 ('Luc', FIG. 5). These data demonstrate that a single intrastriatal injection of cholesterol-conjugated siRNA targeting huntingtin results in functional improvement, and therefore, represents a novel approach to providing effective treatment of Huntington's disease.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. An isolated iRNA agent comprising a sense strand and an antisense strand, wherein the sense strand and the antisense strand form an RNA duplex, wherein the antisense strand comprises a nucleotide sequence that differs by no more than four nucleotides from an antisense sequence of SEQ ID NO: 12, wherein the iRNA agent is conjugated to a cholesterol moiety, and wherein the iRNA agent further comprises a phosphorothioate or a 2'-OMe modification.

2. The iRNA agent of claim 1, wherein the sense strand comprises a sequence of SEQ ID NO: 11.

3. The isolated iRNA agent of claim 1, wherein the cholesterol is conjugated to the sense strand.

4. The isolated iRNA agent of claim 3, wherein the cholesterol is conjugated to the 3' end of the sense strand.

5. The isolated iRNA agent of claim 1, which is at least 21 nucleotides in length.

6. The isolated iRNA agent of claim 1, wherein the duplex region of the iRNA agent is about 18-25 nucleotides in length.

7. The isolated iRNA agent of claim 1, wherein the iRNA agent comprises a nucleotide overhang having 1 to 4 unpaired nucleotides.

8. A pharmaceutical composition, comprising:
(i) the isolated iRNA agent of claim 1; and
(ii) a pharmaceutically acceptable carrier.

9. The pharmaceutical composition of claim 8, comprising the sense strand of the iRNA agent comprises a sequence of SEQ ID NO: 11.

10. A method of downregulating expression of huntingtin (htt) mRNA in a neural cell distal to the site of administration, the method comprising contacting the iRNA agent of claim 1 with the neural cell for a time sufficient to allow uptake of the iRNA agent into the cell.

11. The method of claim 10, wherein the cell is contacted for a time sufficient to allow axonal transport of said iRNA.

12. The method of claim 10, wherein the iRNA agent is provided in a solution comprising a transfection reagent.

13. The method of claim 10 for treating a human further comprising identifying a human having Huntington's disease, and administering to the human the iRNA agent.

14. The method of claim 13, wherein the iRNA agent comprises a nucleotide overhang having 1 to 4 unpaired nucleotides.

15. The method of claim 13, wherein the iRNA agent is administered as a sustained dose formulation, administered in multiple doses over a prolonged time period, or as a single dose.

16. The method of claim 13, comprising the administration of a second iRNA agent, wherein (i) the second iRNA agent comprises a sense and an antisense strand that form an RNA duplex, and (ii) the antisense strand of the iRNA agent comprises a nucleotide sequence sufficiently complementary to a second target sequence of about 18 to 25 nucleotides of the mRNA expressed from the htt gene.

17. The method of claim 10, wherein the neural cell is present in a subject and/or wherein the amount of huntingtin (htt) mRNA in the subject is reduced.

18. The method of claim 17, wherein the cells are contacted for a time sufficient to allow axonal transport of said iRNA.

19. A method of downregulating expression of htt mRNA in a neural cell, the method comprising contacting the iRNA agent of claim 1 with the neural cell for a time sufficient to allow uptake of the iRNA agent into the cell.

20. The method of claim 19 for treating a human further comprising identifying a human having Huntington's disease, and administering to the human the iRNA agent.

\* \* \* \* \*

SEQUENCE LISTING

<160> NUMBER OF SEQ ID NOS: 60

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cccuggaaaa gcugaugacg g                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uucaucagcu uuccagggu c                                               21

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cccuggaaaa gcugaugacg                                                20

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uucaucagcu uuccagggu c                                               21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cccucaucca cugugugccc u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugcacacagu ggaugaggga g                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cccucaucca cugugugccc u                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugcacacagu ggaugaggga g                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugugcugacu cugaggaaaa g                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
guuccucaga gucagcacau c                                              21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ugugcugacu cugaggaaaa g                                              21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
guuccucaga gucagcacau c                                              21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cccuggaaaa gcugaugaag g                                              21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uucaucagcu uuccagggu c                                               21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cccuggaaaa gcugaugaag g                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uucaucagcu uuccagggu c                                               21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 17
cccuggaaaa gcugaugacg g                                              21

<210> SEQ ID NO 18

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 18
uucaucagcu uuuccagggu c                                            21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (18)..(19)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 19
cccuggaaaa gcugaugacg g                                            21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (18)..(19)
<223> OTHER INFORMATION: Phosphorothioate linkage
<220> FEATURE:
<221> NAME/KEY: misc_feature
<222> LOCATION: (19)..(20)
```

```
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 20
uucaucagcu uuuccagggu c                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 21
ugugcugacu cugaggaaaa g                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 22
guuccucaga gucagcacau c                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (18)..(19)
```

```
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 23
ugugcugacu cugaggaaaa g                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (18)..(19)
<223> OTHER INFORMATION: Phosphorothioate linkage

<400> SEQUENCE: 24
guuccucaga gucagcacau c                                              21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (4)
<223> OTHER INFORMATION: 2'-O-methyl sugar
<220> FEATURE:
<221> NAME/KEY: modified_base
<222> LOCATION: (13)
<223> OTHER INFORMATION: 2'-O-methyl sugar
<220> FEATURE:
<221> NAME/KEY: modified_base
<222> LOCATION: (16)
<223> OTHER INFORMATION: 2'-O-methyl sugar
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 25
cccuggaaaa gcugaugacg g                                              21

<210> SEQ ID NO 26
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: 2'-O-methyl sugar
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (3)
<223> OTHER INFORMATION: 2'-O-methyl sugar
<220> FEATURE:
<221> NAME/KEY: modified_base
<222> LOCATION: (6)
<223> OTHER INFORMATION: 2'-O-methyl sugar
<220> FEATURE:
<221> NAME/KEY: modified_base
<222> LOCATION: (12)
<223> OTHER INFORMATION: 2'-O-methyl sugar
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 26
ugugcugacu cugaggaaaa g                                           21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ccacaugaag cagcacgacu u                                           21

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(22)
<223> OTHER INFORMATION: 2'-O-methyl sugar

<400> SEQUENCE: 28
aagucgugcu gcuucaugug guc                                         23

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
```

```
<223> OTHER INFORMATION: Phosphorothioate linkage
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 29
cccuggaaaa gcugaugacg g                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 30
cccuggaaaa gcugaugacg g                                              21

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Gln Ile Lys Ile Trp Phe Gln Asn Arg Arg Met Lys Trp Lys Lys
 1               5                  10                  15

<210> SEQ ID NO 32
<211> LENGTH: 14
<212> TYPE: PRT
<213> ORGANISM: Human immunodeficiency virus

<400> SEQUENCE: 32

Gly Arg Lys Lys Arg Arg Gln Arg Arg Pro Pro Gln Cys
 1               5                  10

<210> SEQ ID NO 33
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ala Leu Phe Leu Gly Trp Leu Gly Ala Ala Gly Ser Thr Met Gly
 1               5                  10                  15

Ala Trp Ser Gln Pro Lys Lys Lys Arg Lys Val
            20                  25

<210> SEQ ID NO 34
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Leu Ile Ile Leu Arg Arg Arg Ile Arg Lys Gln Ala His Ala His
1               5                   10                  15

Ser Lys

<210> SEQ ID NO 35
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Leu Ala Leu Lys Leu Ala Leu Lys Ala Leu Lys Ala Ala Leu Lys
1               5                   10                  15

Leu Ala

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Arg Arg Arg Arg Arg Arg Arg Arg
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Phe Phe Lys Phe Phe Lys Phe Phe Lys
1               5                   10

<210> SEQ ID NO 39
<211> LENGTH: 37
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 39

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 40
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
            35

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 43

Arg Lys Cys Arg Ile Val Val Ile Arg Val Cys Arg
1               5                   10

<210> SEQ ID NO 44
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 44

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 45

Ile Leu Pro Trp Lys Trp Pro Trp Trp Pro Trp Arg Arg
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ala Val Ala Leu Leu Pro Ala Val Leu Leu Ala Leu Leu Ala Pro
1               5                   10                  15

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ala Leu Leu Pro Val Leu Leu Ala Ala Pro
1               5                   10

<210> SEQ ID NO 48
<211> LENGTH: 13
<212> TYPE: PRT
<213> ORGANISM: Human immunodeficiency virus

<400> SEQUENCE: 48
```

-continued

```
Gly Arg Lys Lys Arg Arg Gln Arg Arg Arg Pro Pro Gln
 1               5                  10
```

<210> SEQ ID NO 49
<211> LENGTH: 16
<212> TYPE: PRT
<213> ORGANISM: Drosophila sp.

<400> SEQUENCE: 49

```
Arg Gln Ile Lys Ile Trp Phe Gln Asn Arg Arg Met Lys Trp Lys Lys
 1               5                  10                  15
```

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 50
cccuggaaaa gcugaugacg g                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 51
cccucaucca cugugugccc u                                              21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 52
cccucaucca cugugugccc u                                              21

<210> SEQ ID NO 53

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ccacaugaag cagcacgacu u                                                21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 54
cccuggaaaa gcugaugacg g                                                21

<210> SEQ ID NO 55
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(22)
<223> OTHER INFORMATION: 2'-O-methyl sugar

<400> SEQUENCE: 55
aagucgugcu gcuucaugug guc                                              23

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 56
cccuggaaaa gcugaugacg g                                                21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (20)..(21)
<223> OTHER INFORMATION: Phosphorothioate linkage

<400> SEQUENCE: 57
cccuggaaaa gcugaugacg g                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 58
ugcacacagu ggaugaggga g                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (20)..(21)
<223> OTHER INFORMATION: Phosphorothioate linkage

<400> SEQUENCE: 59
uucaucagcu uuuccagggu c                                              21

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Phe Leu Gly
 1
```